US012617785B2

(12) United States Patent
Gnedeva et al.

(10) Patent No.: US 12,617,785 B2
(45) Date of Patent: May 5, 2026

(54) PYRROLO[2,3-b]PYRIDINE-3-CARBOXAMIDE COMPOSITIONS AND METHODS FOR AMELIORATING HEARING LOSS

(71) Applicant: The Rockefeller University, New York, NY (US)

(72) Inventors: Ksenia Gnedeva, Malibu, CA (US); A. James Hudspeth, New York, NY (US); Nathaniel Kastan, New York, NY (US); Rui Liang, East Brunswick, NJ (US); Peter T. Meinke, Scotch Plains, NJ (US); David John Huggins, New York, NY (US); Nigel John Liverton, San Antonio, TX (US); Leigh Ashley Baxt, New York, NY (US); John David Ginn, New York, NY (US); Robert Walter Myers, Cresskill, NJ (US)

(73) Assignee: The Rockefeller University, New York, NY (US)

( * ) Notice: Subject to any disclaimer, the term of this patent is extended or adjusted under 35 U.S.C. 154(b) by 839 days.

(21) Appl. No.: 17/760,143

(22) PCT Filed: Feb. 5, 2021

(86) PCT No.: PCT/US2021/016848

§ 371 (c)(1),
(2) Date: Aug. 4, 2022

(87) PCT Pub. No.: WO2021/158936

PCT Pub. Date: Aug. 12, 2021

(65) Prior Publication Data

US 2023/0137893 A1 May 4, 2023

Related U.S. Application Data

(60) Provisional application No. 62/970,425, filed on Feb. 5, 2020.

(51) Int. Cl.
*C07D 471/04* (2006.01)

(52) U.S. Cl.
CPC .................................. *C07D 471/04* (2013.01)

(58) Field of Classification Search
CPC .................................................... C07D 471/04
See application file for complete search history.

(56) References Cited

U.S. PATENT DOCUMENTS

| | | | |
|---|---|---|---|
| 8,592,398 | B2 | 11/2013 | Kumar et al. |
| 2007/0129364 | A1 | 6/2007 | Dong et al. |
| 2011/0082144 | A1 | 4/2011 | Lau et al. |
| 2011/0092538 | A1 | 4/2011 | Spevak et al. |

FOREIGN PATENT DOCUMENTS

| | | | |
|---|---|---|---|
| WO | 2021158936 | A1 | 8/2021 |

OTHER PUBLICATIONS

American Chemical Society. Chemical Abstract Service. RN 1942057-09-1. Entered into STN: Jun. 29, 2016. (Year: 2016).*

Registry No. 1424635-83-5, CAS Registry Apr. 18, 2013.

Pubchem CID 154857855, Create date: Dec. 15, 2020 (Dec. 15, 2020), entire document, especially p. 2, compound listed Dec. 15, 2020.

U et al. "Discovery of 4-Substituted Methoxybenzoyl-aryl-thiazole as Novel Anticancer Agents: Synthesis, Biological Evaluation, and Structure-Activity Relationships" J. Med.Chem 52, 1701-1711(2009) 2009.

International Search Report and Written Opinion in International Application No. PCT/US2021/016848 mailed Jul. 8, 2021.

Pubchem SID: 438701942 deposited on Dec. 15, 2020, pp. 1-8. pg. 2.

Kastan et al. "Small-Molecule Inhibition of Lats Kinase Promotes Yap-dependent proliferation in Postmitotic Mammalian Tissues", bioRxiv, Apr. 16, 2020, pp. 1-42.

* cited by examiner

*Primary Examiner* — John S Kenyon
(74) *Attorney, Agent, or Firm* — Heslin Rothenberg Farley & Mesiti P.C.

(57) ABSTRACT

N-(3-Substituted thiazol-2(3H)-ylidene)-1H-pyrrolo[2,3-b]pyridine-3-carboxamides and N-(3-substituted oxazol-2(3H)-ylidene)-1H-pyrrolo[2,3-b]pyridine-3-carboxamides

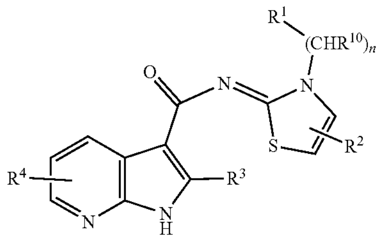

and

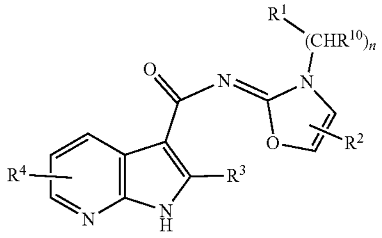

are disclosed. The compounds activate Yap and inhibit Lats kinases. They are therefore useful for treating hearing loss.

25 Claims, No Drawings

PYRROLO[2,3-b]PYRIDINE-3-CARBOXAMIDE COMPOSITIONS AND METHODS FOR AMELIORATING HEARING LOSS

CROSS REFERENCE TO RELATED APPLICATIONS

This application is a national phase filing under 35 U.S.C. § 371 of PCT International Application PCT/US2021/016848, filed Feb. 5, 2021. PCT/US2021/016848 claimed priority from U.S. Provisional Application No. 62/970,425, filed Feb. 5, 2020. The contents of the prior applications are incorporated by reference herein in their entirety.

GOVERNMENT RIGHTS STATEMENT

This invention was made with government support under grant number T32GM007739 awarded by National Institutes of Health. The government has certain rights in the invention.

BACKGROUND OF THE INVENTION

Technical Field

The present application relates generally to N-(3-substituted thiazol-2(3H)-ylidene)-1H-pyrrolo[2,3-b]pyridine-3-carboxamides and N-(3-substituted oxazol-2(3H)-ylidene)-1H-pyrrolo[2,3-b]pyridine-3-carboxamides that inhibit Lats kinases and thus increase Yap activity. The compounds are useful for inducing the proliferation of supporting cells in the inner ear, and thus potentially for treating hearing loss.

Background Information

Initiated in response to injury, regeneration is a complex process that can restore the structure and function of damaged tissue. Some adult mammalian tissues retain a gradually declining regenerative capability beyond development. Regeneration occurs either by activation and amplification of resident stem cells, as in the epithelia of the skin and intestine, or through cellular dedifferentiation and proliferation, as in the liver. In other instances, such as central nervous and cardiac-muscle tissues, cells exhibit little or no potential for regeneration after injury.

In view of its fundamental roles in development, proliferation, stem-cell maintenance, and dedifferentiation, Hippo signaling is an inviting target for driving regeneration. The regenerative potential of the Hippo pathway has become abundantly clear in numerous organs, including the heart, retina, liver, and intestine. Hippo signaling limits the size of the developing murine utricle, a sensory organ in the vestibular portion of the inner ear, and the Yap-Tead complex is active during—and necessary for—proliferative regeneration in the neonatal utricle. These observations suggest that chemical activation of Yap signaling might engender supporting-cell proliferation in adult tissue, a key missing step in the regeneration of the mammalian inner ear.

In an effort to identify activators of Yap, we conducted a small-molecule screen on cultured cells. We identified the compound, which we found to function as an inhibitor of Lats kinases. To test our original hypothesis, we treated utricles explanted from adult mice with the substance and found that a few days' exposure caused supporting cells to reenter the cell cycle, a critical step towards robust hair-cell regeneration.

SUMMARY OF THE INVENTION

The invention is directed to N-(3-substituted azol-2(3H)-ylidene)-1H-pyrrolo[2,3-b]pyridine-3-carboxamides, pharmaceutical compositions and methods for inhibiting Lats or activating Yap, and thereby stimulating regeneration of target cells, particularly hair-cells.

The present invention relates, in a first aspect, to compounds of formula I:

I

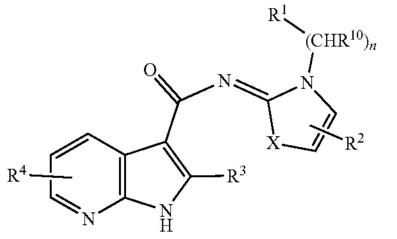

wherein:

$R^1$ is selected from the group consisting of $(C_1\text{-}C_6)$alkyl, carboxy, $(C_3\text{-}C_7)$carbomonocyclyl, $(C_9\text{-}C_{11})$carbobicyclyl, heteromonocyclyl, and heterobicyclyl, wherein said $(C_1\text{-}C_6)$alkyl, $(C_3\text{-}C_7)$carbomonocyclyl, $(C_9\text{-}C_{11})$carbobicyclyl, heteromonocyclyl, and heterobicyclyl may be optionally substituted with from one to three substituents selected independently from the group consisting of halogen, cyano, hydroxy, nitro, amino, acetoxy, carboxy, $(C_1\text{-}C_7)$hydrocarbyl, halo$(C_1\text{-}C_6)$alkyl, $(C_1\text{-}C_3)$alkoxy, halo$(C_1\text{-}C_3)$alkoxy, $(C_1\text{-}C_6)$acyl, $(C_1\text{-}C_3)$alkoxy$(C_1\text{-}C_3)$alkyl, hydroxy$(C_1\text{-}C_3)$alkyl, heteroaryl, benzenesulfonyl, $(C_1\text{-}C_3)$alkoxycarbonyl, aminocarbonyl, $(C_1\text{-}C_3)$alkylaminocarbonyl, di$(C_1\text{-}C_3)$alkylaminocarbonyl, $(C_1\text{-}C_3)$alkylamino, di$(C_1\text{-}C_3)$alkylamino, amino$(C_1\text{-}C_3)$alkyl, $(C_1\text{-}C_3)$alkylamino$(C_1\text{-}C_3)$alkyl $(C_1\text{-}C_3)$dialkylamino$(C_1\text{-}C_3)$alkyl, $(C_1\text{-}C_3)$alkylthio, $(C_1\text{-}C_3)$alkylsulfonylamino, $(C_1\text{-}C_3)$alkylsulfinyl, $(C_1\text{-}C_3)$alkylsulfonyl, phenoxy, and benzyloxy;

$R^2$ is selected from the group consisting of hydrogen, halogen, $(C_1\text{-}C_7)$hydrocarbyl, halo$(C_1\text{-}C_6)$alkyl, $(C_1\text{-}C_6)$acyl, hydroxy$(C_1\text{-}C_3)$alkyl, $-C(=O)O(C_1\text{-}C_6)$alkyl, $-C(=O)NR^{20}R^{21}$, and $(C_1\text{-}C_6)$oxaalkyl;

$R^3$ is selected from the group consisting of hydrogen, halogen, $(C_1\text{-}C_6)$hydrocarbyl, halo$(C_1\text{-}C_6)$alkyl, $(C_1\text{-}C_6)$acyl, and $(C_1\text{-}C_3)$alkoxy;

$R^4$ is selected from the group consisting of hydrogen, halogen, $(C_1\text{-}C_6)$hydrocarbyl, halo$(C_1\text{-}C_6)$alkyl, $(C_1\text{-}C_6)$acyl, and $(C_1\text{-}C_3)$alkoxy;

$R^{10}$ is selected independently in each instance from the group consisting of hydrogen and methyl;

$R^{20}$ is selected from the group consisting of hydrogen and $(C_1\text{-}C_6)$hydrocarbyl;

$R^{21}$ is selected from the group consisting of hydrogen, $(C_1\text{-}C_6)$hydrocarbyl, $(C_1\text{-}C_6)$oxaalkyl, amino$(C_1\text{-}C_6)$alkyl, $(C_1\text{-}C_3)$alkylamino$(C_1\text{-}C_6)$alkyl, di$(C_1\text{-}C_3)$alkylamino$(C_1\text{-}C_6)$alkyl, and $-(CH_2)_m$-Het, wherein Het is an aliphatic mono- or bicyclic heterocycle, optionally substituted with a substituent selected from the group consisting hydroxy, amino, acetoxy, carboxy, $(C_1\text{-}C_7)$hydrocarbyl, halo$(C_1\text{-}C_6)$alkyl, $(C_1\text{-}C_3)$alkoxy, halo$(C_1\text{-}C_3)$alkoxy, $(C_1\text{-}C_6)$acyl, $(C_1\text{-}C_3)$alkoxy$(C_1\text{-}C_3)$alkyl, hydroxy$(C_1\text{-}C_3)$alkyl, aminocarbonyl, $(C_1\text{-}C_3)$ alkylaminocarbonyl, di($C_1$-$C_3$)alkylaminocarbonyl, ($C_1$-$C_3$)alkylamino, and di($C_1$-$C_3$)alkylamino;

or, taken together with the nitrogen to which they are attached, $R^{20}$ and $R^{21}$ form an aliphatic heterocyle;

n is zero, one or two;

m is zero, one or two; and

X is S; or, when n is 1 and $R^1$ is optionally substituted phenyl, X may additionally be O; with the proviso that, when $R^1$ is phenyl, X is sulfur, and n is one, at least one of $R^2$, $R^3$, $R^4$, and $R^{10}$ other than hydrogen.

In another aspect, the invention relates to pharmaceutical compositions comprising a pharmaceutically acceptable carrier and a compound as described herein.

In another aspect, the invention relates to a method of for activating YAP in a cell expressing YAP comprising exposing the cell to a compound as described herein.

In another aspect, the invention relates to a method for LATS inhibition in a cellpopulation expressing LATS comprising exposing the cell population to a compound as described herein.

In another aspect, the invention relates to a method for LATS inhibition in a cell population comprising exposing the cell population to a compound as described herein.

In another aspect, the invention relates to a method for stimulating hair cell regeneration comprising exposing a supporting-cell population to a compound as described herein.

DETAILED DESCRIPTION OF THE INVENTION

It has been found that compounds of formula I

Ia

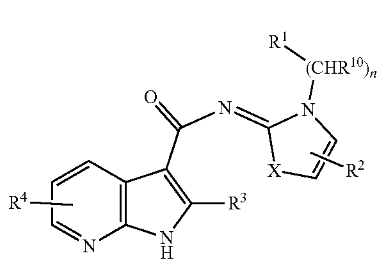

are useful for inhibiting Lats or activating Yap and are therefore potential therapeutic agents for stimulating regeneration of target cells, particularly hair-cells. Such compounds would be useful for treating hearing loss. The genus I can be broken down into two subgenera.

In a first subgenus, X is sulfur, and compounds are thiazol-2(3H)-ylidene)-1H-pyrrolo[2,3-b]pyridine-3-carboxamides of formula II:

II

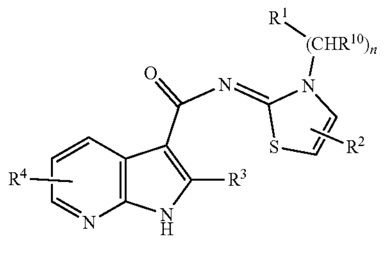

In a second subgenus, X is oxygen, and compounds are oxazol-2(3H)-ylidene)-1H-pyrrolo[2,3-b]pyridine-3-carboxamides of formula III:

III

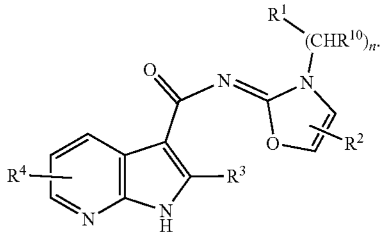

wherein n is one and $R^1$ is optionally substituted phenyl.

In some embodiments of the formulae I and II, n may be zero. In other embodiments of the formulae I-III, n may be one. In these embodiments, $R^{10}$ may be hydrogen.

In some embodiments, $R^1$ is optionally substituted ($C_1$-$C_4$)alkyl, carboxy, phenyl, cyclohexyl, 5-membered heterocyclyl, 6-membered heterocyclyl or heterobicyclyl. In particular, $R^1$ may be methyl, ethyl, aminobutyl, and carboxyethyl. In other embodiments, $R^1$ is optionally substituted cyclohexyl, or $R^1$ is optionally substituted phenyl, or $R^1$ is optionally substituted heterocyclyl, for example, pyridinyl, pyrazolyl, piperidinyl, tetrahydropyranyl, tetrahydrofuranyl, or tetrahydroisoquinolinyl. When $R^1$ is optionally substituted phenyl, it may carry one or two substituents chosen independently from halogen, cyano, hydroxy, amino, carboxy, ($C_1$-$C_6$)hydrocarbyl, trifluoromethyl, methoxy, acetyl, formyl, hydroxy($C_1$-$C_3$)alkyl, methoxycarbonyl [—C(═O)OCH$_3$], carboxamido [—C(═O)NH$_2$], methanesulfonylamino, and amino($C_1$-$C_3$)alkyl. When $R^1$ is pyridinyl, pyrazolyl, piperidinyl, tetrahydropyranyl, or tetrahydroisoquinolinyl, each heterocycle may be optionally substituted with one or two substituents chosen independently from amino, hydroxy and ($C_1$-$C_6$)hydrocarbyl.

In some embodiments $R^1$ is selected from the group consisting of carboxy and optionally substituted ($C_1$-$C_4$) alkyl, phenyl, cyclohexyl, 5-membered heterocyclyl, 6-membered heterocyclyl and heterobicyclyl. In some of these $R^1$ is selected from the group consisting of methyl, ethyl, aminobutyl, and carboxyethyl. In others $R^1$ is optionally substituted cyclohexyl. In some of these $R^1$ is optionally substituted heterocyclyl. The heterocycle may be pyridinyl, pyrazolyl, piperidinyl, tetrahydropyranyl, tetrahydrofuranyl, and tetrahydroisoquinolinyl, each optionally substituted. Optional substituents may include one or two substituents selected independently from the group consisting of amino, hydroxy and ($C_1$-$C_6$)hydrocarbyl.

In some embodiments, $R^1$ is optionally substituted phenyl. The phenyl may be substituted with one or two substituents selected independently from the group consisting of halogen, cyano, hydroxy, amino, carboxy, ($C_1$-$C_6$)hydrocarbyl, trifluoromethyl, methoxy, acetyl, formyl, hydroxy($C_1$-$C_3$)alkyl, methoxycarbonyl, carboxamido, methanesulfonylamino, and amino($C_1$-$C_3$)alkyl. In some of these embodiments, $R^1$ is phenyl substituted at the ortho position and n is zero; in others $R^1$ is optionally substituted phenyl and n is one.

In some embodiments, $R^2$ is selected from the group consisting of —C(═O)O($C_1$-$C_6$)alkyl, —C(═O)NR$^{20}$R$^{21}$, and ($C_1$-$C_6$)oxaalkyl. In some of these embodiments $R^{20}$ is chosen from hydrogen and methyl, and and $R^{21}$ is chosen from hydrogen, methyl, $(C_1\text{-}C_6)$oxaalkyl, dimethylamino $(C_1\text{-}C_6)$alkyl, and —$(CH_2)_2$-Het. In others, $R^{20}$ and $R^{21}$ taken together with the nitrogen to which they are attached form a 4-7-membered aliphatic heterocycle. Exemplary aliphatic heterocycles include piperidine, piperazine, morpholine, pyrrolidine, azetidine, azepine and the like.

In some embodiments $R^2$ is chosen from hydrogen, methyl, ethyl, propyl, cyclopropyl, hydroxymethyl, and trifluoromethyl.

In some embodiments $R^3$ and $R^4$ are chosen from hydrogen, chloro and methyl.

It is to be understood that in various embodiments, the pharmaceutical compositions of the present inventions comprise one or more pharmaceutically acceptable excipients, including, but not limited to, one or more binders, bulking agents, buffers, stabilizing agents, surfactants, wetting agents, lubricating agents, diluents, disintegrants, viscosity enhancing or reducing agents, emulsifiers, suspending agents, preservatives, antioxidants, opacifying agents, glidants, processing aids, colorants, sweeteners, taste-masking agents, perfuming agents, flavoring agents, diluents, polishing agents, polymer matrix systems, plasticizers and other known additives to provide an elegant presentation of the drug or aid in the manufacturing of a medicament or pharmaceutical product comprising a composition of the present inventions. Examples of carriers and excipients well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005.

In various embodiments, non-limiting examples of excipients include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), hydroxypropyl cellulose, titanium dioxide, talc, calcium carbonate (e.g., granules or powder), microcrystalline cellulose, powdered cellulose, dextrates, kaolin, silicic acid, sorbitol, starch, pre-gelatinized starch, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, a syloid silica gel (AEROSIL200, manufactured by W. R. Grace Co. of Baltimore, MD), a coagulated aerosol of synthetic silica (marketed by Degussa Co. of Plano, TX), CAB-O-SIL (a pyrogenic silicon dioxide product sold by Cabot Co. of Boston, MA), colorants and mixtures thereof.

The terms "subject" or "subject in need thereof" are used interchangeably herein. These terms refer to a patient who has been diagnosed with the underlying disorder to be treated. Ordinarily, the patient will be a human. The subject may currently be experiencing symptoms associated with the disorder or may have experienced symptoms in the past. Additionally, a "subject in need thereof" may be a patient at risk of developing a particular disease, or to a patient reporting one or more of the physiological systems of a disease, even though a diagnosis of this disease may not have been made.

As used herein, the terms "treatment" or "treating" are used interchangeably. These terms refer to an approach for obtaining beneficial or desired results including, but not limited to, therapeutic benefit. Therapeutic benefit includes eradication or amelioration of the underlying disorder being treated; it also includes the eradication or amelioration of one or more of the symptoms associated with the underlying disorder such that an improvement is observed in the patient, notwithstanding that the patient may still be afflicted with the underlying disorder.

As used herein, the term "optionally substituted" may be used interchangeably with "unsubstituted or substituted". The term "substituted" refers to the replacement of one or more hydrogen atoms in a specified group with a specified radical. For example, substituted aryl, heterocyclyl etc. refer to aryl or heterocyclyl wherein one or more H atoms in each residue are replaced with halogen, haloalkyl, alkyl, $(C_1\text{-}C_8)$ hydrocarbyl, acyl, alkoxyalkyl, hydroxyloweralkyl, carbonyl, phenyl, heteroaryl, benzenesulfonyl, hydroxy, loweralkoxy, haloalkoxy, oxaalkyl, carboxy, alkoxycarbonyl [i.e. —C(=O)O-alkyl], carboxamido [i.e. —C(=O)$NH_2$], alkylaminocarbonyl [i.e. —C(=O)NH-alkyl], cyano, acetoxy, nitro, amino, alkylamino, dialkylamino, dialkylaminoalkyl, dialkylaminoalkoxy, heterocyclylalkoxy, arylalkyl, (cycloalkyl)alkyl, heterocyclyl, heterocyclylalkyl, alkylaminoalkyl, heterocyclylaminoalkyl, heterocyclylalkylaminoalkyl, cycloalkylaminoalkyl, cycloalkylalkylaminoalkyl, arylaminoalkyl, and arylalkylaminoalkyl, mercapto, alkylthio, alkylsulfinyl, benzyl, heterocyclyl, phenoxy, benzyloxy, heteroaryloxy, aminosulfonyl, amidino, guanidino, ureido, —$SO_2$alkyl, —$SO_2NH_2$, or —$SO_2$NHalkyl. Preferred subsitutents are halogen, cyano, hydroxy, nitro, amino, acetoxy, carboxy, $(C_1\text{-}C_7)$hydrocarbyl, halo$(C_1\text{-}C_6)$alkyl, $(C_1\text{-}C_3)$ alkoxy, halo$(C_1\text{-}C_3)$alkoxy, $(C_1\text{-}C_6)$acyl, $(C_1\text{-}C_3)$alkoxy$(C_1\text{-}C_3)$alkyl, hydroxy$(C_1\text{-}C_3)$alkyl, heteroaryl, benzenesulfonyl, $(C_1\text{-}C_3)$alkoxycarbonyl [i. e. —C(=O)O$(C_1\text{-}C_3)$alkyl], carboxamido [i.e. —C(=O)$NH_2$], $(C_1\text{-}C_3)$alkylaminocarbonyl [i.e. —C(=O)NH—$(C_1\text{-}C_3)$alkyl], $(C_1\text{-}C_3)$alkylamino, di$(C_1\text{-}C_3)$alkylamino, amino$(C_1\text{-}C_3)$alkyl, $(C_1\text{-}C_3)$ alkylamino$(C_1\text{-}C_3)$alkyl $(C_1\text{-}C_3)$dialkylamino$(C_1\text{-}C_3)$alkyl, $(C_1\text{-}C_3)$alkylthio, $(C_1\text{-}C_3)$alkylsulfonylamino, $(C_1\text{-}C_3)$alkylsulfinyl, $(C_1\text{-}C_3)$alkylsulfonyl, phenoxy, and benzyloxy.

Unless otherwise specified, alkyl is a linear or branched hydrocarbyl. Unless otherwise specified, an unsubstituted alkyl has from 1 to 20 carbon atoms (e.g., 1 to 6 carbon atoms). Examples of alkyl groups include methyl, ethyl, propyl, isopropyl, butyl, s- and t-butyl and the like.

Ahydrocarbon or hydrocarbyl (as a substituent) includes alkyl, cycloalkyl, polycycloalkyl, alkenyl, alkynyl, aryl and combinations thereof. Examples include cyclopropylmethyl, benzyl, phenethyl, cyclohexylmethyl, camphoryl and naphthylethyl. Hydrocarbon refers to any substituent comprised of hydrogen and carbon as the only elemental constituents. Cycloalkyl is a subset of hydrocarbyl and includes cyclic hydrocarbon groups of from 3 to 8 carbon atoms. Examples of cycloalkyl groups include c-propyl, c-butyl, c-pentyl, norbornyl and the like.

Unless otherwise specified, the term "carbocycle" is a ring system in which the ring atoms are all carbon but of any oxidation state. Thus $(C_3\text{-}C_8)$ carbocycle refers to both non-aromatic and aromatic systems, including such systems as cyclopropane, benzene and cyclohexene; ($C_8$-$C_{12}$) carbopolycycle refers to such systems as norbornane, decalin, indane and naphthalene. Carbocycle, if not otherwise limited, refers to monocycles, bicycles and polycycles.

Oxaalkyl refers to alkyl residues in which one or more carbons (and their associated hydrogens) have been replaced by oxygen. Examples include methoxypropoxy, 3,6,9-trioxadecyl and the like. The term oxaalkyl is intended as it is understood in the art [see Naming and Indexing of Chemical Substances for Chemical Abstracts, published by the American Chemical Society, 196, but without the restriction of 127(a)], i.e. it refers to compounds in which the oxygen is bonded via a single bond to its adjacent atoms (forming ether bonds); it does not refer to doubly bonded oxygen, as would be found in carbonyl groups. Alkoxy or alkoxyl is a subset of oxaalkyl that refers to groups of from 1 to 8 carbon atoms of a straight or branched configuration attached to the parent structure through an oxygen. Examples include methoxy, ethoxy, propoxy, isopropoxy, cyclopropyloxy, cyclohexyloxy and the like. Lower-alkoxy refers to groups containing one to four carbons. For the purpose of this application, alkoxy and lower alkoxy include methylenedioxy and ethylenedioxy Unless otherwise specified, acyl refers to formyl and to groups of 1, 2, 3, 4, 5, 6, 7 and 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include formyl, acetyl, benzoyl, propionyl, isobutyryl, t-butoxycarbonyl, benzyloxycarbonyl and the like. Lower-acyl refers to groups containing one to four carbons. The double bonded oxygen, when referred to as a substituent itself is called "oxo".

Aryl and heteroaryl mean (i) a phenyl group (or benzene) or a monocyclic 5- or 6-membered heteroaromatic ring containing 1-4 heteroatoms selected from O, N, or S; (ii) a bicyclic 9- or 10-membered aromatic or heteroaromatic ring system containing 0-4 heteroatoms selected from O, N, or S; or (iii) a tricyclic 13- or 14-membered aromatic or heteroaromatic ring system containing 0-5 heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole. As used herein aryl and heteroaryl refer to residues in which one or more rings are aromatic, but not all need be.

Arylalkyl refers to a substituent in which an aryl residue is attached to the parent structure through alkyl. Examples are benzyl, phenethyl and the like. Heteroarylalkyl refers to a substituent in which a heteroaryl residue is attached to the parent structure through alkyl. In one embodiment, the alkyl group of an arylalkyl or a heteroarylalkyl is an alkyl group of from 1 to 6 carbons. Examples include, e.g., pyridinylmethyl, pyrimidinylethyl and the like.

Heterocycle means a cycloalkyl or aryl carbocycle residue in which from one to four carbons is replaced by a heteroatom selected from the group consisting of N, O and S. The nitrogen and sulfur heteroatoms may optionally be oxidized, and the nitrogen heteroatom may optionally be quaternized. Unless otherwise specified, a heterocycle may be non-aromatic (i.e. aliphatic) or aromatic. Examples of heterocycles include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. It is to be noted that heteroaryl is a subset of heterocycle in which the heterocycle is aromatic. Examples of heteroaromatic rings include: furan, benzofuran, isobenzofuran, pyrrole, indole, isoindole, thiophene, benzothiophene, imidazole, benzimidazole, purine, pyrazole, indazole, oxazole, benzoxazole, isoxazole, benzisoxazole, thiazole, benzothiazole, triazole, tetrazole, pyridine, quinoline, isoquinoline, pyrazine, quinoxaline, acridine, pyrimidine, quinazoline, pyridazine, cinnoline, phthalazine, and triazine. Examples of heterocyclyl residues additionally include piperazinyl, 2-oxopiperazinyl, 2-oxopiperidinyl, 2-oxo-pyrrolidinyl, 2-oxoazepinyl, azepinyl, 4-piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl, benzothienyl, thiamorpholinyl, thiamorpholinylsulfoxide, thiamorpholinylsulfone, oxadiazolyl, triazolyl and tetrahydroquinolinyl.

An oxygen heterocycle is a heterocycle containing at least one oxygen in the ring; it may contain additional oxygens, as well as other heteroatoms. A sulphur heterocycle is a heterocycle containing at least one sulphur in the ring; it may contain additional sulphurs, as well as other heteroatoms. Oxygen heteroaryl is a subset of oxygen heterocycle; examples include furan and oxazole. Sulphur heteroaryl is a subset of sulphur heterocycle; examples include thiophene and thiazine. A nitrogen heterocycle is a heterocycle containing at least one nitrogen in the ring; it may contain additional nitrogens, as well as other heteroatoms. Aliphatic nitrogenous heterocycles include piperidine, piperazine, morpholine, pyrrolidine, thiomorpholine, azetidine, azepine, and oxazepine. Nitrogen heteroaryl is a subset of nitrogen heterocycle; examples include pyridine, pyrrole and thiazole.

As used herein, and as would be understood by the person of skill in the art, the recitation of "a compound"—unless expressly further limited—is intended to include salts of that compound. Thus, for example, the recitation "a compound of formula I" as depicted above, would include T32 as a free base and as its salt:

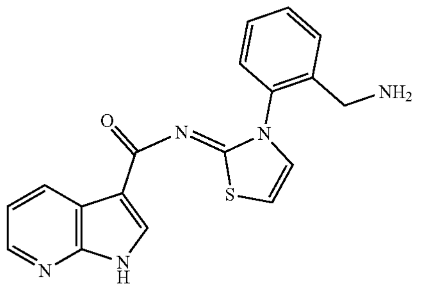

-continued

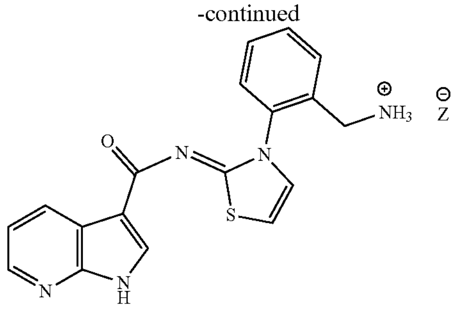

in which Z is any counterion. In a particular embodiment, the term "compound of formula I" refers to the compound or a pharmaceutically acceptable salt thereof. The term "pharmaceutically acceptable salt" refers to salts prepared from pharmaceutically acceptable non-toxic acids or bases including inorganic acids and bases and organic acids and bases. When the compounds of the present invention are basic, as shown in the depiction above in this paragraph, salts may be prepared from pharmaceutically acceptable non-toxic acids including inorganic and organic acids. Suitable pharmaceutically acceptable acid addition salts for the compounds of the present invention include acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like. When the compounds contain an acidic side chain, for example when $R^1$ is COOH as in T34, suitable pharmaceutically acceptable base addition salts for the compounds of the present invention include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine) and procaine. Further pharmaceutically acceptable salts include, when appropriate, nontoxic ammonium cations and carboxylate, sulfonate and phosphonate anions attached to alkyl having from 1 to 20 carbon atoms.

Methods of Treatment

The compositions described herein may be administered to a subject having or at risk of developing hearing loss (e.g., sensorineural hearing loss) and/or vestibular dysfunction by a variety of routes, such as local administration to the middle or inner ear (e.g., administration to or through the oval window, round window, or semicircular canal (e.g., the horizontal canal), or by transtympanic or intratympanic injection), intravenous, parenteral, intradermal, transdermal, intramuscular, intranasal, subcutaneous, percutaneous, intratracheal, intraperitoneal, intraarterial, intravascular, inhalation, perfusion, lavage, and oral administration. The most suitable route for administration in any given case will depend on the particular composition administered, the patient, pharmaceutical formulation methods, administration methods (e.g., administration time and administration route), the patient's age, body weight, sex, severity of the disease being treated, the patient's diet, and the patient's excretion rate. Compositions may be administered once, or more than once (e.g., once annually, twice annually, three times annually, bi-monthly, monthly, or bi-weekly).

Subjects that may be treated as described herein are subjects having or at risk of developing hearing loss and/or vestibular dysfunction (e.g., subjects having or at risk of developing hearing loss, vestibular dysfunction, or both). The compositions and methods described herein can be used to treat subjects having or at risk of developing damage to cochlear hair cells (e.g., damage related to acoustic trauma, disease or infection, head trauma, ototoxic drugs, or aging), subjects having or at risk of developing damage to vestibular hair cells (e.g., damage related to disease or infection, head trauma, ototoxic drugs, or aging), subjects having or at risk of developing sensorineural hearing loss, deafness, or auditory neuropathy, subjects having or at risk of developing vestibular dysfunction (e.g., dizziness, vertigo, loss of balance, bilateral vestibulopathy, oscillopsia, or a balance disorder), subjects having tinnitus (e.g., tinnitus alone, or tinnitus that is associated with sensorineural hearing loss or vestibular dysfunction), subjects having a genetic mutation associated with hearing loss and/or vestibular dysfunction, or subjects with a family history of hereditary hearing loss, deafness, auditory neuropathy, tinnitus, or vestibular dysfunction. In some embodiments, the subject has or is at risk of developing hearing loss and/or vestibular dysfunction that is associated with or results from loss of hair cells (e.g., cochlear or vestibular hair cells). The methods described herein may include a step of screening a subject for one or more mutations in genes known to be associated with hearing loss and/or vestibular dysfunction prior to treatment with or administration of the compositions described herein. A subject can be screened for a genetic mutation using standard methods known to those of skill in the art (e.g., genetic testing). The methods described herein may also include a step of assessing hearing and/or vestibular function in a subject prior to treatment with or administration of the compositions described herein. Hearing can be assessed using standard tests, such as audiometry, auditory brainstem response (ABR), electrocochleography (ECOG), and otoacoustic emissions. Vestibular function may be assessed using standard tests, such as eye movement testing (e.g., electronystagmogram (ENG) or videonystagmogram (VNG)), tests of the vestibulo-ocular reflex (VOR) (e.g., the head impulse test (Halmagyi-Curthoys test), which can be performed at the bedside or using a video-head impulse test (VHIT), or the caloric reflex test), posturography, rotary-chair testing, ECOG, vestibular evoked myogenic potentials (VEMP), and specialized clinical balance tests, such as those described in Mancini and Horak, Eur J Phys Rehabil Med, 46:239 (2010). These tests can also be used to assess hearing and/or vestibular function in a subject after treatment with or administration of the compositions described herein. The compositions and methods described herein may also be administered as a preventative treatment to patients at risk of developing hearing loss and/or vestibular dysfunction, e.g., patients who have a family history of hearing loss or vestibular dysfunction (e.g., inherited hearing loss or vestibular dysfunction), patients carrying a genetic mutation associated with hearing loss or vestibular dysfunction who do not yet exhibit hearing impairment or vestibular dysfunction, or patients exposed to risk factors for acquired hearing loss (e.g., acoustic trauma, disease or infection, head trauma, ototoxic drugs, or aging) or vestibular dysfunction (e.g., disease or infection, head trauma, ototoxic drugs, or aging).

The compositions and methods described herein can be used to induce or increase hair cell regeneration in a subject (e.g., cochlear and/or vestibular hair cell regeneration). Subjects that may benefit from compositions that induce or increase hair cell regeneration include subjects suffering from hearing loss or vestibular dysfunction as a result of loss of hair cells (e.g., loss of hair cells related to trauma (e.g., acoustic trauma or head trauma), disease or infection, ototoxic drugs, or aging), and subjects with abnormal hair cells (e.g., hair cells that do not function properly when compared to normal hair cells), damaged hair cells (e.g., hair cell damage related to trauma (e.g., acoustic trauma or head trauma), disease or infection, ototoxic drugs, or aging), or reduced hair cell numbers due to genetic mutations or congenital abnormalities.

The compositions and methods described herein can also be used to prevent or reduce hearing loss and/or vestibular dysfunction caused by ototoxic drug-induced hair cell damage or death (e.g., cochlear hair cell and/or vestibular hair cell damage or death) in subjects who have been treated with ototoxic drugs, or who are currently undergoing or soon to begin treatment with ototoxic drugs. Ototoxic drugs are toxic to the cells of the inner ear, and can cause sensorineural hearing loss, vestibular dysfunction (e.g., vertigo, dizziness, imbalance, bilateral vestibulopathy, oscillopsia, or a balance disorder), tinnitus, or a combination of these conditions. Drugs that have been found to be ototoxic include aminoglycoside antibiotics (e.g., gentamycin, neomycin, streptomycin, tobramycin, kanamycin, vancomycin, and amikacin), viomycin, antineoplastic drugs (e.g., platinum-containing chemotherapeutic agents, such as cisplatin, carboplatin, and oxaliplatin), loop diuretics (e.g., ethacrynic acid and furosemide), salicylates (e.g., aspirin, particularly at high doses), and quinine. In some embodiments, the methods and compositions described herein can be used to treat bilateral vestibulopathy or oscillopsia. Bilateral vestibulopathy and oscillopsia can be induced by aminoglycosides (e.g., the methods and compositions described herein can be used to promote or increase hair cell regeneration in a subject having or at risk of developing aminoglycoside-induced bilateral vestibulopathy or oscillopsia).

Treatment may include administration of a composition containing a compound described herein in various unit doses. Each unit dose will ordinarily contain a predetermined-quantity of the therapeutic composition. The quantity to be administered, and the particular route of administration and formulation, are within the skill of those in the clinical arts. A unit dose need not be administered as a single injection but may include continuous infusion over a set period of time. Dosing may be performed using a syringe pump to control infusion rate in order to minimize damage to the inner ear (e.g., the cochlea and/or vestibular system).

The compositions described herein are administered in an amount sufficient to improve hearing, improve vestibular function (e.g., improve balance or reduce dizziness or vertigo), reduce tinnitus, treat bilateral vestibulopathy, treat oscillopsia, treat a balance disorder, increase or induce hair cell regeneration (e.g., cochlear and/or vestibular hair cell regeneration), increase hair cell numbers, activate YAP, and/or inhibit LATS. Hearing may be evaluated using standard hearing tests (e.g., audiometry, ABR, electrocochleography (ECOG), and otoacoustic emissions) and may be improved compared to hearing measurements obtained prior to treatment. Vestibular function may be evaluated using standard tests for balance and vertigo (e.g., eye movement testing (e.g., ENG or VNG), posturography, VOR testing (e.g., head impulse testing (Halmagyi-Curthoys testing, e.g., VHIT), or calorie reflex testing), rotary-chair testing, ECOG, VEMP, and specialized clinical balance tests) and may be improved compared to measurements obtained prior to treatment. In some embodiments, the compositions are administered in an amount sufficient to improve the subject's ability to understand speech. The compositions described herein may also be administered in an amount sufficient to slow or prevent the development or progression of sensorineural hearing loss and/or vestibular dysfunction (e.g., in subjects who carry a genetic mutation associated with hearing loss or vestibular dysfunction, who have a family history of hearing loss or vestibular dysfunction (e.g., hereditary hearing loss or vestibular dysfunction), or who have been exposed to risk factors associated with hearing loss or vestibular dysfunction (e.g., ototoxic drugs, head trauma, disease or infection, or acoustic trauma) but do not exhibit hearing impairment or vestibular dysfunction (e.g., vertigo, dizziness, or imbalance), or in subjects exhibiting mild to moderate hearing loss or vestibular dysfunction). These effects may occur, for example, within 1 week, 2 weeks, 3 weeks, 4 weeks, 5 weeks, 6 weeks, 7 weeks, 8 weeks, 9 weeks, 10 weeks, 15 weeks, 20 weeks, 25 weeks, or more, following administration of the compositions described herein. The patient may be evaluated 1 month, 2 months, 3 months, 4 months, 5 months, 6 months or more following administration of the composition depending on the dose and route of administration used for treatment. Depending on the outcome of the evaluation, the patient may receive additional treatments.

Preparation of Compounds

The following abbreviations are used in the synthetic routes: THF (tetrahydrofuran), MeOH (methanol), DCM (dicholoromethane), DMF (N,N-dimethylformamide), ACN (acetonitrile), EtOH (ethanol), EtOAc (ethyl acetate), IPA (2-propanol), DMSO (dimethyl sulfoxide), MTBE (methyl tert-butyl ether), TEA (triethylamine), DIPEA (N,N-diisopropylethylamine), TMEDA (tetramethylethylenediamine), DMAP (N,N-dimethylpyridin-4-amine), EDCI (N-(3-Dimethylaminopropyl)-N'-ethylcarbodiimide hydrochloride), HOBt (1-Hydroxybenzotriazole hydrate), HBTU ((2-(1H-benzotriazol-1-yl)-1,1,3,3-tetramethyluronium hexafluorophosphate), $T_3P$ (propanephosphonic acid anhydride), TBAI (tetrabutylammonium iodide), LAH (lithium aluminum hydride), XPhos (2-dicyclohexylphosphino-2', 4', 6'-triisopropylbiphenyl), TFA (trifluoroacetic acid).

Preparative HPLC purification refers to the use of a water/acetonitrile gradient with or without the use of additives such as HCl, formic acid, TFA, or $NH_4HCO_3$ using an appropriate hydrophobic stationary phase.

The compounds of the present invention can be prepared as illustrated in the General Schemes I-IV and in greater details in Schemes 1-69 below. Detailed description for the synthesis of the intermediates and exemplified compounds are also disclosed below.

Scheme I

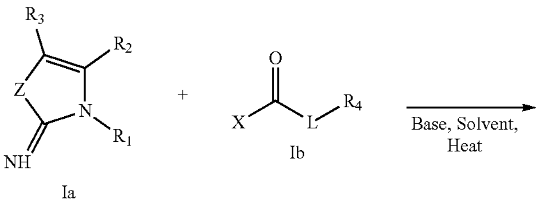

-continued

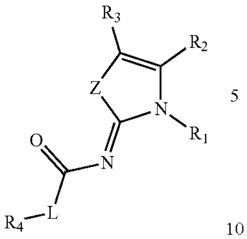

Formula I

As shown in Scheme I, compounds of formula (Ia) containing an imine group when treated with compounds of formula (Ib), where X is chloro, bromo or —OH under coupling conditions known to one skilled in the art, will provide compounds of Formula I. Typical conditions for the reaction of compounds of formula (Ib) wherein X is chloro and compounds of formula (Ia) include but not limiting to stirring an equimolar mixture of the compounds in solvents such as chloroform or dichloromethane in the presence of a base such as but not limited to triethylamine and N,N-dimethylpyridin-4-amine (DMAP) at 5-25° C. for 1-12 hours. Acid coupling conditions of compounds of formula (Ib), wherein X is —OH and compounds of formula (Ia) include but are not limited to stirring an equimolar mixture of the compounds with a coupling reagent such as but not limited to N-(3-Dimethylaminopropyl)-N'-ethylcarbodiimide hydrochloride (EDCI), 1-Hydroxybenzotriazole hydrate (HOBt), ((2-(1H-benzotriazol-1-yl)-1,1,3,3-tetramethyluronium hexafluorophosphate(HBTU), propanephosphonic acid anhydride ($T_3P$), in the presence of a base such as but not limited to N,N-diisopropylethylamine (DIPEA) in solvents such as but not limited to DMF, EtOAc and pyridne. Typical reactions can be carried out between 25-110° C. for 1-12 hours.

Scheme II

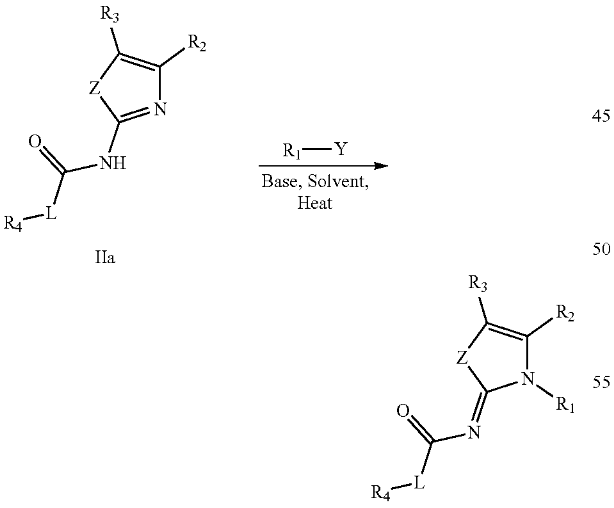

IIa

Formula I

As shown in Scheme II, compounds of formula (IIa) may be converted into compounds of Formula I which are representative compounds of the present invention. Typical conditions include, but not limited to, the treatment of compounds of formula (IIa) with potassium carbonate ($K_2CO_3$) in DMF at 25° C., followed by the addition of reagents such as $R_1$—Y, where $R_1$ is defined in Formula I and Y is chloro, bromo, iodo, mesyl or tosylate. Typical reactions can be carried out at 100° C. in a microwave reactor to facilitate the alkylation.

Scheme III

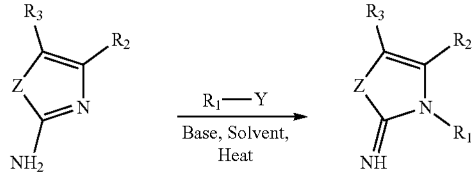

IIIa

IIIb/Ia

Compounds of formula (Ia) in Scheme I may be prepared according to the methods outlined in Scheme III. Compounds of formula (IIIa) when treated with potassium carbonate ($K_2CO_3$) in DMF at 25° C., followed by the addition of reagents such as $R_1$—Y, where $R_1$ is defined in Formula I and Y is chloro, bromo, iodo, mesyl or tosylate will provide compounds of formula (IIIb/Ia). Typical reactions can be carried out at 100° C. in a microwave reactor to facilitate the alkylation.

Scheme IV

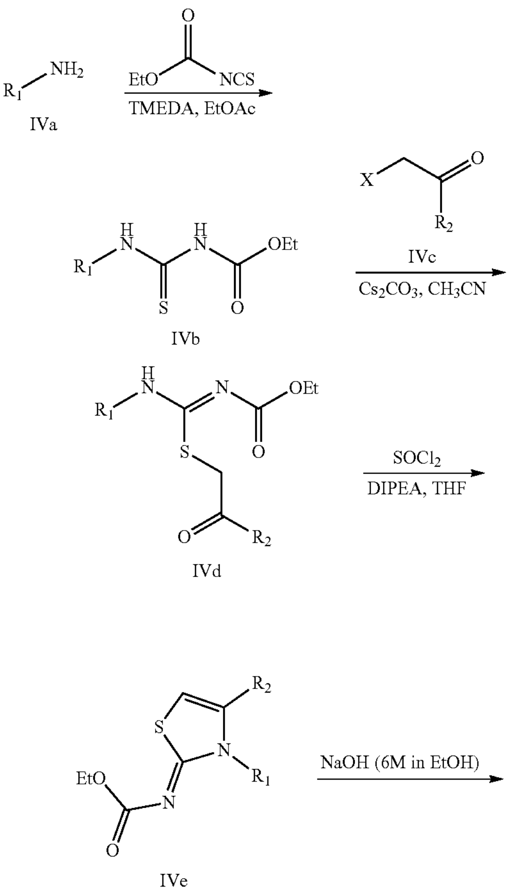

-continued

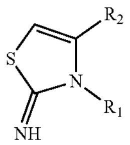

IVf/Ia

Scheme IV describeds another alternative method of preparation of compounds of formula (Ia) in Scheme I. Compounds of formula (IVa) when treated with ethyl N-(thioxomethylene)carbamate and tetramethylethylenediamine (TMEDA) will provide compound formula (IVb). Compounds of formula (IVb) when treated with compounds of formula (IVc) in the present of cesium carbonate ($Cs_2CO_3$) in acetonitrile will provide compounds of formula (IVd). Compounds of formula (IVd) when treated with sulfonyl chloride ($SOCl_2$) in the presence of N,N-diisopropylethylamine (DIPEA) will provide compounds of formula (IVe). Compounds of formula (IVe) when treated with sodium hydroxide (NaOH) will provide compounds of formula (IVf/Ia).

The acids Ib used in Scheme I are depicted in Table A. For acids that are known, the CAS number is shown in the Reference column. Synthetic schemes for all other acids are depicted in the application.

TABLE A

| Acid | Structure | Reference |
|---|---|---|
| A | 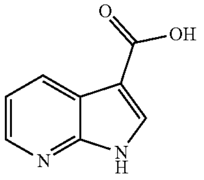 [SMILES: O=C(O)c1c[nH]c2ncccc12] | 156270-06-3 |
| B | 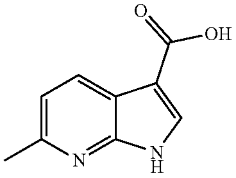 | 1000340-27-1 |

TABLE A-continued

| Acid | Structure | Reference |
|---|---|---|
| C | 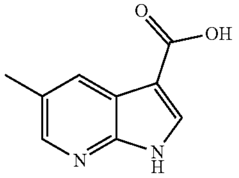 | 1198095-99-6 |
| D | 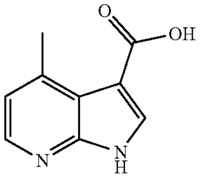 | prepared |
| E | 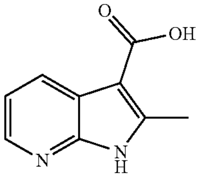 | 933717-06-7 |
| F | 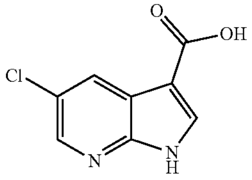 [SMILES: O=C(O)c1c[nH]c2ncc(Cl)cc12] | 1203498-99-0 |
| L | 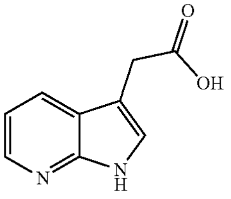 [SMILES: O=C(O)Cc1c[nH]c2ncccc12] | 1912-42-1 |

Intermediates Ia/IIIb used in Scheme I and prepared with methods outlined in Scheme III are depicted in Table B.

TABLE B

| Intermediate | Structure | LCMS | 1H NMR |
|---|---|---|---|
| B1 | 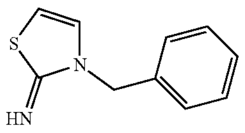 [SMILES: N=c1sccn1Cc1ccccc1] | NA | ($CDCl_3$, 400 MHz) δ 7.48-7.27 (m, 5H), 6.67-6.54 (m, 1H), 6.34-6.32 (m, 1H), 5.75-5.74 (m, 1H), 4.89 (s, 2H). |
| B2 | 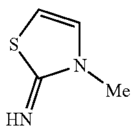 | NA | (DMSO-$d_6$, 400 MHz) δ 7.44 (br s, 1H), 6.71 (d, J = 5.1 Hz, 1H), 5.91 (d, J = 4.9 Hz, 1H), 3.12 (s, 3H). |

TABLE B-continued

| Intermediate | Structure | LCMS | 1H NMR |
|---|---|---|---|
| B3 | 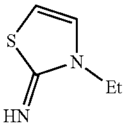 | NA | (DMSO-$d_6$, 400 MHz) δ 7.39 (br s, 1H), 6.74 (d, J = 5.0 Hz, 1H), 5.91 (d,J = 5.0 Hz, 1H), 3.65-3.56 (m, 2H), 1.14 (t, J = 7.1 Hz, 2H), 1.17-1.10 (m, 1H). |
| B4 | 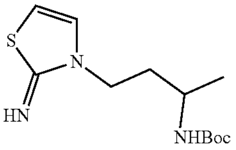 [SMILES: CC(CCn1ccsc1=N)NC(=O)OC(C)(C)C] | NA | (METHANOL-$d_4$, 400 MHz) δ 6.67 (br d, J = 4.6 Hz, 1H), 6.02 (d, J = 4.9 Hz, 1H), 3.82-3.72 (m, 1H), 3.66 (br dd, J = 7.5, 14.6 Hz, 1H), 3.60 (br d, J = 10.1 Hz, 1H), 1.88-1.77 (m, 1H), 1.77-1.66 (m, 1H), 1.44 (s, 9H), 1.12 (d, J = 6.4 Hz, 3H). |
| B5 | 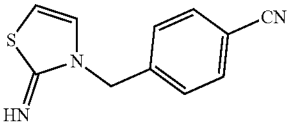 [SMILES: N#Cc1ccc(Cn2ccsc2=N)cc1] | NA | (DMSO-$d_6$, 400 MHz) δ 9.72 (br s, 2H), 7.91 (d, J = 8.3 Hz, 2H), 7.54 (d, J = 4.6 Hz, 1H), 7.47 (d, J =8.3 Hz, 2H), 7.11 (d, J = 4.5 Hz, 1H), 5.45 (s, 2H). |
| B6 | 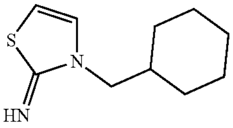 [SMILES: N=c1sccn1CC1CCCCC1] | NA | ($CDCl_3$, 400 MHz) δ 6.46 (d, J = 4.9 Hz, 1H), 5.98 (d, J = 4.8 Hz, 1H), 3.70 (d, J = 7.4 Hz, 2H), 1.91-1.79 (m, 1H), 1.77-1.64 (m, 6H), 1.53-1.42 (m, 2H), 1.27-1.17 (m, 2H). |
| B7 | 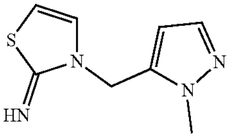 | NA | (DMSO-$d_6$, 400 MHz) δ 9.95 (br s, 2H), 7.40 (d, J = 1.8 Hz, 1H), 7.32 (d, J = 4.6 Hz, 1H), 7.02 (d, J = 4.5 Hz, 1H), 6.09 (d, J = 1.5 Hz, 1H), 5.44 (s, 2H), 3.84 (s, 3H). |
| B8 | 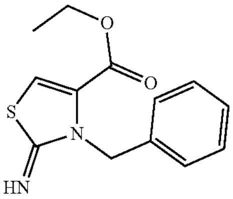 [SMILES: CCOC(=O)c1csc(=N)n1Cc1ccccc1] | 263.2 | (DMSO-$d_6$, 400 MHz) δ 9.97 (br.s, 1H), 7.98 (s, 1H), 7.40-7.37 (m, 2H), 7.34-7.29 (m, 1H), 7.13 (d, J = 7.2 Hz, 2H), 5.59 (s, 2H), 4.22(q, J = 7.2 Hz, 2H), 1.19(t, J = 7.2 Hz, 3H). |
| B9 | 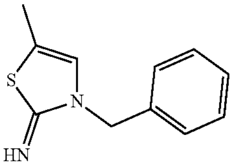 | 205.1 | (DMSO-$d_6$, 400 MHz) δ 9.61 (brs, 2H), 7.33-7.41 (m, 5H), 7.22 (m, 1H), 5.24 (s, 2H), 2.22 (s, 3 H). |
| B10 | 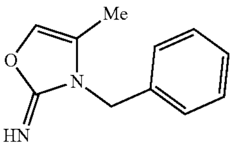 [SMILES: Cc1coc(=N)n1Cc1ccccc1] | 188.9 | (DMSO-$d_6$, 400 MHz) δ 9.71 (br. s, 2H), 7.71 (s, 1H), 7.42-7.40 (m, 2H), 7.38-7.36 (m, 1H), 7.27-7.26 (m, 2H), 5.14 (s, 2H), 1.98 (s, 3H). |
| B11 | 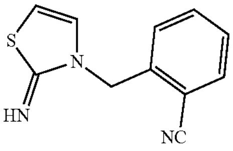 [SMILES: N#Cc1ccccc1Cn1ccsc1=N] | 216.1 | NA |

TABLE B-continued
| Intermediate | Structure | LCMS | 1H NMR |
| --- | --- | --- | --- |
| B12 | 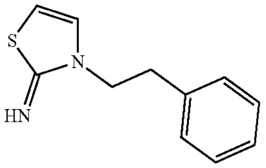 [SMILES: N=c1sccn1CCc1ccccc1] | 205.1 | NA |
| B13 | 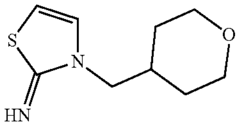 [SMILES: N=c1sccn1CC1CCOCC1] | NA | NA |
| B14 | 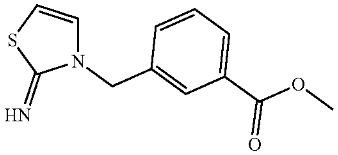 [SMILES: COC(=O)c1cccc(Cn2ccsc2=N)c1] | NA | NA |
| B15 | 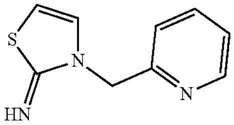 [SMILES: N=c1sccn1Cc1ccccn1] | NA | NA |
| B16 | 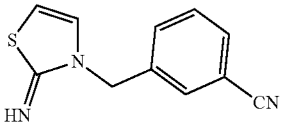 [SMILES: N#Cc1cccc(Cn2ccsc2=N)c1] | NA | NA |
| B17 | 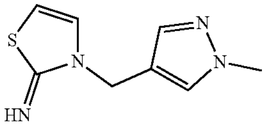 | NA | NA |
| B18 | 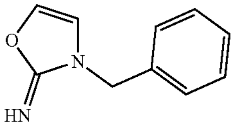 [SMILES: N=c1occn1Cc1ccccc1] | NA | NA |
| B19 | 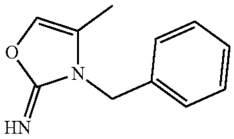 | 188.9 | (DMSO-$d_6$, 400 MHz) δ 9.71 (br. s, 2H), 7.71 (s, 1H), 7.42-7.40 (m, 2H), 7.38-7.36 (m, 1H), 7.27-7.26 (m, 2H), 5.14 (s, 2H), 1.98 (s, 3H). |
| B20 | 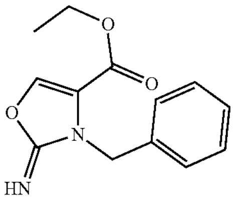 [SMILES: CCOC(=O)c1coc(=N)n1Cc1ccccc1] | NA | (DMSO-$d_6$, 400 MHz) δ 10.23 (br. s, 1H), 8.82 (s, 1H), 7.41-7.29 (m, 5H), 5.36 (s, 2H), 4.24 (q, J = 7.2 Hz, 2H), 1.18 (t, J = 7.2 Hz, 3H). |

Intermediates Ia/IVf used in Scheme I and prepared with methods outlined in Scheme IV are depicted in Table C.

TABLE C

| Intermediate | Structure | LCMS | 1H NMR |
|---|---|---|---|
| C1 | 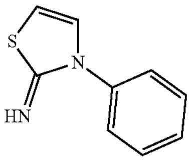 [SMILES: N=c1sccn1-c1ccccc1] | 176.2 | NA |
| C2 | 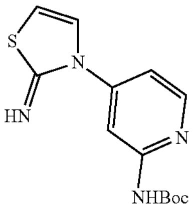 [SMILES: CC(C)(C)OC(=O)Nc1cc(-n2ccsc2=N)ccn1] | NA | (METHANOL-$d_4$, 400 MHz) δ 8.32-8.22 (m, 1H), 8.07 (br s, 1 H), 7.30 (br s, 1H), 6.97-6.90(m, 1H), 6.31-6.17 (m, 1H), 1.54 (s, 9H). |
| C3 | 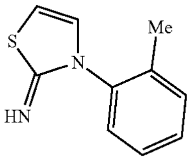 [SMILES: Cc1ccccc1-n1ccsc1=N] | 191.1 | ($CDCl_3$, 400 MHz) δ 7.40-7.27 (m, 4H), 6.42 (d, J = 5.2 Hz, 1H), 5.94 (d, J = 5.2 Hz, 1H), 4.73 (br d, J = 2.4 Hz, 1H), 2.27 (s, 3H). |
| C4 | 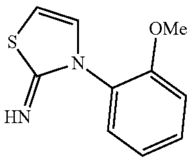 [SMILES: COc1ccccc1-n1ccsc1=N] | 207.2 | (DMSO-$d_6$, 400 MHz) δ 7.62 (br.s, 1H), 7.39-7.35 (m, 1H), 7.33-7.30 (m, 1H), 7.17 (d, J = 8.4 Hz, 1H), 7.01 (t, J = 7.2 Hz, 1H), 6.66 (d, J = 5.2 Hz, 1H), 6.05(d, J = 5.2 Hz, 1H), 3.79 (s, 3H). |
| C5 | 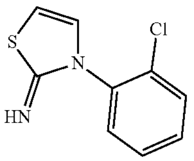 [SMILES: N=c1sccn1-c1ccccc1Cl] | 211.1 | (DMSO-$d_6$, 400 MHz) δ 7.82 (br.s, 1H), 7.65-7.61 (m, 1H), 7.51-7.43 (m, 3H), 6.76 (d, J = 4.8 Hz, 1H), 6.17 (d, J = 5.2 Hz, 1H). |
| C6 | 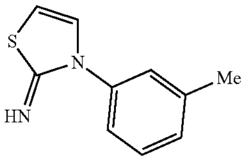 [SMILES: Cc1cccc(-n2ccsc2=N)c1] | 191.1 | (DMSO-$d_6$, 400 MHz) δ 8.01 (br.s, 1H), 7.36-7.28 (m, 3H), 7.10-7.08 (m, 1H), 6.95 (d, J = 5.2 Hz, 1H), 6.14 (d, J = 5.2 Hz, 1H), 2.32 (s, 3H). |
| C7 | 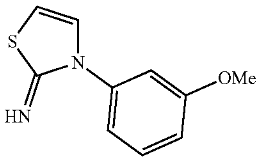 [SMILES: COc1cccc(-n2ccsc2=N)c1] | 207.1 | ($CDCl_3$, 400 MHz) δ 7.44-7.33 (m, 1H), 7.06-6.97 (m, 2H), 6.91-6.88 (m, 1H), 6.60 (d, J = 5.2 Hz, 1H), 5.93 (d, J = 5.2 Hz, 1H), 3.84 (s, 3H). |
| C8 | 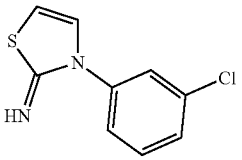 [SMILES: N=c1sccn1-c1cccc(Cl)c1] | 211.1 | (DMSO-$d_6$, 400 MHz) δ 8.30 (br.s, 1H), 7.80 (s, 1H), 7.56-7.54(m, 1H), 7.45(t, J = 8.0 Hz, 1H), 7.32-7.30 (m, 1H), 7.08 (d, J = 5.2 Hz, 1H), 6.21 (d, J = 5.2 Hz, 1H). |

TABLE C-continued

| Intermediate | Structure | LCMS | 1H NMR |
|---|---|---|---|
| C9 | 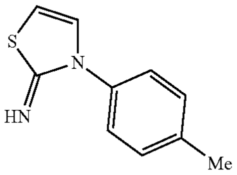 [SMILES: Cc1ccc(-n2ccsc2=N)cc1] | 191.0 | ($CDCl_3$, 400 MHz) δ 7.35-7.31 (m, 2H), 7.29-7.27 (m, 2H), 6.57 (d, J = 5.2 Hz, 1H), 5.92 (d, J = 5.2 Hz, 1H). |
| C10 | 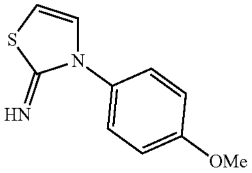 [SMILES: COc1ccc(-n2ccsc2=N)cc1] | 207.2 | (DMSO-$d_6$, 400 MHz) δ 8.16 (br. s, 1H), 7.46-7.40 (m, 2H), 7.03-6.97 (m, 2H), 6.96 (d, J = 5.2 Hz, 1H), 6.22 (d, J = 5.2 Hz, 1H), 3.78 (s, 3H). |
| C11 | 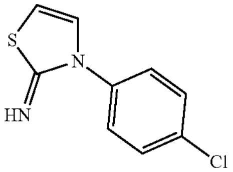 [SMILES: N=c1sccn1-c1ccc(Cl)cc1] | 211.1 | (DMSO-$d_6$, 400 MHz) δ 8.20 (br. s, 1H), 7.64 (d, J = 8.8 Hz, 2H), 7.48 (d, J = 8.8 Hz, 2H), 7.03 (d, J = 5.2 Hz, 1H), 6.20 (d, J = 5.2 Hz, 1H). |
| C12 | 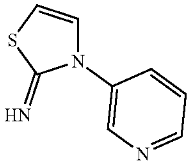 [SMILES: N=c1sccn1-c1cccnc1] | NA | (DMSO-$d_6$, 400 MHz) δ 8.80 (d, J = 2.0 Hz, 1H), 8.45 (d, J = 4.0 Hz, 1H), 8.28 (br. s, 1H), 8.06 (d, J = 7.6 Hz, 1H),7.51-7.43 (m, 1H), 7.12 (d, J = 5.2 Hz, 1H), 6.25 (d, J = 5.2 Hz, 1H). |
| C13 | 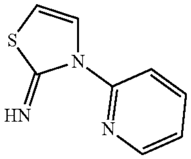 [SMILES: N=c1sccn1-c1ccccn1] | 177.9 | (DMSO-$d_6$, 400 MHz) δ 8.82 (s, 1H), 8.62-8.60 (m, 1H), 8.41 (d, J = 4.0 Hz, 1H), 7.89-7.86 (m, 1H), 7.60 (s, 1H), 7.24-7.21(m, 1H), 7.26 (d, J = 5.2 Hz, 1H). |
| C14 | 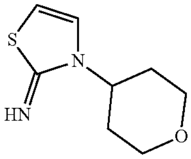 [SMILES: N=c1sccn1C1CCOCC1] | 184.9 | (METHANOL-$d_4$, 400 MHz) δ 7.40 (d, J = 4.4 Hz, 1H), 6.84 (d, J = 4.8 Hz, 1H), 4.48-4.35 (m, 1H), 4.11 -4.02 (m, 2H), 3.58-3.51 (m, 2H), 2.00-1.95 (m, 4H). |
| C15 | 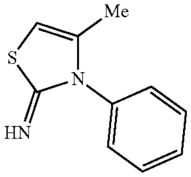 [SMILES: Cc1csc(=N)n1-c1ccccc1] | 191.1 | ($CDCl_3$, 400 MHz) δ 7.55-7.50 (m, 2H), 7.46-7.42 (m, 1H), 7.29-7.28 (m, 1H), 7.27-7.26(m, 1H), 5.56 (d, J = 1.2 Hz, 1H), 1.78 (d, J = 1.2 Hz, 3H). |
| C16 | 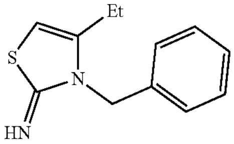 [SMILES: CCc1csc(=N)n1Cc1ccccc1] | 219.1 | (DMSO-$d_6$, 400 MHz) δ 7.80 (br. s, 1H), 7.32 (t, J = 6.8 Hz, 2H), 7.24 (t, J = 7.6 Hz, 1H), 7.17 (d, J = 6.8 Hz, 2H), 5.68 (s, 1H), 4.95 (s, 2H), 2.27-2.21 (m, 2H), 1.02 (t, J J = 7.2 Hz, 3H). |
| C17 | 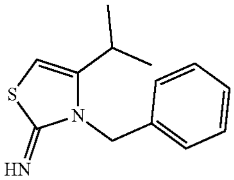 [SMILES: CC(C)c1csc(=N)n1Cc1ccccc1] | 233.2 | (DMSO-$d_6$, 400 MHz) δ 7.36-7.29 (m, 2H), 7.27-7.20 (m, 1H), 7.12 (d, J = 7.6 Hz, 2H), 5.79 (br. s, 1H), 4.98 (s, 2H), 2.56-2.53 (m, 1H), 1.01 (d, J = 6.4 Hz, 6H). |

TABLE C-continued
| Intermediate | Structure | LCMS | 1H NMR |
|---|---|---|---|
| C18 | 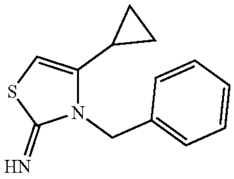 [SMILES: N=c1scc(C2CC2)n1Cc1ccccc1] | 233.2 | (DMSO-$d_6$, 400 MHz) δ 7.57 (br.s, 1H), 7.36-7.30 (m, 2H), 7.27-7.20 (m, 3H), 5.64 (s, 1H), 5.04 (s, 2H), 1.48 1.36 (m, 1H), 0.72-0.64 (m, 2H), 0.52-0.42 (m, 2H). |
| C19 | 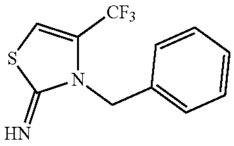 [SMILES: N=c1scc(C(F)(F)F)n1Cc1ccccc1] | 258.8 | ($CDCl_3$, 400 MHz) δ 7.35-7.31 (m, 2H), 7.30-7.26 (m, 2H), 7.24-7.22 (m, 2H), 6.50 (brs, 1H), 5.07 (s, 2H). $^{19}F$ NMR ($CDCl_3$, 400 MHz) δ 63.14 (s, 3F). |
| C20 | 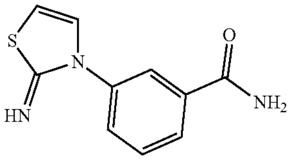 [SMILES: N=c1sccn1-c1cccc(C(N)=O)c1] | 220.0 | NA |
| C21 | 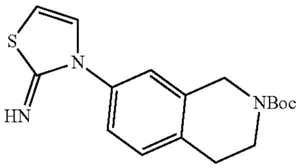 [SMILES: CC(C)(C)OC(=O)N1CCc2ccc(-n3ccsc3=N)cc2C1] | 332.1 | NA |
| C22 | 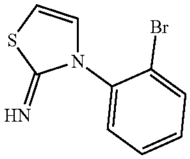 [SMILES: N=c1sccn1-c1ccccc1Br] | 255.1 | NA |
| C23 | 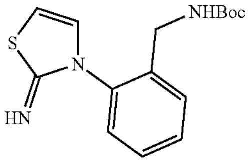 [SMILES: CC(C)(C)OC(=O)NCc1ccccc1-n1ccsc1=N] | 306.0 | NA |
| C24 | 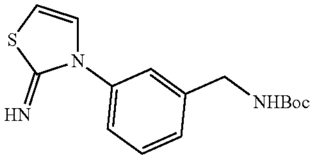 [SMILES: CC(C)(C)OC(=O)NCc1cccc(-n2ccsc2=N)c1] | NA | NA |
| C25 | 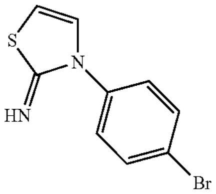 [SMILES: N=c1sccn1-c1ccc(Br)cc1] | NA | NA |
| C26 | 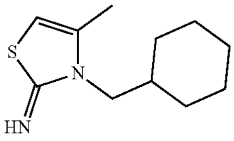 | 210.9 | (DMSO-$d_6$, 400 MHz) δ 7.40 (br. s, 1H), 5.60 (d, J = 1.2 Hz, 1H), 3.42 (d, J = 7.2 Hz, 2H), 2.01 (s, 3H), 1.88-1.77 (m, 1H), 1.68-1.59 (m, 3H), 1.57-1.54(m, 2H), 1.18-1.09 (m, 3H), 0.98-0.92 (m, 2H). |

TABLE C-continued

| Intermediate | Structure | LCMS | 1H NMR |
|---|---|---|---|
| C27 | 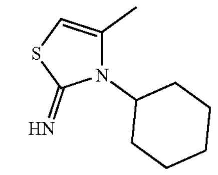 | 197.0 | (METHANOL-$d_4$, 400 MHz) δ 5.80 (s, 1H), 2.22 (s, 3H), 2.20-2.09 (m, 1H), 1.94-1.64 (m, 6H), 1.52-1.39 (m, 2H), 1.38-1.23 (m, 2H). |
| C28 | 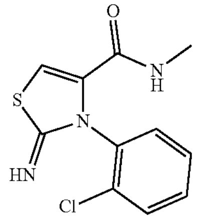 [SMILES: CNC(=O)c1csc(=N)n1-c1ccccc1Cl] | 268.0 | (DMSO-$d_6$, 400 MHz) δ 8.36 (br. s, 1H), 7.54-7.51 (m, 1H), 7.50-7.46 (m, 1H), 7.40-7.35 (m, 3H), 6.83 (br. s, 1H), 2.53 (s, 3H). |
| C29 | 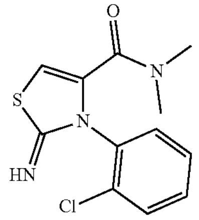 [SMILES: CN(C)C(=O)c1csc(=N)n1-c1ccccc1Cl] | 304.0 | (DMSO-$d_6$, 400 MHz) δ 8.04 (s, 1H), 7.53-7.51 (m, 1H), 7.38-7.36 (m, 3H), 6.52 (s, 1H), 3.11 (s, 3H), 2.71 (s, 3H). |

Preparation of Intermediates in Table D is depicted in Schemes 51-52.

TABLE D

| Intermediate | Structure | LCMS | 1H NMR |
|---|---|---|---|
| D1 | 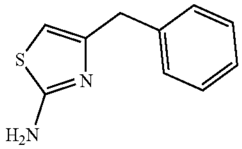 [SMILES: Nc1nc(Cc2ccccc2)cs1] | | (DMSO-$d_6$, 400 MHz) δ 7.31-7.12 (m, 5H), 6.83 (s, 2H), 6.12 (s, 1H), 3.71 (s, 2H). |
| D3 | 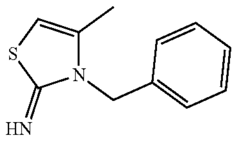 | NA | (DMSO-$d_6$, 400 MHz) δ 10.08 (brs, 2H), 7.40-7.44 (m, 2H), 7.35-7.37 (m, 1H), 7.15 (d, J = 7.2 Hz, 2H), 6.79 (s, 1H), 5.42 (s, 2H), 2.13 (s, 3H). |

Preparation of Intermediate B1

Scheme 1

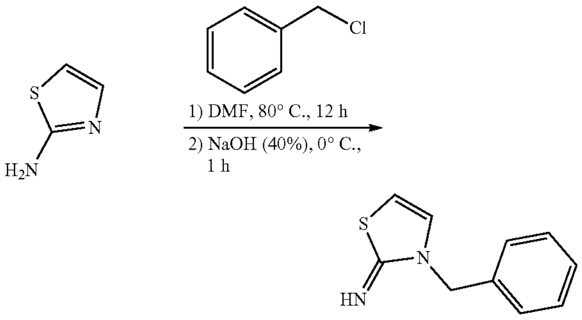

B1

To a solution of 2-thiazolamine (10.00 g, 99.86 mmol, 1.0 eq) in DMF (200 mL) was added chloromethylbenzene (18.96 g, 149.8 mmol, 1.5 eq). The reaction mixture was heated to 80° C. and stirred for 12 hours. The reaction mixture was concentrated under reduced pressure. The resulting residue was diluted with EtOAc (200 mL). Aqueous NaOH (100 mL, 40% w %) was added at 0° C. and stirred for 1 hour at 0° C. The mixture was extracted with EtOAc (3×100 mL). The combined organic layers were washed with brine (3×100 mL), dried by $Na_2SO_4$, filtered and concentrated under reduced pressure to give a residue, which was purified by column chromatography on silica gel (Petroleum ether/EtOAc=5:1 to 1:1) to obtain 3-benzylthiazol-2(3H)-imine B1 (13.00 g, crude) as a yellow oil.

Alternative Method to Prepare Intermediate B1

Scheme 2

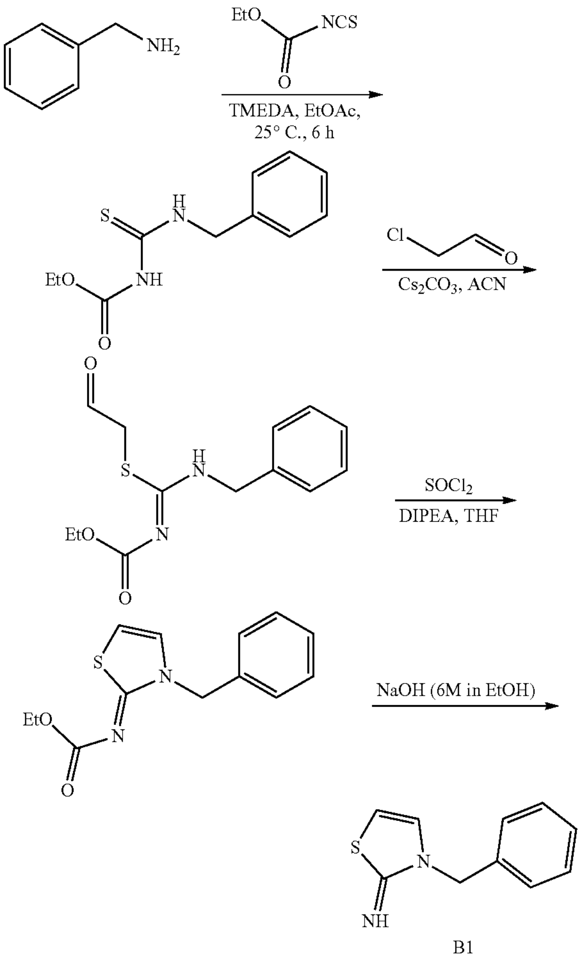

B1

Ethyl N-(benzylcarbamothioyl)carbamate

To a solution of phenylmethanamine (5.00 g, 46.7 mmol, 1.0 eq) and O-ethyl carbonisothiocyanatidate (6.43 g, 49.0 mmol, 1.05 eq) in ethyl acetate (40 mL) was added TMEDA (0.54 g, 4.67 mmol, 0.1 eq) at 25° C. under nitrogen atmosphere. The mixture was stirred at 25° C. for 6 hours, and then concentrated under reduced pressure. The residue was tritrated from a solution of petroleum ether and ethyl acetate (v/v=10/1, 55 mL) twice to afford 10.0 g of the ethyl N-(benzylcarbamothioyl)carbamate as a yellow solid. $^{1}H$ NMR (400 MHz, DMSO-$d_6$) δ 11.04 (br. s, 1H), 10.22 (br. t, J=5.6 Hz, 1H), 7.39-7.23 (m, 5H), 4.81 (d, J=5.6 Hz, 2H), 4.14 (q, J=7.2 Hz, 2H), 1.21 (t, J=7.2 Hz, 3H).

(Z)-Ethyl ((benzylamino)((2-oxoethyl)thio)methylene)carbamate

To a mixture of ethyl N-(benzylcarbamothioyl)carbamate (4.00 g, 16.8 mmol, 1.0 eq) and cesium carbonate (13.7 g, 42.0 mmol, 2.5 eq) in acetonitrile (50 mL) was added 2-chloroacetaldehyde (13.2 g, 67.2 mmol, 4.0 eq). The reaction mixture was stirred at 25° C. for 12 hours, poured into ice-water (20 mL), and then extracted with MTBE (2×200 mL). The combined organic phase was washed with brine (2×20 mL), dried over anhydrous sodium sulfate, filtered and concentrated under reduced pressure. The residue was purified by column chromatography on silica gel (Petroleum ether/Ethyl acetate=100:1 to 3:1) to afford 5.00 g of (Z)-ethyl ((benzylamino)((2-oxoethyl)thio)methylene) carbamate as a yellow solid. LCMS (m/z $[M+H]^+$): 280.9.

(Z)-Ethyl (3-benzylthiazol-2(3H)-ylidene)carbamate

To a mixture of (Z)-ethyl ((benzylamino)((2-oxoethyl) thio)methylene)carbamate (5.00 g, 12.4 mmol, 1.0 eq) and diisopropylethylamine (4.81 g, 37.2 mmol, 3.0 eq) in tetrahydrofuran (50 mL) was added thionyl chloride (1.48 g, 12.4 mmol, 1.0 eq). The mixture was stirred at 25° C. for 16 hours, then poured into ice-water (20 mL) and extracted with ethyl acetate (3×100 mL). The combined organic phase was washed with brine (20 mL), dried over anhydrous sodium sulfate, filtered and concentrated under reduced pressure. The residue was purified by column chromatography on silica gel (Petroleum ether/Ethyl acetate=100:1 to 4:1) to afford 2.80 g of (Z)-ethyl (3-benzylthiazol-2(3H)-ylidene) carbamate as a yellow solid. $^{1}H$ NMR (400 MHz, $CD_3OD$) δ 7.36-7.28 (m, 5H), 7.22 (d, J=4.8 Hz, 1H), 6.84 (d, J=4.8 Hz, 1H), 5.31 (s, 2H), 4.20 (q, J=7.2 Hz, 2H), 1.30 (t, J=7.2 Hz, 3H). LCMS (m/z $[M+H]^+$): 262.9.

Intermediate B1

A mixture (Z)-ethyl (3-benzylthiazol-2(3H)-ylidene)carbamate (2.80 g, 9.06 mmol, 1.0 eq) and sodium hydroxide (7.25 g, 181 mmol, 20 eq) in ethanol (20 mL) was stirred at 50° C. for 1.5 hours. The mixture was poured into ice-water (20 mL) and extracted with ethyl acetate (5×100 mL). The combined organic phase was washed with brine (20 mL), dried over anhydrous sodium sulfate, filtered and concentrated under reduced pressure to afford 1.60 g of 3-benzylthiazol-2(3H)-imine B1 as a yellow gum.

Preparation of Intermediate B2

Scheme 3

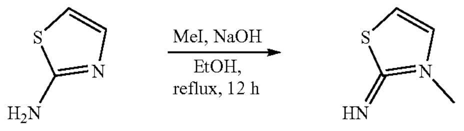

B2

To a solution of 2-thiazolamine (1.00 g, 9.99 mmol, 1.0 eq) in EtOH (10 mL) was added MeI (1.84 g, 13.0 mmol, 808 μL, 1.3 eq). The reaction mixture was stirred at 90° C. for 12 hours. The suspension was filtered, and the solid was washed with EtOH (60 mL), dried under reduced pressure. The solid was collected and diluted with 40% NaOH aqueous solution (10 mL) and extracted with EtOAc (3×10 mL). The combined organic layers were washed with 40% NaOH aqueous solution (3×10 mL) and brine (3×10 mL), dried over anhydrous $Na_2SO_4$, filtered and concentrated under reduced pressure to give a residue to afford 160 mg of 3-methyl-thiazol-2-amine B2.

Preparation of Intermediate B3

Scheme 4

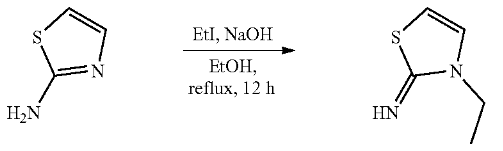

B3

A mixture of 2-thiazolamine (3.00 g, 30.0 mmol, 1.0 eq) and ethyl iodide EtI (6.07 g, 38.9 mmol, 1.3 eq) in EtOH (30 mL) was degassed and purged with $N_2$ for 3 times and stirred at 90° C. for 12 hours under $N_2$ atmosphere. The reaction mixture was diluted with 40% NaOH aqueous solution (50 mL) and extracted with EtOAc (2x30 mL). The combined organic layers were washed with 40% NaOH aqueous solution (3x20 mL) and brine (3x20 mL), dried over anhydrous $Na_2SO_4$, filtered and concentrated under reduced pressure to afford 2.80 g o f 3-ethylthiazol-2(3H)-imine B3 as a dark red oil.

Preparation of Intermediate B4

Scheme 5

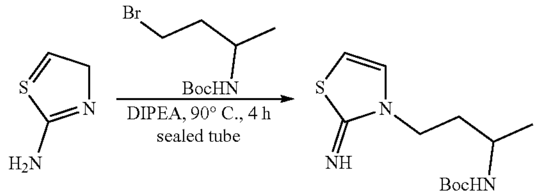

B4

A mixture of 2-thiazolamine (120 mg, 1.20 mmol, 1.0 eq), tert-butyl (4-bromobutan-2-yl)carbamate (302 mg, 1.20 mmol, 1.0 eq) and DIPEA (170 mg, 1.32 mmol, 230 □L, 1.1 eq) was stirred at 90° C. for 4 hours in a 5 mL sealed tube. The reaction mixture was diluted with MeOH (1 mL) and the mixture was purified by column chromatography on silica gel (Petroleum ether/Ethyl acetate=1/1 to 0/1, then Ethyl acetate/Ammonium hydroxide (25%)=50/1) to give 30 mg of tert-butyl (4-(2-iminothiazol-3(2H)-yl)butan-2-yl)carbamate B4 as a yellow oil.

Preparation of Intermediate B5

Scheme 6

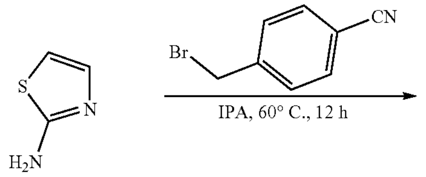

-continued

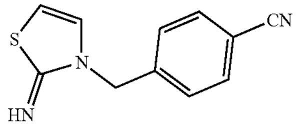

B5

A mixture of 2-thiazolamine (1.00 g, 10.0 mmol, 1.0 eq) and 4-(bromomethyl)benzonitrile (1.96 g, 10.0 mmol, 1.0 eq) in i-PrOH (20 mL) was stirred at 60° C. for 12 hr. The reaction mixture was filtered to collect the solid, which was washed with 20 mL of EtOAc and dried in vacuum to give 2.1 g of 2-amino-3-(4-cyanobenzyl)thiazol-3-ium B5 as a yellow solid.

Preparation of Intermediate B6

Scheme 7

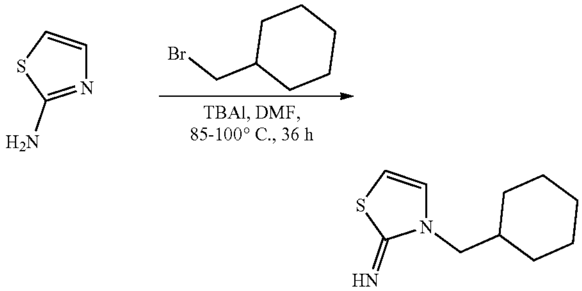

B6

To a solution of 2-thiazolamine (1.00 g, 9.99 mmol, 1.0 eq) and (bromomethyl)cyclohexane (1.77 g, 9.99 mmol, 1.39 mL, 1.0 eq) in DMF (10 mL) was added TBAI (1.84 g, 4.99 mmol, 0.5 eq) at room temperature. Then the reaction mixture was stirred at 85° C. for 12 h under $N_2$. Additional 1.0 eq of (bromomethyl)cyclohexane was added into the mixture and the reaction mixture was stirred at 100° C. for additional 24 h under $N_2$. The reaction mixture was diluted with sat. aq $NaHCO_3$ solution (100 mL) and extracted with EtOAc (3x50 mL). The combined organic layers were washed with brine (3x50 mL), dried over $Na_2SO_4$, filtered and the filtrate was concentrated under reduced pressure. The residue was purified by column chromatography on silica gel (Petroleum ether/Ethyl acetate/MeOH=0:1:0 to 0:1:1) to give 428 mg of 3-(cyclohexylmethyl)thiazol-2 (3H)-imine B6 as a yellow solid.

Preparation of Intermediate B7

Scheme 8

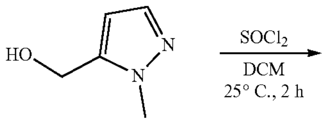

-continued

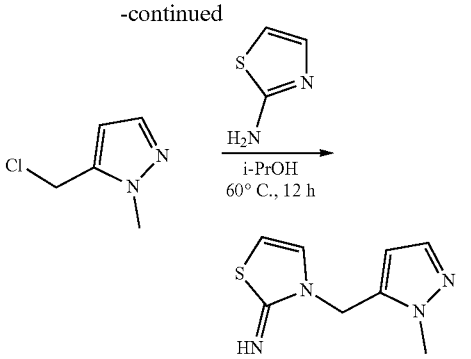

B7

5-(Chloromethyl)-1-methyl-1H-pyrazole

To a stirred solution of (1-methyl-1H-pyrazol-5-yl)methanol (200 mg, 1.78 mmol, 1.0 eq) in DCM (4 mL) was added $SOCl_2$ (0.32 mL) dropwise at 25° C. Then the reaction mixture was stirred at 25° C. for 2 h under $N_2$. The reaction mixture was diluted with water (20 mL) and adjusted to pH 8 with sat. aq $NaHCO_3$ solution. The solution was extracted with EtOAc (3×20 mL), and the combined organic layers were washed with brine (3×10 mL), dried over $Na_2SO_4$, filtered. The filtrate was concentrated under reduced pressure to give 200 mg of the crude 5-(chloromethyl)-1-methyl-1H-pyrazole as yellow oil. $^1H$ NMR: (400 MHz, CHLOROFORM-d) δ 7.41 (d, J=1.8 Hz, 1H), 6.28 (d, J=1.8 Hz, 1H), 4.62 (s, 2H), 3.93 (s, 3H).

Intermediate B7

To a solution of 5-(chloromethyl)-1-methyl-1H-pyrazole (120 mg, 919 μmol, 1.0 eq) in i-PrOH (1 mL) was added 2-thiazolamine (74 mg, 735 μmol, 0.8 eq) at room temperature and then stirred at 60° C. for 12 h under $N_2$. The reaction mixture was concentrated under reduced pressure. The residue was purified by column chromatography on silica gel (Petroleum ether/Ethyl acetate/MeOH=1:1:0 to 0:1:0 to 0:1:9) to give 76 mg of 3-((1-methyl-1H-pyrazol-5-yl)methyl)thiazol-2(3H)-imine B7 as a yellow solid.

Preparation of Intermediate B8

Scheme 9

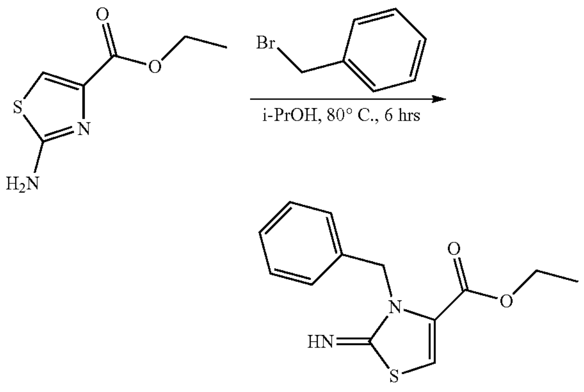

B8

To a solution of ethyl 2-aminothiazole-4-carboxylate (2.00 g, 11.6 mmol, 1.0 eq) in i-PrOH (20 mL) was added (bromomethyl)benzene (1.38 mL, 11.6 mmol, 1.0 eq) at 25° C. The mixture was heated to 80° C. and stirred for 6 hours. The reaction mixture was cooled to room temperature and allowed to stand for 3 days. The precipitate was collected by filtration, and the filter cake was dried in high vacuum to afford 0.80 g of the ethyl 3-benzyl-2-imino-2, 3-dihydrothiazole-4-carboxylate B8 as a white solid.

Preparation of Intermediate B9

Scheme 10

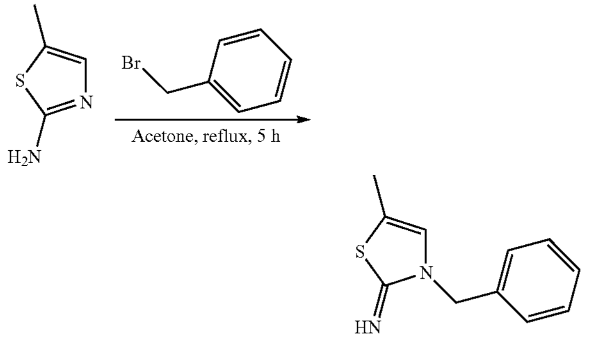

B9

To a solution of 5-methyl-2-thiazolamine (1.00 g, 8.76 mmol, 1.0 eq) in acetone (15 mL) was added bromomethylbenzene (1.65 g, 9.63 mmol, 1.1 eq) at 25° C. The reaction mixture was heated to 70° C. and stirred for 5 hours. The reaction mixture was cooled to 25° C. and adjusted to pH>7.0 by addition of aqueous NaOH (2N). The reaction mixture was filtered and the filter cake was washed with acetone (5 mL), MTBE (10 mL), dried under reduced pressure to afford 1.1 g of the crude 3-benzyl-5-methylthiazol-2(3H)-imine B9 as a brown solid. Structure was confirmed with NOE.

Preparation of Intermediate B10

Scheme 11

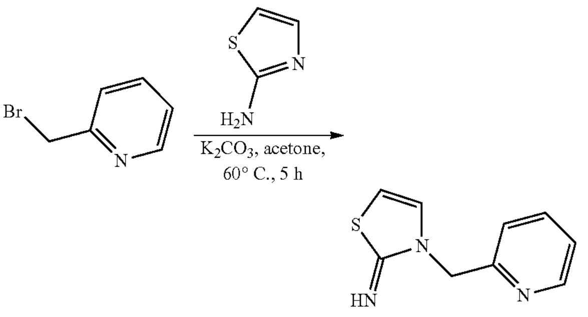

B10

A mixture of 2-thiazolamine (100 mg, 998 μmol, 1.0 eq), 2-(bromomethyl)pyridine (278 mg, 1.10 mmol, 1.1 eq, HBr) and $K_2CO_3$ (152 mg, 1.10 mmol, 1.1 eq) in acetone (5 mL) was degassed and purged with $N_2$ for 3 times, and then the reaction mixture was stirred at 60° C. for 5 hr under $N_2$ atmosphere. The result mixture was concentrated under reduced pressure. The residue was purified by prep-HPLC to give 100 mg of compound 3-(pyridin-2-ylmethyl)thiazol-2(3H)-imine B10 as a white solid.

Preparation of Intermediate B11

Scheme 12

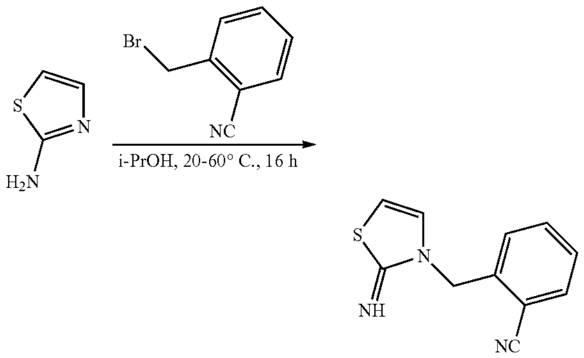

B11

To a solution of 2-thiazolamine (0.30 g, 3.0 mmol, 1.0 eq) in i-PrOH (5 mL) was added 2-(bromomethyl)benzonitrile (587 mg, 3.00 mmol, 1.0 eq). The reaction mixture was stirred at 25° C. for 12 hours, then heated to 60° C. and stirred for additional 4 hours. The reaction mixture was concentrated directly under reduced pressure to afford a residue which was purified by flash column chromatography on silica gel (Ethyl acetate/MeOH) to afford 0.41 g of 2-((2-iminothiazol-3(2H)-yl)methyl)benzonitrile B11 as a yellow solid.

Preparation of Intermediate B12

Scheme 13

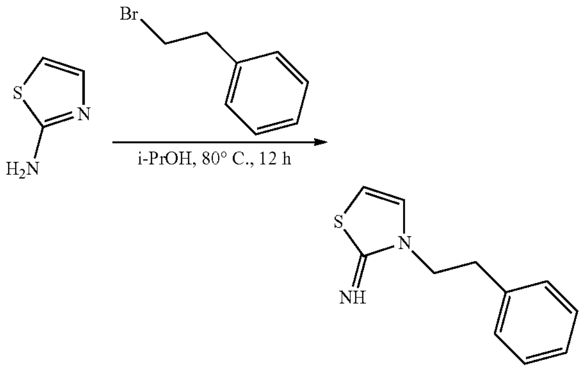

B12

To a solution of 2-bromoethylbenzene (3.70 g, 20.0 mmol, 1.0 eq) in i-PrOH (35 mL) was added 2-thiazolamine (2.00 g, 20.0 mmol, 1.0 eq). The reaction mixture was stirred at 80° C. for 12 hours. The reaction mixture was cooled to room temperature and then concentrated directly to give a residue, which was purified by reverse phase column chromatography to afford 2.00 g of the compound 3-phenethylthiazol-2(3H)-imine B12 as a light yellow solid.

Preparation of Intermediate B13

Scheme 14

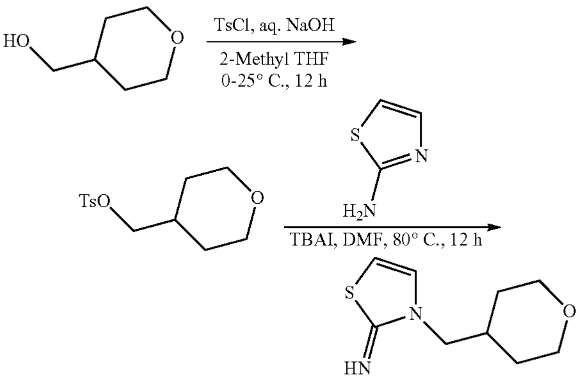

B13

(Tetrahydro-2H-pyran-4-yl)methyl 4-methylbenzenesulfonate

To a solution of (tetrahydro-2H-pyran-4-yl)methanol (2.00 g, 17.2 mmol, 1.0 eq) in 2-methyltetrahydrofuran (20 mL) was added NaOH (4.13 g, 51.6 mmol, 50% purity, 3.0 eq), followed by dropwise addition of a solution of 4-methylbenzenesulfonyl chloride (5.91 g, 31.0 mmol, 1.8 eq) in 2-methyltetrahydrofuran (6 mL) at 0° C. The reaction mixture was then stirred at 25° C. for 12 h. The reaction mixture was diluted with aq HCl (6 M), and then 3.0 mL cyclohexane was added. The solution was stirred at 0° C. for 0.5 h but no solid precipitate out. Then the mixture was extracted with EtOAc (3×60 mL), the combined organic layers were washed with brine (100 mL), dried over $Na_2SO_4$, filtered and the filtrate was concentrated under reduced pressure to give 4.2 g of crude (tetrahydro-2H-pyran-4-yl)methyl 4-methylbenzenesulfonate as a white solid. LCMS (m/z $[M+H]^+$): 271.1.

Intermediate B13

To a solution of (Tetrahydro-2H-pyran-4-yl)methyl 4-methylbenzenesulfonate (2.70 g, 9.99 mmol, 1.0 eq) and 2-thiazolamine (1.00 g, 9.99 mmol, 1.0 eq) in DMF (10 mL) was added TBAI (1.84 g, 4.99 mmol, 0.5 eq) at room temperature. The reaction mixture was stirred at 80° C. for 12 h under $N_2$. The reaction mixture was diluted with water (80 mL) and extracted with EtOAc (3×60 mL), the combined organic layers were discarded and the water phase was adjusted to pH=9 with NaOH (50% purity). The the aqueous solution was extracted with EtOAc (3×50 mL), the combined organic layers were washed with brine (100 mL), dried over $Na_2SO_4$, filtered. The filtrate was concentrated under reduced pressure to give 500 mg of 3-((tetrahydro-2H-pyran-4-yl)methyl)thiazol-2(3H)-imine B13 as a yellow solid.

Preparation of Intermediate B14

Scheme 15

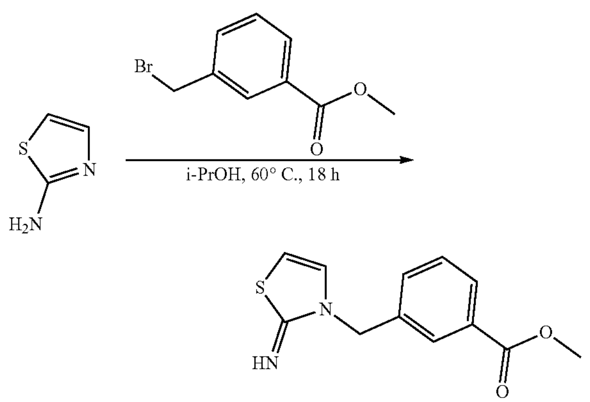

B14

To a solution of 2-thiazolamine (0.60 g, 5.99 mmol, 1.0 eq) in i-PrOH (10 mL) was added methyl 3-(bromomethyl) benzoate (1.37 g, 5.99 mmol, 1.0 eq). The reaction mixture was stirred at 60° C. for 12 hours. The reaction mixture was cooled to 25° C. and diluted with MTBE. The suspension was decaned and dried under reduced pressure to afford 1.5 g of the crude product methyl 3-((2-iminothiazol-3(2H)-yl) methyl)benzoate B14 as a brown solid.

Preparation of Intermediate B15

Scheme 16

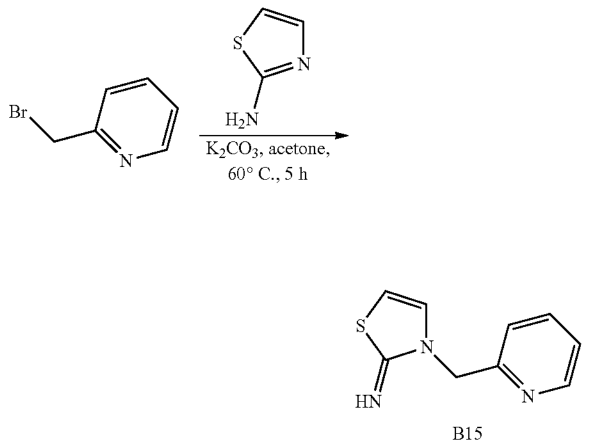

B15

A mixture of 2-thiazolamine (100 mg, 1.00 mmol, 1.0 eq), 2-(bromomethyl)pyridine (278 mg, 1.10 mmol, 1.1 eq, HBr) and $K_2CO_3$ (152 mg, 1.10 mmol, 1.1 eq) in acetone (5 mL) was degassed and purged with $N_2$ for 3 times. The reaction mixture was stirred at 60° C. for 5 hr under $N_2$ atmosphere. The resulting mixture was concentrated under reduced pressure. The residue was purified by prep-HPLC to give 100 mg of 3-(pyridin-2-ylmethyl)thiazol-2(3H)-imine B15 as a white solid.

Preparation of Intermediate B16

Scheme 17

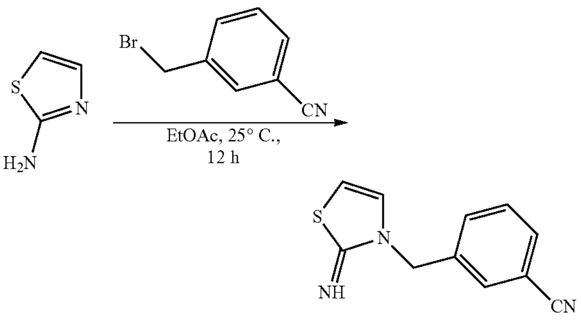

B16

To a solution 2-thiazolamine (1.00 g, 9.99 mmol, 1.0 eq) in EtOAc (20 mL) was added 3-(bromomethyl)benzonitrile (1.96 g, 9.99 mmol, 1.0 eq) at 25° C. The reaction mixture was then stirred for 12 hours at 25° C. The reaction mixture was diluted with EtOAc (100 mL), and then NaOH (100 mL, 40%) was added at 0° C. The resulting mixture was stirred for 1 hour at 0° C. The solution was extracted with EtOAc (3×100 mL). The combined organic layers were washed with brine (3×100 mL), dried by $Na_2SO_4$, filtered and concentrated in vacuum. The residue was purified by column chromatography on silica gel (Petroleum ether/EtOAc=5:1 to EtOAc:$NH_3$·$H_2O$ (25%)=100:1) to give 500 mg of 3-((2-iminothiazol-3(2H)-yl)methyl)benzonitrile B16 as a yellow oil.

Preparation of Intermediate B17

Scheme 18

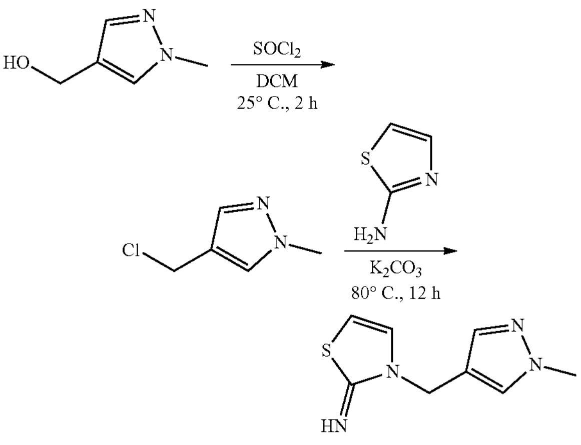

B17

4-(Chloromethyl)-1-methyl-1H-pyrazole

To a stirred solution of (1-methyl-1H-pyrazol-4-yl)methanol (500 mg, 4.46 mmol, 1.0 eq) in DCM (1.6 mL) was added $SOCl_2$ (2.39 g, 20.1 mmol, 1.46 mL, 4.5 eq) dropwise at 25° C. The reaction mixture was stirred at 25° C. for 2 h under $N_2$. The reaction mixture was concentrated under reduced pressure to give 500 mg of 4-(chloromethyl)-1-methyl-1H-pyrazole as a white solid. $^1H$ NMR (400 MHz, DMSO-$d_6$) δ 7.79 (s, 1H), 7.48 (s, 1H), 4.68 (s, 2H), 3.81 (s, 3H).

Intermediate B17

To a solution of 4-(chloromethyl)-1-methyl-1H-pyrazole (450 mg, 3.45 mmol, 1.0 eq) in DMF (4.5 mL) was added 2-thiazolamine (345 mg, 3.45 mmol, 1.0 eq), followed by addition of $K_2CO_3$ (953 mg, 6.89 mmol, 2.0 eq) at room temperature. The mixture was then stirred at 80° C. for 12 h under $N_2$. The reaction mixture was diluted with water (30 mL) and extracted with EtOAc (3×20 mL), the organic layer was washed with brine (30 mL), dried over $Na_2SO_4$, filtered and the filtrate was concentrated under reduced pressure. The residue was purified by column chromatography on silica gel (Petroleum ether/Ethyl acetate/MeOH=1:1:0 to 0:1:1) to give 50 mg of 3-((1-methyl-1H-pyrazol-4-yl)methyl)thiazol-2(3H)-imine B17 as a yellow solid.

Preparation of Intermediate B18

Scheme 19

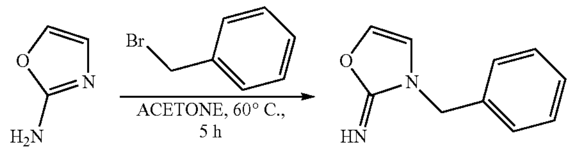

B18

To a solution of 2-oxazolamine (0.50 g, 5.95 mmol, 1.0 eq) in acetone (10 mL) was added bromomethylbenzene (1.12 g, 6.54 mmol, 777 μL, 1.1 eq) and the mixture was stirred at 60° C. for 5 h. The reaction mixture was concentrated under reduced pressure to give 0.70 g of 3-Benzyloxazol-2(3H)-imine B18 as a yellow gelatinous oil.

Preparation of Intermediate B19

Scheme 20

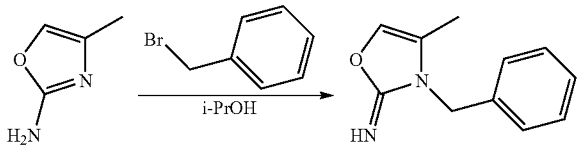

B19

To a solution of 4-methyl-2-oxazolamine (0.400 g, 3.26 mmol, 1.0 eq) in i-PrOH (2 mL) was added dropwise (bromomethyl)benzene (0.387 mL 3.26 mmol, 1.0 eq) at 20° C. The reaction mixture was heated to 80° C. and stirred for 3 hours. The mixture was concentrated under reduced pressure, the residue was purified by prep-HPLC to afford 0.20 g of 3-benzyl-4-methyloxazol-2(3H)-imine 2,2,2-trifluoroacetate B19 as a yellow oil.

Preparation of Intermediate B20

Scheme 21

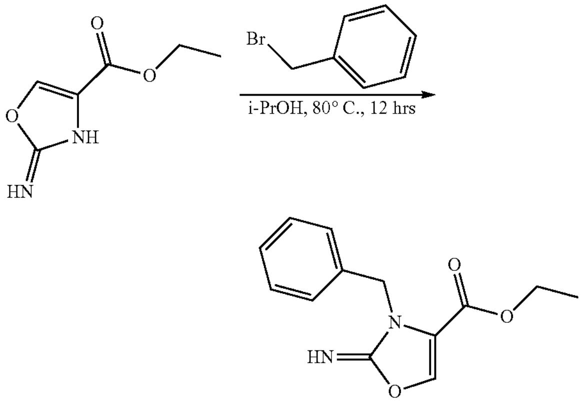

B20

To a solution of ethyl 2-imino-3H-oxazole-4-carboxylate (1.35 g, 8.65 mmol) in isopropyl alcohol (14 mL) was added bromomethylbenzene (1.03 mL, 8.65 mmol) at 25° C. and the mixture was stirred at 80° C. for 12 hours. The reaction mixture was cooled to room temperature and the precipitate was collected by filtration. The filter cake was dried under reduced pressure to afford 1.20 g of ethyl 3-benzyl-2-imino-2, 3-dihydrooxazole-4-carboxylate B20 as a white solid.

Preparation of Intermediate C1

Scheme 22

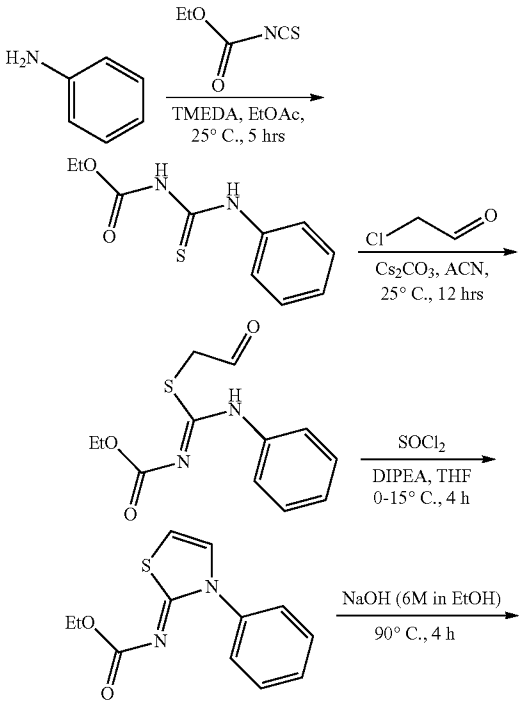

-continued

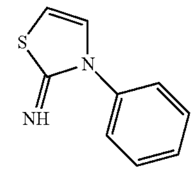

C1

Ethyl N-(phenylcarbamothioyl)carbamate

To a solution of aniline (2.00 g, 21.48 mmol, 1.0 eq) in EtOAc (20 mL) was added ethyl N-(thioxomethylene)carbamate (2.82 g, 21.48 mmol, 1.0 eq) and TMEDA (250 mg, 2.15 mmol, 0.1 eq). The reaction mixture was stirred at 25° C. for 5 hours. The reaction mixture was concentrated directly under reduced pressure to afford a yellow solid. The solid was re-dissolved in EtOH (10 mL) and stirred for 0.5 hour and then filtered. The filter cake was washed with EtOH (2×5 mL), dried in vacuum to afford 3.70 g of ethyl N-(phenylcarbamothioyl)carbamate as a white solid.

(Z)-Ethyl (((2-oxoethyl)thio)(phenylamino)methylene)carbamate

To a solution of ethyl N-(phenylcarbamothioyl)carbamate (2.70 g, 12.0 mmol, 1.0 eq) and $Cs_2CO_3$ (6.67 g, 20.5 mmol, 1.7 eq) in $CH_3CN$ (40 mL) was added 2-chloroacetaldehyde (2.95 g, 15.0 mmol, 1.3 eq), maintaining the temperature blow 25° C. After addition, the reaction mixture was stirred at 25° C. for 12 hours. The reaction mixture was diluted with MTBE (80 mL) at 20° C., washed with saturated aqueous $NaHCO_3$ (75 ml), brine (75 mL), dried over $Na_2SO_4$ and filtered. The filtrate was concentrated under reduced pressure to afford 0.32 g of crude product (Z)-ethyl (((2-oxoethyl)thio)(phenylamino)methylene)carbamate as a brown oil.

(Z)-Ethyl (3-phenylthiazol-2(3H)-ylidene)carbamate

To a solution of ethyl (Z)-ethyl (((2-oxoethyl)thio)(phenylamino)methylene)carbamate (3.20 g, 12.0 mmol, 1.0 eq) in THF (40 mL) was added DIPEA (4.66 g, 36.0 mmol, 3.0 eq) and $SOCl_2$ (1.43 g, 12.0 mmol, 1.0 eq) at 0° C. The reaction mixture was stirred below 15° C. for 4 hours. The reaction mixture was concentrated under reduced pressure. The residue was re-dissolved in MTBE (100 mL) and adjusted to pH 8.0 by addition of saturated aqueous $NaHCO_3$. The organic layer was washed with brine, dried over $Na_2SO_4$, concentrated in vacuum. The residue was purified by flash silica gel chromatography (Ethyl acetate/Petroleum ether) to afford 1.40 g of (Z)-ethyl (3-phenylthiazol-2(3H)-ylidene)carbamate as a yellow solid.

Intermediate C1

To a solution of (Z)-ethyl (3-phenylthiazol-2(3H)-ylidene)carbamate (0.80 g, 3.22 mmol, 1.0 eq) in EtOH (10 mL) was added 6N NaOH (10 mL, 60.0 mmol, 19 eq). The reaction mixture was stirred at 90° C. for 4 hours. The reaction mixture was diluted with water (25 mL), extracted with EtOAc (2×25 mL). The combined organic layers were dried over $Na_2SO_4$ and concentrated to afford 0.60 g of crude 3-phenylthiazol-2-imine C1 as a brown solid. The crude product was purified by reverse phase MPLC to afford 0.23 g of pure 3-phenylthiazol-2(3H)-imine C1 as a brown oil.

Preparation of Intermediate C2

Scheme 23

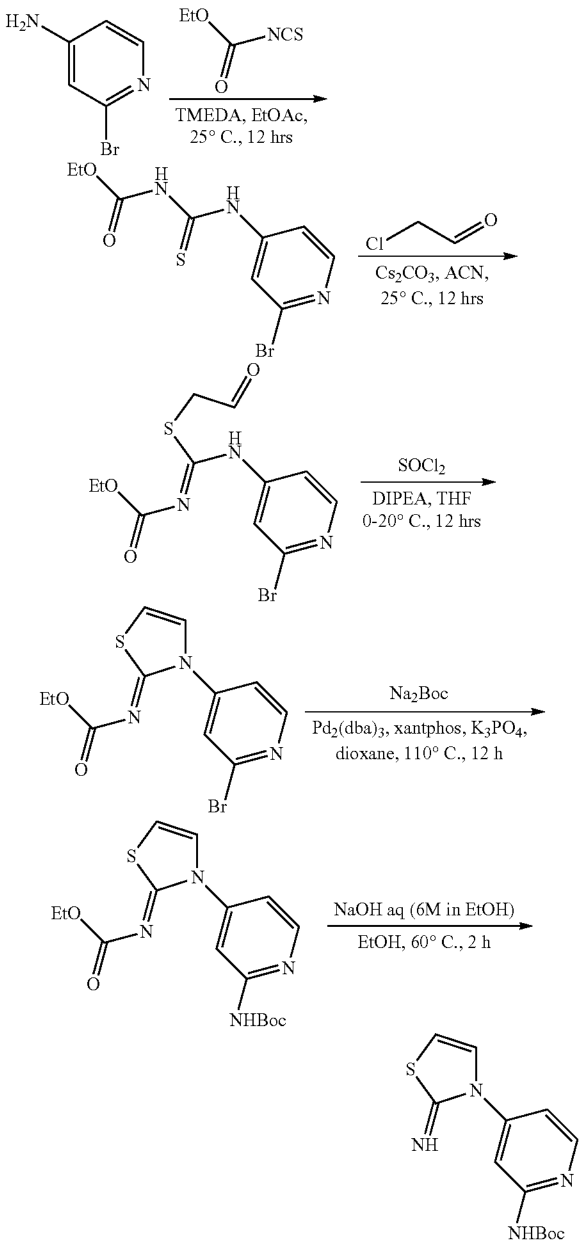

C2

Ethyl N-[(2-bromo-4-pyridyl)carbamothioyl]carbamate

A mixture of 2-bromopyridin-4-amine (5.00 g, 28.9 mmol, 1.0 eq), ethyl N-(thioxomethylene)carbamate (3.79 g, 28.9 mmol, 3.41 mL, 1.0 eq) and TMEDA (336 mg, 2.89 mmol, 436 uL, 0.1 eq) in EtOAc (50 mL) was degassed and purged with $N_2$ for 3 times at room temperature, and then the reaction mixture was stirred at 25° C. for 12 h under $N_2$ atmosphere. The mixture was concentrated directly under reduced pressure to afford a yellow solid. The solid was redissolved in EtOH (30 mL) and stirred for 10 min and then filtered. The filter cake was washed with EtOH (2×5 mL), and then concentrated under reduced pressure to give 4.2 g of ethyl N-[(2-bromo-4-pyridyl)carbamothioyl]carbamate as a light yellow solid.

(Z)-Ethyl (((2-bromopyridin-4-yl)amino)((2-oxoethyl)thio)methylene)carbamate

To a solution of ethyl N-[(2-bromo-4-pyridyl)carbamothioyl]carbamate (1.50 g, 4.93 mmol, 1.0 eq) and $Cs_2CO_3$ (2.73 g, 8.38 mmol, 1.7 eq) in MeCN (30 mL) was added 2-chloroacetaldehyde (484 mg, 6.16 mmol, 397 □L, 1.2 eq) at room temperature. After addition, the reaction mixture was stirred at 25° C. for 12 hours. The mixture was diluted with water (50 mL) and extracted with ethyl acetate (3×30 mL). The combined organic phase was washed with brine (30 mL), dried with anhydrous $Na_2SO_4$, filtered and concentrated in vacuum. (Z)-ethyl (((2-bromopyridin-4-yl)amino)((2-oxoethyl)thio)methylene)carbamate (1.60 g, crude) was obtained as a brown oil.

(Z)-Ethyl (3-(2-bromopyridin-4-yl)thiazol-2(3H)-ylidene)carbamate

To a solution of (Z)-ethyl (((2-bromopyridin-4-yl)amino)((2-oxoethyl)thio) methylene)carbamate (1.60 g, 4.62 mmol, 1.0 eq) in THF (20 mL) was added DIPEA (1.79 g, 13.9 mmol, 2.42 mL, 3.0 eq) and $SOCl_2$ (550 mg, 4.62 mmol, 335 □L, 1.0 eq) at 0° C. The reaction mixture was stirred below 20° C. for 12 h. The mixture was quenched with saturated $NaHCO_3$ aqueous solution (50 mL) and extracted with dichloromethane (3×20 mL). The combined organic layers were washed with brine, dried over $Na_2SO_4$ and concentrated to give 1.40 g of (Z)-ethyl (3-(2-bromopyridin-4-yl) thiazol-2(3H)-ylidene)carbamate as a brown oil.

(Z)-Ethyl (3-(2-((tert-butoxycarbonyl)amino)pyridin-4-yl)thiazol-2(3H)-ylidene)carbamate A mixture of (Z)-ethyl (3-(2-bromopyridin-4-yl)thiazol-2 (3H)-ylidene)carbamate (700 mg, 2.13 mmol, 1.0 eq), $NH_2$Boc (750 mg, 6.40 mmol, 3.0 eq), $K_3PO_4$ (1.81 g, 8.53 mmol, 4.0 eq), $Pd_2(dba)_3$ (195 mg, 213 μmol, 0.1 eq) and Xantphos (123 mg, 213 □mol, 0.1 eq) in dioxane (10 mL) was degassed and purged with $N_2$ for 3 times, and then the reaction mixture was stirred at 110° C. for 12 h under $N_2$ atmosphere. The mixture was poured into water (30 mL) and extracted with ethyl acetate (3×20 mL). The combined organic layers were washed with brine (30 mL), dried with anhydrous $Na_2SO_4$, filtered and concentrated in vacuum. The residue was purified by column chromatography on silica gel (Petroleum ether/Ethyl acetate=50/1 to 1/1) to give 140 mg of (Z)-ethyl (3-(2-((tert-butoxycarbonyl)amino) pyridin-4-yl)thiazol-2(3H)-ylidene)carbamate as a yellow solid. $^1$H NMR (400 MHz, METHANOL-$d_4$) δ 8.37 (d, J=5.50 Hz, 1H), 8.09 (s, 1H), 7.43 (d, J=4.75 Hz, 1H), 7.29 (dd, J=5.50, 1.75 Hz, 1H), 7.01 (d, J=4.88 Hz, 1H), 4.18 (q, J=7.13 Hz, 2H), 1.54 (s, 9H), 1.26 (t, J=7.07 Hz, 3H).

Intermediate C2

To a solution of (Z)-ethyl (3-(2-((tert-butoxycarbonyl) amino)pyridin-4-yl) thiazol-2(3H)-ylidene)carbamate (110 mg, 302 μmol, 1.0 eq) in EtOH (4 mL) was added NaOH (6 M, 4.0 mL, 80 eq). The reaction mixture was stirred at 60° C. for 2 h. The mixture was diluted with water (30 mL), extracted with THF (2×20 mL). The combined organic layers were washed with brine (30 mL), dried over $Na_2SO_4$, filtered and concentrated under reduced pressure to give intermediate C2 tert-butyl (4-(2-iminothiazol-3(2H)-yl)pyridin-2-yl)carbamate (100 mg, crude) as a brown solid.

Preparation of Intermediate C3

Scheme 24

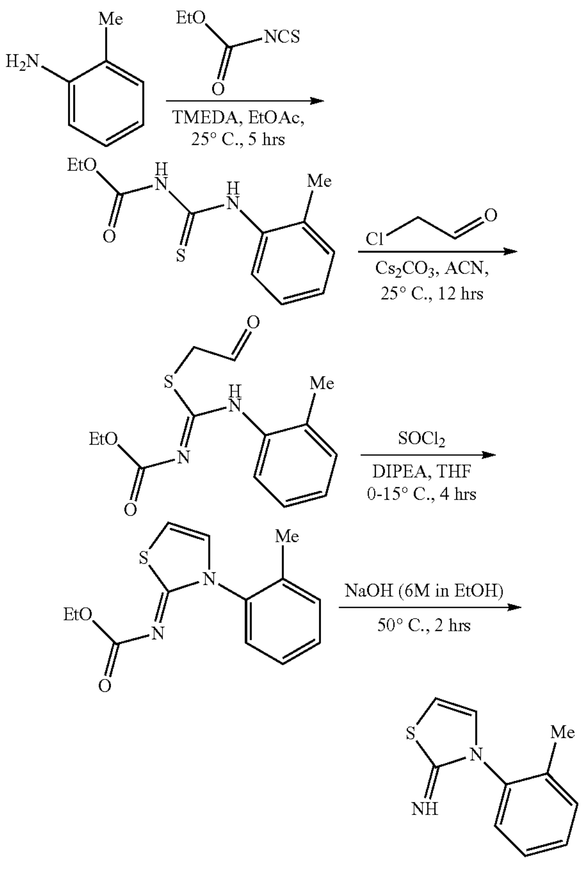

C3

Ethyl N-(o-tolylcarbamothioyl)carbamate

To a solution of o-toluidine (2.00 g, 18.7 mmol, 1.0 eq) in ethyl acetate (20 mL) was added TMEDA (0.217 g, 1.87 mmol, 0.1 eq) and O-ethyl carbonisothiocyanatidate (2.45 g, 18.7 mmol, 1.0 eq) at 25° C. The mixture was stirred at 25° C. for 2 hours then evaporated under reduce pressure. The residue was triturated in ethanol (10 mL) to afford 3.90 g of ethyl N-(o-tolylcarbamothioyl)carbamate as a white solid. $^1$H NMR (400 MHz, $CDCl_3$) δ 11.18 (br. s, 1H), 8.36 (br. s, 1H), 7.71-7.58 (m, 1H), 7.38-7.20 (m, 3H), 4.31 (q, J=7.2 Hz, 2H), 2.34 (s, 3H), 1.37 (t, J=7.2 Hz, 3H). LCMS (m/z $[M+H]^+$):239.1.

(Z)-Ethyl (((2-oxoethyl)thio)(o-tolylamino)methylene)carbamate

To a solution of ethyl N-(o-tolylcarbamothioyl)carbamate (3.90 g, 16.3 mmol, 1.0 eq) and $Cs_2CO_3$ (9.05 g, 27.8 mmol.

1.7 eq) in acetonitrile (40 mL) was added 2-chloroacetaldehyde (3.85 g, 19.6 mmol, 40% of water solution, 1.2 eq) maintaining the temperature blow 25° C. After addition, the mixture was stirred at 25° C. for 12 hours then diluted with MTBE (100 mL), washed with a saturated aqueous solution of $NaHCO_3$ (100 ml), followed by brine (50 mL), dried over $Na_2SO_4$ and filtered. The filtrate was concentrated under reduced pressure to afford 5.80 g of crude (Z)-ethyl (((2-oxoethyl)thio)(o-tolylamino)methylene)carbamate as a brown gum. $^1$H NMR (400 MHz, $CDCl_3$) δ 7.40-7.27 (m, 5H), 5.39 (d, J=5.2 Hz, 1H), 4.16 (q, J=7.2 Hz, 2H), 3.65 (dd, J=6.0, 12.4 Hz, 1H), 3.28 (d, J=12.4 Hz, 1H), 2.20 (s, 3H), 1.26 (t, J=7.2 Hz, 3H). LCMS (m/z $[M+]^+$): 281.1.

(Z)-Ethyl (3-(o-tolyl)thiazol-2(3H)-ylidene)carbamate

To a solution of (Z)-ethyl (((2-oxoethyl)thio)(o-tolylamino)methylene)carbamate (5.80 g, 12.1 mmol, 1.0 eq) and DIEA (6.32 mL, 36.3 mmol, 3.0 eq) in THF (60 mL) was added dropwise $SOCl_2$ (0.878 mL, 12.1 mmol, 1.0 eq) at 0° C. The mixture was stirred for 4 hrs at 0° C. then quenched with water (100 mL) and extracted with ethyl acetate (30 mL×3). The combined organic layers were dried over sodium sulfate, filtered and concentrated. The residue was purified by column chromatography on silica gel (Petroleum ether:Ethyl acetate=10:1 to 3:1) to afford 2.70 g of (Z)-ethyl (3-(o-tolyl)thiazol-2(3H)-ylidene)carbamate as yellow oil. $^1$H NMR (400 MHz, $CDCl_3$) δ 7.41-7.28 (m, 3H), 7.25-7.19 (m, 1H), 6.85 (d, J=4.8 Hz, 1H), 6.69 (d, J=4.8 Hz, 1H), 4.21 (q, J=7.2 Hz, 2H), 2.14 (s, 3H), 1.29 (t, J=7.2 Hz, 3H). LCMS (ink $[M+H]^+$): 263.1.

Intermediate C3

A solution of (Z)-ethyl (3-(o-tolyl)thiazol-2(3H)-ylidene) carbamate (0.500 g, 1.79 mmol, 1.0 eq) and NaOH (1.43 g, 35.8 mmol, 20 eq) in ethanol (6 mL) was stirred at 50° C. for 1 hour. The mixture was cooled to room temperature and diluted in ethyl acetate (20 mL), washed with water (20 mL), followed by brine (20 mL), dried over anhydrous sodium sulfate, filtered and concentrated under reduce pressure. The residue was purified by column chromatography on silica gel (Dichloromethane:Methanol=20:1) to afford 0.23 g of 3-(o-tolyl)thiazol-2(3H)-imine C3 as a yellow oil.

Preparation of Intermediate C4

Scheme 25

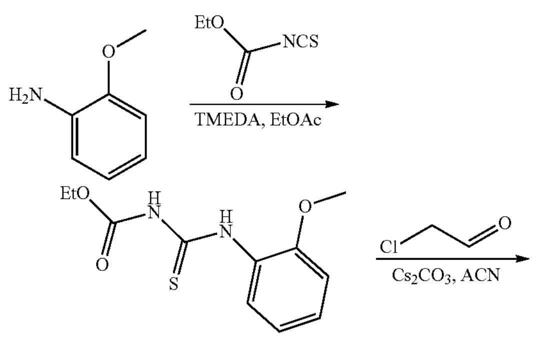

-continued

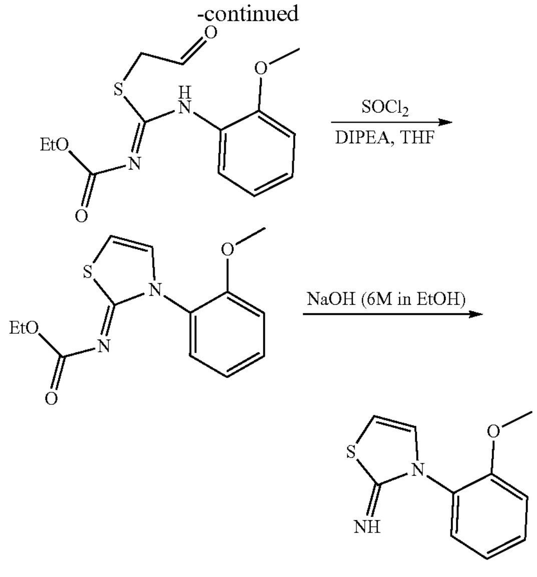

C4

Ethyl N-[(2-methoxyphenyl)carbamothioyl]carbamate

To a solution of 2-methoxyaniline (2.00 g, 16.2 mmol, 1.0 eq) in ethyl acetate (20 mL) was added O-ethyl carbonisothiocyanatidate (1.92 mL, 16.2 mmol, 1.0 eq) and tetramethylethylenediamine (0.245 mL, 1.62 mmo, 0.1 eq) at 25° C. The mixture was stirred at this temperature for 5 hours. The mixture was concentrated under reduced pressure to remove ethyl acetate. The residue was triturated with ethanol (5 mL) twice to afford 3.40 g of ethyl N-[(2-methoxyphenyl) carbamothioyl]carbamate as an off-white solid. $^1$H NMR (400 MHz, DMSO-$d_6$) δ 11.90 (br. s, 1H), 11.25 (br. s, 1H), 8.48 (dd, J=8.0, 1.2 Hz, 1H), 7.19 (dt, J=8.4, 1.6 Hz, 1H), 7.10 (dd, J=8.0, 1.2 Hz, 1H), 6.96 (dt, J=8.0, 1.2 Hz, 1H), 4.22 (q, J=7.2 Hz, 2H), 3.85 (s, 3H), 1.25 (t, J=7.2 Hz, 3H).

(Z)-Ethyl (((2-methoxyphenyl)amino)((2-oxoethyl) thio)methylene)carbamate

To a suspension of ethyl N-[(2-methoxyphenyl)carbamothioyl]carbamate (3.40 g, 13.4 mmol, 1.0 eq) and cesium carbonate (7.41 g, 22.7 mmol, 1.7 eq) in acetonitrile (40 mL) was added dropwise 2-chloroacetaldehyde (2.69 mL, 16.7 mmol, 1.2 eq) at 25° C. The resulting mixture was stirred for 12 hours at this temperature. Additional 2-chloroacetaldehyde (1.08 mL, 6.68 mmol, 0.5 eq) was added dropwise into the mixture at 25° C. and stirred for another 2 hours. The mixture was poured into water (150 mL), extracted with MTBE (100 mL×3), the combined organic layers were washed with brine (75 mL), dried over anhydrous sodium sulfate, filtered. The filtrate was concentrated under reduced pressure to afford 4.60 g of (Z)-ethyl (((2-methoxyphenyl) amino)((2-oxoethyl)thio)methylene)carbamate as a brown oil. $^1$H NMR (400 MHz, DMSO-$d_6$): δ 7.37 (dt, J=8.4, 1.6 Hz, 1H), 7.19 (dd, J=7.6, 1.6 Hz, 1H), 7.13 (dd, J=8.4, 0.8 Hz, 1H), 7.00 (dt, J=7.6, 1.2 Hz, 1H), 6.75 (d, J=7.2 Hz, 1H), 5.46 (dt, J=7.6, 2.4 Hz, 1H), 3.93 (q, J=7.2 Hz, 2H), 3.77 (s, 3H), 3.59 (dd, J=12.4, 6.4 Hz, 1H), 1.12-1.10 (m, 3H). LCMS (m/z $[M+H]^+$): 296.8.

(Z)-Ethyl (3-(2-methoxyphenyl)thiazol-2(3H)-ylidene) carbamate

To a solution of (Z)-ethyl (((2-methoxyphenyl)amino)((2-oxoethyl)thio)methylene) carbamate (2.60 g, 6.10 mmol, 1.0 eq) in THF (20 mL) was added diisopropylethylamine (3.19 mL, 18.3 mmol, 3.0 eq), followed by $SOCl_2$ (0.442 mL, 6.10 mmol, 1.0 eq) at 0° C. The mixture was stirred below 15° C. for 4 hours. The mixture was added to a saturated aqueous solution of sodium bicarbonate (20 mL) and stirred for 5 minutes, extracted with ethyl acetate (100 mL×3). The combined organic layers were washed with brine (50 mL), dried over anhydrous sodium sulfate, filtered and concentrated under reduced pressure. The residue was purified by column chromatography on silica gel (petroleum ether/ethyl acetate=10/1 to 5/1) to afford 1.00 g of (Z)-ethyl (3-(2-methoxyphenyl)thiazol-2(3H)-ylidene) carbamate as an off-white solid. $^1$H NMR (400 MHz, DMSO-$d_6$): δ 7.51-7.47 (m, 1H), 7.35 (dd, J=6.8, 1.6 Hz, 1H), 7.32 (d, J=4.8 Hz, 1H), 7.25 (dd, J=8.4, 0.8 Hz, 1H), 7.10-7.06 (m, 1H), 6.99 (d, J=4.8 Hz, 1H), 3.98 (q, J=7.2 Hz, 2H), 3.76 (s, 3H), 1.13 (t, J=7.2 Hz, 3H). LCMS (m/z $[M+H]^+$): 278.8.

Intermediate C4

To a solution of ethyl (3-(2-methoxyphenyl)thiazol-2(3H)-ylidene)carbamate (0.500 g, 1.80 mmol, 1.0 eq) in ethanol (5 mL) was added sodium hydroxide (1.44 g, 35.9 mmol, 20 eq) in one portion at 25° C. and the mixture was stirred for 1 hour. The mixture was poured into water (20 mL), extracted with ethyl acetate (50 mL×3). The combined organic layers were washed with brine (25 mL), dried over anhydrous sodium sulfate, filtered and concentrated under reduced pressure to afford 0.350 g of 3-(2-methoxyphenyl)thiazol-2(3H)-imine C4 as a brown oil.

Preparation of Intermediate C5

Scheme 26

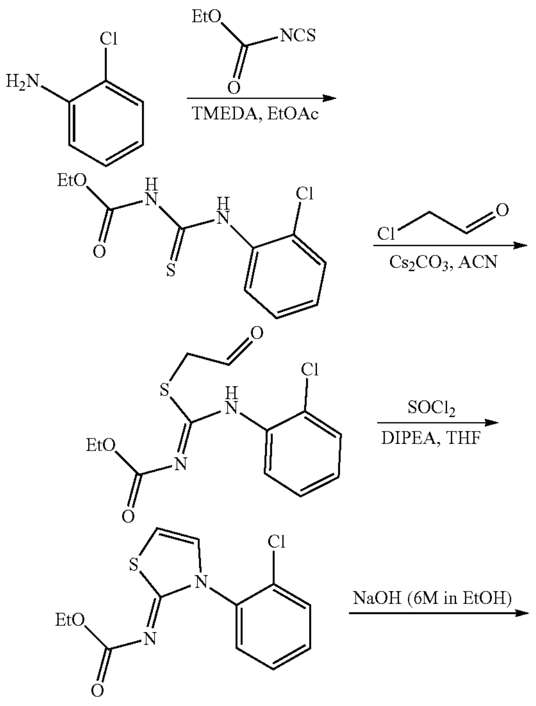

-continued

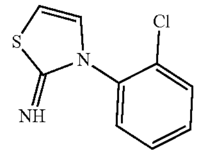

C5

Ethyl N-[(2-chlorophenyl)carbamothioyl]carbamate

To a solution of 2-chloroaniline (2.20 g, 17.3 mmol, 1.0 eq), O-ethyl carbonisothiocyanatidate (2.26 g, 17.3 mmol, 1.0 eq) in ethyl acetate (20 mL) was added tetramethylethylenediamine (0.200 g, 1.72 mmol, 0.1 eq) at 0° C. The resulting mixture was stirred at 25° C. for 2 hours, and then concentrated under reduced pressure. The residue was triturated with methanol (30 mL) to afford 3.00 g of ethyl N-[(2-chlorophenyl)carbamothioyl]carbamate as a white solid. $^1$H NMR (400 MHz, DMSO-$d_6$) δ 11.60 (s, 1H), 11.48 (s, 1H), 7.94 (dd, J=8.0, 1.6 Hz, 1H), 7.56 (dd, J=8.0, 1.6 Hz, 1H), 7.40-7.36 (m, 1H), 7.33-7.29 (m, 1H), 4.23 (q, J=7.2 Hz, 2H), 1.26 (t, J=7.2 Hz, 3H).

(Z)-Ethyl (((2-chlorophenyl)amino)((2-oxoethyl)thio)methylene)carbamate

To a suspension of ethyl N-[(2-chlorophenyl)carbamothioyl]carbamate (3.00 g, 11.6 mmol, 1.0 eq) and $Cs_2CO_3$ (6.42 g, 19.7 mmol, 12 eq) in acetonitrile (40 mL) was added 2-chloroacetaldehyde (2.84 g, 14.5 mmol, 1.2 eq), maintaining the temperature blow 25° C. The reation mixture was stirred at 25° C. for 12 hours. The mixture was poured into water (100 mL), extracted with methyl TBME (150 mL×2), the combined organic layers were washed with brine (200 mL), dried over anhydrous sodium sulfate, filtered, and the filtrate was concentrated under reduced pressure to afford 3.80 g of crude (Z)-ethyl (((2-chlorophenyl)amino)((2-oxoethyl)thio)methylene)carbamate as a brown gum. $^1$H NMR (400 MHz, DMSO-$d_6$) δ 7.66-7.58 (m, 1H), 7.49-7.35 (m, 3H), 6.99 (d, J=6.4 Hz, 1H), 5.53-5.42 (m, 1H), 4.00-3.90 (m, 2H), 3.70-3.65 (m, 1H), 3.23-3.15 (m, 1H), 1.11 (t, J=7.2 Hz, 3H).

(Z)-Ethyl (3-(2-chlorophenyl)thiazol-2(3H)-ylidene) carbamate

To a solution of (Z)-ethyl (((2-chlorophenyl)amino)((2-oxoethyl)thio)methylene)carbamate (1.80 g, 5.98 mmol, 1.0 eq) in THF (20 mL) was added diisopropylethylamine (2.32 g, 17.9 mmol, 3.0 eq) and thionyl chloride (0.710 g, 5.98 mmol, 1.0 eq) at 0° C. The mixture was stirred at 15° C. for 4 hours, then poured into water (100 mL) and extracted with ethyl acetate (150 mL×4). The combined organic phase was washed with brine (100 mL), dried over anhydrous sodium sulfate, filtered and concentrated under reduce pressure. The residue was purified by column chromatography on silica gel (petroleum ether/ethyl acetate=1/0 to 10/1) to afford 1.101 g of (Z)-ethyl (3-(2-chlorophenyl)thiazol-2(3H)-ylidene)carbamate as a yellow solid. $^1$H NMR (400 MHz, DMSO-$d_6$) δ 7.73-7.71 (m, 1H), 7.60-7.53 (m, 3H), 7.45 (d, J=4.8 Hz, 1H), 7.09 (d, J=4.8 Hz, 1H), 4.00 (q, J=6.8 Hz, 2H), 1.14 (t, J=7.2 Hz, 3H). LCMS (m/z $[M+H]^+$): 282.9.

Intermediate C5

To a solution (Z)-ethyl (3-(2-chlorophenyl)thiazol-2(3H)-ylidene)carbamate (0.80 g, 2.75 mmol, 1.0 eq) in ethanol (10 mL) was added sodium hydroxide (2.34 g, 58.4 mmol, 21 eq) at 25° C. The mixture was heated to 50° C. and stirred for 1 hour, then poured into water (80 mL) and extracted with ethyl acetate (120 mL×4). The combined organic layers were washed with brine (100 mL), dried over anhydrous sodium sulfate, filtered. The filtrate was concentrated under reduced pressure to afford 0.54 g of 3-(2-chlorophenyl) thiazol-2(3H)-imine C5 as a yellow solid.

Preparation of Intermediate C6

Scheme 27

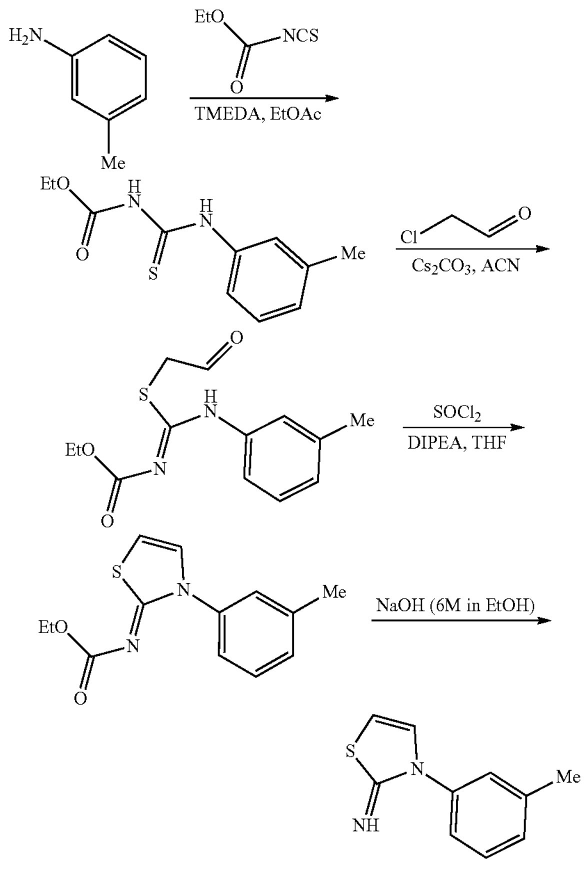

C6

Ethyl N-(m-tolylcarbamothioyl)carbamate

To a solution of m-toluidine (2.00 g, 18.6 mmol, 1.0 eq) in ethyl acetate (20 mL) was added O-ethyl carbonisothiocyanatidate (2.21 mL, 18.6 mmol, 1.0 eq) and tetramethylethylenediamine (0.282 mL, 1.87 mmol, 0.1 eq). The mixture was stirred at 25° C. for 5 hours. The mixture was concentrated under reduced pressure to remove ethyl acetate. The residue was triturated with ethanol (5 mL) twice to afford 3.00 g of ethyl N-(m-tolylcarbamothioyl)carbamate as a white solid. $^1$H NMR (400 MHz, DMSO-$d_6$) δ 11.51 (br. s, 1H), 11.23 (br. s, 1H), 7.43-7.38 (m, 2H), 7.26 (t, J=7.6 Hz, 1H), 7.05 (d, J=7.6 Hz, 1H), 4.20 (q, J=8.0, 7.2 Hz, 2H), 2.30 (s, 3H), 1.25 (t, J=6.8 Hz, 3H).

(Z)-Ethyl (((2-oxoethyl)thio)(m-tolylamino)methylene)carbamate

To a suspension of ethyl N-(m-tolylcarbamothioyl)carbamate (3.00 g, 12.6 mmol, 1.0 eq) and cesium carbonate (6.97 g, 21.4 mmol, 1.7 eq) in acetonitrile (40 mL) was added dropwise 2-chloroacetaldehyde (2.53 mL, 15.7 mmol, 1.25 eq) at 25° C. and the mixture was stirred for 12 hours. The mixture was poured into water (150 mL), extracted with methyl tert-butyl ether (100 mL×3), the combined organic layers were washed with brine (75 mL), dried over sodium sulfate, filtered. The filtrate was concentrated under reduced pressure to afford 4.00 g of (Z)-ethyl (((2-oxoethyl)thio)(m-tolylamino)methylene)carbamate as a brown oil. $^1$H NMR (400 MHz, DMSO-$d_6$) δ 7.34-7.30 (m, 1H), 7.16-7.13 (m, 3H), 6.85 (d, J=7.2 Hz, 1H), 5.60 (dt, J=7.2, 1.6 Hz, 1H), 3.96 (q, J=7.2 Hz, 2H), 2.32 (s, 3H), 1.14-1.10 (m, 3H). LCMS (m/z [M+H]$^+$): 280.9.

(Z)-Ethyl (3-(m-tolyl)thiazol-2(3H)-ylidene)carbamate

To a solution of (Z)-ethyl (((2-oxoethyl)thio)(m-tolylamino)methylene)carbamate (2.00 g, 5.58 mmol, 1.0 eq) in THF (20 mL) was added diisopropylethylamine (2.92 mL, 16.8 mmol, 3.0 eq), followed by $SOCl_2$ (0.405 mL, 5.58 mmol, 1.0 eq) at 0° C. under nitrogen atmosphere. The mixture was stirred below 15° C. for 4 hours. The mixture was poured into a saturated aqueous solution of sodium bicarbonate to adjust pH=8, then extracted with ethyl acetate (100 mL×3). The combined organic layers were washed with brine (100 mL), dried over anhydrous sodium sulfate, filtered and concentrated under reduced pressure. The residue was purified by column chromatography on silica gel (petroleum ether/ethyl acetate=10/1) to afford 1.00 g of (Z)-ethyl (3-(m-tolyl)thiazol-2(3H)-ylidene)carbamate as a yellow oil. $^1$H NMR (400 MHz, DMSO-$d_6$) δ 7.49 (d, J=4.8 Hz, 1H), 7.42 (t, J=8.0 Hz, 1H), 7.30-7.28 (m, 3H), 7.05 (d, J=4.8 Hz, 1H), 4.04-3.99 (m, 2H), 2.37 (s, 3H), 1.15 (t, J=7.2 Hz, 3H). LCMS (m/z [M+H]$^+$): 262.8.

Intermediate C6

To a solution of (Z)-ethyl (3-(m-tolyl)thiazol-2(3H)-ylidene)carbamate (0.200 g, 0.762 mmol, 1.0 eq) in ethanol (2 mL) was added sodium hydroxide (0.610 g, 15.2 mmol, 20 eq) in one portion at 25° C., then the mixture was heated to 50° C. and stirred for 1 hour. The mixture was added into water (50 mL), extracted with ethyl acetate (50 mL×4). The combined organic layers were washed with brine (20 mL), dried over anhydrous sodium sulfate, filtered and concentrated under reduced pressure to afford 140 mg of 3-(m-tolyl)thiazol-2(3H)-imine C6 as a brown oil.

Preparation of Intermediate C7

Scheme 28

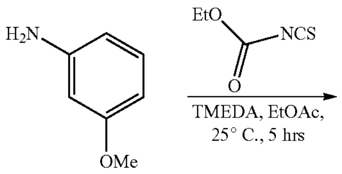

-continued

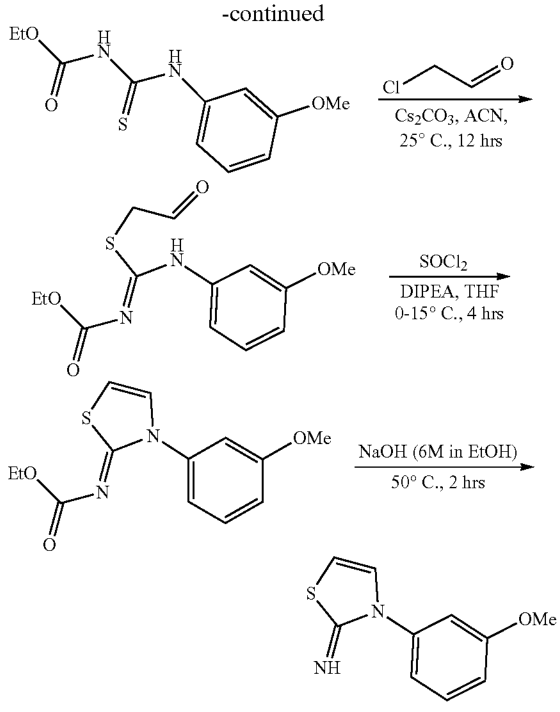

C7

Ethyl N-[(3-methoxyphenyl)carbamothioyl]carbamate

To a solution of 3-methoxyaniline (2.00 g, 16.2 mmol, 1.0 eq) in ethyl acetate (10 mL) was added TMEDA (0.189 g, 1.62 mmol, 0.1 eq) and O-ethyl carbonisothiocyanatidate (2.13 g, 16.2 mmol, 1.0 eq) at 25° C. The mixture was stirred at 25° C. for 2 hours then evaporated under reduce pressure. The residue was crystallized from petroleum ether/ethyl acetate (v/v=5:1, 10 mL) to afford 3.70 g of ethyl N-[(3-methoxyphenyl)carbamothioyl]carbamate as a yellow solid. $^1H$ NMR (400 MHz, $CDCl_3$) δ 11.48 (br. s, 1H), 8.11 (br. s, 1H), 7.41 (t, J=2.0 Hz, 1H), 7.30 (t, J=8.0 Hz, 1H), 7.14 (dd, J=1.6, 8.0 Hz, 1H), 6.82 (ddd, J=0.8, 2.4, 8.4 Hz, 1H), 4.30 (q, J=7.2 Hz, 2H), 3.83 (s, 3H), 1.36 (t, J=7.2 Hz, 3H). LCMS (m/z $[M+H]^+$): 255.1.

(Z)-Ethyl (((3-methoxyphenyl)amino)((2-oxoethyl)thio)methylene)carbamate

To a solution of ethyl N-[(3-methoxyphenyl)carbamothioyl]carbamate (3.70 g, 14.5 mmol, 1.0 eq) and $Cs_2CO_3$ (8.01 g, 24.6 mmol, 1.7 eq) in acetonitrile (40 mL) was added 2-chloroacetaldehyde (3.40 g, 17.3 mmol, 40% solution of water, 1.2 eq) maintaining the temperature blow 25° C. The mixture was stirred at 25° C. for 12 hours, then diluted with MTBE (100 mL) and washed with a saturated aqueous solution of $NaHCO_3$ (100 ml), followed by brine (50 mL), dried over $Na_2SO_4$ and filtered. The filtrate was concentrated under reduced pressure to afford 5.00 g of (Z)-ethyl (((3-methoxyphenyl)amino)((2-oxoethyl)thio)methylene)carbamate as a yellow oil. $^1H$ NMR (400 MHz, $CDCl_3$) δ 7.33 (t, J=8.0 Hz, 1H), 7.04-6.95 (m, 2H), 6.87 (ddd, J=0.8, 2.4, 8.4 Hz, 1H), 5.61 (d, J=5.2 Hz, 1H), 4.18 (q, J=7.2 Hz, 2H), 3.81 (s, 3H), 3.60 (dd, J=5.6, 12.0 Hz, 1H), 3.22 (dd, J=1.2, 12.4 Hz, 1H), 1.28 (t, J=7.2 Hz, 3H). LCMS (m/z 297.1 $[M+H]^+$): 297.1.

(Z)-Ethyl (3-(3-methoxyphenyl)thiazol-2(3H)-ylidene)carbamate

To a solution of (Z)-ethyl (((3-methoxyphenyl)amino)((2-oxoethyl)thio)methylene)carbamate (5.00 g, 11.3 mmol, 1.0 eq) and DIEA (4.37 g, 33.8 mmol, 3.0 eq) in THF (60 mL) was added dropwise $SOCl_2$ (0.818 mL, 11.3 mmol, 1.0 eq) at 0° C. The mixture was stirred for 4 hrs at 0° C. then quenched with water (100 mL) and extracted with ethyl acetate (30 mL×3). The combined organic layers were dried over sodium sulfate, filtered and concentrated. The residue was purified by column chromatography on silica gel (petroleum ether/ethyl acetate=10:1 to 3:1) to afford 2.70 g of (Z)-ethyl (3-(3-methoxyphenyl)thiazol-2(3H)-ylidene)carbamate as a yellow oil. $^1H$ NMR (400 MHz, $CDCl_3$) δ 7.38 (t, J=8.0 Hz, 1H), 7.07-6.98 (m, 3H), 6.94 (dd, J=2.0, 8.0 Hz, 1H), 6.66 (d, J=4.8 Hz, 1H), 4.22 (q, J=7.2 Hz, 2H), 3.83 (s, 3H), 1.30 (t, J=7.2 Hz, 3H). LCMS (m/z $[M+H]^+$): 279.1.

Intermediate C7

A solution of (Z)-ethyl (3-(3-methoxyphenyl)thiazol-2(3H)-ylidene)carbamate (0.500 g, 1.70 mmol, 1.0 eq) and NaOH (1.36 g, 34.1 mmol, 20 eq) in ethanol (6 mL) was stirred at 50° C. for 1 hour. The mixture was cooled to room temperature and diluted in ethyl acetate (20 mL), washed with water (20 mL), followed by brine (20 mL), dried over anhydrous sodium sulfate, filtered and concentrated under reduce pressure. The residue was purified by column chromatography on silica gel (dichloromethane:methanol=20:1) to afford 230 mg of 3-(3-methoxyphenyl)thiazol-2(3H)-imine C7 as yellow oil.

Preparation of Intermediate C8

Scheme 29

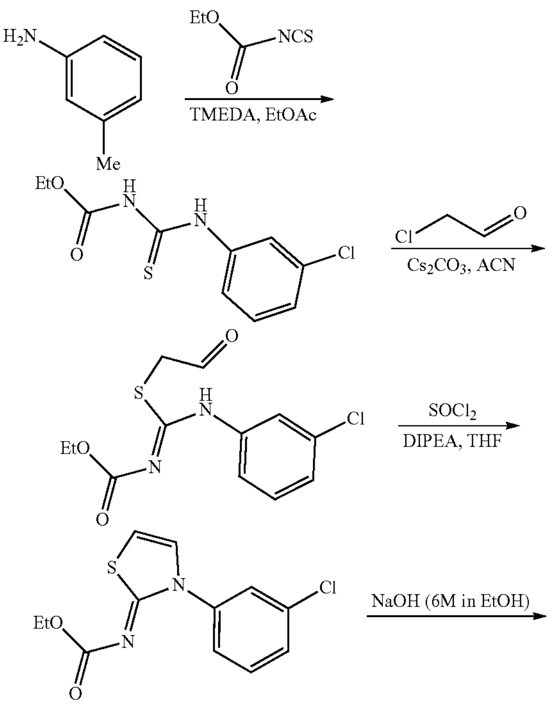

-continued

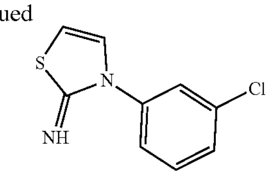

C8

Ethyl N-[(3-chlorophenyl)carbamothioyl]carbamate

To a solution of 3-chloroaniline (2.00 g, 15.7 mmol, 1.0 eq) in ethyl acetate (20 mL) was added O-ethyl carbonisothiocyanatidate (1.85 mL, 15.7 mmol, 1.0 eq) and tetramethylethylenediamine (0.237 mL, 1.57 mmol, 0.1 eq). The mixture was stirred at 25° C. for 5 hours. The mixture was concentrated under reduced pressure. The residue was triturated with petroleum ether/ethyl acetate (v/v=10/1, 11 mL) twice to afford 3.20 g of ethyl N-[(3-chlorophenyl)carbamothioyl]carbamate as a yellow solid. $^1$H NMR (400 MHz, DMSO-$d_6$): δ 11.55 (br. s, 1H), 11.35 (br. s, 1H), 7.84 (s, 1H), 7.49-7.47 (m, 1H), 7.41 (t, J=7.6 Hz, 1H), 7.32-7.30 (m, 1H), 4.21 (q, J=7.6 Hz, 2H), 1.25 (t, J=7.2 Hz, 3H).

(Z)-Ethyl (((3-chlorophenyl)amino)((2-oxoethyl)thio)methylene)carbamate

To a suspension of ethyl N-[(3-chlorophenyl)carbamothioyl]carbamate (3.20 g, 12.4 mmol, 1.0 eq) and cesium carbonate (6.85 g, 21.0 mmol, 1.7 eq) in acetonitrile (40 mL) was added dropwise 2-chloroacetaldehyde (2.49 mL, 15.4 mmol, 1.25 eq) at 25° C. The resulting mixture was stirred for 12 hours at this temperature. The mixture was poured into water (150 mL), extracted with MTBE (100 mL×3) at 25° C. The combined organic layers were washed with brine (75 mL), dried over anhydrous sodium sulfate, filtered and the filtrate was concentrated under reduced pressure to afford 3.80 g of (Z)-ethyl (((3-chlorophenyl)amino)((2-oxoethyl)thio)methylene)carbamate as a brown oil. $^1$H NMR (400 MHz, DMSO-$d_6$): δ 7.50-7.46 (m, 2H), 7.43-7.40 (m, 1H), 7.38-7.36 (m, 1H), 6.95 (br. s, 1H), 5.69-5.68 (m, 1H), 3.98 (t, J=7.6 Hz, 2H), 3.68-3.55 (m, 1H), 3.10-3.05 (m, 1H), 1.14 (t, J=7.6 Hz, 3H). LCMS (m/z [M+H]$^+$): 300.8.

(Z)-Ethyl (3-(3-chlorophenyl)thiazol-2(3H)-ylidene)carbamate

To a solution of (Z)-ethyl (((3-chlorophenyl)amino)((2-oxoethyl)thio)methylene)carbamate (1.80 g, 3.68 mmol, 1.0 eq) in THF (20 mL) was added diisopropylethylamine (1.92 mL, 11.0 mmol, 3.0 eq), followed by $SOCl_2$ (0.267 mL, 3.68 mmol, 1.0 eq) at 0° C. under nitrogen atmosphere. The mixture was stirred below 15° C. for 4 hours. $SOCl_2$ (0.134 mL, 1.84 mmol, 0.5 eq) was added dropwise into the mixture at 0° C. and the reaction mixture was stirred at 15° C. for 2 hours. The mixture was added into a saturated aqueous solution of sodium bicarbonate to adjust pH=8, extracted with ethyl acetate (100 mL×3). The combined organic layers were washed with brine (100 mL), dried over anhydrous sodium sulfate, filtered and concentrated under reduced pressure. The residue was purified by column chromatography on silica gel (petroleum ether/ethyl acetate=10/1 to 5/1) to afford 0.95 g of (Z)-ethyl (3-(3-chlorophenyl)thiazol-2(3H)-ylidene)carbamate as an off-white solid. $^1$H NMR (400 MHz, DMSO-$d_6$): δ 7.70 (s, 1H), 7.58-7.54 (m, 3H), 7.53-7.51 (m, 1H), 7.07 (d, J=4.8 Hz, 1H), 4.03 (q, J=7.2 Hz, 2H), 1.16 (t, J=7.2 Hz, 3H). LCMS (m/z [M+H]$^+$): 282.8.

Intermediate C8

To a solution of (Z)-ethyl (3-(3-chlorophenyl)thiazol-2(3H)-ylidene)carbamate (0.200 g, 0.707 mmol, 1.0 eq) in ethanol (2 mL) was added sodium hydroxide (0.566 g, 14.2 mmol, 20 eq) in one portion at 25° C. And the mixture was stirred for 1 hour at this temperature. The mixture was added into water (50 mL), extracted with ethyl acetate (50 mL×4). The combined organic layers were washed with brine (20 mL), dried over anhydrous sodium sulfate, filtered and concentrated under reduced pressure to afford 130 mg of 3-(3-chlorophenyl)thiazol-2(3H)-imine C8 as an brown solid.

Preparation of Intermediate C9

Scheme 30

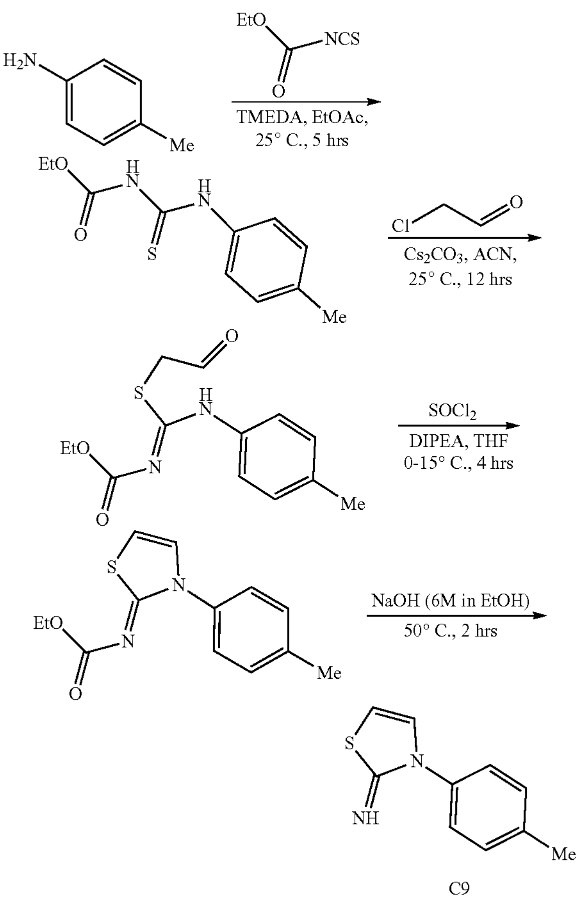

C9

To a solution of p-toluidine (2.00 g, 18.7 mmol, 1.0 eq) in ethyl acetate (10 mL) was added TMEDA (0.217 g, 1.87 mmol, 0.1 eq) and O-ethyl carbonisothiocyanatidate (2.45 g, 18.7 mmol, 1.0 eq) at 25° C. The mixture was stirred at 25° C. for 2 hours then evaporated under reduce pressure. The residue was triturated in ethanol (10 mL) to afford 3.70 g of the ethyl N-(p-tolylcarbamothioyl)carbamate as a yellow solid. $^1$H NMR (400 MHz, $CDCl_3$) δ 11.35 (br s, 1H), 8.21

(br s, 1H), 7.48 (d, J=8.4 Hz, 2H), 7.21 (d, J=8.0 Hz, 2H), 4.29 (q, J=7.2 Hz, 2H), 2.37 (s, 3H), 1.35 (t, J=7.2 Hz, 3H). LCMS (m/z $[M+H]^+$): 239.1.

(Z)-Ethyl (((2-oxoethyl)thio)(p-tolylamino)methylene)carbamate

To a solution of ethyl N-(p-tolylcarbamothioyl)carbamate (3.70 g, 15.5 mmol, 10 eq) and $Cs_2CO_3$ (8.59 g, 26.4 mmol, 1.7 eq) in acetonitrile (40 mL) was added 2-chloroacetaldehyde (3.65 g, 18.6 mmol, 40% solution of water, 1.2 eq) maintaining the temperature blow 25° C. After addition, the mixture was stirred at 25° C. for 12 hours then diluted with MTBE (100 mL), washed with a saturated aqueous solution of $NaHCO_3$ (100 ml), followed by brine (50 mL), dried over $Na_2SO_4$ and filtered. The filtrate was concentrated under reduced pressure to afford 5.30 g of the crude (Z)-ethyl (((2-oxoethyl)thio)(p-tolylamino)methylene)carbamate as yellow oil. $^1$H NMR (400 MHz, $CDCl_3$) δ 7.39-7.18 (m, 5H), 5.56 (dd, J=0.5, 5.6 Hz, 1H), 4.16 (q, J=7.2 Hz, 2H), 3.57 (dd, J=5.6, 12.4 Hz, 1H), 3.19 (dd, J=1.2, 12.0 Hz, 1H), 2.35 (s, 3H), 1.26(t, J=7.2 Hz, 3H). LCMS (m/z $[M+H]^+$): 281.1.

(Z)-Ethyl (3-(p-tolyl)thiazol-2(3H)-ylidene)carbamate

To a solution of (Z)-ethyl (((2-oxoethyl)thio)(p-tolylamino)methylene)carbamate (5.30 g, 10.8 mmol, 1.0 eq) and DIEA (4.19 g, 32.4 mmol, 3.0 eq) in THF (60 mL) was added dropwise $SOCl_2$ (0.783 mL, 10.8 mmol, 1.0 eq) at 0° C. The mixture was stirred for 4 hrs at 0° C. then quenched with water (100 mL) and extracted with ethyl acetate (30 mL×3). The combined organic layers were dried over sodium sulfate, filtered and concentrated. The residue was purified by column chromatography on silica gel (petroleum ether/ethyl acetate=10:1 to 3:1) to afford 2.20 g of (Z)-ethyl (3-(p-tolyl)thiazol-2(3H)-ylidene)carbamate as yellow oil. $^1$H NMR (400 MHz, $CDCl_3$) δ 7.26 (d, J=8.4 Hz, 2H), 7.21 (d, J=8.4 Hz, 2H), 6.93 (d, J=4.8 Hz, 1H), 6.58 (d, J=4.8 Hz, 1H), 4.14 (q, J=7.2 Hz, 2H), 2.32 (s, 3H), 1.22 (t, J=7.2 Hz, 3H). LCMS o(m/z $[M+H]^+$): 263.1.

Intermediate C9

A solution of (Z)-ethyl (3-(p-tolyl)thiazol-2(3H)-ylidene) carbamate (0.500 g, 1.86 mmol, 1.0 eq) and NaOH (1.49 g, 37.2 mmol, 20 eq) in ethanol (6 mL) was stirred at 50° C. for 1 hour. The mixture was cooled to room temperature and diluted in ethyl acetate (20 mL), washed with water (20 mL), followed by brine (20 mL), dried over anhydrous sodium sulfate, filtered and concentrated under reduce pressure. The residue was purified by column chromatography on silica gel (dichloromethane/methanol=20:1) to afford 230 mg of 3-(p-tolyl)thiazol-2(3H)-imine C9 as a yellow oil.

Preparation of Intermediate C10

Scheme 31

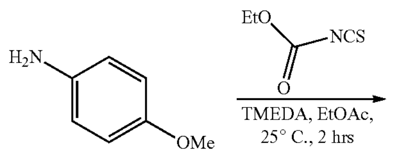

-continued

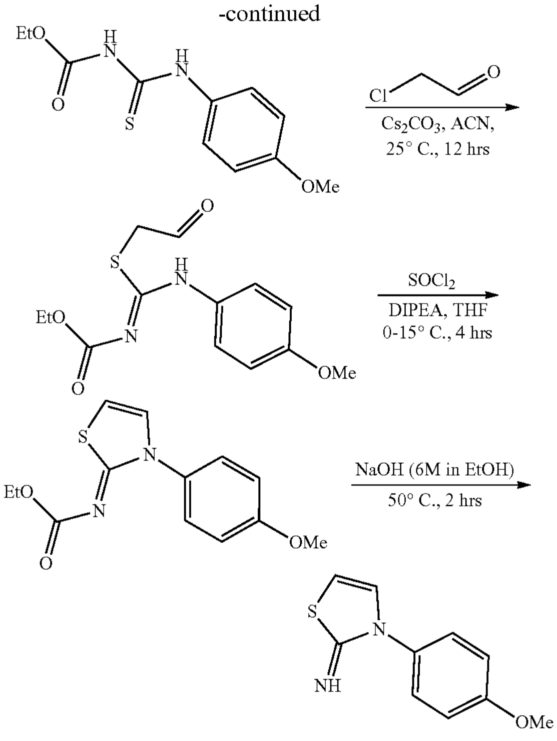

C10

Ethyl N-[(4-methoxyphenyl)carbamothioyl]carbamate

To a solution of 4-methoxyaniline (2.00 g, 16.2 mmol, 1.0 eq) and O-ethyl carbonisothiocyanatidate (2.13 g, 16.2 mmol, 1.0 eq) in ethyl acetate (20 mL) was added tetramethylethylendiamine (0.189 g, 1.62 mmol, 0.1 eq) at 25° C., the mixture was stirred at 25° C. for 2 hours. The mixture was concentrated in vacuum, and the residue was triturated with ethanol (8 mL), the precipitate was dried in vacuum to afford 3.50 g of ethyl N-[(4-methoxyphenyl)carbamothioyl] carbamate as a white solid. $^1$H NMR (400 MHz, $CDCl_3$): δ 11.37 (br. s, 1H), 11.18 (br. s, 1H), 7.44 (d, J=8.8 Hz, 2H), 6.94 (d, J=8.8 Hz, 2H), 4.20 (q, J=7.2 Hz, 2H), 3.76 (s, 1H), 1.26 (t, J=6.8 Hz, 3H).

(Z)-Ethyl (((4-methoxyphenyl)amino)((2-oxoethyl)thio)methylene)carbamate

To a solution of ethyl N-[(4-methoxyphenyl)carbamothioyl]carbamate (3.50 g, 13.7 mmol, 1.0 eq) and cesium carbonate (7.62 g, 23.4 mmol, 1.7 eq) in acetonitrile (40 mL) was added 2-chloroacetaldehyde (3.38 g, 17.2 mmol, 1.25 eq), maintaining the temperature blow 25° C. After addition, the mixture was stirred at 25° C. for 12 hours. The mixture was poured into water (150 mL), extracted with TBME (150 mL×2). The combined organic layers were washed with brine (200 mL), dried over sodium sulfate, filtered. The filtrate was concentrated under reduced pressure to afford 3.80 g of (Z)-ethyl (((4-methoxyphenyl)amino)((2-oxoethyl)thio)methylene)carbamate as a brown gum. 1H NMR (400 MHz, DMSO-$d_6$): δ 7.28-7.20 (m, 2H), 7.02-6.95 (m, 2H), 6.92 (d, J=7.2 Hz, 1H), 5.59-5.54 (m, 1H), 3.95 (q, J=7.2 Hz, 2H), 3.78 (s, 3H), 1.12 (t, J=7.2 Hz, 3H). LCMS (m/z $[M+H]^+$): 297.0.

(Z)-Ethyl (3-(4-methoxyphenyl)thiazol-2(3H)-ylidene)carbamate

To a solution of (Z)-ethyl (((4-methoxyphenyl)amino)((2-oxoethyl)thio)methylene)carbamate (1.80 g, 6.07 mmol, 1.0 eq) in tetrahydrofuran (20 mL) was added DIEA (2.36 g, 18.2 mmol, 3.0 eq), followed by thionyl chloride (0.723 g, 6.07 mmol, 1.0 eq) at 0° C. After the addition, the mixture was warmed to 15° C. and stirred for 4 hours. The mixture was concentrated directly under reduced pressure. The residue was dissolved in ethyl acetate (100 mL) and adjusted to pH=8.0 by addition of saturated aqueous sodium bicarbonate. The organic layer was separated and washed with brine (20 mL), dried over sodium sulfate, filtered and concentrated under reduce pressure. The residue was purified by column chromatography on silica gel (petroleum ether/ethyl acetate=10/1 to 5/1) to afford 1.20 g of (Z)-ethyl (3-(4-methoxyphenyl)thiazol-2(3H)-ylidene)carbamate as a yellow solid. $^1H$ NMR (400 MHz, $CDCl_3$) δ 7.47 (d, J=4.8 Hz, 1H), 7.41 (d, J=5.2 Hz, 2H), 7.07 (d, J=4.8 Hz, 2H), 7.04 (d, J=4.8 Hz, 1H), 4.01 (q, J=6.8 Hz, 2H), 3.82 (s, 3H), 1.16 (t, J=7.2 Hz, 3H).

Intermediate C10

To a solution of ethyl (3-(4-methoxyphenyl)thiazol-2(3H)-ylidene)carbamate (0.200 g, 0.718 mmol, 1.0 eq) in ethanol (2 mL) was added sodium hydroxide (0.575 g, 14.4 mmol, 20 eq). The mixture was stirred at 50° C. for 2 hours. The mixture was diluted with water (30 mL), extracted with ethyl acetate (15 mL×2). The combined organic layers were dried over sodium sulfate, filtered and the filtrate was concentrated under reduce pressure. The residue was purified by column chromatography on silica gel (dichloromethane/methanol=0/1) to afford 100 mg of 3-(4-methoxyphenyl) thiazol-2(3H)-imine C10 as yellow oil.

Preparation of Intermediate C11

Scheme 32

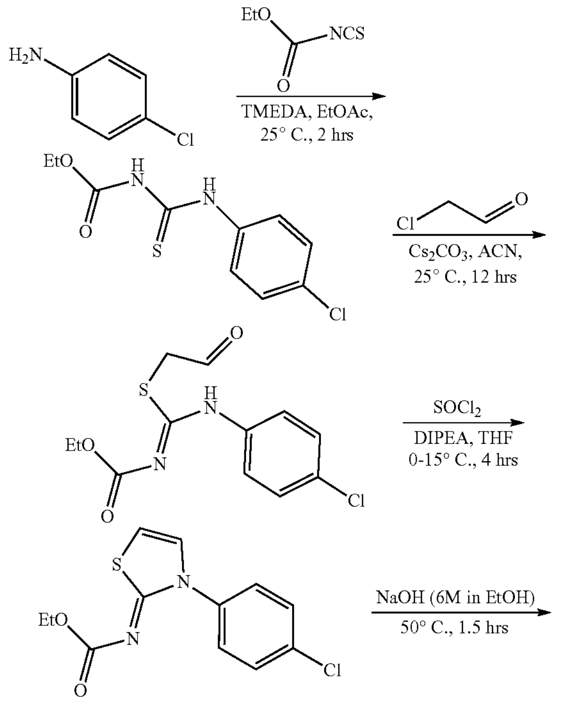

-continued

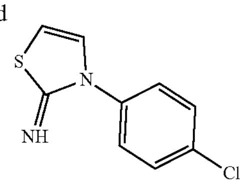

C11

Ethyl N-[(4-chlorophenyl)carbamothioyl]carbamate

To a solution of 4-chloroaniline (2.00 g, 15.7 mmol, 1.0 eq) and O-ethyl carbonisothiocyanatidate (2.06 g, 15.7 mmol, 1.0 eq) in ethyl acetate (20 mL) was added tetramethylethylenediamine (0.182 g, 1.57 mmol, 0.1 eq) at 25° C., the resulting mixture was stirred at 25° C. for 2 hours. The mixture was concentrated in reduced pressure. The residue was triturated with ethanol (8 mL) to afford 3.00 g of ethyl N-[(4-chlorophenyl)carbamothioyl]carbamate as a white solid. $^1H$ NMR (400 MHz, $CDCl_3$-d): δ 11.51 (br. s, 1H), 11.31 (br. s, 1H), 7.62 (d, J=8.8 Hz, 2H), 7.44 (d, J=8.8 Hz, 2H), 4.21 (q, J=7.2 Hz, 2H), 1.26 (t, J=6.8 Hz, 3H).

(Z)-Ethyl (((4-chlorophenyl)amino)((2-oxoethyl)thio)methylene)carbamate

To a suspension of ethyl ethyl N-[(4-chlorophenyl)carbamothioyl]carbamate (3.00 g, 11.60 mmol, 1.0 eq) and cesium carbonate (6.42 g, 19.7 mmol, 1.7 eq) in acetonitrile (40 mL) was added dropwise 2-chloroacetaldehyde (2.84 g, 14.5 mmol, 1.25 eq), maintaining the temperature blow 25° C. After the addition, the mixture was stirred at 25° C. for 12 hours. The mixture was diluted with tert-butyl methyl ether (150 mL×2), washed with brine (50 mL), dried over sodium sulfate, filtered. The filtrate was concentrated under reduced pressure to afford 3.50 g of (Z)-ethyl (((4-chlorophenyl)amino)((2-oxoethyl)thio)methylene)carbamate as a brown gum. $^1H$ NMR (400 MHz, DMSO-$d_6$) δ 7.57-7.46 (m, 2H), 7.43-7.33 (m, 2H), 6.92 (d, J=7.2 Hz, 1H), 5.70-5.61 (m, 1H), 3.98 (q, J=6.8 Hz, 2H), 1.13 (t, J=7.2 Hz, 3H). LCMS (m/z $[M+H]^+$): 301.0.

(Z)-Ethyl (3-(4-chlorophenyl)thiazol-2(3H)-ylidene)carbamate

To a solution of (Z)-ethyl (((4-chlorophenyl)amino)((2-oxoethyl)thio)methylene)carbamate (1.80 g, 5.78 mmol, 1.0 eq) in tetrahydrofuran (20 mL) was added N-ethyl-N-isopropylpropan-2-amine (2.24 g, 17.3 mmol, 3.0 eq) and thionyl chloride (0.687 g, 5.78 mmol, 1.0 eq) at 0° C. The mixture was stirred at 25° C. for 4 hours. The mixture was concentrated directly under reduced pressure. The residue was dissolved in ethyl acetate (100 mL) and adjusted to pH=8.0 by addition of a saturated aqueous solution of sodium bicarbonate. The organic layer was separated and washed with brine (20 mL), dried over sodium sulfate, filtered and concentrated under reduced pressure. The residue was purified by column chromatography on silica gel (petroleum ether/ethyl acetate=10/1 to 5/1) to afford 1.10 g of (Z)-ethyl (3-(4-chlorophenyl)thiazol-2(3H)-ylidene)carbamate as a yellow solid. $^1H$ NMR (400 MHz, $CDCl_3$-d): δ 7.65-7.55 (m, 4H), 7.54 (d, J=4.4 Hz, 1H), 7.07 (d, J=4.4 Hz, 1H), 4.03 (q, J=7.2 Hz, 2H), 1.16 (t, J=7.2 Hz, 3H).

Intermediate C11

To a solution of (Z)-ethyl (3-(4-chlorophenyl)thiazol-2(3H)-ylidene)carbamate (0.200 g, 0.707 mmol, 1.0 eq) in ethanol (2 mL) was added sodium hydroxide (0.569 g, 14.2 mmol, 20 eq) at 25° C. Then the reaction mixture was heated to 50° C. and stirred for 1.5 hours. The mixture was diluted with water (80 mL), extracted with ethyl acetate (50 mL×2). The combined organic layers were dried over sodium sulfate, filtered and the filtrate was concentrated under reduced pressure to afford 120 mg of 3-(4-chlorophenyl)thiazol-2(3H)-imine C11 as a yellow oil.

Preparation of Intermediate C12

Scheme 33

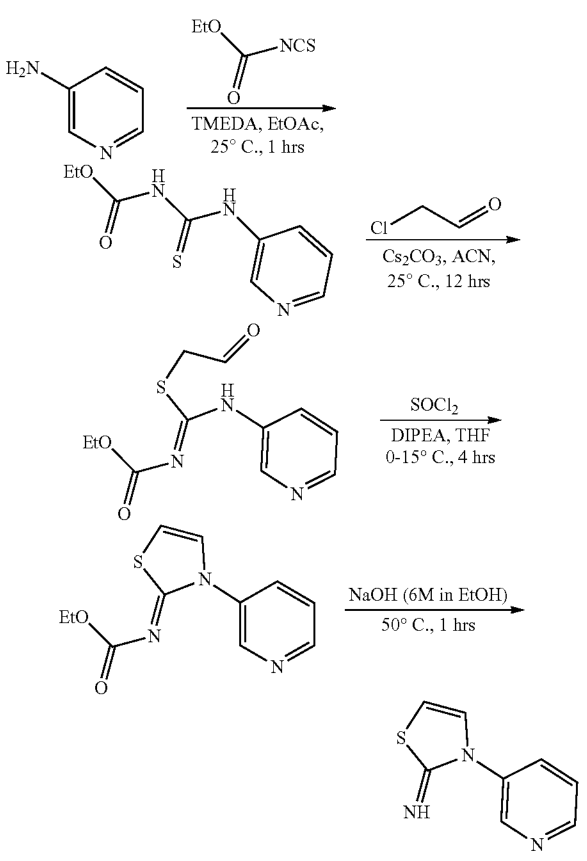

C12

Ethyl N-(3-pyridylcarbamothioyl) carbamate

To a solution of pyridin-3-amine (1.00 g, 10.6 mmol, 1.0 eq) and O-ethyl carbonisothiocyanatidate (1.39 g, 10.6 mmol, 1.0 eq) in ethyl acetate (10 mL) was added tetramethylethylenediamine (0.123 g, 1.06 mmol, 0.1 eq) at 25° C., then the mixture was stirred at this temperature for 1 hour. The mixture was concentrated, and the residue was triturated with ethanol (10 mL), the precipitate was collected by filtration, dried in reduced pressure to afford 1.80 g of ethyl N-(3-pyridylcarbamothioyl) carbamate as a white solid. $^1$H NMR (400 MHz, $CDCl_3$) δ 11.56 (br. s, 1H), 8.70 (d, J=2.4 Hz, 1H), 8.52 (dd, J=4.8 Hz, 1.6 Hz, 1H), 8.30 (br. s, 1H), 8.28-8.23 (m, 1H), 7.39-7.33 (m, 1H), 4.33 (q, J=7.2 Hz, 2H), 1.38 (t, J=7.2 Hz, 3H).

(Z)-Ethyl (((2-oxoethyl)thio)(pyridin-3-ylamino) methylene)carbamate

To a suspension of ethyl N-(3-pyridylcarbamothioyl)carbamate (0.60 g, 2.66 mmol, 1.0 eq) and cesium carbonate (1.48 g, 4.53 mmol, 1.7 eq) in acetonitrile (10 mL) was added dropwise 2-chloroacetaldehyde (1.05 g, 5.33 mmol, 2.0 eq), maintaining the temperature at 25° C. After the addition, the mixture was stirred at this temperature for 12 hours. The mixture was poured into water (100 mL) and extracted with ethyl acetate (50 mL×3). The combined organic layers were washed with brine (100 mL), dried over anhydrous sodium sulfate, filtered, and the filtrate was concentrated under reduced pressure to afford 0.40 g of (Z)-ethyl (((2-oxoethyl)thio)(pyridin-3-ylamino)methylene) carbamate as a white solid. $^1$H NMR (400 MHz, DMSO-$d_6$) δ 8.58 (d, J=2.0 Hz, 1H), 8.52 (dd, J=1.6 Hz, 4.8 Hz, 1H), 7.83-7.80 (m, 1H), 7.50 (q, J=4.8 Hz, 1H), 7.00 (d, J=7.2 Hz, 1H), 5.72 (t, J=6.0 Hz, 1H), 4.04-3.96 (m, 2H), 3.66-3.61 (m, 1H), 3.15 (dd, J=12.4 Hz, 1.2 Hz, 1H), 1.13 (t, J=6.8 Hz, 3H). LCMS (m/z $[M+H]^+$): 268.1.

(Z)-Ethyl (3-(pyridin-3-yl)thiazol-2(3H)-ylidene) carbamate

To a solution of (Z)-ethyl (((2-oxoethyl)thio)(pyridin-3-ylamino)methylene)carbamate (0.570 g, 2.13 mmol, 1.0 eq) in tetrahydrofuran (6 mL) was added diisopropylethylamine (0.830 g, 6.40 mmol, 3.0 eq) and thionyl chloride (0.250 g, 2.13 mmol, 1.0 eq) at 0° C. The mixture was stirred at 25° C. for 4 hours. The mixture was concentrated directly under reduced pressure. The residue was dissolved in ethyl acetate (100 mL) and adjusted to pH=8.0 by a saturated aqueous solution of sodium bicarbonate. The organic layer was separated and washed with brine (20 mL), dried over sodium sulfate, filtered and concentrated in reduced pressure to afford 0.40 g of (Z)-ethyl (3-(pyridin-3-yl)thiazol-2(3H)-ylidene)carbamate as a yellow solid. $^1$H NMR (400 MHz, DMSO-$d_6$) δ 8.77 (d, J=2.4 Hz, 1H), 8.65 (dd, J=4.8 Hz, 1.6 Hz, 1H), 8.07-8.00 (m, 1H), 7.63 (d, J=4.8 Hz, 1H), 7.63-7.59 (m, 1H), 7.12 (d, J=4.8 Hz, 1H), 4.03 (q, J=7.2 Hz, 2H), 1.15 (t, J=7.2 Hz, 3H).

Intermediate C12

To a solution of ethyl (3-(pyridin-3-yl)thiazol-2(3H)-ylidene)carbamate (0.200 g, 0.800 mmol, 1.0 eq) in ethanol (2 mL) was added sodium hydroxide (0.640 g, 16.1 mmol, 20 eq) at 25° C., then the mixture was heated to 50° C. and stirred at for 1 hour. The mixture was diluted with water (50 mL), extracted with ethyl acetate (50 mL×2). The combined organic layers were dried over sodium sulfate, filtered and concentrated to afford 140 mg of 3-(pyridin-3-yl) thiazol-2(3H)-imine C12 as a brown oil. $^1$H NMR (400 MHz, DMSO-$d_6$, 400 MHz) δ 8.80 (d, J=2.0 Hz, 1H), 8.45 (d, J=4.0 Hz, 1H), 8.28 (br. s, 1H), 8.06 (d, J=7.6 Hz, 1H), 7.51-7.43 (m, 1H), 7.12 (d, J=5.2 Hz, 1H), 6.25 (d, J=5.2 Hz, 1H).

Preparation of Intermediate C13

Scheme 34

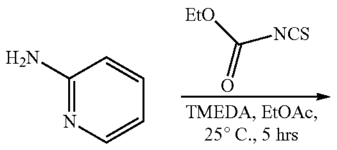

-continued

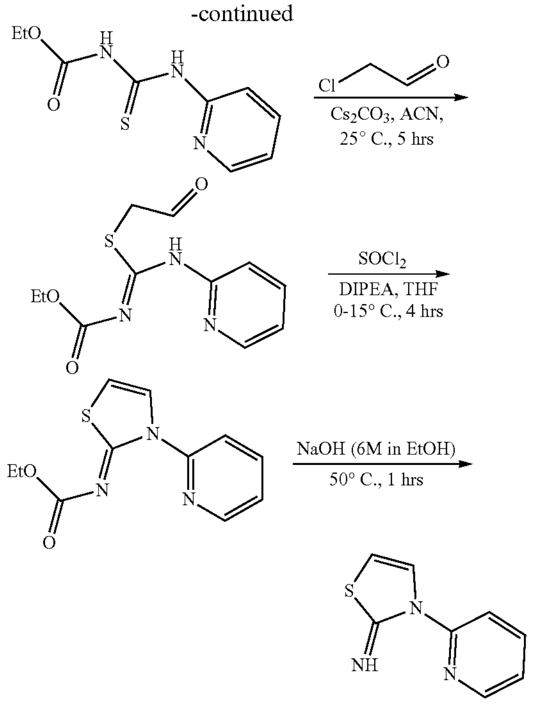

C13

Ethyl N-(2-pyridylcarbamothioyl) carbamate

To a solution of pyridin-2-amine (1.00 g, 10.6 mmol, 1.0 eq) in ethyl acetate (10 mL) was added O-ethyl carbonisothiocyanatidate (1.26 mL, 10.6 mmol, 1.0 eq) and N1,N1,N2,N2-tetramethylethane-1,2-diamine (0.160 mL, 1.06 mmol, 0.1 eq) at 25° C. Then the mixture was stirred at this temperature for 5 hours. The mixture was concentrated under reduced pressure. The residue was triturated with ethanol (10 mL) three times to afford 0.95 g of ethyl N-(2-pyridylcarbamothioyl) carbamate as an off-white solid. $^1$H NMR (400 MHz, $CDCl_3$) δ 12.06 (br.s, 1H), 8.80 (d, J=8.0 Hz, 1H), 8.41 (d, J=4.0 Hz, 1H), 8.07 (br. s, 1H), 7.79-7.74 (m, 1H), 7.16-7.13 (m, 1H), 4.31 (q, J=7.2 Hz, 2H), 1.35 (t, J=7.2 Hz, 3H). LCMS (m/z $[M+H]^+$): 225.8.

(Z)-Ethyl (((2-oxoethyl)thio)(pyridin-2-ylamino) methylene) carbamate

To a suspension of ethyl N-(2-pyridylcarbamothioyl)carbamate (0.800 g, 3.55 mmol, 1.0 eq) and cesium carbonate (1.97 g, 6.04 mmol, 1.7 eq) in acetonitrile (8 mL) was added 2-chloroacetaldehyde (0.714 mL, 4.44 mmol, 1.25 eq) dropwise at 25° C. After the addition, the mixture was stirred for 5 hours. Then 2-chloroacetaldehyde (0.285 mL, 1.78 mmol, 0.5 eq) was added into the mixture and stirred for a further 2 hours. The mixture was poured into water (20 mL), extracted with ethyl acetate (70 mL×3). The combined organic layers were washed with brine (50 mL), dried over anhydrous sodium sulfate, filtered and concentrated under reduced pressure to afford (Z)-ethyl (((2-oxoethyl)thio)(pyridin-2-ylamino)methylene) carbamate (1.00 g) as brown oil. $^1$H NMR (400 MHz, $CDCl_3$): δ 8.34-8.32 (m, 1H), 8.06 (d, J=8.4 Hz, 1H), 7.93-7.79 (m, 1H), 7.17-7.14 (m, 1H), 6.19 (d, J=6.4 Hz, 1H), 5.44 (s, 1H), 4.28-4.22 (m, 2H), 3.51-3.47 (m, 1H), 3.28-3.24 (m, 1H), 1.33 (t, J=7.2 Hz, 3H).

(Z)-Ethyl (3-(pyridin-2-yl)thiazol-2(3H)-ylidene) carbamate

To a solution of (Z)-ethyl (((2-oxoethyl)thio)(pyridin-2-ylamino)methylene)carbamate (0.500 g, 1.87 mmol, 1.0 eq) in THF (5 mL) was added N-ethyl-N-isopropylpropan-2-amine (0.977 mL, 5.61 mmol, 3.0 eq), followed by $SOCl_2$ (136 μL, 1.87 mmol, 1.0 eq) at 0° C. The mixture was stirred below 15° C. for 4 hours. The mixture was poured into water (10 mL) and extracted with ethyl acetate (40 mL×3). The combined organic layers were washed with brine (25 mL), dried over anhydrous sodium sulfate, filtered and concentrated under reduced pressure. The residue was purified by column chromatography on silica gel (petroleum ether/ethyl acetate=20/1 to 10/1) to afford 210 mg of (Z)-ethyl (3-(pyridin-2-yl)thiazol-2(3H)-ylidene)carbamate as a brown solid. $^1$H NMR (400 MHz, $CDCl_3$) δ 8.51-8.49 (m, 1H), 8.42 (d, J=8.4 Hz, 1H), 7.92-7.88 (m, 1H), 7.80 (d, J=5.2 Hz, 1H), 7.31-7.28 (m, 1H), 0.65 (d, J=5.2 Hz, 1H), 4.28 (q, J=7.2 Hz, 2H), 1.36 (t, J=7.2 Hz, 3H). LCMS (m/z $[M+H]^+$): 249.8.

Intermediate C13

To a solution of sodium hydroxide (0.674 g, 16.8 mmol, 20.0 eq) in ethanol (3 mL) was added (Z)-ethyl (3-(pyridin-2-yl)thiazol-2(3H)-ylidene)carbamate (0.210 g, 0.842 mmol, 1.0 eq) at 25° C. Then the mixture was heated to 50° C. and stirred for 1 hour. The mixture was poured into water (15 mL) and stirred for 3 minutes, and extracted with ethyl acetate (40 mL×3). The combined organic phase was washed with brine (15 mL×2), dried over anhydrous sodium sulfate, filtered and concentrated under reduced pressure to afford 130 mg of 3-(pyridin-2-yl)thiazol-2(3H)-imine C13 as a brown oil. $^1$H NMR (400 MHz, DMSO-$d_6$) δ 8.82 (s, 1H), 8.62-8.60 (m, 1H), 8.41 (d, J=4.0 Hz, 1H), 7.89-7.86 (m, 1H), 7.60 (s, 1H), 7.24-7.21 (m, 1H), 7.26 (d, J=5.2 Hz, 1H). LCMS (m/z $[M+H]^+$): 177.9.

Preparation of Intermediate C14

Scheme 35

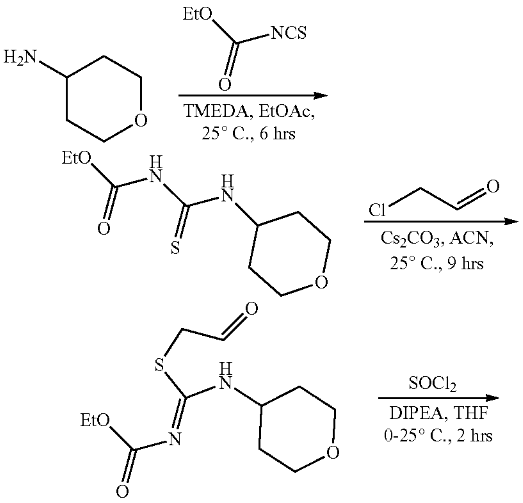

-continued

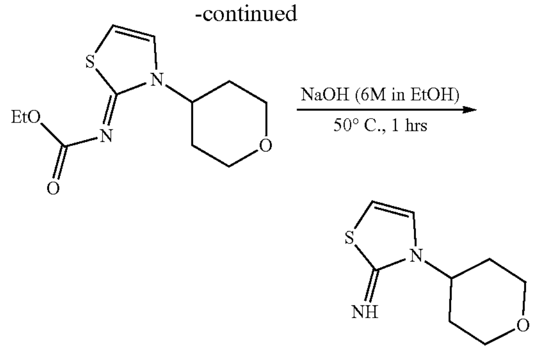

C14

Ethyl N-(tetrahydropyran-4-ylcarbamothioyl)carbamate

To a mixture of tetrahydro-2H-pyran-4-amine (0.800 g, 7.91 mmol, 1.0 eq) and O-ethyl carbonisothiocyanatidate (1.09 g, 8.30 mmol, 1.05 eq) in ethyl acetate (10 mL) was added TMEDA (92 mg, 0.791 mmol, 0.1 eq). The mixture was stirred at 25° C. for 6 hours then concentrated under reduced pressure. The residue was triturated with a solution of petroleum ether/ethanol (v/v=20/1, 21 mL) twice to afford 1.80 g of ethyl N-(tetrahydropyran-4-ylcarbamothioyl)carbamate as a yellow solid. $^1$H NMR (400 MHz, DMSO-$d_6$) δ 10.99 (br. s, 1H), 9.83 (d, J=7.2 Hz, 1H), 4.40-4.26 (m, 1H), 4.12 (q, J=7.2 Hz, 2H), 3.87-3.73 (m, 2H), 3.48-3.36 (m, 2H), 1.97-1.86 (m, 2H), 1.59-1.45 (m, 2H), 1.21(t, J=7.2 Hz, 3H).

(Z)-Ethyl (((2-oxoethyl)thio)((tetrahydro-2H-pyran-4-yl)amino)methylene)carbamate To a mixture of ethyl N-(tetrahydropyran-4-ylcarbamothioyl)carbamate (0.800 g, 3.44 mmol, 1.0 eq) and cesium carbonate (1.91 g, 5.85 mmol, 1.7 eq) in acetonitrile (10 mL) was added 2-chloroacetaldehyde (2.09 g, 10.66 mmol, 3.1 eq). The resulting mixture was stirred at 25° C. for 9 hours then poured into ice-water (10 mL), and extracted with ethyl acetate (100 mL×2). The combined organic phase was washed with brine (20 mL×2), dried over anhydrous sodium sulfate, filtered and concentrated under reduced pressure. The residue was purified by column chromatography on silica gel (petroleum ether/ethyl acetate=100/1 to 0/1) to afford 0.30 g of (Z)-ethyl (((2-oxoethyl)thio)((tetrahydro-2H-pyran-4-yl)amino)methylene)carbamate as a yellow solid. LCMS (m/z [M+H]$^+$): 274.9.

(Z)-Ethyl (3-(tetrahydro-2H-pyran-4-yl)thiazol-2(3H)-ylidene)carbamate

To a mixture of (Z)-ethyl (((2-oxoethyl)thio)((tetrahydro-2H-pyran-4-yl)amino)methylene)carbamate (0.30 g, 0.52 mmol, 1.0 eq) and diisopropylethylamine (133 mg, 1.03 mmol, 2.0 eq) in tetrahydrofuran (10 mL) was added thionyl chloride (61 mg, 0.52 mmol, 1.0 eq). The mixture was stirred at 25° C. for 2 hours then poured into ice-water (20 mL) and extracted with ethyl acetate (100 mL×3). The combined organic layers were washed with brine (20 mL), dried over anhydrous sodium sulfate, filtered and concentrated under reduced pressure. The residue was purified by column chromatography on silica gel (petroleum ether/ethyl acetate=100/1 to 0/1) to afford 120 mg of (Z)-ethyl (3-(tetrahydro-2H-pyran-4-yl)thiazol-2(3H)-ylidene)carbamate as a yellow solid. $^1$H NMR (400 MHz, $CD_3OD$) δ 7.41 (d, J=4.8 Hz, 1H), 6.87 (d, J=4.8 Hz, 1H), 5.02-4.91 (m, 1H), 4.20 (q, J=7.2 Hz, 2H), 4.09-4.04 (m, 2H), 3.62-3.58 (m, 2H), 1.99-1.89 (m, 4H), 1.31 (t, J=7.2 Hz, 3H). LCMS (m/z [M+H]$^+$): 256.9.

Intermediate C14

A mixture (Z)-ethyl (3-(tetrahydro-2H-pyran-4-yl)thiazol-2(3H)-ylidene)carbamate (0.120 g, 0.468 mmol, 1.0 eq) and sodium hydroxide (0.374 g, 9.36 mmol, 20 eq) in ethanol (1 mL) was stirred at 50° C. for 1 hour. The mixture was concentrated under reduced pressure, the residue was purified by column chromatography on silica gel (dichloromethane/methanol=100/1 to 10/1) to afford 80 mg of 3-(tetrahydro-2H-pyran-4-yl)thiazol-2(3H)-imine C14 as a yellow solid.

Preparation of Intermediate C15

Scheme 36

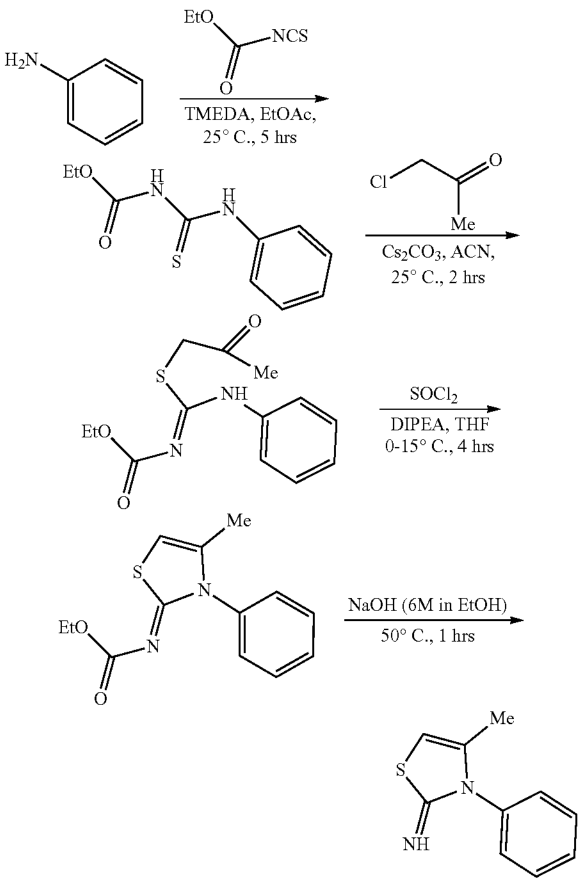

C15

Ethyl N-(phenylcarbamothioyl)carbamate

To a solution of aniline (1.96 mL, 21.5 mmol, 1.0 eq) in ethyl acetate (20 mL) was added O-ethyl carbonisothiocyanatidate (2.54 mL, 21.5 mmol, 1.0 eq) and tetramethylethylenediamine (0.324 mL, 2.15 mmol, 0.1 eq). The mixture was stirred at 25° C. for 4 hours, and then concentrated directly under reduced pressure. The residue was triturated with petroleum ether (8 ml) to afford 4.20 g of ethyl N-(phenylcarbamothioyl)carbamate as a yellow oil. $^1H$ NMR (400 MHz, DMSO-$d_6$) δ 11.55 (br. s, 1H), 11.25 (br. s, 1H), 7.61-7.59 (m, 2H), 7.41-7.37 (m, 2H), 7.26-7.22 (m, 1H), 4.21 (q, J=7.2 Hz, 2H), 1.26 (t, J=7.2 Hz, 3H).

(Z)-Ethyl (((2-oxopropyl)thio)(phenylamino)methylene)carbamate

To a solution of N-(phenylcarbamothioyl)carbamate (4.20 g, 18.7 mmol, 1.0 eq) and cesium carbonate (10.4 g, 31.8 mmol, 1.7 eq) in acetonitrile (50 mL) was added 1-chloropropan-2-one (2.17 g, 23.4 mmol, 1.25 eq), maintaining the temperature blow 25° C. After the addition, the mixture was stirred at 25° C. for 2 hours, then diluted with MTBE (120 mL) and washed with a saturated aqueous solution of sodium bicarbonate solution (100 ml), followed by brine (100 mL), dried over anhydrous sodium sulfate and filtered. The filtrate was concentrated under reduced pressure. The residue was purified by column chromatography on silica gel (petroleum ether/ethyl acetate=50:1 to 4:1) to afford 1.80 g of (Z)-ethyl (((2-oxopropyl)thio)(phenylamino)methylene)carbamate as a brown oil. $^1H$ NMR (400 MHz, $CDCl_3$) δ 7.46-7.42 (m, 2H), 7.40-7.36 (m, 1H), 7.28-7.27 (m, 1H), 7.27-7.26(m, 1H), 4.14 (q, J=7.2.0 Hz, 2H), 3.47(d, J=12.0 Hz, 1H), 3.65 (d, J=12.0 Hz, 1H), 1.47 (s, 3H), 1.26 (t, J=7.6 Hz, 4H). LCMS (m/z $[M+H]^+$): 280.9.

(Z)-Ethyl (4-methyl-3-phenylthiazol-2(3H)-ylidene) carbamate

To a solution of (Z)-ethyl (((2-oxopropyl)thio)(phenylamino)methylene)carbamate (0.600 g, 2.09 mmol, 1.0 eq) in THF (6 mL) was added diisopropylethylamine (0.810 g, 6.27 mmol, 3.0 eq) and thionyl chloride (0.167 mL, 2.30 mmol, 1.1 eq) at 0° C. The mixture was stirred at 20° C. for 4 hours, and then concentrated under reduced pressure. The residue was diluted with a saturated aqueous solution of sodium bicarbonate (40 mL) and extracted with ethyl acetate (30 mL×3). The combined organic phases were washed with brine (60 mL), dried over anhydrous sodium sulfate, filtered and concentrated under reduced pressure. The residue was purified by reversed-phase HPLC to give 0.32 g of (Z)-ethyl (4-methyl-3-phenylthiazol-2(3H)-ylidene)carbamate as a yellow oil. $^1H$ NMR (400 MHz, $CDCl_3$) δ 7.68(s, 3H), 7.45 (s, 2H), 6.92(s, 1H), 4.34(q, J=7.2 Hz, 2H), 2.08(s, 3H), 1.34 (t, J=7.2 Hz, 3H). LCMS (m/z $[M+H]^+$): 263.3.

Intermediate C15

To a solution of (Z)-ethyl (4-methyl-3-phenylthiazol-2(3H)-ylidene)carbamate (0.240 g, 0.891 mmol, 1.0 eq) in ethanol (4 mL) was added sodium hydroxide (0.713 g, 17.8 mmol, 20 eq) at 25° C. The mixture was heated to 60° C. and stirred for 1 hour, then diluted with water (40 mL) and extracted with ethyl acetate (30 mL×3). The combined organic layers were washed with brine (50 mL), dried over anhydrous sodium sulfate, filtered and concentrated under reduce pressure to afford 180 mg of 4-methyl-3-phenylthiazol-2(3H)-imine C15 as a yellow solid.

Preparation of Intermediate C16

Scheme 37

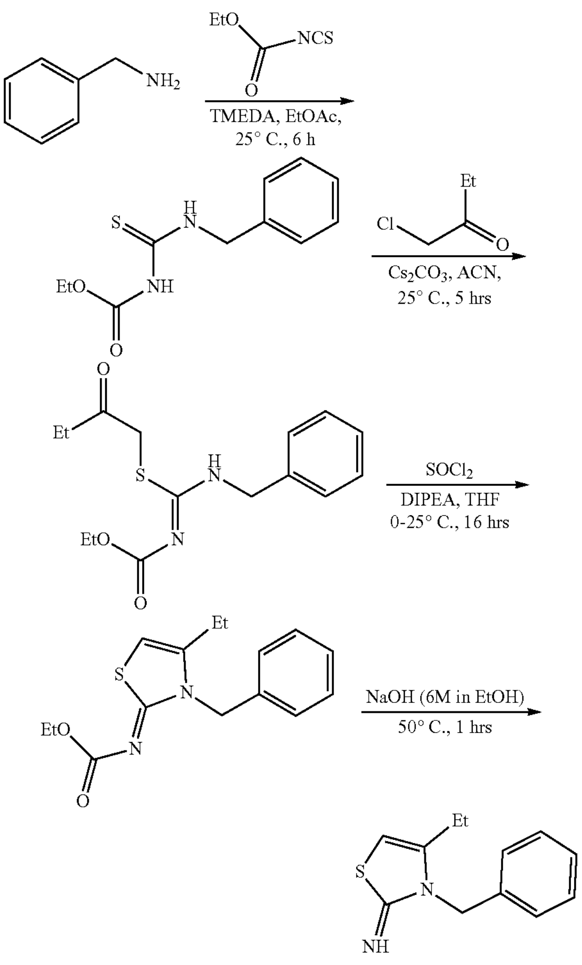

C16

Ethyl N-(benzylcarbamothioyl)carbamate

To a solution of phenylmethanamine (5.00 g, 46.7 mmol, 1.0 eq) and O-ethyl carbonisothiocyanatidate (6.43 g, 49.0 mmol, 1.05 eq) in ethyl acetate (40 mL) was added TMEDA (0.542 g, 4.67 mmol, 1.0 eq) at 25° C. under nitrogen atmosphere. The mixture was stirred at 25° C. for 6 hours, and then concentrated under reduced pressure. The residue was triturated from a solution of petroleum and ethyl acetate (v/v=10/1, 55 mL) twice to afford 10.0 g of the ethyl N-(benzylcarbamothioyl)carbamate as a yellow solid. $^1H$ NMR (400 MHz, DMSO-$d_6$) δ 11.04 (br. s, 1H), 10.22 (br. t, J=5.6 Hz, 1H), 7.39-7.23 (m, 5H), 4.81 (d, J=5.6 Hz, 2H), 4.14 (q, J=7.2 Hz, 2H), 1.21 (t, J=7.2 Hz, 3H).

(Z)-Ethyl ((benzylamino)((2-oxobutyl)thio)methylene)carbamate

To a suspension of ethyl N-(benzylcarbamothioyl)carbamate (3.00 g, 12.6 mmol, 1.0 eq) and $Cs_2CO_3$ (6.97 g, 21.4 mmol, 1.7 eq) in acetonitrile (45 mL) was added 1-bromobutan-2-one (2.38 g, 15.7 mmol, 1.25 eq) mataining the temperature blow 25° C. After the addition, the mixture was stirred at 25° C. for 5 hours, then poured into water (80 mL) and extracted with ethyl acetate (120 mL×3). The combined organic layers were washed with brine (100 mL×2), dried over anhydrous sodium sulfate, filtered and concentrated under reduced pressure. The residue was purified by column chromatography on silica gel (petroleum ether/ethyl acetate=1:0 to 5:1) to afford 2.50 g of (Z)-ethyl ((benzylamino)((2-oxobutyl)thio)methylene)carbamate as yellow oil. $^1$H NMR (400 MHz, $CDCl_3$) δ 7.32-7.27 (m, 3H), 7.25-7.22 (m, 2H), 4.96 (d, J=15.6 Hz, 1H), 4.71 (d, J=15.6 Hz, 1H), 4.18 (q, J=7.2 Hz, 2H), 3.28 (d, J=12.0 Hz, 1H), 3.11 (d, J=12.0 Hz, 1H), 1.97-1.92(m, 1H),1.67-1.62 (m, 1H), 1.31-1.28 (m, 3H), 0.88 (t, J=7.6 Hz, 3H). LCMS (m/z $[M+H]^+$): 308.9.

(Z)-Ethyl (3-benzyl-4-ethylthiazol-2(3H)-ylidene) carbamate

To a solution of ethyl (Z)-ethyl ((benzylamino)((2-oxobutyl)thio)methylene)carbamate (2.50 g, 8.11 mmol, 1.0 eq) in THF (38 mL) was added diisopropylethylamine (3.14 g, 24.3 mmol, 3.0 eq) and $SOCl_2$ (0.964 g, 8.11 mmol, 1.0 eq) at 0° C. The mixture was stirred at 25° C. for 16 hours, then poured into water (80 mL) and extracted with ethyl acetate (100 mL×3). The combined organic layers were washed with brine (100 mL×2), dried over anhydrous sodium sulfate, filtered and concentrated under reduced pressure to afford 2.20 g of (Z)-ethyl (3-benzyl-4-ethylthiazol-2(3H)-ylidene)carbamate as black brown oil. $^1$H NMR (400 MHz, DMSO-$d_6$) δ 7.37-7.33 (m, 2H), 7.29-7.27 (m, 1H), 7.09 (d, J=7.2 Hz, 2H), 6.61 (s, 1H), 5.36-5.34 (m, 2H), 4.07-4.03 (m, 2H), 2.46 (dd, J=2.0 Hz,7.6 Hz, 2H), 1.17 (t, J=7.2 Hz, 3H), 1.11 (t, J=7.2 Hz, 3H). LCMS (m/z $[M+H]^+$): 291.1.

Intermediate C16

To a solution of (Z)-ethyl (3-benzyl-4-ethylthiazol-2(3H)-ylidene)carbamate (1.00 g, 3.44 mmol, 1.0 eq) in ethanol (10 mL) was added 6N NaOH (2.75 g, 68.9 mmol, 20 eq) at 25° C. The mixture was heated to 50° C. and stirred for 1 hour, then poured into water (80 mL), and extracted with ethyl acetate (100 mL×3). The combined organic layers were washed with brine (100 mL×2), dried over anhydrous sodium sulfate, filtered and concentrated under reduced pressure. The residue was purified by column chromatography on silica gel (Petroleum ether/Ethyl acetate=1:0 to 5:1) to afford 0.49 g of 3-benzyl-4-ethylthiazol-2(3H)-imine C16 as a dark brown oil.

Preparation of Intermediate C17

Scheme 38

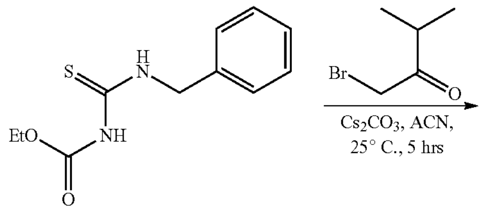

-continued

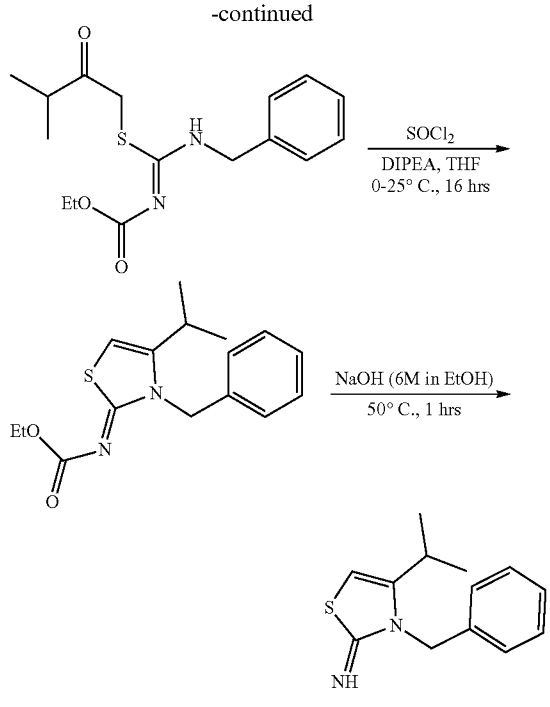

C17

(Z)-Ethyl ((benzylamino)((3-methyl-2-oxobutyl) thio)methylene)carbamate

To a mixture of ethyl N-(benzylcarbamothioyl)carbamate (0.500 g, 2.10 mmol, 1.0 eq) and cesium carbonate (1.16 g, 3.57 mmol, 1.7 eq) in acetonitrile (5 mL) was added 1-bromo-3-methylbutan-2-one (0.519 g, 3.15 mmol, 1.5 eq) at 25° C. The mixture was stirred for 5 hours, then poured into water (10 mL) and extracted with MTBE (100 mL×2). The combined organic phase was washed with brine (20 mL×2), dried over anhydrous sodium sulfate, filtered and concentrated under reduced pressure to afford 0.67 g of the crude (Z)-ethyl ((benzylamino)((3-methyl-2-oxobutyl)thio) methylene)carbamate as a yellow solid. LCMS (m/z $[M+H]^+$): 323.0.

Ethyl (Z)-ethyl (3-benzyl-4-isopropylthiazol-2(3H)-ylidene)carbamate

To a solution of (Z)-ethyl ((benzylamino)((3-methyl-2-oxobutyl)thio)methylene)carbamate (0.670 g, 2.08 mmol, 1.0 eq) and diisopropylethylmine (1.09 mL, 6.23 mmol, 3.0 eq) in THF (10 mL) was added thionyl chloride (0.247 g, 2.08 mmol, 1.0 eq). The mixture was stirred at 25° C. for 16 hours, then poured into water (20 mL) and extracted with ethyl acetate (100 mL×3). The combined organic layers were washed with brine (20 mL), dried over anhydrous sodium sulfate, filtered and concentrated under reduced pressure. The residue was purified by column chromatography on silica gel (petroleum ether/ethyl acetate=100/1 to 4/1) to afford 0.53 g of ethyl (Z)-ethyl (3-benzyl-4-isopropylthiazol-2(3H)-ylidene)carbamate as a yellow solid. $^1$H NMR (400 MHz, DMSO-$d_6$) δ 7.38-7.24 (m, 3H), 7.04(d, J=7.2 Hz, 2H), 6.70 (s, 1H), 5.39 (s, 2H), 4.04 (q, J=7.2 Hz, 2H), 2.87-2.77 (m, 1H), 1.16 (t, J=7.2 Hz, 3H), 1.08 (d, J=6.8 Hz, 6H). LCMS (m/z: 305.1$[M+H]^+$): 305.1.

Intermediate C17

A mixture ethyl (Z)-ethyl (3-benzyl-4-isopropylthiazol-2(3H)-ylidene)carbamate (0.300 g, 0.830 mmol) and sodium hydroxide (0.664 g, 16.61 mmol) in ethanol (5 mL) was stirred at 50° C. for 1 hour. The mixture was poured into water (10 mL) and extracted with ethyl acetate (100 mL×3). The combined organic layers were washed with brine (10 mL), dried over anhydrous sodium sulfate, filtered and concentrated under reduced pressure. The residue was purified by column chromatography on silica gel (dichloromethane/methanol=100/1 to 10/1) to afford 150 mg of 3-benzyl-4-isopropylthiazol-2(3H)-imine C17 as a yellow solid.

Preparation of Intermediate C18

Scheme 39

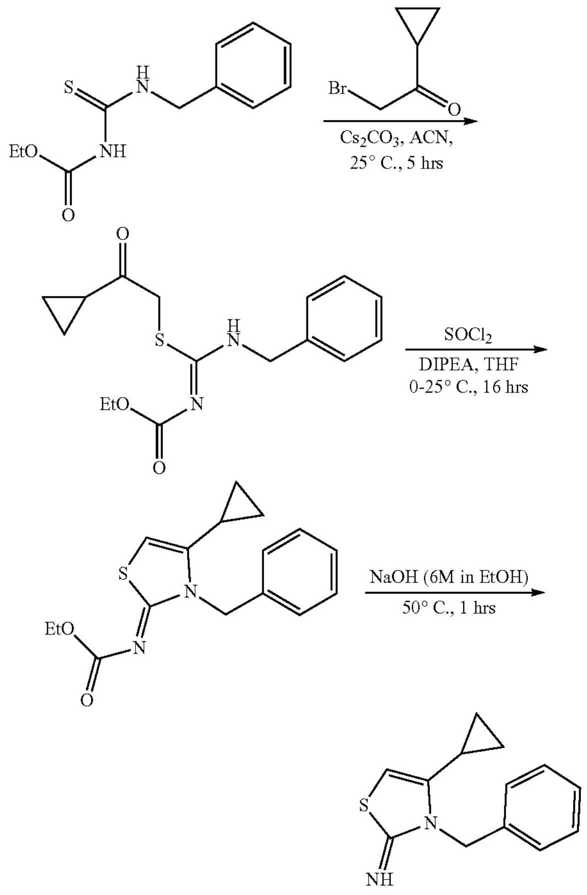

C18

(Z)-Ethyl ((benzylamino)((2-cyclopropyl-2-oxo-ethyl)thio)methylene)carbamate

To a mixture of ethyl N-(benzylcarbamothioyl)carbamate (0.500 g, 2.10 mmol, 1.0 eq) and cesium carbonate (1.16 g, 3.57 mmol, 1.7 eq) in acetonitrile (5 mL) was added 2-bromo-1-cyclopropyl-ethanone (0.513 g, 3.15 mmol, 1.5 eq). The resulting mixture was stirred at 25° C. for 5 hours then poured into ice-water (10 mL) and extracted with MTBE (100 mL×2). The combined organic layers were washed with brine (20 mL×2), dried with anhydrous sodium sulfate, filtered and concentrated under reduced pressure to afford (Z)-ethyl ((benzylamino)((2-cyclopropyl-2-oxoethyl)thio)methylene)carbamate (0.670 g, crude) as a yellow solid. LCMS (m/z $[M+H]^+$): 321.1.

Ethyl (Z)-ethyl (3-benzyl-4-cyclopropylthiazol-2(3H)-ylidene)carbamate

To a mixture of (Z)-ethyl ((benzylamino)((2-cyclopropyl-2-oxoethyl)thio)methylene)carbamate (0.670 g, 2.08 mmol, 1.0 eq) and diisopropylethylamine (0.810 g, 6.27 mmol, 3.0 eq) in tetrahydrofuran (10 mL) was added thionyl chloride (0.248 g, 2.09 mmol, 1.2 eq). The mixture was stirred at 25° C. for 16 hours then poured into ice-water (20 mL), and extracted with ethyl acetate (100 mL×3). The combined organic layers were washed with brine (20 mL), dried over anhydrous sodium sulfate, filtered and concentrated under reduced pressure. The residue was purified by column chromatography on silica gel (petroleum ether/ethyl acetate=100/1 to 4/1) to afford 0.25 g of ethyl (Z)-ethyl (3-benzyl-4-cyclopropylthiazol-2(3H)-ylidene)carbamate as a yellow gum. $^1$H NMR (400 MHz, DMSO-$d_6$): δ 7.40-7.24 (m, 3H), 7.14 (d, J=7.2 Hz, 2H), 6.59 (s, 1H), 5.48(s, 2H), 4.03 (q, J=7.2 Hz, 2H), 1.69-1.60 (m, 1H), 1.17 (t, J=7.2 Hz, 3H), 0.82-0.75 (m, 2H), 0.60-0.54 (m, 2H). LCMS (m/z $[M+H]^+$): 305.1.

Intermedtate C18

A mixture ethyl(Z)-ethyl (3-benzyl-4-cyclopropylthiazol-2(3H)-ylidene)carbamate (0.200 g, 0.661 mmol, 1.0 eq) and 6N sodium hydroxide (0.529 g, 13.23 mmol, 20 eq) in ethanol (4 mL) was stirred at 50° C. for 1 hour. The mixture was poured into ice-water (10 mL) and extracted with ethyl acetate (100 mL×3). The combined organic layers were washed with brine (10 mL), dried over anhydrous sodium sulfate, filtered and concentrated under reduced pressure to afford 160 mg of 3-benzyl-4-cyclopropylthiazol-2(3H)-imine C18 as a yellow solid. $^1$H NMR (400 MHz, DMSO-$d_6$) δ 7.57 (br. s, 1H), 7.36-7.30 (m, 2H), 7.27-7.20 (m, 3H), 5.64 (s, 1H), 5.04 (s, 2H), 1.48-1.36 (m, 1H), 0.72-0.64 (m, 2H), 0.52-0.42 (m, 2H). LCMS (m/z $[M+H]^+$): 233.2.

Preparation of Intermediate C19

Scheme 40

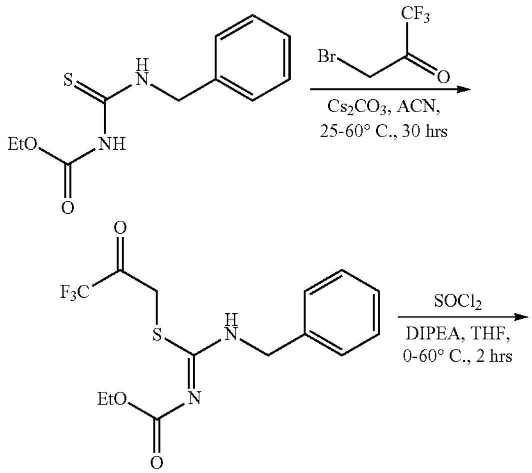

-continued

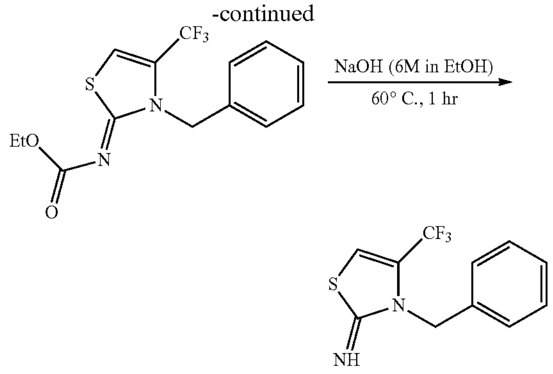

C19

(Z)-Ethyl ((benzylamino)((3,3,3-trifluoro-2-oxopropyl)thio)methylene)carbamate

To a suspension of ethyl N-(benzylcarbamothioyl)carbamate (0.500 g, 2.10 mmol, 1.0 eq) and cesium carbonate (1.16 g, 3.57 mmol, 1.7 eq) in acetonitrile (8 mL) was added 3-bromo-1,1,1-trifluoropropan-2-one (0.654 mL, 6.30 mmol, 3.0 eq) maintaining the temperature blow 25° C. After the addition, the mixture was stirred at 25° C. for 12 hours, then poured into water (40 mL) and extracted with MTBE (30 mL×3). The combined organic layers were washed with brine (50 mL), dried over anhydrous sodium sulfate and filtered. The filtrate was concentrated under reduced pressure. The residue was purified by column chromatography on silica gel (petroleum ether/ethyl acetate=50:1: to 10:1) to afford 0.75 g of (Z)-ethyl ((benzylamino)((3,3,3-trifluoro-2-oxopropyl)thio)methylene)carbamate as a yellow oil. $^{1}$H NMR (400 MHz, $CDCl_3$) δ 7.35-7.28 (m, 5H), 5.37 (d, J=15.6 Hz,1H), 4.62 (d, J=16.0 Hz, 1H), 4.27-4.18 (m, 2H), 3.79 (br. s, 1H), 3.69 (d, J=12.8 Hz, 1H), 3.25 (dd, J=12.0 Hz, 0.8 Hz, 1H), 1.35-1.31 (m, 3H). $^{19}$F NMR (400 MHz, $CDCl_3$) δ −79.04 (s, 3F). LCMS (m/z $[M+H]^+$): 348.9.

(Z)-Ethyl (3-benzyl-4-(trifluoromethyl)thiazol-2(3H)-ylidene)carbamate

To a solution of (Z)-ethyl ((benzylamino)((3,3,3-trifluoro-2-oxopropyl)thio)methylene)carbamate (0.550 g, 1.44 mmol, 1.0 eq) in THF (20 mL) was added diisopropylethylamine (0.754 mL, 4.33 mmol, 3.0 eq) and thionyl chloride (0.115 mL, 1.59 mmol, 1.1 eq) at 0° C. The mixture was heated to 60° C. and stirred for 2 hours, then added into a saturated aqueous solution of sodium bicarbonate (40 mL) and extracted with ethyl acetate (30 mL×3). The combined organic layers were washed with brine (60 mL), dried over anhydrous sodium sulfate, filtered and concentrated under reduced pressure. The residue was purified by column chromatography on silica gel (petroleum ether/ethyl acetate=50:1 to 10:1) to afford 0.40 g of (Z)-ethyl (3-benzyl-4-(trifluoromethyl)thiazol-2(3H)-ylidene)carbamate as brown oil. $^{1}$H NMR (400 MHz, $CDCl_3$): δ 7.34-7.28 (m, 3H), 7.18-7.13 (m, 3H), 5.48 (s, 2H), 4.26 (q, J=7.2 Hz, 2H), 1.34 (t, J=6.8 Hz, 3H). LCMS (m/z $[M+H]^+$): 330.9.

Intermediate C19

To a solution of (Z)-ethyl (3-benzyl-4-(trifluoromethyl)thiazol-2(3H)-ylidene)carbamate (0.300 g, 0.884 mmol, 1.0 eq) in ethanol (5 mL) was added sodium hydroxide (0.707 g, 17.7 mmol, 20 eq) at 25° C. The mixture was heated to 60° C. and stirred for 1 hour, then poured into water (40 mL) and extracted with ethyl acetate (30 mL×3). The combined organic layers were washed with brine (50 mL), dried over anhydrous sodium sulfate, filtered and concentrated reduced pressure. The residue was purified by column chromatography on silica gel (petroleum ether/ethyl acetate=20:1) to give 150 mg of 3-benzyl-4-(trifluoromethyl)thiazol-2(3H)-imine C19 as a brown oil.

Preparation of Intermediate C20

Scheme 41

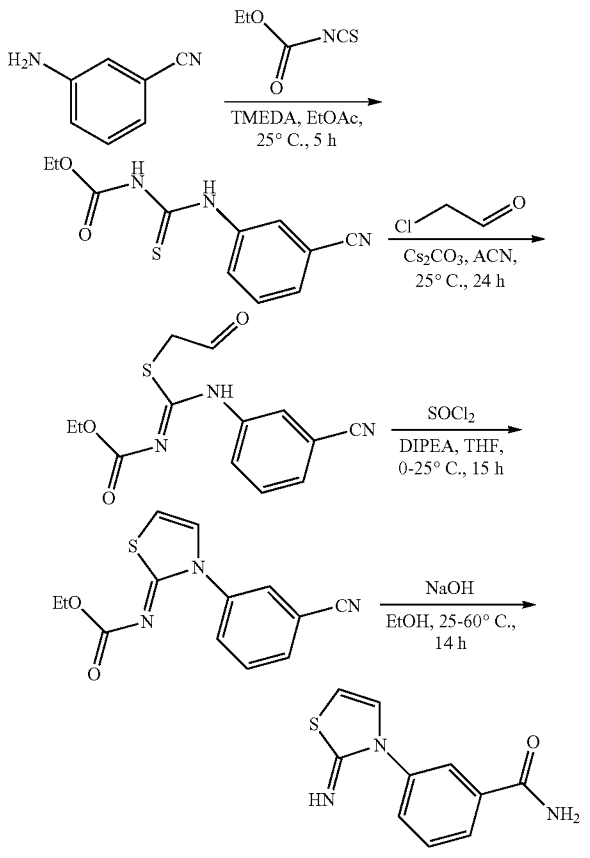

C20

Ethyl N-[(3-cyanophenyl)carbamothioyl]carbamate

To a stirred mixture of 3-aminobenzonitrile (2.50 g, 21.16 mmol, 1.0 eq) in EtOAc (25 mL) was added O-ethyl carbonisothiocyanatidate (2.78 g, 21.16 mmol, 1.0 eq) and TMEDA (246 mg, 2.12 mmol, 319 uL, 0.1 eq) at 25° C. Then the reaction mixture was stirred at 25° C. for 5 h under $N_2$. The reaction mixture was concentrated under reduced pressure. EtOH (50 mL) was added into the mixture and the resulting mixture was stirred at 25° C. for 0.5 h. The mixture was filtered and the filter cake was dried under reduced pressure to give 2.80 g of ethyl N-[(3-cyanophenyl)carbamothioyl]carbamate as a yellow solid.

(Z)-Ethyl (((3-cyanophenyl)amino)((2-oxoethyl)thio)methylene)carbamate

To a mixture of ethyl N-[(3-cyanophenyl)carbamothioyl]carbamate (2.80 g, 11.2 mmol, 1.0 eq) and $Cs_2CO_3$ (6.22 g, 19.1 mmol, 1.7 eq) in MeCN (40 mL) was added 2-chloroacetaldehyde (2.76 g, 14.0 mmol, 2.26 mL, 1.2 eq) at 25° C. The reaction mixture was stirred at 25° C. for 12 h under $N_2$. Additional 1.0 eq of 2-chloroacetaldehyde was added and the reaction mixture was stirred at 25° C. for another 12 h. The reaction mixture was diluted with MTBE (100 mL) and washed with $NaHCO_3$ solution (2×50 mL). The organic layer was washed with brine (50 mL), dried over $Na_2SO_4$, filtered. The filtrate was concentrated under reduced pressure to give 2.80 g of (Z)-ethyl (((3-cyanophenyl)amino)((2-oxoethyl)thio)methylene)carbamate as a brown solid.

(Z)-Ethyl (3-(3-cyanophenyl)thiazol-2(3H)-ylidene)carbamate

To a mixture of (Z)-ethyl (((3-cyanophenyl)amino)((2-oxoethyl)thio)methylene) carbamate (2.80 g, 9.61 mmol, 1.0 eq) in THF (30 mL) was added DIPEA (3.73 g, 28.8 mmol, 5.02 mL, 3.0 eq) and $SOCl_2$ (1.14 g, 9.61 mmol, 697 μL, 1.0 eq) at 0° C. The reaction mixture was then stirred at 25° C. for 15 h under $N_2$. The reaction mixture was concentrated under reduced pressure. The residue was dissolved in MTBE (200 mL) and the mixture was adjusted to pH=8 with sat. aq $NaHCO_3$ solution, the organic layer was discarded. The aqueous phase was extracted with EtOAc (3×100 mL), and the organic layer was washed with brine (100 mL), dried over $Na_2SO_4$, filtered and the filtrate was concentrated under reduced pressure. MTBE (10 mL) was added into the mixture and the mixture was stirred at 25° C. for 0.5 h. Then the mixture was filtered and the filter cake was dried under reduced pressure to give 1.30 g of ethyl (Z)-ethyl (3-(3-cyanophenyl)thiazol-2(3H)-ylidene)carbamate as a brown solid. $^1H$ NMR: (400 MHz, DMSO-$d_6$) δ 8.12 (s, 1H), 7.99-7.91 (m, 2H), 7.79-7.74 (m, 1H), 7.61 (d, J=4.8 Hz, 1H), 7.11 (d, J=4.8 Hz, 1H), 4.09-3.98 (m, 2H), 1.17 (t, J=7.1 Hz, 3H).

Intermediate C20

To a mixture of (Z)-ethyl (3-(3-cyanophenyl)thiazol-2(3H)-ylidene)carbamate (400 mg, 1.46 mmol, 1.0 eq) in EtOH (4 mL) was added NaOH (6 M, 4.00 mL, 16.4 eq) at 25° C. Then the reaction mixture was stirred for 12 h at 25° C. and 2 h at 60° C. under $N_2$. The reaction mixture was adjusted pH=7 with con. HCl at 0° C., and then the resulted solution was filtered and the filtrate was concentrated under reduced pressure. The residue was purified by prep-HPLC to give 130 mg of 3-(2-iminothiazol-3(2H)-yl)benzamide C20 as a brown solid.

Preparation of Intermediate C21

Scheme 42

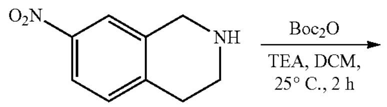

-continued

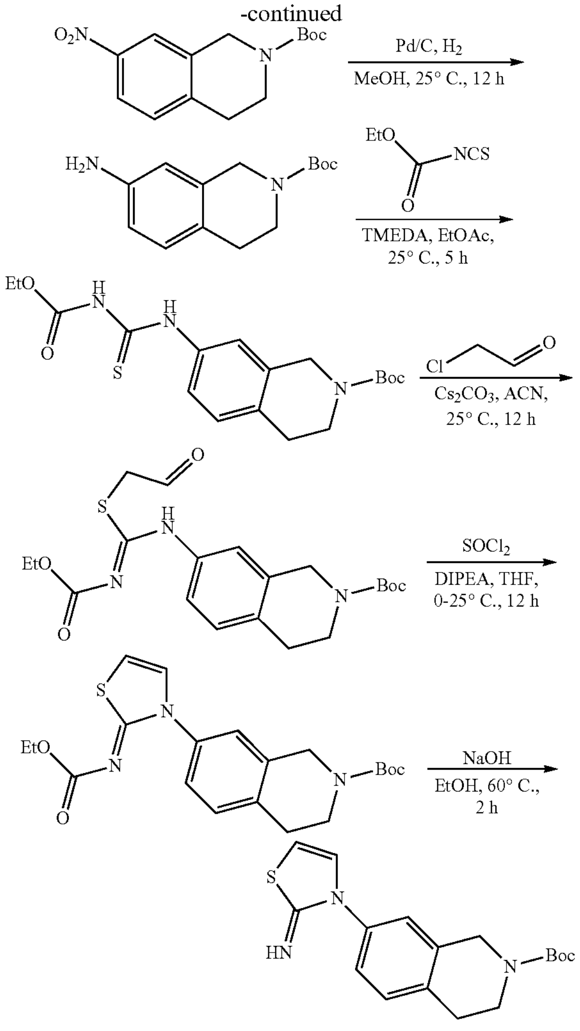

C21

Tert-Butyl 7-nitro-3,4-dihydroisoquinoline-2(1H)-carboxylate

To a solution of 7-nitro-1,2,3,4-tetrahydroisoquinoline (4.00 g, 22.4 mmol, 1.0 eq) in DCM (40 mL) was added TEA (4.54 g, 44.9 mmol, 6.25 mL, 2.0 eq) and di-tert-butyl dicarbonate (5.39 g, 24.7 mmol, 5.67 mL, 1.1 eq) at 25° C. The reaction mixture was stirred at 25° C. for 2 hr. The reaction mixture was diluted with water (100 mL) and extracted with EtOAc (4×200 mL). The combined organic layers were washed with brine (100 mL), dried over $Na_2SO_4$, filtered and concentrated under reduced pressure to give a residue. The residue was purified by flash silica gel chromatography (Eluent of 0-17% Ethylacetate/Petroleum ether gradient at 100 mL/min) to give 5.30 g of tert-butyl 7-nitro-3,4-dihydroisoquinoline-2(1H)-carboxylate as a yellow oil. $^1H$ NMR (400 MHz, DMSO-$d_6$) δ 8.12 (s, 1H), 8.02 (dd, J=1.9, 8.4 Hz, 1H), 7.45 (d, J=8.4 Hz, 1H), 4.63 (br s, 2H), 3.64-3.52 (m, 2H), 2.97-2.80 (m, 2H), 1.43 (s, 9H).

Tert-Butyl 7-amino-3,4-dihydroisoquinoline-2(1H)-carboxylate

To a solution of tert-butyl 7-nitro-3,4-dihydroisoquinoline-2(1H)-carboxylate (5.9 g, 21.2 mmol, 1.0 eq) in MeOH (50 mL) was added Pd/C (2.5 g, 10% purity) at 25° C. under $N_2$. The suspension was degassed under vacuum and purged with $H_2$ three times. The reaction mixture was stirred under $H_2$ (15 psi) at 25° C. for 12 hours. The reaction mixture was filtered, and the filtrate was concentrated under reduced pressure to give tert-butyl 7-amino-3,4-dihydroisoquinoline-2(1H)-carboxylate (4.5 g, crude) as red oil.

Tert-Butyl 7-(3-(ethoxycarbonyl)thioureido)-3,4-dihydroisoquinoline-2(1H)-carboxylate To a mixture of tert-butyl 7-amino-3,4-dihydroisoquinoline-2(1H)-carboxylate (1.00 g, 4.03 mmol, 1.0 eq) in EtOAc (10 mL) was added O-ethyl carbonisothiocyanatidate (528 mg, 4.03 mmol, 1.0 eq) and TMEDA (47 mg, 0.40 mmol, 61 µL, 0.1 eq) at 25° C. Then the reaction mixture was stirred at 25° C. for 5 h under $N_2$. The reaction mixture was concentrated under reduced pressure to remove the solvent. The residue was dissolved in EtOH (10 mL) and the mixture was stirred at 25° C. for 0.5 h. The mixture was filtered and the filter cake was dried under reduced pressure to give 1.20 g of tert-butyl 7-(3-(ethoxycarbonyl)thioureido)-3,4-dihydroisoquinoline-2(1H)-carboxylate as white solid. LCMS (m/z $[M+Na]^+$): 402.2.

(Z)-tert-Butyl 7-((((ethoxycarbonyl)imino)((2-oxoethyl)thio)methyl)amino)-3,4-dihydroisoquinoline-2(1H)-carboxylate To a mixture of tert-butyl 7-(3-(ethoxycarbonyl)thioureido)-3,4-dihydroisoquinoline-2(1H)-carboxylate (1.80 g, 4.74 mmol, 1.0 eq) in MeCN (20 mL) was added $Cs_2CO_3$ (2.63 g, 8.06 mmol, 1.7 eq) and 2-chloroacetaldehyde (1.16 g, 5.93 mmol, 954 µL, 1.25 eq) at 25° C. The reaction mixture was then stirred at 25° C. for 12 h under $N_2$. The reaction mixture was diluted with MTBE (100 mL), and then the mixture was washed with sat. aq $NaHCO_3$ solution (2×50 mL). The organic layer was washed with brine (50 mL), dried over $Na_2SO_4$, filtered and the filtrate was concentrated under reduced pressure to give (Z)-tert-butyl 7-((((ethoxycarbonyl)imino)((2-oxoethyl)thio)methyl)amino)-3,4-dihydroisoquinoline-2(1H)-carboxylate (2.4 g, crude) as brown oil.

Tert-Butyl 7-[(2Z)-2-ethoxycarbonyliminothiazol-3-yl]-3,4-dihydro-1H-isoquinoline-2-carboxylate To a mixture of (Z)-tert-butyl 7-((((ethoxycarbonyl)imino)((2-oxoethyl)thio)methyl) amino)-3,4-dihydroisoquinoline-2(1H)-carboxylate (2.40 g, 5.69 mmol, 1.0 eq) in THF (30 mL) was added DIPEA (2.21 g, 17.1 mmol, 2.98 mL, 3.0 eq) and $SOCl_2$ (677 mg, 5.69 mmol, 413 µL, 1.0 eq) at 0° C. The reaction mixture was then stirred at 25° C. for 12 h under $N_2$. The reaction mixture was diluted with water (100 mL) and extracted with EtOAc (3×50 mL). The organic layer was washed with brine (100 mL), dried over $Na_2SO_4$, filtered and the filtrate was concentrated under reduced pressure. The residue was purified by flash silica gel chromatography (ISCO®; 20 g SepaFlash® Silica Flash Column, Eluent of 0-40% Ethyl acetate/Petroleum ethergradient @75 mL/min) to give 1.0 go of (Z)-tert-butyl 7-((((ethoxycarbonyl)imino)((2-oxoethyl)thio)methyl) amino)-3,4-dihydroisoquinoline-2(1H)-carboxylate as a brown oil.

Intermediate C21

To a mixture of (Z)-tert-butyl 7-((((ethoxycarbonyl)imino)((2-oxoethyl)thio)methyl) amino)-3,4-dihydroisoquinoline-2(1H)-carboxylate (800 mg, 1.98 mmol, 1.0 eq) in EtOH (8 mL) was added NaOH (6 M, 8.00 mL, 24 eq) at room temperature. The reaction mixture was then stirred at 60° C. for 2 h under $N_2$. The reaction mixture was filtered, and the filter cake was washed with EtOAc (3×20 mL), then the filtrate was concentrated under reduced pressure. The residue was purified by reversed-phase column to give 170 mg of tert-butyl 7-(2-iminothiazol-3(2H)-yl)-3,4-dihydroisoquinoline-2(1H)-carboxylate C21 as a yellow solid.

Preparation of Intermediate C22

Scheme 43

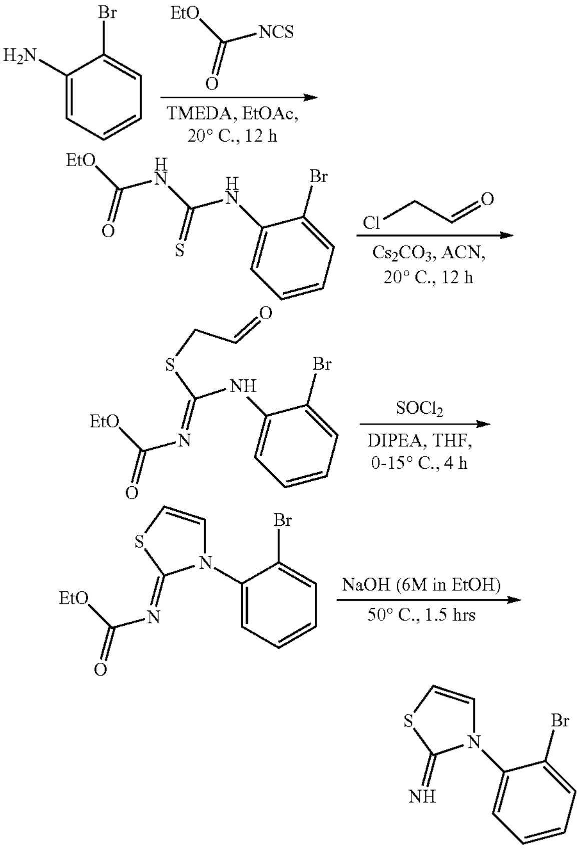

C22

Ethyl N-[(2-bromophenyl)carbamothioyl]carbamate

To a solution of 2-bromoaniline (10.00 g, 58.1 mmol, 1.0 eq) in EtOAc (100 mL) was added ethyl N-(thioxomethylene)carbamate (7.62 g, 58.1 mmol, 1.0 eq) and TMEDA (675 mg, 5.81 mmol, 877 µL, 0.1 eq) at room temperature. The mixture was stirred at 20° C. for 12 hr. The reaction mixture was concentrated under reduced pressure. The residue was triturated with EtOH (50 mL) for 0.5 hr. The mixture was filtered, and the filter cake was washed with EtOH (2×30 mL). The filter cake was collected to give 16.0 g of ethyl N-[(2-bromophenyl)carbamothioyl] carbamate as a white solid.

(Z)-Ethyl (((2-bromophenyl)amino)((2-oxoethyl)thio)methylene)carbamate

To a solution of ethyl N-[(2-bromophenyl)carbamothioyl] carbamate (16.0 g, 52.8 mmol, 1.0 eq) in ACN (200 mL) was added $Cs_2CO_3$ (31.0 g, 95.0 mmol, 1.8 eq) and 2-chloroacetaldehyde (20.7 g, 106 mmol, 17.0 mL, 2.0 eq) at room temperature. The mixture was stirred at 20° C. for 12 hr. The reaction mixture was quenched by addition water (500 mL) and extracted with ethyl acetate (3×500 mL). The combined organic layers were dried over $Na_2SO_4$, filtered and concentrated under reduced pressure to give 24.0 g of (Z)-ethyl (((2-bromophenyl)amino)((2-oxoethyl)thio)methylene)carbamate as a light yellow solid.

(Z)-Ethyl (3-(2-bromophenyl)thiazol-2(3H)-ylidene) carbamate

To a solution of (Z)-ethyl (((2-bromophenyl)amino)((2-oxoethyl)thio)methylene)carbamate (24.0 g, 69.5 mmol, 1.0 eq) in THF (240 mL) was added DIPEA (27.0 g, 209 mmol, 36.3 mL, 3.0 eq) and $SOCl_2$ (8.27 g, 69.5 mmol, 5.0 mL, 1.0 eq) at 0° C. The mixture was stirred at 15° C. for 4 hr. The reaction mixture was quenched by addition saturated $NaHCO_3$ solution (400 mL) and extracted with ethyl acetate (3×400 mL). The combined organic layers were dried over $Na_2SO_4$, filtered and concentrated under reduced pressure to give a residue. The residue was purified by column chromatography on silica gel (petroleum ether/ethyl acetate=3/1 to 1/1) to give 13.43 g of (Z)-ethyl (3-(2-bromophenyl) thiazol-2(3H)-ylidene) carbamate. LCMS: (m/z [M+H$^+$]): 329.0.

Intermediate C22

To a solution of (Z)-ethyl (3-(2-bromophenyl)thiazol-2(3H)-ylidene)carbamate (2.00 g, 6.11 mmol, 1.0 eq) in EtOH (20 mL) was added 6N NaOH (4.89 g, 122 mmol, 20 eq) at room temperature. The mixture was stirred at 50° C. for 1.5 hr under $N_2$. The reaction mixture was quenched by addition water (40 mL) and extracted with ethyl acetate (3×40 mL). The combined organic layers were dried over $Na_2SO_4$, filtered and concentrated under reduced pressure to give 1.56 g of 3-(2-bromophenyl)thiazol-2(3H)-imine C22 as a yellow oil. LCMS (m/z [M+H]$^+$): 255.1.

Preparation of Intermediate C23

Scheme 44

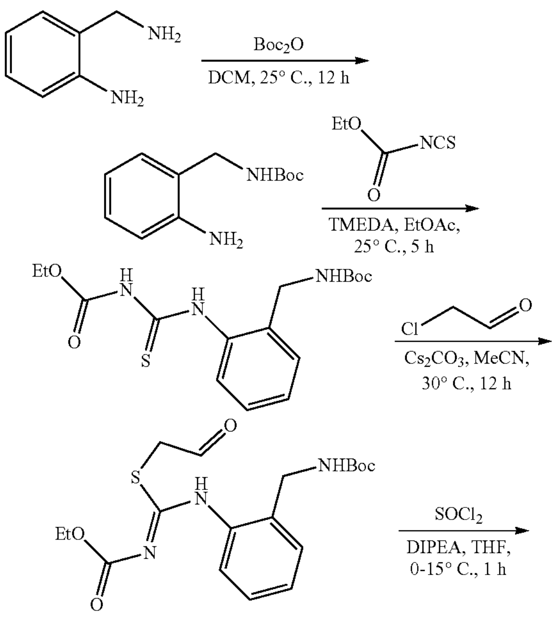

-continued

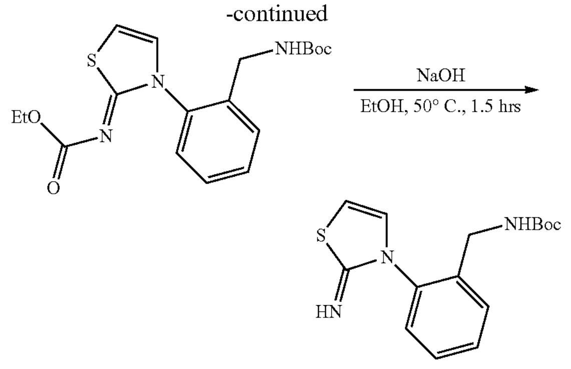

C23

Tert-Butyl 2-aminobenzylcarbamate

To a solution of 2-(aminomethyl)aniline (5.00 g, 40.9 mmol, 1.0 eq) in DCM (50 mL) was added $BOC_2O$ (8.93 g, 40.9 mmol, 9.40 mL, 1.0 eq) in DCM (20 mL). The reaction mixture was stirred at 25° C. for 12 hr under $N_2$ atmosphere. The reaction mixture was extracted with $H_2O$ (25 mL). The combined organic layers were washed with brine (25 mL), dried over $Na_2SO_4$, filtered and concentrated under reduced pressure to give 8.36 g of tert-butyl 2-aminobenzylcarbamatenyl)methyl]carbamate as a light yellow solid. $^1H$ NMR (400 MHz, DMSO-$d_6$) δ 7.18 (s, 1H), 7.19-7.18 (m, 1H), 7.05-7.00 (m, 1H), 7.02 (dt, J=1.3, 7.6 Hz, 1H), 6.95 (d, J=7.3 Hz, 1H), 6.65-6.53 (m, 2H), 4.19-4.14 (m, 1H), 4.19-4.11 (m, 1H), 4.16 (d, J=6.4 Hz, 2H), 1.36-1.36 (m, 1H), 1.37 (s, 9H). LCMS (m/z [M+H]$^+$): 166.9.

Ethyl N-[[2-[tert-butoxycarbonylamino)methyl]phenyl]carbamothioyl]carbamate

To a solution of tert-butyl 2-aminobenzylcarbamatenyl) methyl]carbamate (5.00 g, 22.5 mmol, 1.0 eq) in EtOAc (50 mL) was added TMEDA (2.61 g, 22.5 mmol, 3.39 mL, 1.0 eq) and ethyl N-(thioxomethylene)carbamate (4.43 g, 33.7 mmol, 1.5 eq). The reaction mixture was stirred at 25° C. for 5 hr. The mixture was concentrated directly under reduced pressure to afford yellow oil. The oil was dissolved in MTBE (20 mL) and stirred for 0.5 hr, and then filtered. The filter cake was washed with MTBE (2×10 mL), dried in vacuum to afford 7.75 g of ethyl N-[[2-[(tert-butoxycarbonylamino) methyl]phenyl]carbamothioyl] carbamate as a yellow solid. $^1H$ NMR (400 MHz, DMSO-$d_6$) δ 11.18 (br s, 1H), 11.21-11.15 (m, 1H), 11.24-11.09 (m, 1H), 11.24-11.09 (m, 1H), 7.35-7.31 (m, 1H), 7.29-7.19 (m, 3H), 7.12-7.03 (m, 1H), 7.12-7.02 (m, 1H), 7.13-7.00 (m, 1H), 4.62 (s, 1H), 4.65-4.55 (m, 1H), 4.29-4.12 (m, 2H), 4.10-4.02 (m, 2H), 1.37 (s, 9H), 1.28-1.19 (m, 1H), 1.23 (td, J=7.2, 16.0 Hz, 3H). LCMS (m/z [M+H]$^+$): 298.1.

(Z)-Ethyl(((2-(((tert-butoxycarbonyl)amino)methyl) phenyl)amino)((2-oxoethyl)thio) methylene)carbamate To a solution of ethyl N-[[2-[(tert-butoxycarbonylamino) methyl]phenyl]carbamothioyl] carbamate (3.70 g, 10.5 mmol, 1.0 eq) in MeCN (50 mL) was added $Cs_2CO_3$ (5.80 g, 17.8 mmol, 1.7 eq), then 2-chloroacetaldehyde (2.57 g, 13.1 mmol, 2.10 mL, 1.25 eq) was added at 10° C. The reaction mixture was stirred at 20° C. for 12 hr. The reaction mixture was filtered and concentrated under reduced pressure. The residue was diluted with water (50 mL) and extracted with EtOAc (3x20 mL). The combined organic layers were washed with brine (50 mL), dried over $Na_2SO_4$, filtered and concentrated under reduced pressure. The residue was purified by column chromatography on silica gel (petroleum ether/ethyl acetate=1/0 to 1/1) to give 3.0 g of (Z)-ethyl (((2-(((tert-butoxycarbonyl)amino) methyl)phenyl)amino)((2-oxoethyl)thio)methylene)carbamate as a yellow solid. LCMS (m/z $[M+H]^+$):396.1.

(Z)-Ethyl (3-(2-(((tert-butoxycarbonyl)amino) methyl)phenyl)thiazol-2(3H)-ylidene carbamate To a solution of (Z)-ethyl (((2-(((tert-butoxycarbonyl) amino)methyl)phenyl)amino) ((2-oxoethyl)thio)methylene) carbamate (2.00 g, 5.06 mmol, 1.0 eq) in THF (40 mL) was added DIPEA (1.96 g, 15.2 mmol, 2.64 mL, 3.0 eq) and $SOCl_2$ (602 mg, 5.06 mmol, 367 μL, 1.0 eq) at 0° C. The reaction mixture was stirred at 15° C. for 1 hr under $N_2$ atmosphere. The reaction mixture was concentrated under reduced pressure to remove solvent. The residue was diluted with saturated aqueous $NaHCO_3$ (25 mL) and extracted with MTBE (3x25 mL). The combined organic layers were washed with brine (25 mL), dried over $Na_2SO_4$, filtered and concentrated under reduced pressure to give a residue. The residue was purified by column chromatography on silica gel (petroleum ether/ethyl acetate=1/0 to 2/1) to give 1.06 g of (Z)-ethyl (3-(2-(((tert-butoxycarbonyl)amino)methyl) phenyl)thiazol-2(3H)-ylidene)carbamate as a yellow solid. $^1$H NMR (400 MHz, DMSO-$d_6$) δ 7.55-7.47 (m, 1H), 7.42 (br s, 1H), 7.46-7.39 (m, 1H), 7.37 (d, J=4.6 Hz, 1H), 7.28 (d, J=7.7 Hz, 1H), 7.24 (br t, J=5.6 Hz, 1H), 7.08 (d, J=4.9 Hz, 1H), 4.07-3.93 (m, 2H), 3.88 (br d, J=6.0 Hz, 2H), 1.40-1.21 (m, 9H), 1.20-1.09 (m, 3H). LCMS (m/z $[M+H]^+$): 378.3.

Intermediate C23

To a solution of (Z)-ethyl (3-(2-(((tert-butoxycarbonyl) amino)methyl)phenyl)thiazol-2(3H)-ylidene)carbamate (340 mg, 901 μmol, 1.0 eq) in EtOH (3.4 mL) was added NaOH (831 mg, 20.8 mmol, 23 eq). The reaction mixture was stirred at 50° C. for 1.5 hr under $N_2$ atmosphere. The reaction mixture was diluted with water (20 mL) and extracted with EtOAc (3x20 mL). The combined organic layers were washed with brine (20 mL), dried over $Na_2SO_4$, filtered and concentrated under reduced pressure. The residue was purified by prep-HPLC to give 133 mg of tert-butyl 2-(2-iminothiazol-3(2H)-yl)benzylcarbamate C23 as a light yellow solid.

Preparation of Intermediate C24

Scheme 45

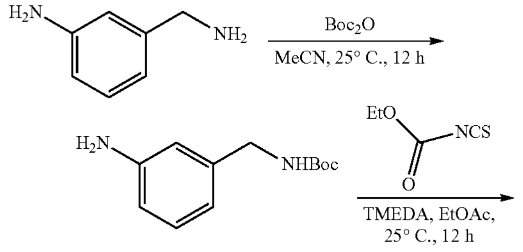

-continued

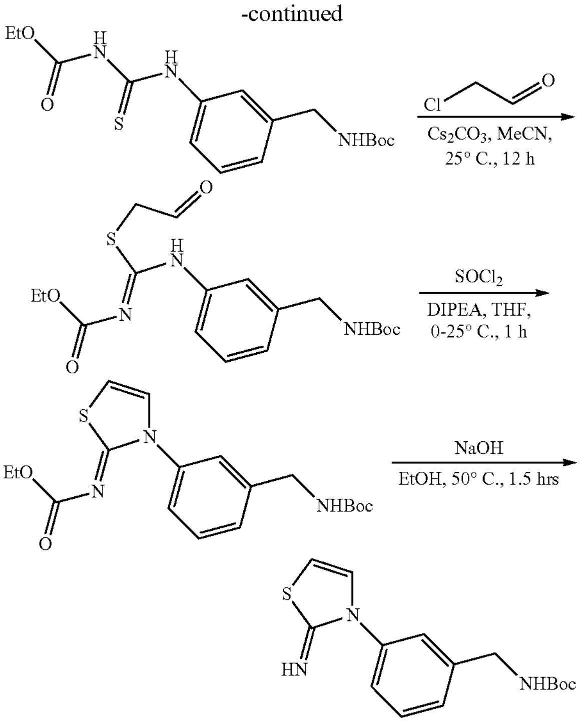

C24

Tert-Butyl 3-aminobenzylcarbamate

A solution of 3-(aminomethyl)aniline (5.00 g, 40.9 mmol, 1.0 eq) in MeCN (50 mL) was added a MeCN (50 mL) solution of $Boc_2O$ (8.13 g, 37.2 mmol, 8.56 mL, 0.9 eq) dropwise at 25° C. Then the reaction mixture was stirred at 25° C. for 12 h under $N_2$. The reaction mixture was diluted with ethyl acetate (100 mL) and filtered through a silica gel layer, and then the silica gel layer was washed with ethyl acetate (500 mL). The filtrate was concentrated under reduced pressure to give 9.4 g of tert-butyl 3-aminobenzylcarbamate as a yellow oil. $^1$H NMR (400 MHz, DMSO-$d_6$) δ 7.23 (br t, J=5.9 Hz, 1H), 6.95 (t, J=7.6 Hz, 1H), 6.48-6.38(m, 3H), 4.99 (s, 2H), 4.00 (br d, J=6.1 Hz, 2H), 1.42 (s, 9H).

Ethyl N-[[3-[tert-butoxycarbonylamino)methyl]phenyl]carbamothioyl]carbamate

To a solution of tert-butyl 3-aminobenzylcarbamate (5.00 g, 22.5 mmol, 1.0 eq) in EtOAc (50 mL) was added ethyl O-ethyl carbonisothiocyanatidate (2.95 g, 22.5 mmol, 1.0 eq) and TMEDA (261 mg, 2.25 mmol, 339 μL, 0.1 eq) at 25° C. The reaction mixture was stirred at 25° C. for 12 h under $N_2$. The reaction mixture was concentrated under reduced pressure. The residue was diluted with MTBE (50 mL) and stirred for 0.5 h at 25° C., which was filtered to collect 4.3 g of ethyl N-[[3-[(tert-butoxycarbonylamino)methyl]phenyl]carbamothioyl]carbamate as a white solid. $^1$H NMR (400 MHz, DMSO-$d_6$) δ 11.55 (s, 1H), 11.22 (br s, 1H), 7.53 (br d, J=7.8 Hz, 1H), 7.46-7.38 (m, 2H), 7.33 (t, J=7.8 Hz, 1H), 7.11 (d, J=7.6 Hz, 1H), 4.22 (q, J=7.1 Hz, 2H), 4.13 (br d, J=6.1 Hz, 2H), 1.40 (s, 9H), 1.27 (t, J=7.1 Hz, 3H).

(Z)-Ethyl (((3-(((tert-butoxycarbonyl)amino)methyl) phenyl)amino)((2-oxoethyl)thio)methylene)carbamate To a solution of ethyl N-[[3-[(tert-butoxycarbonylamino) methyl]phenyl]carbamothioyl]carbamate (4.30 g, 12.2 mmol, 1.0 eq) and $Cs_2CO_3$ (6.74 g, 20.7 mmol, 1.7 eq) in MeCN (44 mL) was added 2-chloroacetaldehyde (2.98 g, 15.2 mmol, 2.45 mL, 1.25 eq), mantaining the temperature blow 25° C. After the addition, the reaction mixture was stirred at 25° C. for 12 hr under $N_2$. The reaction mixture was diluted with MTBE (80 mL), washed with saturated aq $NaHCO_3$ (75 ml), brine (75 mL), dried over $Na_2SO_4$ and filtered. The filtrate was concentrated under reduced pressure to give 4.7 g of (Z)-ethyl (((3-(((tert-butoxycarbonyl) amino)methyl)phenyl)amino)((2-oxoethyl)thio)methylene) carbamate as a brown solid.

(Z)-Ethyl (3-(3-(((tert-butoxycarbonyl)amino) methyl)phenyl)thiazol-2(3H)-ylidene)carbamate To a solution of (Z)-ethyl (((3-(((tert-butoxycarbonyl) amino)methyl)phenyl)amino)((2-oxoethyl)thio)methylene) carbamate (4.70 g, 11.9 mmol, 1.0 eq) in THF (47 mL) was added DIPEA (4.61 g, 35.6 mmol, 6.21 mL, 3.0 eq) and $SOCl_2$ (1.41 g, 11.9 mmol, 862 μL, 1.0 eq) at 0° C. The reaction mixture was stirred at 25° C. for 1 hr under $N_2$. The reaction mixture was concentrated under reduced pressure. The residue was dissolved in EtOAc (20 mL), diluted with sat aq. $NaHCO_3$ (60 mL) and extracted with EtOAc (3×80 mL). The combined organic layers were washed with brine (80 mL), dried over $Na_2SO_4$, filtered. The filtrate was concentrated under reduced pressure. The residue was purified by flash silica gel chromatography (eluted with 0-40% Ethyl acetate/Petroleum ethergradient at 75 mL/min) to give 2.4 g of (Z)-ethyl (3-(3-(((tert-butoxycarbonyl)amino) methyl)phenyl)thiazol-2(3H)-ylidene)carbamate as a white solid. $^1$H NMR (400 MHz, DMSO-$d_6$) δ 7.53-7.47 (m, 2H), 7.41-7.33 (m, 3H), 7.08 (d, J=4.8 Hz, 1H), 4.21 (br d, J=6.1 Hz, 2H), 4.06-4.00 (m, 2H), 1.40(s, 9H), 1.16 (t, J=7.1 Hz, 3H).

Intermediate C24

To a solution of (Z)-ethyl (3-(3-(((tert-butoxycarbonyl) amino)methyl)phenyl)thiazol-2(3H)-ylidene)carbamate (1.00 g, 2.65 mmol, 1.0 eq) in EtOH (10 mL) was added 6N NaOH (2.40 g, 60.0 mmol, 23.0 eq) at room temperature. The reaction mixture was stirred at 60° C. for 5 hr under $N_2$. The reaction mixture was adjusted to pH 7 with aq HCl (6M). Then the neutralized solution was filtered, and the filter cake was washed with EtOH (200 mL). The filtrate was concentrated under reduced pressure. The crude product was purified by reversed-phase column to give 300 mg of tert-butyl 3-(2-iminothiazol-3(2H)-yl)benzylcarbamate C24 as a yellow solid.

Preparation of Intermediate C25

Scheme 46

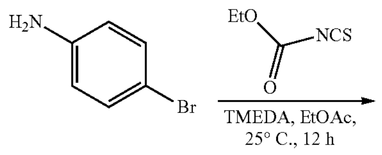

-continued

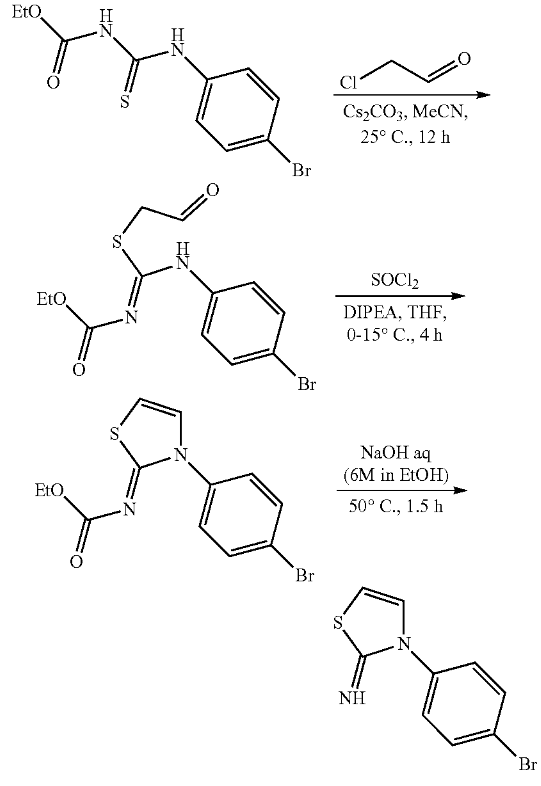

C25

Ethyl N-[(4-bromophenyl)carbamothioyl]carbamate

To a solution of 4-bromoaniline (5.00 g, 29.1 mmol, 1.0 eq) in EtOAc (50 mL) was added ethyl N-(thioxomethylene) carbamate (3.81 g, 29.1 mmol, 1.0 eq) and TMEDA (338 mg, 2.91 mmol, 439 μL, 0.1 eq) at room temperature. The reaction mixture was stirred at 20° C. for 12 hr. The reaction mixture was concentrated under reduced pressure to give a residue. The residue was triturated with EtOH (25 mL) for 0.5 hr. The mixture was filtered and the filter cake was washed with EtOH (2×25 mL) and dried to give 7.5 g of ethyl N-[(4-bromophenyl)carbamothioyl]carbamate as a white solid.

(Z)-Ethyl (((4-bromophenyl)amino)((2-oxoethyl) thio)methylene)carbamate

To a solution of ethyl N-[(4-bromophenyl)carbamothioyl] carbamate (7.50 g, 24.7 mmol, 1.0 eq) in $CH_3CN$ (100 mL) was added $Cs_2CO_3$ (13.70 g, 42.0 mmol, 1.7 eq) and 2-chloroacetaldehyde (6.07 g, 30.9 mmol, 4.97 mL, 1.25 eq) at room temperature. The reaction mixture was stirred at 20° C. for 12 hr under $N_2$. $Cs_2CO_3$ (8.06 g, 24.7 mmol, 1.0 eq) and 2-chloroacetaldehyde (3.64 g, 18.6 mmol, 2.98 mL, 0.75 eq) were added to the reaction solution. The reaction mixture was stirred at 20° C. for 4 hr under $N_2$. The reaction mixture was quenched by addition water (300 mL) and extracted with ethyl acetate (3×300 mL). The combined organic layers were dried over $Na_2SO_4$, filtered and concentrated under reduced pressure to give 10 g of (Z)-ethyl (((4-bromophenyl)amino)((2-oxoethyl)thio)methylene)carbamate as a light yellow solid. LCMS (m/z $[M+H]^+$): 345.0.

(Z)-Ethyl (3-(4-bromophenyl)thiazol-2(3H)-ylidene) carbamate

To a solution of (Z)-ethyl (((4-bromophenyl)amino)((2-oxoethyl)thio)methylene)carbamate (10.00 g, 28.97 mmol, 1.0 eq) in THF (120 mL) was added DIPEA (11.23 g, 86.90 mmol, 15.14 mL, 3.0 eq) and $SOCl_2$ (3.45 g, 28.97 mmol, 2.10 mL, 1.0 eq) at 0° C. The reaction mixture was stirred at 15° C. for 4 hr. The reaction mixture was quenched by addition saturated $NaHCO_3$ solution (200 mL) and extracted with ethyl acetate (3×200 mL). The combined organic layers were dried over $Na_2SO_4$, filtered and concentrated under reduced pressure to give a residue. The residue was purified by column chromatography on silica gel (petroleum ether/rthyl acetate=3/1 to 1/1) to give compound 3.60 g of (Z)-ethyl (3-(4-bromophenyl)thiazol-2(3H)-ylidene)carbamate as a yellow solid. $^1H$ NMR (400 MHz, DMSO-$d_6$) δ 7.75 (d, J=8.63 Hz, 2H), 7.47-7.56 (m, 3H), 7.08 (d, J=4.88 Hz, 1H), 4.03 (q, J=7.09 Hz, 2H), 1.16 (t, J=7.07 Hz, 3H).

Intermediate C25

To a solution of (Z)-ethyl (3-(4-bromophenyl)thiazol-2(3H)-ylidene)carbamate (1.00 g, 3.06 mmol, 1.0 eq) in EtOH (10 mL) was added 6N NaOH (2.44 g, 61.1 mmol, 20 eq). The reaction mixture was stirred at 50° C. for 1.5 hr under $N_2$. The reaction was combined with a previous batch (with 100 mg of starting material). The reaction mixture was quenched by addition water (100 mL) and extracted with ethyl acetate (3×100 mL). The combined organic layers were dried over $Na_2SO_4$, filtered and concentrated under reduced pressure to give 750 mg of 3-(4-bromophenyl)thiazol-2(3H)-imine C25 as a yellow oil.

Preparation of Intermediate C26

Scheme 47

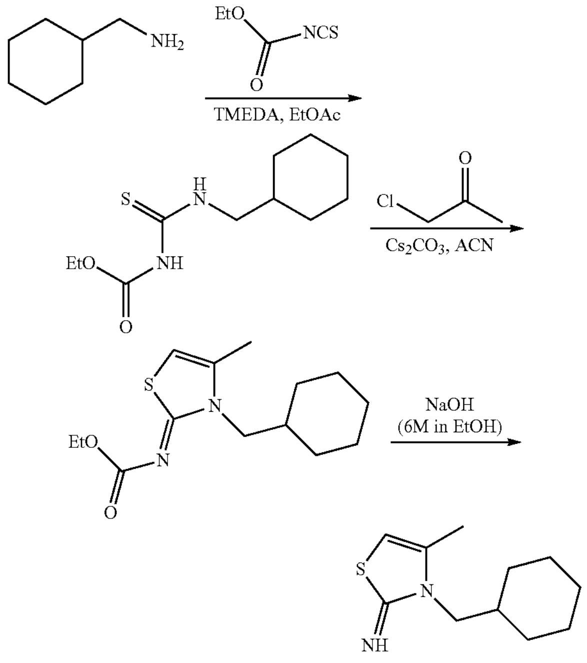

C26

Ethyl N-((cyclohexylmethyl)carbamothioyl)carbamate

To a solution of cyclohexylmethanamine (2.00 g, 17.7 mmol, 1.0 eq) in ethyl acetate (20 mL) was added O-ethyl carbonisothiocyanatidate (2.09 mL, 17.7 mmol, 1.0 eq) and tetramethylethylenediamine (0.267 mL, 1.77 mmol, 0.1 eq) at 25° C. Then the mixture was stirred at this temperature for 5 hours. The mixture was concentrated under reduced pressure, the residue was triturated with ethanol (10 mL) twice to afford 3.50 g of ethyl N-((cyclohexylmethyl)carbamothioyl)carbamate as an off-white solid. $^1H$ NMR (400 MHz, DMSO-$d_6$) δ 10.94 (br. s, 1H), 9.92 (br. t, J=5.2 Hz, 1H), 4.14 (q, J=7.2 Hz, 2H), 3.42-3.39 (m, 2H), 2.83 (s, 1H), 1.69-1.60 (m, 6H), 1.22-1.10 (m, 5H), 0.98-0.90 (m, 2H). LCMS (m/z $[M+H]^+$): 244.9.

(Z)-Ethyl (3-(cyclohexylmethyl)-4-methylthiazol-2(3H)-ylidene)carbamate

The solution of ethyl N-((cyclohexylmethyl)carbamothioyl)carbamate (1.00 g, 4.09 mmol, 1.0 eq) and cesium carbonate (2.27 g, 6.96 mmol, 1.7 eq) in acetonitrile (10 mL) was added 1-chloropropan-2-one (0.568 g, 6.14 mmol, 1.5 eq) dropwise at 25° C. After the addition, the mixture was stirred at this temperature for 2 hours. The mixture was poured into water (30 mL), extracted with ethyl acetate (50 mL×3). The combined organic layers were washed with brine (25 mL×2), dried over anhydrous sodium sulfate, filtered and concentrated under reduced pressure. The residue was purified by column chromatography on silica gel (petroleum ether/ethyl acetate=10/1 to 5/1) to afford 0.80 g of (Z)-ethyl (3-(cyclohexylmethyl)-4-methylthiazol-2(3H)-ylidene)carbamate as a yellow oil. $^1H$ NMR (400 MHz, DMSO-$d_6$) δ 6.44 (s, 1H), 4.01-3.99 (m, 2H), 3.22-3.09 (m, 2H), 3.08-3.05 (m, 1H), 1.65-1.61 (m, 6H), 1.48 (s, 3H), 1.15-1.14 (m, 3H), 1.12-1.10 (m, 2H), 0.90-0.88 (m, 2H). LCMS (m/z $[M+H]^+$): 282.9.

Intermediate C26

The solution of (Z)-ethyl (3-(cyclohexylmethyl)-4-methylthiazol-2(3H)-ylidene)carbamate (0.350 g, 1.08 mmol, 1.0 eq) in ethanol (3 mL) was added 6N sodium hydroxide (0.862 g, 21.5 mmol, 20 eq) in one portion at 25° C. The reaction mixture was heated to 50° C. and stirred for 1 hour. The mixture was added into water (15 mL), extracted with ethyl acetate (30 mL×3). The combined organic phase was washed with brine (25 mL×2), dried over anhydrous sodium sulfate, filtered and concentrated under reduced pressure. The residue was purified by column chromatography on silica gel (petroleum ether/ethyl acetate=10/1 to 0/1) to afford 150 mg of 3-(cyclohexylmethyl)-4-methylthiazol-2(3H)-imine C26 as a yellow oil.

Preparation of Intermediate C27

Scheme 48

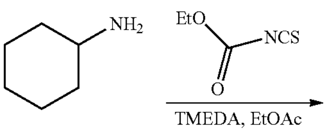

-continued

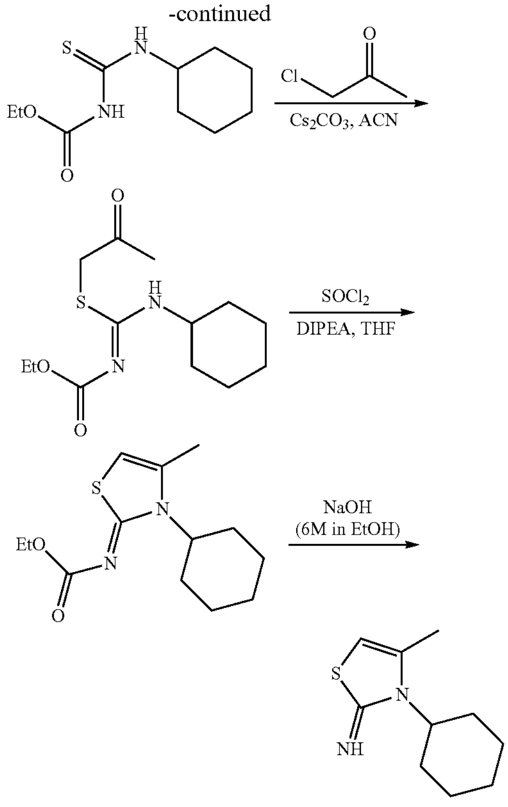

C27

Ethyl N-(cyclohexylcarbamothioyl)carbamate

To a mixture of cyclohexanamine (0.800 g, 8.07 mmol, 1.0 eq) and O-ethyl carbonisothiocyanatidate (1.11 g, 8.47 mmol, 1.05 eq) in ethyl acetate (10 mL) was added TMEDA (93 mg, 0.806 mmol, 1.0 eq) in at 25° C. The mixture was stirred for 6 hours at this temperature, and then concentrated under reduced pressure. The residue was purified by column chromatography on silica gel (column height: 250 mm, diameter: 100 mm, 100-200 mesh silica gel, Petroleum ether/Ethyl acetate=100/1 to 3/1) to afford 1.80 g of ethyl N-(cyclohexylcarbamothioyl)carbamate as a yellow gum. $^1$H NMR (400 MHz, $CD_3Cl$) δ 9.64 (br. s, 1H), 7.96 (br. s, 1H), 4.29-4.22 (m, 2H), 2.09-2.01 (m, 2H), 1.77-1.68 (m, 2H), 1.62-1.63 (m, 1H), 1.49-1.33 (m, 4H), 1.33-1.19 (m, 5H). LCMS (m/z $[M+H]^+$): 231.1.

(Z)-Ethyl ((cyclohexylamino)((2-oxopropyl)thio) methylene)carbamate

To a mixture of ethyl N-(cyclohexylcarbamothioyl)carbamate (0.800 g, 3.47 mmol, 1.0 eq) and cesium carbonate (1.92 g, 5.90 mmol, 1.7 eq) in acetonitrile (10 mL) was added 1-chloropropan-2-one (0.353 g, 3.82 mmol, 1.1 eq) at 25° C. The resulting mixture was stirred for 4 hours and this temperature then poured into ice-water (10 mL) and extracted with MTBE (100 mL×2). The combined organic phase was washed with brine (20 mL×2), dried over anhydrous sodium sulfate, filtered and concentrated under reduced pressure to afford 900 mg of the crude (Z)-ethyl ((cyclohexylamino)((2-oxopropyl)thio)methylene)carbamate as a yellow solid, which was used for next step directly without purification. LCMS (m/z $[M+H]^+$): 287.1.

(Z)-Ethyl (3-cyclohexyl-4-methylthiazol-2(3H)-ylidene)carbamate

To a mixture of (Z)-ethyl ((cyclohexylamino)((2-oxopropyl)thio)methylene)carbamate (0.900 g, 3.14 mmol, 1.0 eq) and diisopropylethylamine (0.812 g, 6.29 mmol, 2.2 eq) in tetrahydrofuran (20 mL) was added thionyl chloride (0.224 g, 1.89 mmol, 0.6 eq) at 0° C. The mixture was stirred at 25° C. for 2 hours then poured into ice-water (20 mL) and extracted with ethyl acetate (100 mL×3). The combined organic phase was washed with brine (20 mL), dried over anhydrous sodium sulfate, filtered and concentrated under reduced pressure. The residue was purified by column chromatography on silica gel (petroleum ether/ethyl acetate=100/1 to 4/1) to afford 0.50 g of (Z)-ethyl (3-cyclohexyl-4-methylthiazol-2(3H)-ylidene)carbamate as a yellow solid. $^1$H NMR (400 MHz, DMSO-$d_6$) δ 6.54 (br. s, 1H), 4.09-4.03 (m, 2H), 2.29-2.25 (m, 3H), 1.82-1.62 (m, 6H), 1.36-1.23 (m, 3H), 1.21-1.19 (m, 5H). LCMS (m/z $[M+H]^+$): 268.9.

Intermediate C27

To a mixture of (Z)-ethyl (3-cyclohexyl-4-methylthiazol-2(3H)-ylidene)carbamate (0.200 g, 0.745 mmol, 1.0 eq) in ethanol (4 mL) was added NaOH (0.596 g, 14.90 mmol, 20 eq) at 25° C. The mixture was heated to 50° C. and stirred for 1 hour, and then poured into ice-water (50 mL) and extracted with ethyl acetate (50 mL×5). The combined organic phase was washed with brine (10×2 mL), dried over anhydrous sodium sulfate, filtered and concentrated under reduced pressure to afford 120 mg of 3-cyclohexyl-4-methylthiazol-2(3H)-imine C27 as a yellow solid.

Preparation of Intermediate C28

Scheme 49

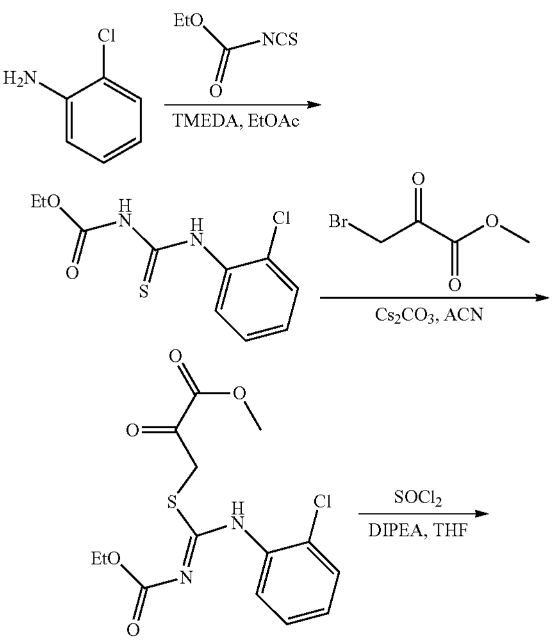

-continued

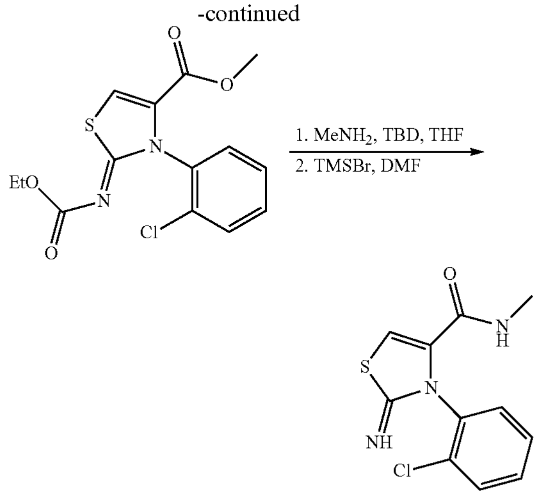

C28

Ethyl N-[(2-chlorophenyl)carbamothioyl]carbamate

To a solution of 2-chloroaniline (8.26 mL, 78.4 mmol) in ethyl acetate (100 mL) was added O-ethyl carbonisothiocyanatidate (10.3 g, 78.4 mmol) and tetramethylethylenediamine (1.18 mL, 7.84 mmol) at 0° C. slowly, then the mixture was stirred at 50° C. for 5 hours. The reaction mixture was cooled to room temperature and quenched with 100 mL of methanol dropwise. The precipitated solid was collected by filtration and then triturated with methanol (100 mL) at 25° C. for 10 minutes to afford 16.5 g of ethyl N-[(2-chlorophenyl)carbamothioyl]carbamate as a white solid. $^1$H NMR (DMSO-$d_6$, 400 MHz) δ 11.60 (br. s, 1H), 11.47 (br. s, 1H), 7.94 (d, J=8.0 Hz, 1H), 7.57-7.55 (m, 1H), 7.41-7.36 (m, 1H), 7.33-7.29 (m, 1H), 4.23 (q, J=7.2 Hz, 2H), 1.27 (t, J=7.2 Hz, 3H). LCMS (m/z [M+H]$^+$): 258.9.

(Z)-Methyl 3-((N-(2-chloro phenyl)-N'-(ethoxycarbonyl)carbamimidoyl)thio)-2-oxopropanoate To a solution of ethyl N-[(2-chlorophenyl)carbamothioyl] carbamate (5.00 g, 19.3 mmol) and cesium carbonate (7.56 g, 23.2 mmol) in acetonitrile (100 mL) was added methyl 3-bromo-2-oxopropanoate (2.67 mL, 25.1 mmol) at 25° C., then the mixture was stirred at 25° C. for 2 hours. The reaction mixture was quenched with water (100 mL) at 25° C., and extracted with ethyl acetate (200 mL×3). The combined organic layers were washed with brine (200 mL×2), dried over anhydrous $Na_2SO_4$ and filtered. The filtrate was concentrated under reduced pressure. The residue was purified by column chromatography ($SiO_2$, petroleum ether/ethyl acetate=10/1~2/1) to afford 2.80 g of (Z)-methyl 3-((N-(2-chloro phenyl)-N'-(ethoxycarbonyl) carbamimidoyl)thio)-2-oxopropanoate as brown oil. $^1$H NMR ($CDCl_3$, 400 MHz) δ 7.53-7.49 (m, 1H), 7.47-7.44 (m, 1H), 7.35-7.31 (m, 2H), 4.90 (br. s, 1H), 4.16 (q, J=7.2 Hz, 2H), 4.00 (d, J=11.6 Hz, 1H), 3.75 (s, 3H), 3.47-3.42 (m, 1H), 1.26 (t, J=7.2 Hz, 3H). LCMS (m/z [M+H]$^+$): 358.9.

(Z)-Methyl 3-(2-chlorophenyl)-2-((ethoxycarbonyl) imino)-2,3-dihydrothiazole-4-carboxylate To a mixture of (Z)-methyl 3-((N-(2-chlorophenyl)-N'-(ethoxycarbonyl)carbamimidoyl) thio)-2-oxopropanoate (2.80 g, 7.80 mmol) and DIPEA (2.04 mL, 11.7 mmol) in THF (15 mL) was added sulfurous dichloride (0.85 mL, 11.7 mmol) at 0° C. The mixture was stirred at 25° C. for 2 hours under nitrogen atmosphere. The reaction mixture was quenched with water (100 mL) at 25° C. and extracted with ethyl acetate (200 mL×3). The combined organic layers were washed with brine (200 mL×2), dried over anhydrous $Na_2SO_4$ and filtered. The filtrate was concentrated under reduced pressure to afford 2.20 g of (Z)-methyl 3-(2-chlorophenyl)-2-((ethoxycarbonyl)imino)-2,3-dihydrothiazole-4-carboxylate as yellow oil, which was used for the next step without further purification. $^1$H NMR (CDC13, 400 MHz) δ 7.64 (s, 1H), 7.54-7.51 (m, 1H), 7.46-7.41 (m, 2H), 7.40-7.37 (m, 1H), 4.20 (q, J=7.2 Hz, 2H), 3.74 (s, 3H), 1.29 (t, J=7.2 Hz, 3H). LCMS (m/z [M+H]$^+$): 340.9.

(Z)-Ethyl (3-(2-chlorophenyl)-4-(methylcarbamoyl) thiazol-2(3H)-ylidene)carbamate To a mixture of (Z)-methyl 3-(2-chlorophenyl)-2-((ethoxycarbonyl)imino)-2,3-dihydro thiazole-4-carboxylate (1.5 g, 4.40 mmol) in THF (15 mL) was added methylamine (2 M, 22 mL) drop wise and 3, 4, 6, 7, 8, 9-hexahydro-2H-pyrimido[1,2-a] pyrimidine (0.306 g, 2.20 mmol) at 25° C. The mixture was stirred at 60° C. for 2 hours under nitrogen atmosphere, and then poured into ice water (50 mL) slowly, followed by extraction with ethyl acetate (100 mL×3). The combined organic layers were washed with brine (200 mL×2), dried over anhydrous $Na_2SO_4$ and filtered. The filtrate was concentrated under reduced pressure to afford 1.55 g of (Z)-ethyl (3-(2-chlorophenyl)-4-(methylcarbamoyl)thiazol-2(3H)-ylidene)carbamate as a yellow solid. $^1$H NMR (DMSO-$d_6$, 400 MHz) δ 8.63 (br. d, J=4.8 Hz, 1H), 7.59 (d, J=7.6 Hz, 1H), 7.54 (s, 1H), 7.49-7.43 (m, 3H), 4.02 (q, J=7.2 Hz, 2H), 2.57 (d, J=4.8 Hz, 3H), 1.19-1.04 (t, J=7.2 Hz, 3H). LCMS (m/z [M+H]$^+$): 339.9.

Intermediate C28

To a solution of (Z)-ethyl (3-(2-chlorophenyl)-4-(methylcarbamoyl)thiazol-2(3H)-ylidene) carbamate (0.360 g, 1.06 mmol) in DMF (7 mL) was added bromotrimethylsilane (0.687 mL, 5.30 mmol) at 25° C. The reaction mixture was stirred at 80° C. for 1 hour, and then poured into ice water (20 mL) slowly. The mixture was neutralized with a saturated aqueous solution of sodium bicarbonate. The mixture was purified by reversed-phase flash (0.1% $NH_3 \cdot H_2O$/MeCN/water) directly to afford 80 mg of 3-(2-chlorophenyl)-2-imino-N-methyl-2,3-dihydrothiazole-4-carboxamide C28 as a yellow solid.

Preparation of Intermediate C29

Scheme 50

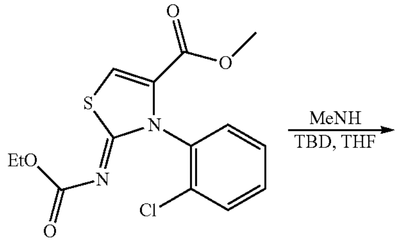

-continued

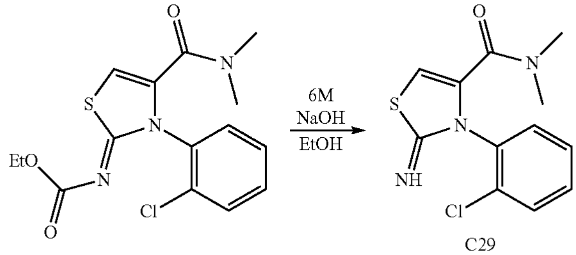

C29

Preparation of Intermediate C29

Ethyl (Z)-(3-(2-chlorophenyl)-4-(dimethylcarbamoyl)thiazol-2(3H)-ylidene)carbamate To a mixture of methyl (Z)-3-(2-chlorophenyl)-2-((ethoxycarbonyl)imino)-2,3-dihydrothiazole-4-carboxylate (0.380 g, 1.12 mmol) and dimethylamine (2 M, 5.6 mL) in THF (1 mL) was added 3, 4, 6, 7, 8, 9-hexahydro-2H-pyrimido[1,2-a]pyrimidine (0.078 g, 0.560 mmol) in one portion at 25° C. under nitrogen atmosphere. The reaction mixture was stirred at 60° C. for 2 hours, and then poured into 100 mL of ice-water carefully. The aqueous phase was extracted with ethyl acetate (50 mL×3), then washed with brine (10 mL). The organic layer was dried over anhydrous $Na_2SO_4$ and filtrated. The filtrate was concentrated under reduced pressure to give a residue, which was purified by reversed-phase flash (0.1% trifluoroacetic acid/MeCN/water) to afford 140 mg of ethyl (Z)-[3-(2-chlorophenyl)-4-(dimethylcarbamoyl)thiazol-2-ylidene]carbamate as a yellow solid. $^1H$ NMR (DMSO-$d_6$, 400 MHz) δ 7.63-7.61 (m, 1H), 7.52-7.43 (m, 3H), 7.36 (s, 1H), 4.04 (m, 2H), 3.11 (s, 3H), 2.76 (s, 3H), 1.14 (t, J=7.2 Hz, 3H). LCMS (m/z $[M+H]^+$): 353.9.

Intermediate C29

To a solution of ethyl (Z)-[3-(2-chlorophenyl)-4-(dimethylcarbamoyl)thiazol-2-ylidene]carbamate (0.390 g, 1.10 mmol) in ethyl alcohol (4 mL) was added sodium hydroxide solid (0.960 g, 24.0 mmol). The mixture was stirred at 50° C. for 2 hours. The crude product was purified by reversed-phase flash directly without any workup (0.1% ammonium hydroxide/MeCN/water) to afford 90 mg of 3-(2-chlorophenyl)-2-imino-N, N-dimethyl-thiazole-4-carboxamide C29 as a yellow solid.

Preparation of Intermediate D1

Scheme 51

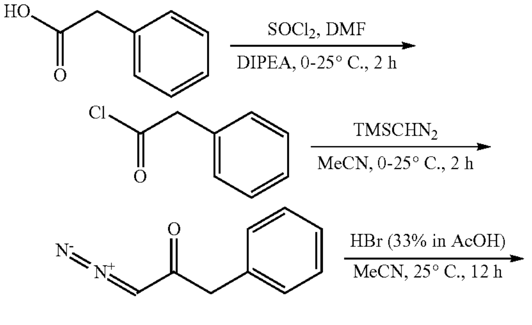

-continued

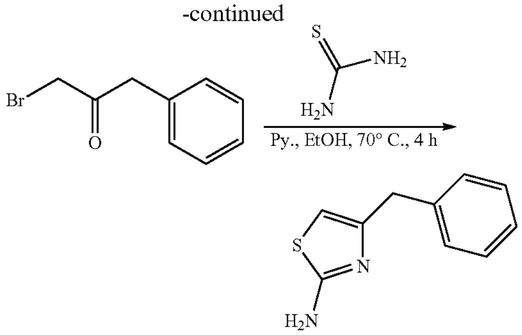

D1

2-Phenylacetyl chloride

To a solution of 2-phenylacetic acid (5.00 g, 36.7 mmol, 4.63 mL, 1.0 eq) in DCM (50 mL) was added DMF (268 mg, 3.67 mmol, 283 μL, 0.1 eq), and then $SOCl_2$ (8.74 g, 73.4 mmol, 5.33 mL, 2.0 eq) was added into the mixture at 0° C. The reaction mixture was stirred at 25° C. for 1 h. The reaction mixture was concentrated under reduced pressure to remove solvent. Compound 2-phenylacetyl chloride (5.68 g, crude) was obtained as colorless oil.

1-Diazo-3-phenylpropan-2-one

To a solution of 2-phenylacetyl chloride (5.68 g, 36.7 mmol, 4.90 mL, 1.0 eq) in MeCN (50 mL) was added $TMSCHN_2$ (2 M, 36.74 mL, 2 eq) at 0° C. Then the reaction mixture was stirred at 25° C. for 2 h. The result yellow solution was used into next step directly without further purification.

1-Bromo-3-phenylpropan-2-one

To a solution of 1-diazo-3-phenylpropan-2-one in MeCN was added HBr (13.5 g, 55.1 mmol, 9.06 mL, 1.5 eq) (33% in AcOH). The mixture was stirred at 25° C. for 12 h. The mixture was poured in water (50 mL) and extracted with EtOAc (3×30 mL). The organic phase was washed with brine (50 mL), dried over $Na_2SO_4$, filtered and concentrated under reduced pressure. The residue was purified by column chromatography on silica gel (petroleum ether/ethyl acetate=0/1 to 6/1) to give 2.30 g of 1-bromo-3-phenylpropan-2-one as red oil.

Intermediate D1

To a solution of thiourea (715 mg, 9.39 mmol, 1.0 eq) in refluxing EtOH (20 mL) was added the 1-bromo-3-phenylpropan-2-one (2.00 g, 9.39 mmol, 1.0 eq) and Pyridine (742 mg, 9.39 mmol, 758 μL, 1.0 eq). The reaction mixture was stirred for 4 h at 70° C. The reaction mixture was concentrated under reduced pressure to remove solvent. The residue was purified by column chromatography on silica gel (petroleum ether/ethyl acetate=50/1 to 1/1) to give 0.6 g crude product. 490 mg of crude product was purified on prep-HPLC to give 160 mg of 4-benzylthiazol-2(3H)-imine D1 as a white solid. $^1H$ NMR: (400 MHz, DMSO-$d_6$) δ 7.31-7.12 (m, 5H), 6.83 (s, 2H), 6.12 (s, 1H), 3.71 (s, 2H). Structure was confirmed with HMBC and HSQC.

Preparation of Intermediate D3

Scheme 52

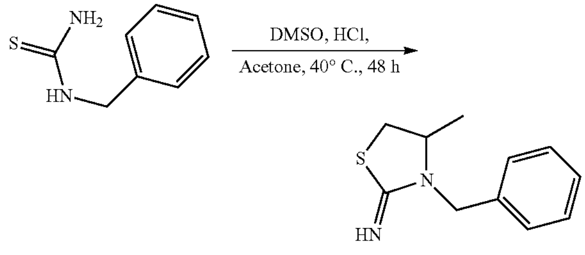

D3

To a solution of benzylthiourea (1.00 g, 6.02 mmol, 1.0 eq) in Acetone (15 mL) was added HCl (1.20 g, 12.0 mmol, 1.18 mL, 36% purity, 2.0 eq) and DMSO (939 mg, 12.0 mmol, 939 μL, 2.0 eq) at 40° C. The reaction mixture was stirred for 48 hours. The reaction mixture was concentrated directly under reduced pressure. The residue was purified by reverse phase MPLC to afford 0.80 g of the 3-benzyl-4-methylthiazol-2(3H)-imine D3 as a white solid.

Preparation of Acid D

Scheme 53

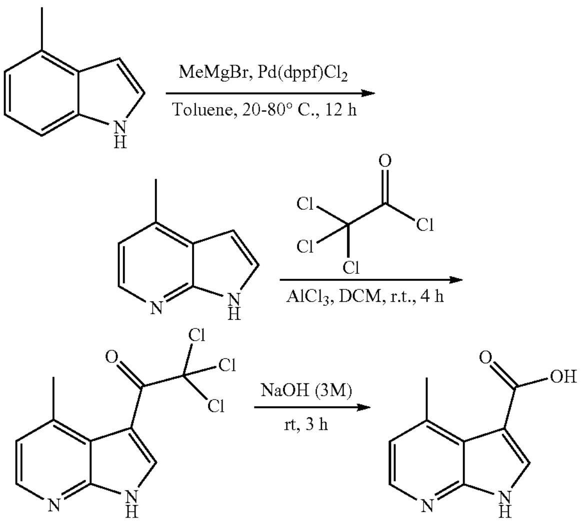

Acid D

4-Methyl-1H-pyrrolo[2,3-b]pyridine

To a solution of 4-chloro-1H-pyrrolo[2,3-b]pyridine (10.00 g, 65.54 mmol, 1.0 eq) and Pd(dppf)$Cl_2$ (1.20 g, 1.64 mmol, 0.025 eq) in toluene (200 mL) was added MeMgBr (3 M, 109 mL, 5.0 eq) drop-wise at 25° C. After the addition, the reaction mixture was stirred at 80° C. for 12 hours, and then cooled to 25° C., quenched by addition of ice-water (300 mL) at 0° C., extracted with EtOAc (2×200 mL). The combined organic layers were washed with saturated aqueous $NH_4Cl$ (400 mL), brine (200 mL), dried over $Na_2SO_4$ and filtered. The filtrate was concentrated under reduced pressure to afford a residue. The residue was purified by flash chromatography on silica gel (eluted with 0-100% ethyl acetate/petroleum ether gradient at 100 mL/min) to afford 7.00 g of 4-methyl-1H-pyrrolo[2,3-b]pyridine as a white solid. LCMS (m/z $[M+H]^+$): 133.1.

2,2,2-Trichloro-1-(4-methyl-1H-pyrrolo[2,3-b]pyridin-3-yl)ethanone

To a solution of 4-methyl-1H-pyrrolo[2,3-b]pyridine (1.00 g, 7.57 mmol, 1.0 eq) in DCM (20 mL) was added $AlCl_3$ (2.52 g, 18.9 mmol, 2.5 eq) at 25° C. The reaction mixture was stirred at 25° C. for 10 minute and then 2,2,2-trichloroacetyl chloride (2.06 g, 11.4 mmol, 1.5 eq) was added. The reaction mixture was stirred at 25° C. for more 3 hours 50 min. The mixture was poured into ice-water (30 mL) and the precipitate was filtered. The filtrate was extracted with DCM (2×30 mL), concentrated under reduced pressure to afford 2.0 g of the crude 2,2,2-trichloro-1-(4-methyl-1H-pyrrolo[2,3-b]pyridin-3-yl)ethanone as a light yellow solid.

4-Methyl-1H-pyrrolo[2,3-b]pyridine-3-carboxylic acid (Acid D)

A mixture of 2,2,2-trichloro-1-(4-methyl-1H-pyrrolo[2,3-b]pyridin-3-yl)ethanone (2.00 g, 7.21 mmol, 1.0 eq) in aqueous NaOH (3 M, 30 mL, 12.5 eq) was stirred at 25° C. for 3 hours under $N_2$ atmosphere. The mixture was cooled to 0° C. and adjusted to pH<6.0 by addition of concentrated aqueous HCl. The precipitate was collected by filtration and the filter cake was washed with $H_2O$ (2×5 mL), dried in vacuum to afford 1.2 g of the crude 4-methyl-1H-pyrrolo[2,3-b]pyridine-3-carboxylic acid (Acid D) as an off-white solid.

Preparation of Example T01

Scheme 54

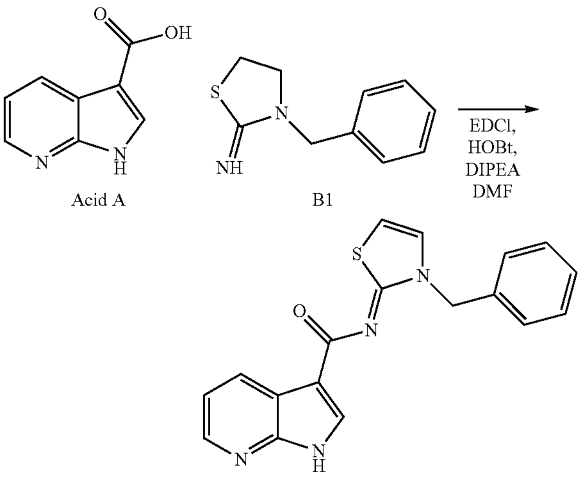

Acid A

B1

T01

To a mixture of 3-benzylthiazol-2(3H)-imine B1 (1.20 g, 6.31 mmol, 1.0 eq), 1H-pyrrolo[2,3-b]pyridine-3-carboxylic acid A (0.818 g, 5.05 mmol, 0.8 eq), HOBt (1.28 g, 9.46 mmol, 1.5 eq) and diisopropylethylamine (2.45 g, 18.9 mmol, 3.0 eq) in dimethylformamide (10 mL) was added EDCI (1.81 g, 9.46 mmol, 1.5 eq). The mixture was stirred at 25° C. for 1.5 hours then poured into ice-water (200 mL). The precipitate was collected by filtration, and the filter cake was washed with acetonitrile (3×30 mL), then tritrated with acetonitrile/methanol=5:1 (5×30 mL), followed by reversed-phase HPLC and re-crystallization from methanol (2×250 mL) to afford 352 mg of (Z)—N-(3-benzylthiazol-2(3H)-ylidene)-1H-pyrrolo[2,3-b]pyridine-3-carboxamide T01 as a white solid. $^{1}$H-NMR (DMSO-$d_6$, 400 MHz) δ 12.18 (br. s, 1H), 8.53-8.50 (m, 1H), 8.25-8.10 (m, 2H), 7.60 (d, J=4.8 Hz, 1H), 7.42-7.40 (m, 5H), 7.36 (d, J=7.2 Hz, 1H), 6.96 (d, J=4.8 Hz, 1H), 5.52 (s, 2H). LCMS (m/z $[M+H]^+$)=335.1.

The following examples in Table E were prepared in a similar fashion to that shown above in Scheme 54 using intermediate B1 and the appropriate Acids from Table A.

TABLE E

| Example | Structure | LCMS | 1H NMR |
|---|---|---|---|
| T02 | 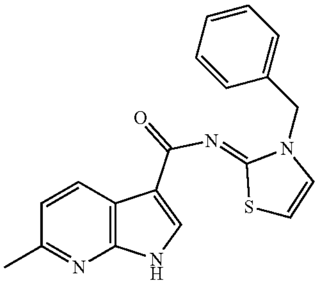 [SMILES: Cc1ccc2c(C(=O)/N=c3\sccn3Cc3ccccc3)c[nH]c2n1] | 349.1 | (DMSO-$d_6$, 400 MHz) δ 12.96 (brs, 1H), 8.80-8.78 (m, 1H), 8.19-8.18 (m, 1H), 7.40-7.39 (m, 1H), 7.37-7.28 (m, 6H), 7.06-7.05 (m, 1H), 5.56 (s, 2H), 2.71 (s, 3H). |
| T03 | 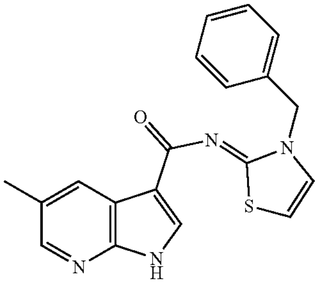 [SMILES: Cc1cnc2[nH]cc(C(=O)/N=c3\sccn3Cc3ccccc3)c2c1] | 349.0 | (DMSO-$d_6$, 400 MHz) δ 12.64 (brs, 1H), 8.58 (s, 1H), 8.23 (s, 2H), 7.66-7.65 (m, 1H), 7.40-7.34 (m, 4H), 7.30-7.28 (m, 1H), 7.04-7.02 (m, 1H), 5.56 (s, 2H), 2.42 (s, 3H). |
| T04 | 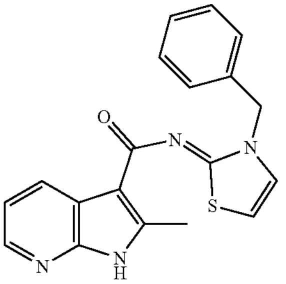 [SMILES: Cc1[nH]c2ncccc2c1C(=O)/N=c1\sccn1Cc1ccccc1] | 349.1 | (METHANOL-$d_4$, 400 MHz) δ 12.00 (s, 1H), 8.49 (d, J = 8.0 Hz, 1H), 8.38 (d, J = 3.2 Hz, 1H), 7.59 (d, J = 4.8 Hz, 1H), 7.33-7.36 (m, 5H), 7.04-7.06 (m, 1H), 6.99 (d, J = 4.8 Hz, 1H), 5.53 (s, 2H), 2.74 (s, 3H). |
| T05 | 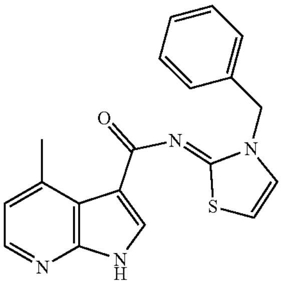 [SMILES: Cc1ccnc2[nH]cc(C(=O)/N=c3\sccn3Cc3ccccc3)c12] | 349.0 | (METHANOL-$d_4$, 400 MHz) δ 8.34 (s, 1H), 8.27 (d, J = 5.6 Hz, 1H), 7.31-7.41 (m, 7H), 6.95 (d, J = 4.8 Hz, 1H), 5.54 (s, 2H), 3.14 (s, 3H). |

TABLE E-continued

| Example | Structure | LCMS | 1H NMR |
|---|---|---|---|
| T06 | 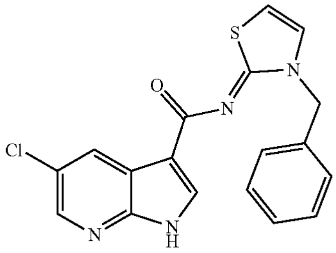 [SMILES: O=C(/N=c1\sccn1Cc1ccccc1)c1c[nH]c2ncc(Cl)cc12] | 369.0 | (DMSO-$d_6$, 400 MHz) δ 12.46 (brs, 1H), 8.51 (s, 1H), 8.26 (m, 2H), 7.66-7.65 (m, 1H), 7.40-7.34 (m, 4H), 7.30-7.28 (m, 1H), 7.03-7.01 (m, 1H), 5.53 (s, 2H). |

Examples in Table F are prepared in a similar fashion to that shown above in Scheme 54 using the appropriate Intermediates in Table B/C and acid A from Table A.

TABLE F

| Example | Structure | LCMS | 1H NMR |
|---|---|---|---|
| T14 | 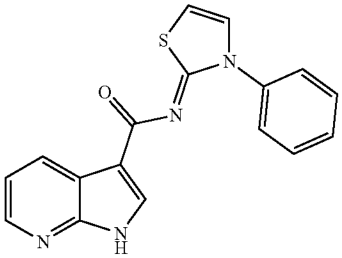 [SMILES: O=C(/N=c1\sccn1-c1ccccc1)c1c[nH]c2ncccc12] | 321.1 | (DMSO-$d_6$, 400 MHz) δ 12.36 (brs, 1H), 8.26-8.29 (m, 2H), 8.99 (s, 1H), 7.68-7.73 (m, 5H), 7.59 (m, 1H), 7.15 (s, 1H), 7.14 (m, 1H). |
| T19 | 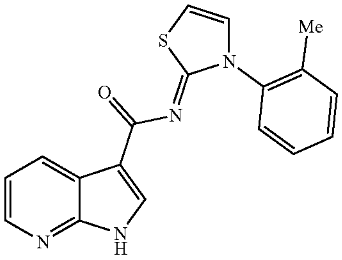 [SMILES: Cc1ccccc1-n1ccs/c1=N\C(=O)c1c[nH]c2ncccc12] | 335.1 | (DMSO-$d_6$, 400 MHz) δ 12.11 (br.s, 1H), 8.16 (dd, J = 4.8, 1.6 Hz, 1H), 7.88 (s, 1H), 7.85-7.77 (m, 1H), 7.60-7.52 (m, 3H), 7.50-7.41 (m, 2H), 7.13 (d, J = 4.8 Hz, 1H), 6.87 (dd, J = 8.0, 4.8 Hz, 1H), 2.09 (s, 3H). |
| T20 | 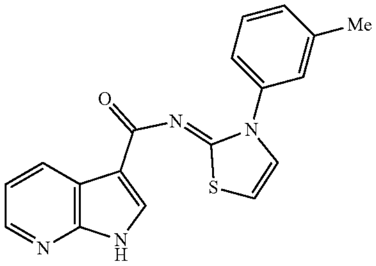 [SMILES: Cc1cccc(-n2ccs/c2=N\C(=O)c2c[nH]c3ncccc23)c1] | 335.0 | (METHANOL-$d_4$, 400 MHz) δ 8.28 (dd, J = 7.6, 1.6 Hz, 1H), 8.17 (dd, J = 4.8, 1.6 Hz, 1H), 8.00 (s, 1H), 7.56-7.52(m, 2H), 7.48 (d, J = 3.6 Hz, 1H), 7.44-7.42(m, 2H), 7.04 6.99 (m, 2H), 2.50 (s, 3H). |
| T21 | 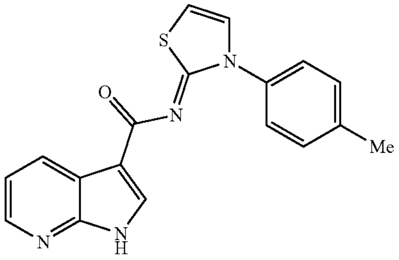 [SMILES: Cc1ccc(-n2ccs/c2=N\C(=O)c2c[nH]c3ncccc23)cc1] | 335.0 | (METHANOL-$d_4$, 400 MHz) δ 8.27 (dd, J = 1.6, 8.0 Hz, 1H), 8.18 (dd, J = 1.6, 4.8 Hz, 1H), 7.99 (s, 1H), 7.57-7.49 (m, 2H), 7.49-7.43 (m, 3H), 7.04-6.97 (m, 2H), 2.52 (s, 3H). |

TABLE F-continued
| Example | Structure | LCMS | 1H NMR |
|---|---|---|---|
| T22 | 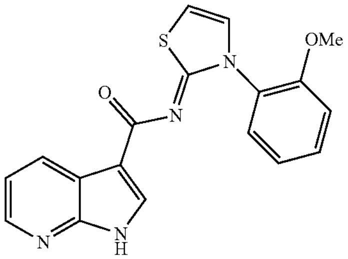 [SMILES: COc1ccccc1-n1ccs/c1=N\C(=O)c1c[nH]c2ncccc12] | 351.1 | (DMSO-$d_6$, 400 MHz) δ 12.11 (br.s, 1H), 8.17 (dd, J = 4.8, 1.6 Hz, 1H), 7.93 (d, J = 7.6 Hz, 1H), 7.88-7.87 (m, 1H), 7.61 (dt, J = 7.2, 1.6 Hz, 1H), 7.53-7.50(m, 2H), 7.35 (d, J = 8 Hz, 1H), 7.22-7.18 (m, 1H), 7.04 (d, J = 4.8 Hz, 1H), 6.90 (dd, J = 8.0, 4.8 Hz, 1H), 3.75 (s, 3H). |
| T23 | 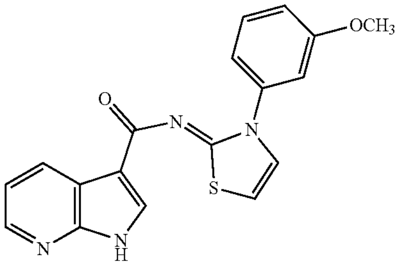 [SMILES: COc1cccc(-n2ccs/c2=N\C(=O)c2c[nH]c3ncccc23)c1] | 351.1 | (DMSO-$d_6$, 400 MHz) δ 12.17 (br.s, 1H), 8.35-8.16 (m, 2H), 7.96 (s, 1H), 7.68 (d, J = 4.4 Hz, 1H), 7.55 (t, J = 8.0 Hz, 1H), 7.33 (s, 1H), 7.27 (d, J = 7.6 Hz, 1H), 7.15 (d J = 7.6 Hz, 1H), 7.10 (d, J = 4.4 Hz, 1H), 7.01 (dd J = 4.8, 7.2 Hz, 1H), 3.84 (s, 3H). |
| T24 | 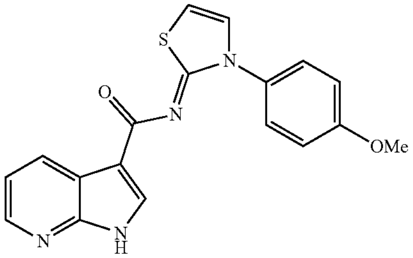 [SMILES: COc1ccc(-n2ccs/c2=N\C(=O)c2c[nH]c3ncccc23)cc1] | 351.2 | (DMSO-$d_6$, 400 MHz) δ 12.13 (br s, 1H), 8.28-8.15 (m, 2H), 7.94 (s, 1H), 7.69-7.48 (m, 3H), 7.22-7.14 (m, 2H), 7.08 (d, J = 4.8 Hz, 1H), 7.02 (dd, J = 4.8, 7.6 Hz, 1H), 3.89 (s, 3H). |
| T25 | 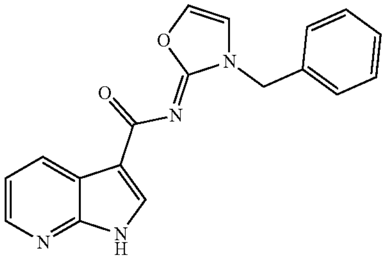 [SMILES: O=C(/N=c1\occn1Cc1ccccc1)c1c[nH]c2ncccc12] | 319.0 | (DMSO-$d_6$, 400 MHz) δ 12.08 (br s, 1H), 8.42 (dd, J = 7.83, 1.47 Hz, 1H), 8.23 (dd, J = 4.65, 1.59 Hz, 1H), 8.06 (s, 1H), 7.66 (d, J = 1.59 Hz, 1H), 7.51 (d, J = 1.59 Hz, 1H), 7.46-7.31 (m, 5H), 7.11 (dd, J = 7.89, 4.71 Hz, 1H), 5.09 (s, 2H). |
| T26 | 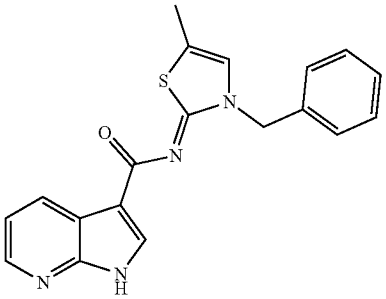 [SMILES: Cc1cn(Cc2ccccc2)/c(=N/C(=O)c2c[nH]c3ncccc23)s1] | 349.1 | (DMSO-$d_6$, 400 MHz) δ 12.71 (brs, 1H), 8.75 (d, J = 7.6 Hz, 1H), 8.37 (d, J = 4.4 Hz, 1H), 8.29 (s, 1H), 7.29-7.43 (m, 7H), 5.50 (s, 2H), 2.25 (s, 3H). |

TABLE F-continued

| Example | Structure | LCMS | 1H NMR |
|---|---|---|---|
| T27 | 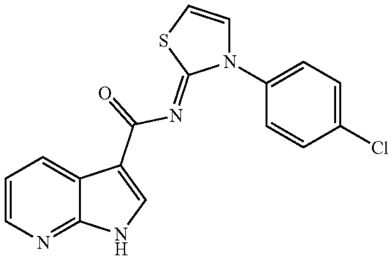 [SMILES: O=C(/N=c1\sccn1-c1ccc(Cl)cc1)c1c[nH]c2ncccc12] | 355.0 | (DMSO-$d_6$, 400 MHz) δ 12.16 (br. s, 1H), 8.26-8.18 (m, 2H), 7.95 (s, 1H), 7.79-7.70 (m, 4H), 7.67 (d, J = 5.2 Hz, 1H), 7.11 (d, J = 4.8 Hz, 1H), 7.08-7.02 (m, 1H). |
| T28 | 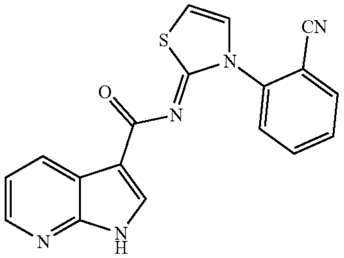 [SMILES: N#Cc1ccccc1-n1ccs/c1=N\C(=O)c1c[nH]c2ncccc12] | | (METHANOL-$d_4$, 400 MHz) δ 8.60 (dd, J = 7.9, 1.1 Hz, 1H), 8.43 (d, J = 4.9 Hz, 1H), 8.16 (s, 1H), 8.10 (dd, J = 7.7, 1.1 Hz, 1H), 8.00-8.06 (m, 1H), 7.85-7.91 (m, 1H), 7.81 (d, J = 7.9 Hz, 1H), 7.61 (d, J = 4.9 Hz, 1H), 7.46 (dd, J = 7.9, 6.0 Hz, 1H), 7.20 (d, J = 4.6 Hz, 1H). |
| T29 | 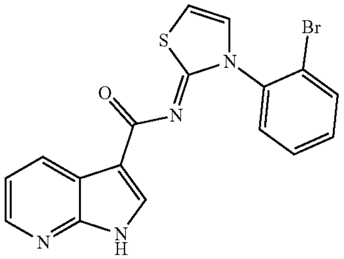 | 401.0 | (DMSO-$d_6$, 400 MHz) δ 12.83 (s, 1H), 8.32 (d, J = 4.2 Hz, 1H), 8.05 (d, J = 7.5 Hz, 1H), 7.95-8.01 (m, 2H), 7.59-7.75 (m, 4H), 7.18 (d, J = 4.6 Hz, 1H), 7.11 (dd, J = 7.8, 5.2 Hz, 1H). |
| T30 | 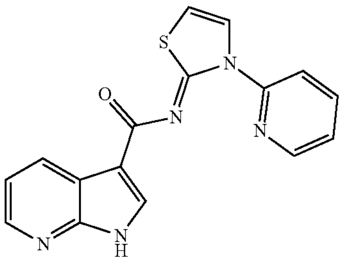 [SMILES: O=C(/N=c1\sccn1-c1ccccn1)c1c[nH]c2ncccc12] | 322.0 | (DMSO-$d_6$, 400 MHz) δ 12.26 (br.s, 1H), 8.66-8.64 (m, 1H), 8.42-8.40(m, 1H), 8.40-8.38 (m, 1H), 8.26 (dd, J = 4.4, 1.6 Hz, 1H), 8.22-8.18 (m, 1H), 8.08 (s, 1H), 7.92 (d, J = 4.8 Hz, 1H), 7.59-7.56 (m, 1H), 7.14 (dd, J = 7.6, 4.4 Hz, 1H), 7.08 (d, J = 4.8 Hz, 1H). |
| T31 | 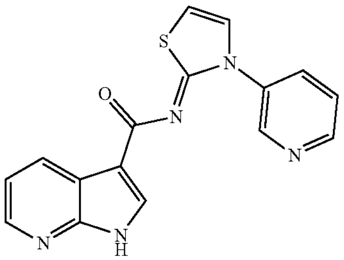 [SMILES: O=C(/N=c1\sccn1-c1cccnc1)c1c[nH]c2ncccc12] | 322.0 | (DMSO-$d_6$, 400 MHz) δ 12.28 (br. s, 1H), 8.98 (d, J = 2.4 Hz, 1H), 8.78 (d, J = 3.6 Hz, 1H), 8.33-8.27 (m, 1H), 8.27-8.21 (m, 2H), 7.96 (d, J = 2.4 Hz, 1H), 7.80-7.73 (m, 2H), 7.17 (d, J = 4.8 Hz, 1H), 7.12-7.07 (m, 1H). |
| T32 | 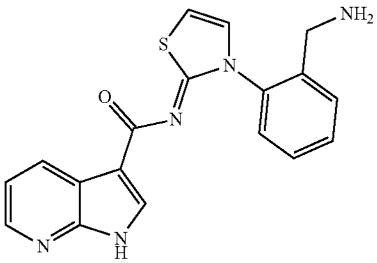 [SMILES: NCc1ccccc1-n1ccs/c1=N\C(=O)c1c[nH]c2ncccc12] | 350.1 | (DMSO-$d_6$, 400 MHz) δ 8.46-8.37 (m, 2H), 8.11 (s, 1H), 7.84 (d, J = 4.0 Hz, 2H), 7.78 (td, J = 4.2, 8.3 Hz, 1H), 7.58 (d, J = 7.7 Hz, 1H), 7.52 (d, J = 4.6 Hz, 1H), 7.37 (dd, J = 5.7, 7.9 Hz, 1H), 7.23 (d, J = 4.6 Hz, 1H), 4.13-4.05 (m, 1H), 3.98-3.88 (m, 1H). |

TABLE F-continued
| Example | Structure | LCMS | 1H NMR |
|---|---|---|---|
| T33 | 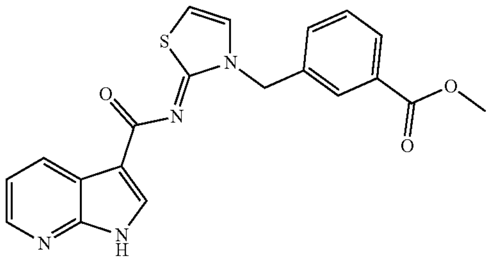 [SMILES: COC(=O)c1cccc(Cn2ccs/c2=N\C(=O)c2c[nH]c3ncccc23)c1] | 393.1 | (DMSO-$d_6$, 400 MHz) δ 12.21 (brs, 1H), 8.52 (d, J = 6.4 Hz, 1H), 8.25-8.26 (m, 1H), 8.21 (d, J = 2.8 Hz, 1H), 8.09 (s, H), 7.87 (m, 1H), 7.67-7.68 (m, 2H), 7.53 (m, 1H), 7.15 (d, J = 3.6 Hz, 1H), 7.09 (d, J = 4.4 Hz, 1H), 5.59 (s, 2H), 3.81 (s, 3H). |
| T34 | 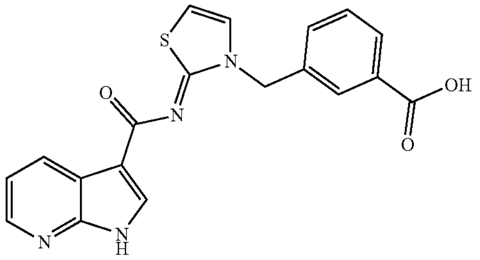 [SMILES: O=C(O)c1cccc(Cn2ccs/c2=N\C(=O)c2c[nH]c3ncccc23)c1] | 379.1 | (DMSO-$d_6$, 400 MHz) δ 12.19 (brs, 1H), 8.50-8.52 (m, 1H), 8.23-8.27 (m, 2H), 8.01 (s, 1H), 7.87 (d, J = 7.6 Hz, 1H) 7.61-7.67 (m, 2H), 7.46 (m, 1H), 7.16 (m, 1H), 7.01 (d, J = 4.8 Hz, 1H), 5.59 (s, 2H) |
| T35 | 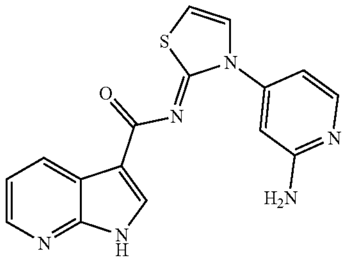 [SMILES: Nc1cc(-n2ccs/c2=N\C(=O)c2c[nH]c3ncccc23)ccn1] | 337.0 | (METHANOL-$d_4$, 400 MHz) δ 12.44 (brs, 1H), 8.50 (brd, J = 7.95 Hz, 1H), 8.44-8.24 (m, 3H), 8.22-8.15 (m, 2H), 7.78 (d, J = 4.89 Hz, 1H), 7.64 (s, 1H), 7.34 (d, J = 6.70 Hz, 1H), 7.23-7.17 (m, 2H). |
| T36 | 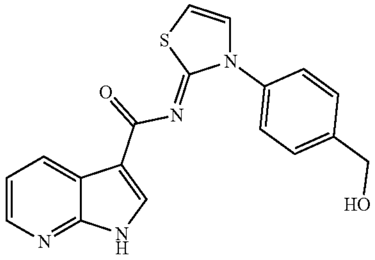 [SMILES: O=C(/N=c1\sccn1-c1ccc(CO)cc1)c1c[nH]c2ncccc12] | 351.0 | (METHANOL-$d_4$, 400 MHz) δ 8.28 (dd, J = 7.88, 1.50 Hz, 1H), 8.17 (dd, J = 4.75, 1.50 Hz, 1H), 7.99 (s, 1H), 7.60-7.68 (m, 4H), 7.49 (d, J = 4.75 Hz, 1H), 7.01-7.07 (m, 2H), 4.79 (s, 2H). |
| T40 | 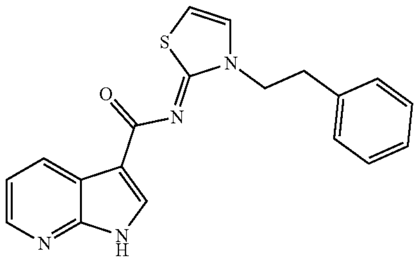 [SMILES: O=C(/N=c1\sccn1CCc1ccccc1)c1c[nH]c2ncccc12] | 349.0 | (DMSO-$d_6$, 400 MHz) δ 8.64-8.67 (m, 1H), 8.28-8.29 (m, 1H), 8.16 (s, 1H), 7.40-7.41 (d, J = 4.4 Hz, 1H), 7.30-7.32 (m, 4H), 7.17-7.20 (m, 2H), 6.88 (d, J = 4.8 Hz, 1H), 4.51-4.55 (t, J = 7.2 Hz, 2H), 3.14-3.18 (t, J = 7.2 Hz, 2H). |

TABLE F-continued

| Example | Structure | LCMS | 1H NMR |
| --- | --- | --- | --- |
| T49 | 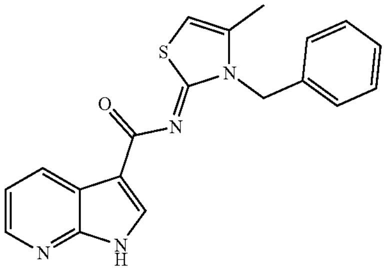 | 349.1 | (DMSO-$d_6$, 400 MHz) δ 12.68 (brs, 1H), 8.70 (d, J = 8.0 Hz, 1H), 8.34-8.36 (m, 1H), 8.22 (s, 1H), 7.26-7.36 (m, 6H), 6.71 (s, 1H), 5.63 (s, 2H), 2.22 (s, 3H). |
| T55 | 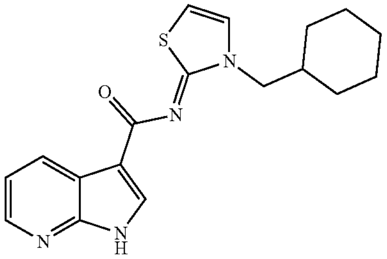 [SMILES: O=C(/N=c1\sccn1CC1CCCCC1)c1c[nH]c2ncccc12] | 341.1 | (DMSO-$d_6$, 400 MHz) δ 12.59 (br s, 1H), 8.85-8.78 (m, 1H), 8.38 (dd, J = 1.3, 4.9 Hz, 1H), 8.24 (s, 1H), 7.54 (d, J = 4.6 Hz, 1H), 7.37 (dd, J = 4.9, 7.9 Hz, 1H), 7.01 (d, J = 4.6 Hz, 1H), 4.20 (br d, J = 7.3 Hz, 2H), 2.02 (br d, J = 7.4 Hz, 1H), 1.79-1.55 (m, 5H), 1.29-1.01 (m, 5H). |
| T56 | 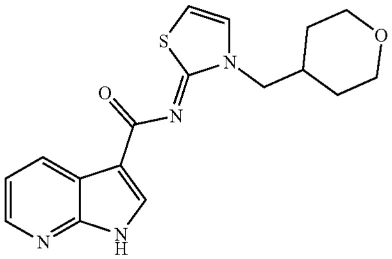 [SMILES: O=C(/N=c1\sccn1CC1CCOCC1)c1c[nH]c2ncccc12] | 343.0 | (DMSO-$d_6$, 400 MHz) δ 8.62 (dd, J = 1.6, 7.9 Hz, 1H), 8.28 (dd, J = 1.5, 4.6 Hz, 1H), 8.17 (s, 1H), 7.50 (d, J = 4.8 Hz, 1H), 7.21 (dd, J = 4.6, 7.9 Hz, 1H), 6.95 (d, J = 4.6 Hz, 1H), 4.22 (d, J = 7.3 Hz, 2H), 3.85 (br dd, J = 2.3, 11.5 Hz, 2H), 3.27 (br s, 1H), 3.26-3.20 (m, 1H), 2.26 (ddd, J = 4.0, 7.3, 11.2 Hz, 1H), 1.54-1.45 (m, 2H), 1.44-1.32 (m, 2H). |
| T58 | 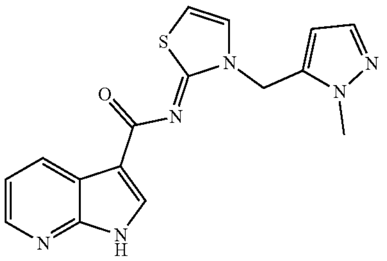 [SMILES: Cn1nccc1Cn1ccs/c1=N\C(=O)c1c[nH]c2ncccc12] | 339.1 | (DMSO-$d_6$, 400 MHz) δ 12.22 (br s, 1H), 8.58 (dd, J = 1.6, 7.8 Hz, 1H), 8.30-8.26 (m, 2H), 7.46 (d, J = 4.8 Hz, 1H), 7.36 (d, J = 1.9 Hz, 1H), 7.20 (dd, J = 4.7, 7.8 Hz, 1H), 6.98 (d, J = 4.8 Hz, 1H), 6.29 (d, J = 1.8 Hz, 1H), 5.65 (s, 2H), 3.92 (s, 3H). |
| T59 | 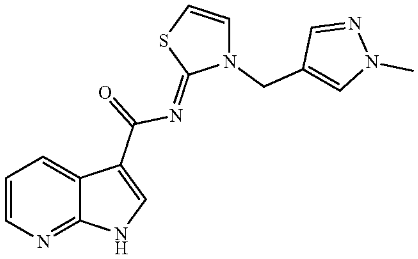 [SMILES: Cn1cc(Cn2ccs/c2=N\C(=O)c2c[nH]c3ncccc23)cn1] | 339.0 | (METHANOL-$d_4$, 400 MHz) δ 9.39 (dd, J = 1.1, 8.0 Hz, 1H), 8.57-8.49 (m, 2H), 7.83 (s, 1H), 7.75 (dd, J = 5.9, 7.9 Hz, 1H), 7.72-7.70 (m, 1H), 7.51 (d, J = 4.8 Hz, 1H), 7.04 (d, J = 4.6 Hz, 1H), 5.53 (s, 2H), 3.88 (s, 3H). |
| T60 | 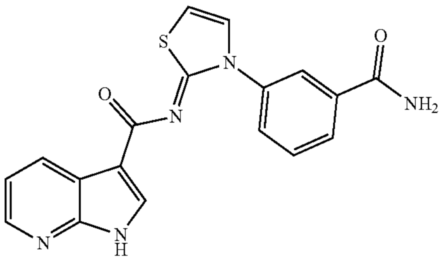 [SMILES: NC(=O)c1cccc(-n2ccs/c2=N\C(=O)c2c[nH]c3ncccc23)c1] | 364.1 | (DMSO-$d_6$, 400 MHz) δ 12.16 (br s, 1H), 8.27 (s, 1H), 8.21 (d, J = 6.1 Hz, 2H), 8.14 (br s, 1H), 8.06 (d, J = 7.8 Hz, 1H), 7.97 (s, 1H), 7.87 (br d, J = 8.0 Hz, 1H), 7.77-7.71 (m, 2H), 7.54 (br s, 1H), 7.14 (d, J = 4.8 Hz, 1H), 7.02-6.98 (m, 1H). |

TABLE F-continued
| Example | Structure | LCMS | 1H NMR |
|---|---|---|---|
| T65 | 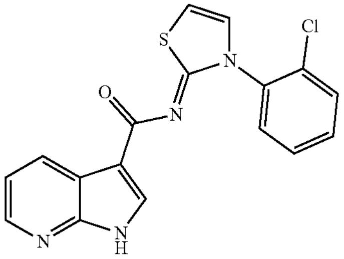 [SMILES: O=C(/N=c1\sccn1-c1ccccc1Cl)c1c[nH]c2ncccc12] | 355.1 | (METHANOL-$d_4$, 400 MHz) δ 8.15 (dd, J = 4.8 Hz, 1.2 Hz, 1H), 7.96-7.94 (m, 2H), 7.78 (d, J = 7.6 Hz, 1H), 7.71-7.63 (m, 3H), 7.40 (d, J = 4.8 Hz, 1H), 7.06 (d, J = 4.8 Hz, 1H), 6.90 (dd, J = 8.0 Hz, 4.8 Hz, 1H). |
| T66 | 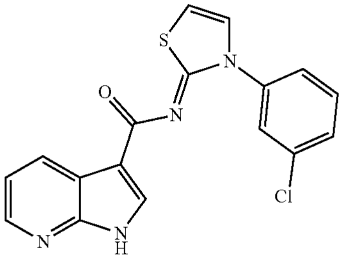 [SMILES: O=C(/N=c1\sccn1-c1cccc(Cl)c1)c1c[nH]c2ncccc12] | 355.0 | (DMSO-$d_6$, 400 MHz) δ 12.19 (br. s, 1H), 8.27-8.24 (m, 1H), 8.23-8.22 (m, 1H), 7.97-7.95 (m, 2H), 7.72 (d, J = 4.4 Hz, 1H), 7.70-7.63 (m, 3H), 7.12 (d, J = 4.8 Hz, 1H), 7.05 (dd, J = 7.6, 4.8 Hz, 1H). |
| T67 | 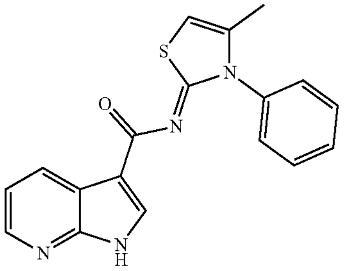 [SMILES: Cc1cs/c(=N\C(=O)c2c[nH]c3ncccc23)n1-c1ccccc1] | 355.1 | (METHANOL-$d_4$, 400 MHz) δ 8.12 (dd, J = 3.2 Hz, 1.6 Hz, 1H), 7.92 (s, 1H), 7.84 (dd, J = 6.4 Hz, 1H), 7.72-7.69 (m, 3H), 7.47-7.45 (m, 2H), 6.87 (dd, J = 4.8 Hz, 3.2 Hz, 1H), 6.68 (d, J = 1.2 Hz, 1H), 2.10 (d, J = 1.2 Hz, 3H). |
| T68 | 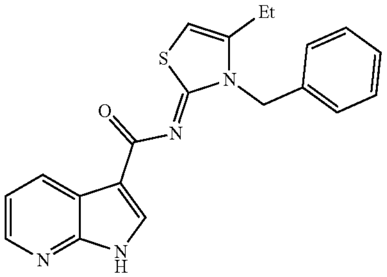 [SMILES: CCc1cs/c(=N\C(=O)c2c[nH]c3ncccc23)n1Cc1ccccc1] | 363.2 | (METHANOL-$d_4$, 400 MHz) δ 8.79 (d, J = 7.2 Hz, 1H), 8.30 (d, J = 5.2 Hz, 1H), 8.18 (s, 1H), 7.38-7.35 (m, 2H), 7.33-7.29 (m, 2H), 7.26-7.24 (m, 2H), 6.66 (s, 1H), 5.71 (s, 2H), 2.68-2.62 (m, 2H), 1.27 (t, J = 7.2 Hz, 3H). |
| T69 | 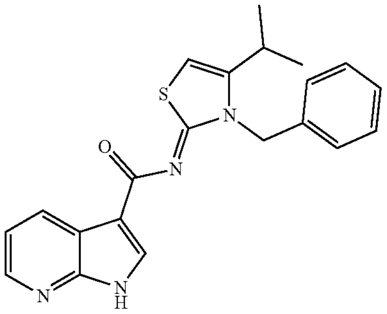 [SMILES: CC(C)c1cs/c(=N\C(=O)c2c[nH]c3ncccc23)n1Cc1ccccc1] | 377.1 | (METHANOL-$d_4$, 400 MHz) δ 8.47 (dd, J = 1.6, 8.0 Hz, 1H), 8.18 (dd, J = 3.2, 4.8 Hz, 1H), 8.06 (s, 1H), 7.40-7.33 (m, 2H), 7.32-7.21 (m, 3H), 7.11-7.06 (m, 1H), 6.66 (s, 1H), 5.74 (s, 2H), 3.07-2.97 (m, 1H), 1.23 (d, J = 6.8 Hz, 6H). |

TABLE F-continued
| Example | Structure | LCMS | 1H NMR |
|---|---|---|---|
| T70 | 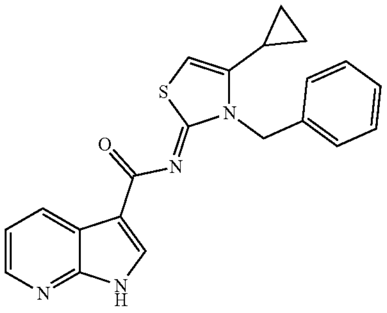 [SMILES: O=C(/N=c1\scc(C2CC2)n1Cc1ccccc1)c1c[nH]c2ncccc12] | 377.1 | (METHANOL-$d_4$, 400 MHz) δ 8.53 (dd, J = 6.8, 1.2 Hz, 1H), 8.19 (dd, J = 6.8, 1.2 Hz, 1H), 8.09 (s, 1H), 7.40-7.25 (m, 5H), 7.15-7.06 (m, 1H), 6.52 (s, 1H), 5.82(s, 2H), 1.82-1.67 (m, 1H), 0.97-0.86 (m, 2H), 0.75-0.63 (m, 2H). |
| T71 | 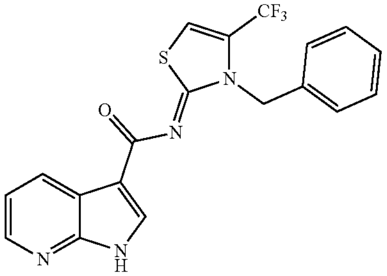 [SMILES: O=C(/N=c1\scc(C(F)(F)F)n1Cc1ccccc1)c1c[nH]c2ncccc12] | 403.1 | (METHANOL-$d_4$, 400 MHz) δ 8.43 (dd, J = 5.6, 1.6 Hz, 1H), 8.21 (dd, J = 3.6, 1.6 Hz, 1H), 8.10 (s, 1H), 7.71 (d, J = 0.8 Hz, 1H), 7.38-7.34 (m, 2H), 7.30-7.25 (m, 3H), 7.13-7.10 (m, 1H), 5.70 (s, 2H). $^{19}$F NMR ($CD_3OD$, 400 MHz) δ - 62.57 (s, 3F). |
| T73 | 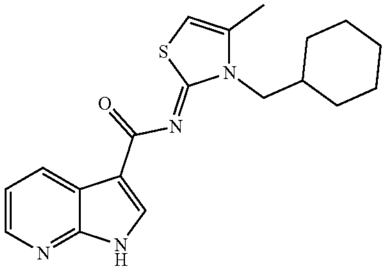 [SMILES: Cc1cs/c(=N\C(=O)c2c[nH]c3ncccc23)n1CC1CCCCC1] | 355.1 | (METHANOL-$d_4$, 400 MHz) δ 8.79 (d, J = 7.6 Hz, 1H), 8.26 (dd, J = 4.8, 1.2 Hz, 1H), 8.12 (s, 1H), 7.25-7.22 (m, 1H), 6.55 (s, 1H), 4.19-4.18 (m, 2H), 2.38 (s, 3H), 2.21-2.19 (m, 1H), 1.77-1.70 (m, 5H), 1.24-1.22 (m, 5H). |
| T74 | 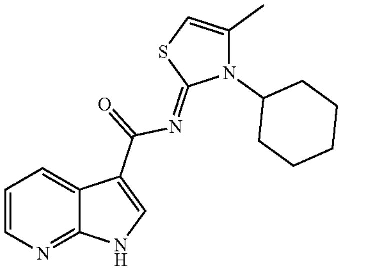 [SMILES: Cc1cs/c(=N\C(=O)c2c[nH]c3ncccc23)n1C1CCCCC1] | 341.3 | (METHANOL-$d_4$, 400 MHz) δ 8.86-8.76 (m, 1H), 8.31-8.24 (m, 1H), 8.10 (s, 1H), 7.30-7.21 (m, 1H), 6.50 (s, 1H), 4.26-4.22 (m, 1H), 2.99-3.34 (m, 2H), 2.47 (s, 3H), 2.07-1.97 (m, 2H), 1.94-1.77 (m, 3H), 1.62-1.43 (m, 3H). |
| T76 | 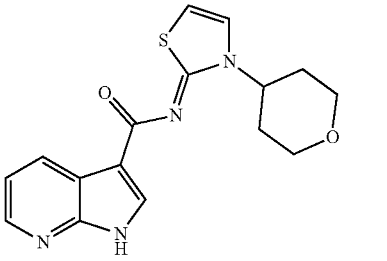 | 329.0 | (METHANOL-$d_4$, 400 MHz) δ 9.36 (d, J = 8.0 Hz, 1H), 8.51 (d, J = 6.0 Hz, 1H), 8.46 (s, 1H), 7.76 (t, J = 5.6 Hz, 1H), 7.64 (d, J = 4.8 Hz, 1H), 7.06 (d, J = 4.8 Hz, 1H), 5.34-5.33 (m, 1H), 4.16 (dd, J = 4.4, 11.6 Hz, 2H), 3.77-3.71 (m, 1H), 2.21-2.03 (m, 4H). |

TABLE F-continued

| Example | Structure | LCMS | 1H NMR |
|---|---|---|---|
| T81 | 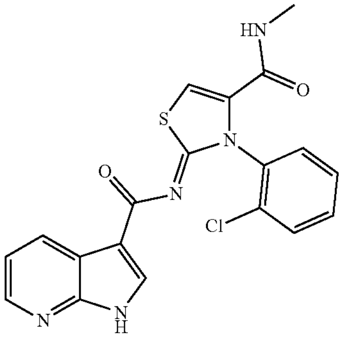 [SMILES: CNC(=O)c1cs/c(=N\C(=O)c2c[nH]c3ncccc23)n1-c1ccccc1Cl] | 411.9 | (DMSO-$d_6$, 400 MHz) δ 12.18 (br. s, 1H), 8.72-8.70 (m, 1H), 8.17 (dd, J = 1.6, 4.8 Hz, 1H), 7.89 (s, 1H), 7.71 (d, J = 7.2 Hz, 1H), 7.64-7.56 (m, 5H), 6.89-6.85 (m, 1H), 2.62 (d, J = 4.4 Hz, 3H). |
| T82 | 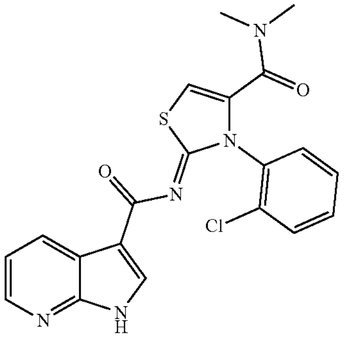 [SMILES: CN(C)C(=O)c1cs/c(=N\C(=O)c2c[nH]c3ncccc23)n1-c1ccccc1Cl] | 426.1 | (DMSO-$d_6$, 400 MHz) δ 12.18 (br. s, J = 2.6 Hz, 1H), 8.17 (dd, J = 1.6, 4.4 Hz, 1H), 7.89 (s, 1H), 7.75-7.70 (m, 2H), 7.66-7.61 (m, 2H), 7.59-7.55 (m, 1H), 7.40 (s, 1H), 6.89 (dd, J = 4.8, 8.0 Hz, 1H), 3.16 (s, 3H), 2.82 (s, 3H). |

Preparation of additional examples in Table G is shown in Scheme 55-71.

TABLE G

| Example | Structure | LCMS | 1H NMR |
|---|---|---|---|
| T37 | 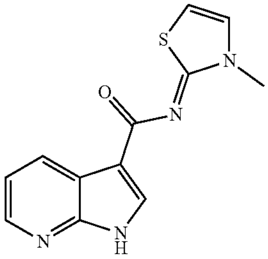 [SMILES: Cn1ccs/c1=N\C(=O)c1c[nH]c2ncccc12] | 259.0 | (DMSO-$d_6$, 400 MHz) δ 12.89 (br s, 1H), 8.91 (br d, J = 7.9 Hz, 1H), 8.45-8.33 (m, 2H), 7.59 (d, J = 4.4 Hz, 1H), 7.44 (br dd, J = 5.4, 6.7 Hz, 1H), 7.07 (br d, J = 4.0 Hz, 1H), 3.88 (s, 3H). |
| T38 | 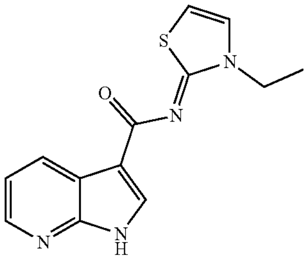 [SMILES: CCn1ccs/c1=N\C(=O)c1c[nH]c2ncccc12] | 273.1 | (DMSO-$d_6$, 400 MHz) δ 12.90 (br s, 1H), 8.89 (br d, J = 7.9 Hz, 1H), 8.42 (br d, J = 5.1 Hz, 1H), 8.31 (s, 1H), 7.62 (d, J = 4.6 Hz, 1H), 7.45 (dd, J = 5.2, 7.8 Hz, 1H), 7.05 (d, J = 4.6 Hz, 1H), 4.38 (q, J = 7.0 Hz, 2H), 1.40 (t, J = 7.2 Hz, 3H). |

TABLE G-continued

| Example | Structure | LCMS | 1H NMR |
|---|---|---|---|
| T39 | 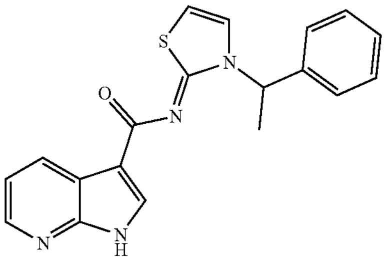 [SMILES: CC(c1ccccc1)n1ccs/c1=N\C(=O)c1c[nH]c2ncccc12] | 349.1 | ($DMSO-d_6$, 400 MHz) δ 12.81 (brs, 1H), 8.83 (d, J = 7.6 Hz, 1H), 8.41 (d, J = 4.8 Hz, 1H), 8.34 (s, 1H), 7.72 (d, J = 4.8 Hz, 1H), 7.39-7.45 (m, 5H), 7.38 (d, J = 7.6 Hz, 1H), 7.05 (d, J = 4.8 Hz, 1H), 6.51 (d, J = 7.2 Hz, 1H), 1.9 (d, J = 7.2 Hz, 3H). |
| T41 | 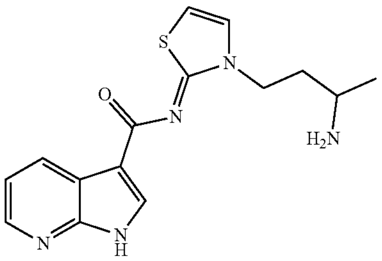 [SMILES: CC(N)CCn1ccs/c1=N\C(=O)c1c[nH]c2ncccc12] | 316.1 | (400 MHz, $D_2O-d_2$) δ 9.02 (d, J = 8.0 Hz, 1H), 8.35 (d, J = 5.9 Hz, 1H), 8.27 (s, 1H), 7.60 (dd, J = 5.9, 8.0 Hz, 1H), 7.38 (d, J = 4.8 Hz, 1H), 7.01 (d, J = 4.6 Hz, 1H), 4.48-4.35 (m, 2H), 3.35-3.24 (m, 1H), 2.27-2.07 (m, 2H), 1.32 (d, J = 6.6 Hz, 3H). |
| T42 | 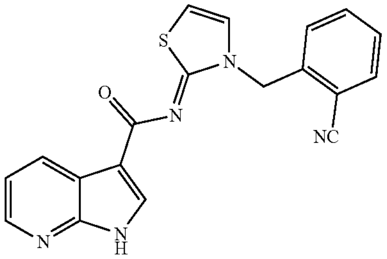 [SMILES: N#Cc1ccccc1Cn1ccs/c1=N\C(=O)c1c[nH]c2ncccc12] | 360.1 | ($DMSO-d_6$, 400 MHz) δ 12.41 (brs, 1H), 8.48 (m, 1H), 8.30 (m, 1H), 8.21 (s, 1H), 7.96 (m, 1H), 7.66-7.69 (m, 2H), 7.52 (m, 1H), 7.20-7.21 (m, 2H), 7.09 d, J = 4.8 Hz, 1H), 5.74 (s, 2H). |
| T43 | 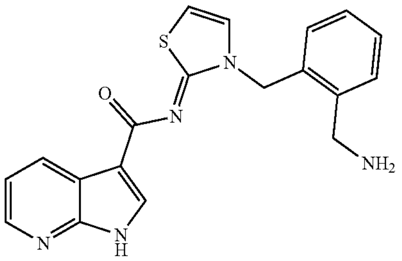 [SMILES: NCc1ccccc1Cn1ccs/c1=N\C(=O)c1c[nH]c2ncccc12] | 364.1 | ($DMSO-d_6$, 400 MHz) δ 12.82 (brs, 1H), 8.70-8.75 (m, 4H), 8.37-8.39 (m, 2H), 7.59 (s, 1H), 7.51 (d, J = 4.8 Hz, 1H), 7.36-7.40 (m, 3H), 7.09 (d, J = 4.8 Hz, 1H), 7.00 (s, 1H), 5.81 (s, 2H), 4.27 (s, 2H). |
| T44 | 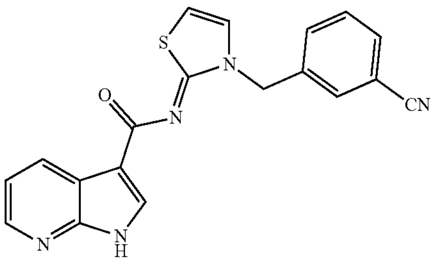 [SMILES: N#Cc1cccc(Cn2ccs/c2=N\C(=O)c2c[nH]c3ncccc23)c1] | 360.0 | ($DMSO-d_6$, 400 MHz) δ 12.22 (br s, 1H), 8.49 (dd, J = 1.5, 7.9 Hz, 1H), 8.26 (dd, J = 1.5, 4.6 Hz, 1H), 8.23 (d, J = 1.6 Hz, 1H), 7.94 (s, 1H), 7.78 (d, J = 7.6 Hz, 1H), 7.72 (d, J = 8.0 Hz, 1H), 7.66 (d, J = 4.8 Hz, 1H), 7.61-7.55 (m, 1H), 7.16 (dd, J = 4.6, 7.9 Hz, 1H), 7.00 (d, J = 4.6 Hz, 1H), 5.57 (s, 2H). |
| T45 | 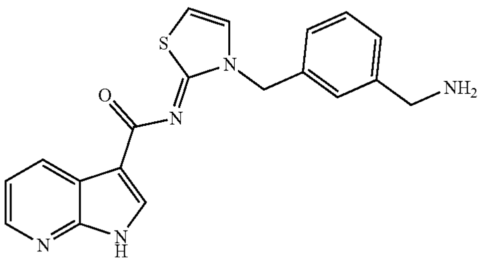 [SMILES: NCc1cccc(Cn2ccs/c2=N\C(=O)c2c[nH]c3ncccc23)c1] | 364.0 | ($DMSO-d_6$, 400 MHz) δ 12.68 (br s, 1H), 8.74 (dd, J = 1.2, 7.8 Hz, 1H), 8.46 (br s, 3H), 8.36 (dd, J = 1.3, 5.0 Hz, 1H), 8.28 (d, J = 1.6 Hz, 1H), 7.62 (d, J = 4.6 Hz, 1H), 7.54 (s, 1H), 7.48-7.40 (m, 3H), 7.35 (dd, J = 5.0, 7.9 Hz, 1H), 7.03 (d, J = 4.6 Hz, 1H), 5.56 (s, 2H), 3.98 (q, J = 5.6 Hz, 2H). |

TABLE G-continued

| Example | Structure | LCMS | 1H NMR |
|---|---|---|---|
| T46 | 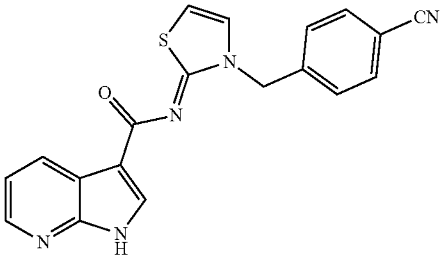 [SMILES: N#Cc1ccc(Cn2ccs/c2=N\C(=O)c2c[nH]c3ncccc23)cc1] | 360.6 | (DMSO-$d_6$, 400 MHz) δ 12.20 (br s, 1H), 8.44 (d, J = 7.9 Hz, 1H), 8.25 (dd, J = 1.5, 4.6 Hz, 1H), 8.17 (s, 1H), 7.85 (d, J = 8.2 Hz, 2H), 7.64 (d, J = 4.6 Hz, 1H), 7.56 (d, J = 8.2 Hz, 2H), 7.15 (dd, J = 4.7, 7.8 Hz, 1H), 7.01 (d, J = 4.6 Hz, 1H), 5.62 (s, 2H). |
| T47 | 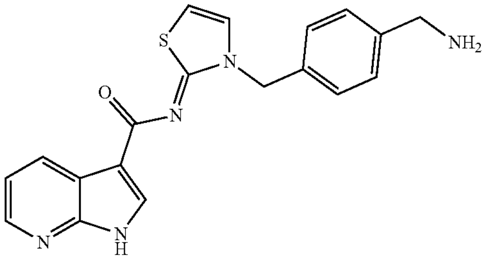 [SMILES: NCc1ccc(Cn2ccs/c2=N\C(=O)c2c[nH]c3ncccc23)cc1] | 364.0 | (DMSO-$d_6$, 400 MHz) δ 12.44 (br s, 1H), 8.66 (dd, J = 1.5, 7.9 Hz, 1H), 8.32 (br dd, J = 1.5, 4.9 Hz, 4H), 8.24 (d, J = 2.3 Hz, 1H), 7.65 (d, J = 4.6 Hz, 1H), 7.50-7.43 (m, 4H), 7.27 (dd, J = 4.9, 7.9 Hz, 1H), 7.00 (d, J = 4.8 Hz, 1H), 5.55 (s, 2H), 3.96 (q, J = 5.8 Hz, 2H). |
| T48 | 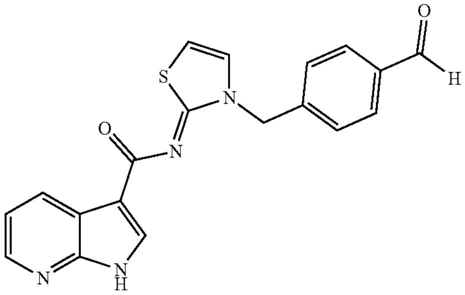 [SMILES: O=Cc1ccc(Cn2ccs/c2=N\C(=O)c2c[nH]c3ncccc23)cc1] | 363.0 | (DMSO-$d_6$, 400 MHz) δ 12.31 (br s, 1H), 9.96 (s, 1H), 8.53 (dd, J = 1.5, 7.9 Hz, 1H), 8.28 (dd, J = 1.6, 4.8 Hz, 1H), 8.19 (d, J = 2.5 Hz, 1H), 7.91 (d, J = 8.1 Hz, 2H), 7.65 (d, J = 4.8 Hz, 1H), 7.58 (d, J = 8.1 Hz, 2H), 7.19 (dd, J = 4.9, 7.9 Hz, 1H), 7.03 (d, J = 4.6 Hz, 1H), 5.64 (s, 2H). |
| T51 | 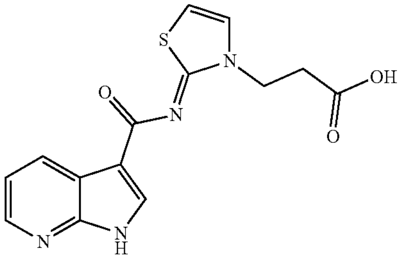 [SMILES: O=C(O)CCn1ccs/c1=N\C(=O)c1c[nH]c2ncccc12] | 315.0 | (DMSO-$d_6$, 400 MHz) δ 8.83 (s, 1H), 8.55-8.57 (m, 1H), 8.40-8.41 (m, 1H), 7.55 (d, J = 3.6 Hz, 1H), 7.32-7.35 (m, 1H), 7.24 (d, J = 3.6 Hz, 1H), 4.53-4.56 (t, J = 6.8 Hz, 2H), 2.92-2.95 (t, J = 6.8 Hz, 2 H). |
| T52 | 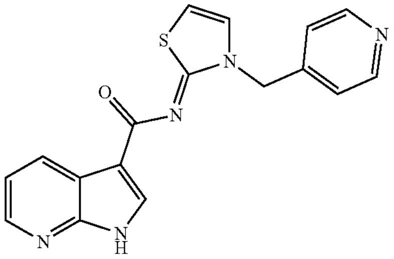 [SMILES: O=C(/N=c1\sccn1Cc1ccncc1)c1c[nH]c2ncccc12] | 336.0 | (DMSO-$d_6$, 400 MHz) δ 12.55 (br s, 1H), 8.89 (d, J = 6.25 Hz, 2H), 8.50 (d, J = 7.75 Hz, 1H), 8.32 (d, J = 4.63 Hz, 1H), 8.16 (s, 1H), 7.92 (d, J = 6.25 Hz, 2H), 7.72 (d, J = 4.75 Hz, 1H), 7.26 (dd, J = 7.82, 4.94 Hz, 1H), 7.11 (d, J = 4.63 Hz, 1H), 5.86 (s, 2H). |

TABLE G-continued

| Example | Structure | LCMS | 1H NMR |
|---|---|---|---|
| T53 | 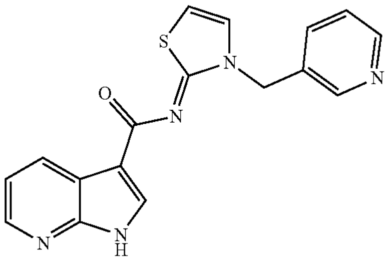 [SMILES: O=C(/N=c1\sccn1Cc1cccnc1)c1c[nH]c2ncccc12] | 336.0 | (DMSO-$d_6$, 400 MHz) δ 12.51 (br s, 1H), 9.06 (s, 1H), 8.81 (d, J = 5.38 Hz, 1H), 8.59 (d, J = 7.63 Hz, 1H), 8.49 (br d, 8.13 Hz, 1H), 8.34 (s, 1H), 8.32 (d, J = 5.03 Hz, 1H), 7.96 (dd, J = 8.00, 5.63 Hz, 1H), 7.75 (d, J = 4.63 Hz, 1H), 7.26 (dd, J = 7.82, 4.82 Hz, 1H), 7.04 (d, J = 4.75 Hz, 1H), 5.72 (s, 2H). |
| T54 | 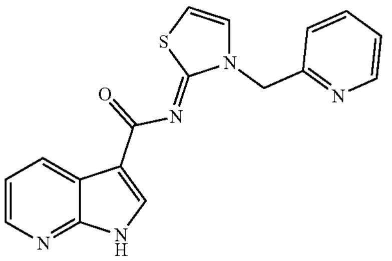 | 336.1 | (DMSO-$d_6$, 400 MHz) δ 3.07 (br s, 1H), 8.85-8.73 (m, 2H), 8.42 (d, J = 5.25 Hz, 1H), 8.38-8.26 (m, 2H), 7.82-7.73 (m, 2H), 7.64 (br d, J = 8.00 Hz, 1H), 7.45 (br dd, J = 7.50, 5.50 Hz, 1H), 7.11 (d, J = 4.63 Hz, 1H), 5.91 (s, 2H). |
| T57 | 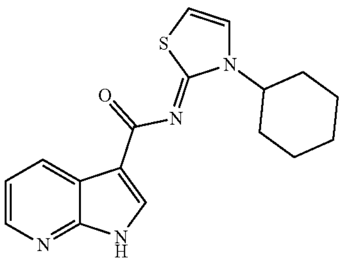 | 327.0 | (METHANOL-$d_4$, 400 MHz) δ 8.78 (d, J = 8.0 Hz, 1H), 8.27 (d, J = 4.9 Hz, 1H), 8.15 (s, 1H), 7.51 (d, J = 4.8 Hz, 1H), 7.30-7.24 (m, 1H), 6.91 (d, J = 4.8 Hz, 1H), 5.11-5.03 (m, 1H), 2.16 (br d, J = 11.3 Hz, 2H), 2.03 (br d, J = 12.5 Hz, 2H), 1.91-1.75 (m, 3H), 1.71-1.56 (m, 2H), 1.48-1.35 (m, 1H). |
| T61 | 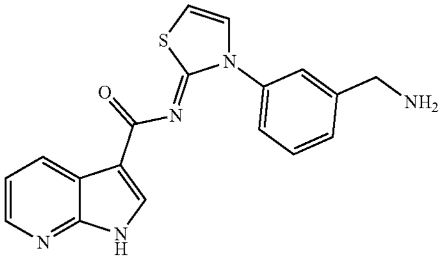 [SMILES: NCc1cccc(-n2ccs/c2=N\C(=O)c2c[nH]c3ncccc23)c1] | 350.1 | (DMSO-$d_6$, 400 MHz) δ 12.35 (br s, 1H), 8.51 (br s, 2H), 8.34 (d, J = 7.9 Hz, 1H), 8.28 (dd, J = 1.6, 4.8 Hz, 1H), 8.01 (d, J = 2.6 Hz, 1H), 7.88-7.82 (m, 2H), 7.76-7.67 (m, 3H), 7.19 (d, J = 4.9 Hz, 1H), 7.14 (dd, J = 4.9, 7.9 Hz, 1H), 4.18 (q, J = 5.7 Hz, 2H). |
| T62 | 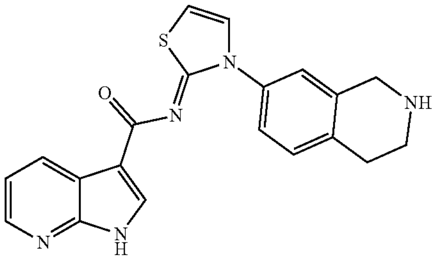 [SMILES: O=C(/N=c1\sccn1-c1ccc2c(c1)CNCC2)c1c[nH]c2ncccc12] | 376.1 | (DMSO-$d_6$, 400 MHz) δ 12.44 (br s, 1H), 9.74 (br s, 2H), 8.37 (d, J = 7.6 Hz, 1H), 8.29 (d, J = 4.5 Hz, 1H), 8.00 (d, J = 1.5 Hz, 1H), 7.68-7.60 (m, 3H), 7.51 (d, J = 8.2 Hz, 1H), 7.25 (dd, J = 4.9, 7.8 Hz, 1H), 7.14 (d, J = 4.8 Hz, 1H), 4.34 (br s, 2H), 3.46 (br d, 4.0 Hz, 2H), 3.17 (br t, J = 5.9 Hz, 2H). |
| T64 | 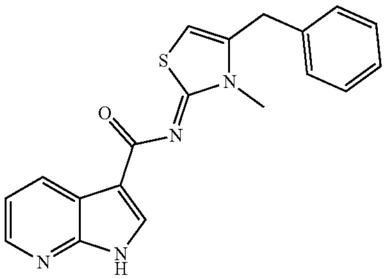 [SMILES: Cn1c(Cc2ccccc2)cs/c1=N\C(=O)c1c[nH]c2ncccc12] | 349.0 | (DMSO-$d_6$, 400 MHz) δ 12.67 (br s, 1H), 8.82 (br d, J = 7.82 Hz, 1H), 8.37 (br d, J = 4.77 Hz, 1H), 8.29 (s, 1H), 7.43-7.33(m, 3H), 7.32-7.25(m, 3H), 6.54 (s, 1H), 4.13 (s, 2H), 3.72-3.71 (m, 3H). |

TABLE G-continued
| Example | Structure | LCMS | 1H NMR |
| --- | --- | --- | --- |
| T72 | 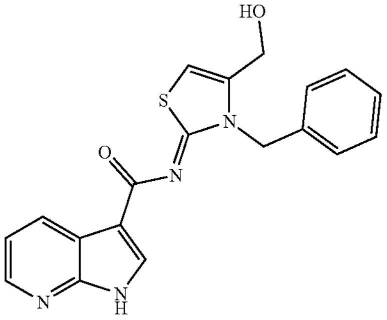 | 365.1 | ($DMSO-d_6$, 400 MHz) δ 12.15 (br. s, 1H), 8.43 (dd, J = 7.6, 1.6 Hz, 1H), 8.22 (dd, J = 5.6, 1.6 Hz, 1H), 8.11 (s, 1H), 7.37-7.33 (m, 2H), 7.29-7.24 (m, 3H), 7.13-7.09 (m, 1H), 6.85 (s, 1H), 5.64 (s, 3H), 4.42 (s, 2H). |
| T75 | 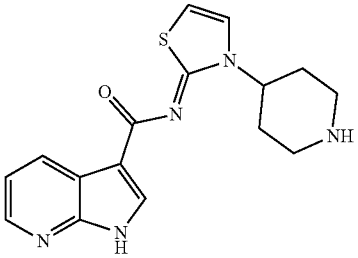 [SMILES: O=C(/N=c1\sccn1C1CCNCC1)c1c[nH]c2ncccc12] | 328.1 | ($DMSO-d_6$, 400 MHz) δ 9.30-9.32 (m, 1H), 8.59 (s, 1H), 8.51-8.52 (m, 1H), 7.73-7.76 (m, 1H), 7.53 (d, J = 4.8 Hz, 1H), 7.06 (d, J = 4.8 Hz, 1H), 5.41-5.45 (m, 1H), 3.66-3.69 (m, 2H), 3.45-3.46 (m, 2H), 2.30-2.44 (m, 4 H) |
| T77 | 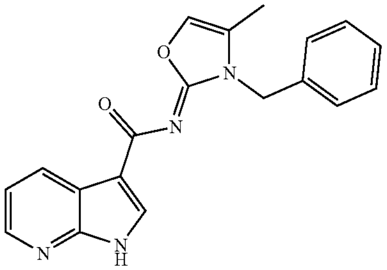 [SMILES: Cc1co/c(=N\C(=O)c2c[nH]c3ncccc23)n1Cc1ccccc1] | 333.1 | ($METHANOL-d_4$, 400 MHz) δ 8.53 (dd, J = 8.0, 1.6 Hz, 1H), 8.20 (dd, J = 4.8, 1.6 Hz, 1H), 8.07 (s, 1H), 7.40-7.32 (m, 6H), 7.11 (dd, J = 7.6, 4.4 Hz, 1H), 5.22 (s, 2H), 2.10 (d, J = 1.2 Hz, 3H). |
| T78 | 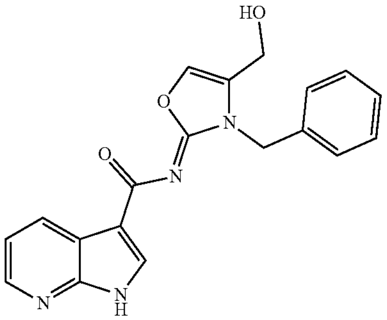 | 349.0 | ($DMSO-d_6$, 400 MHz) δ 12.24 (br. s, 1H), 8.63 (d, J = 7.6 Hz, 1H), 8.27 (d, J = 5.6 Hz, 1H), 8.00 (s, 1H), 7.69 (s, 1H), 7.39-7.38 (m, 4H), 7.34-7.27 (m, 2H), 5.29 (br. t, J = 5.2 Hz, 1H), 5.19 (s, 2H), 4.36 (d, J = 4.4 Hz, 2H). |
| T79 | 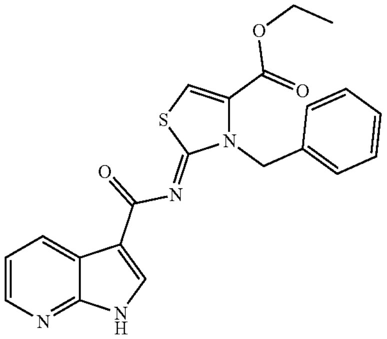 [SMILES: CCOC(=O)c1cs/c(=N\C(=O)c2c[nH]c3ncccc23)n1Cc1ccccc1] | 407.1 | ($DMSO-d_6$, 400 MHz) δ 12.27 (br. s, 1H), 8.44-8.42 (m, 1H), 8.26-8.25 (m, 1H), 8.20 (d, J = 2.4 Hz, 1H), 7.98 (s, 1H), 7.34-7.31 (m, 2H), 7.26-7.24 (m, 3H), 7.16-7.12 (m, 1H), 5.93 (s, 2H), 4.26 (q, J = 7.2 Hz, 2H), 1.24 (t, J = 7.2 Hz, 3H). |

TABLE G-continued

| Example | Structure | LCMS | 1H NMR |
|---|---|---|---|
| T80 | 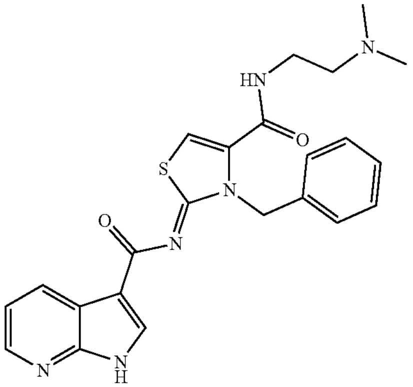 [SMILES: CN(C)CCNC(=O)c1cs/c(=N\C(=O)c2c[nH]c3ncccc23)n1Cc1ccccc1] | 449.2 | (DMSO-$d_6$, 400 MHz) δ 12.25 (br. s, 1H), 8.76 (t, J = 5.6 Hz, 1H), 8.51 (dd, J = 1.6, 7.6 Hz, 1H), 8.27 (dd, J = 1.6, 4.4 Hz, 1H), 8.24 (s, 1H), 7.37 (s, 1H), 7.31 (d, J = 4.4 Hz, 4H), 7.27-7.22 (m, 1H), 7.19-7.15 (m, 1H), 5.88 (s, 2H), 3.29-3.24 (m, 2H), 2.30 (t, J = 6.8 Hz, 2H), 2.14 (s, 6H). |

Preparation of Examples T37, T38

Scheme 55

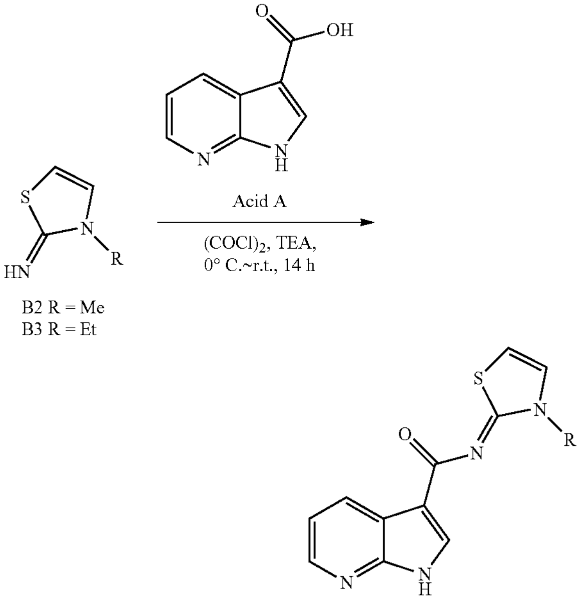

T37 R = Me
T38 R = Et

Example T37

To a solution of 1H-pyrrolo[2, 3-b]pyridine-3-carboxylic acid A (199 mg, 1.23 mmol, 1.0 eq) in DCM (10 mL) was added oxalyl chloride $(COCl)_2$ (156 mg, 1.23 mmol, 107 μL, 1.0 eq) and DMF (1 μL, 12.3 μmol, 0.01 eq) at 0° C. The reaction mixture was stirred at 15° C. for 2 hours, and then TEA (187 mg, 1.84 mmol, 1.5 eq) and 3-methylthiazol-2-imine B2 (140 mg, 1.23 mmol, 1.0 eq) was added. The resulting mixture was stirred at 15° C. for 12 hours. The reaction mixture was quenched by addition $H_2O$ (20 mL), and extracted with EtOAc (3x15 mL). The combined organic layers were washed with brine (3x10 mL), dried over anhydrous $Na_2SO_4$, filtered and concentrated under reduced pressure. The residue was purified by prep-HPLC to give 21 mg of (Z)—N-(3-methylthiazol-2(3H)-ylidene)-1H-pyrrolo[2,3-b]pyridine-3-carboxamide T37 as a white solid.

Example T38

To a solution of 1H-pyrrolo[2,3-b]pyridine-3-carboxylic acid A (379 mg, 2.34 mmol, 1.0 eq) in DCM (10 mL) was added oxalyl chloride $(COCl)_2$ (297 mg, 2.34 mmol, 1.0 eq) and DMF (2 μL, 23.4 μmol, 0.01 eq) at 0° C. The reaction mixture was stirred at 15° C. for 2 hours, and then TEA (355 mg, 3.51 mmol, 1.5 eq) and 3-ethylthiazol-2-imine B3 (300 mg, 2.34 mmol, 1.0 eq) was added. The resulting was stirred at 15° C. for 12 hours. The reaction mixture was quenched by addition water (30 mL) and extracted with EtOAc (3x20 mL). The combined organic layers were washed with brine (2x20 mL), dried over anhydrous $Na_2SO_4$, filtered and concentrated under reduced pressure. The residue was purified by prep-HPLC to afford 24 mg of (Z)—N-(3-ethylthiazol-2(3H)-ylidene)-1H-pyrrolo[2,3-b]pyridine-3-carboxamide T38 as a white solid.

Preparation of Example T39

Scheme 56

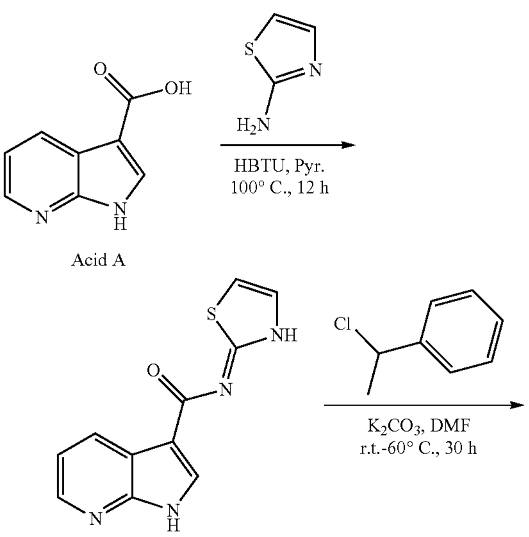

-continued

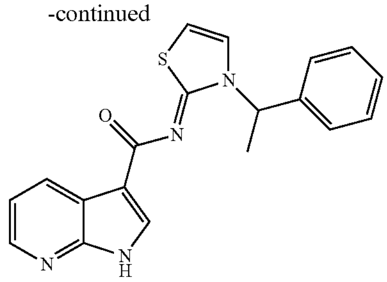

T39

(Z)—N-(Thiazol-2(3H)-ylidene)-1H-pyrrolo[2,3-b] pyridine-3-carboxamide

To a solution of 1H-pyrrolo[2,3-b]pyridine-3-carboxylic acid A (0.60 g, 3.70 mmol, 1.0 eq) in pyridine (5.88 g, 74.3 mmol, 20 eq) was added HBTU (2.81 g, 7.40 mmol, 2.0 eq) and thiazol-2-amine (556 mg, 5.55 mmol, 1.5 eq). The reaction mixture was heated to 100° C. and stirred at 100° C. for 12 hours. The reaction mixture was cooled to 0° C. and poured into ice-water (15 mL). The solid was collected by filtration. The filter cake was washed with water (2×5 mL), dried under reduced pressure to afford a crude product. The crude product was re-crystallized in MeOH/EtOH (4 mL/4 mL) by refluxing at 60° C. for 0.5 hour and then cooled to 25° C. and filtered. The solid was washed with cooled EtOH (5 mL), dried in vacuum to afford 0.41 g of (Z)—N-(thiazol-2(3H)-ylidene)-1H-pyrrolo[2,3-b]pyridine-3-carboxamide as a brown solid.

(Z)—N-(3-(1-Phenylethyl)thiazol-2(3H)-ylidene)-1H-pyrrolo[2,3-b]pyridine-3-carboxamide T39

To a solution of (Z)—N-(thiazol-2(3H)-ylidene)-1H-pyrrolo[2,3-b]pyridine-3-carboxamide (0.20 g, 819 umol, 1.0 eq) in DMF (3 mL) was added $K_2CO_3$ (226 mg, 1.64 mmol, 2.0 eq) and 1-chloroethylbenzene (173 mg, 1.23 mmol, 1.5 eq). The reaction mixture was stirred at 25° C. for 12 hours. The reaction mixture was heated to 60° C. for 18 hours. The reaction mixture was cooled to room temperature and filtered to afford a yellow solution in DMF. The yellow solution was purified by prep-HPLC to afford 25 mg of (Z)—N-(3-(1-phenylethyl)thiazol-2(3H)-ylidene)-1H-pyrrolo[2,3-b]pyridine-3-carboxamide T39 as a light-yellow solid.

Preparation of of Example T41

Scheme 57

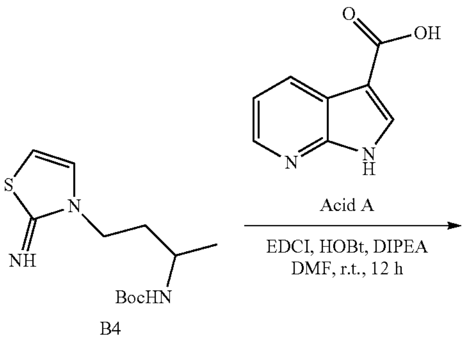

B4

-continued

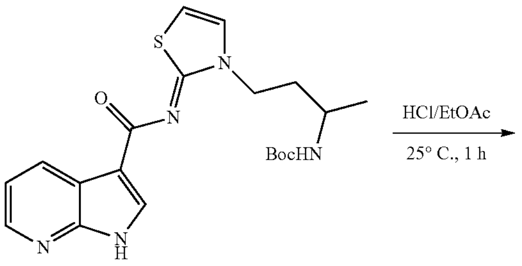

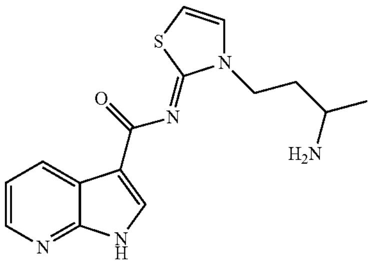

T41

(Z)-Tert-butyl (4-(2-((1H-pyrrolo[2,3-b]pyridine-3-carbonyl)imino)thiazol-3(2H)-yl)butan-2-yl)carbamate To a solution of 1H-pyrrolo[2,3-b]pyridine-3-carboxylic acid A (30 mg, 184 μmol, 1.0 eq), HOBt (37 mg, 276 μmol, 1.5 eq), EDCI (53 mg, 276 μmol, 1.5 eq) and DIPEA (71 mg, 553 μmol, 96 μL, 3.0 eq) in DMF (1 mL) was added tert-butyl (4-(2-iminothiazol-3(2H)-yl)butan-2-yl)carbamate B4 (50 mg, 184 μmol, 1.0 eq). The reaction mixture was stirred at 25° C. for 12 hours. The reaction mixture was diluted with water 20 mL and extracted with EtOAc (3×10 mL). The combined organic layers were washed with brine 20 mL, dried over $Na_2SO_4$, filtered and concentrated under reduced pressure. The residue was purified by prep-TLC on silica gel (petroleum ether/ethyl acetate) to give 40 mg of (Z)-tert-butyl (4-(2-((1H-pyrrolo[2,3-b]pyridine-3-carbonyl)imino)thiazol-3(2H)-yl)butan-2-yl)carbamate as a white solid.

(Z)—N-(3-(3-aminobutyl)thiazol-2(3H)-ylidene)-1H-pyrrolo[2,3-b]pyridine-3-carboxamide T41

A mixture (Z)-tert-butyl (4-(2-((1H-pyrrolo[2,3-b]pyridine-3-carbonyl)imino)thiazol-3(2H)-yl)butan-2-yl)carbamate (40 mg, 96 μmol, 1.0 eq) in HCl/EtOAc (4 M, 2 mL) was stirred at 25° C. for 1 h. The reaction mixture was concentrated under reduced pressure. The residue was purified by prep-HPLC to give 28 mg of (Z)—N-(3-(3-aminobutyl)thiazol-2(3H)-ylidene)-1H-pyrrolo[2,3-b] pyridine-3-carboxamide T41 as a white solid.

Preparation of of Examples T42, T43

Scheme 58

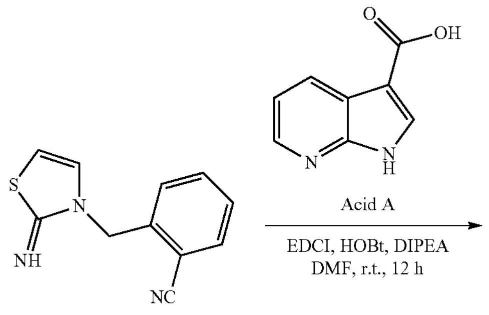

B11

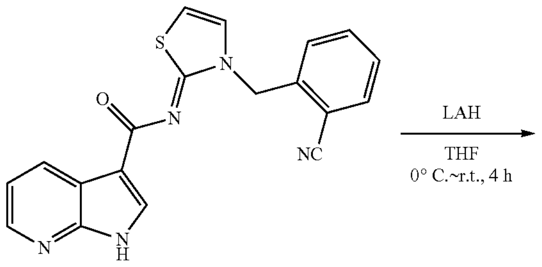

T42

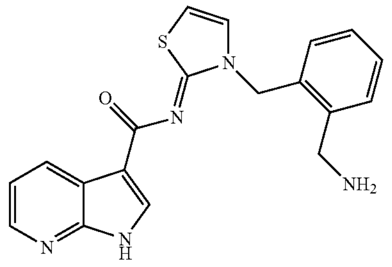

T43

(Z)—N-(3-(2-cyanobenzyl)thiazol-2(3H)-ylidene)-1H-pyrrolo[2,3-b]pyridine-3-carboxamide T42

To a solution of 1H-pyrrolo[2,3-b]pyridine-3-carboxylic acid A (369 mg, 2.28 mmol, 1.0 eq) in DMF (6 mL) was added EDCI (524 mg, 2.73 mmol, 1.2 eq), HOBt (369 mg, 2.73 mmol, 1.2 eq), TEA (691 mg, 6.83 mmol, 3.0 eq) and 2-((2-iminothiazol-3(2H)-yl)methyl)benzonitrile B11 (0.49 g, 2.28 mmol, 1.0 eq). The reaction mixture was stirred at 25° C. for 12 hours. The reaction mixture was quenched by addition of water (15 mL) at 0° C., the precipitate was collected by filtration and washed with water (2×5 mL), dried in vacuum to afford 0.60 g of crude product (Z)—N-(3-(2-cyanobenzyl)thiazol-2(3H)-ylidene)-1H-pyrrolo[2,3-b]pyridine-3-carboxamide T42 as a gray solid. 180 mg of crude product T42 was further purified by prep-HPLC to afford 92 mg of pure (Z)—N-(3-(2-cyanobenzyl)thiazol-2(3H)-ylidene)-1H-pyrrolo [2,3-b]pyridine-3-carboxamide T42 as a light-yellow solid.

(Z)—N-(3-(2-(aminomethyDbenzyl)thiazol-2(3H)-ylidene)-1H-pyrrolo[2,3-b] pyridine-3-carboxamide T43

To a solution of LAH (48 mg, 1.25 mmol, 3.0 eq) in THF (4 mL) was added (Z)—N-(3-(2-cyanobenzyl)thiazol-2 (3H)-ylidene)-1H-pyrrolo [2,3-b]pyridine-3-carboxamide T42 (0.15 g, 417 μmol, 1.0 eq) portionwise at 0° C. After addition, the reaction mixture was warmed to 25° C. slowly and stirred at 25° C. for 4 hours. The reaction mixture was quenched by addition of aqueous HCl (2N, 0.5 mL) at 0° C. and stirred for 0.5 hour. The mixture was diluted with THF/DMF (20 mL/4 mL) and filtered. The filter cake was washed with MeOH (2×5 mL). The combined filtrate was concentrated under reduced pressure. The residue was purified by prep-HPLC to afford 8.3 mg of (Z)—N-(3-(2-(aminomethyl)benzyl)thiazol-2(3H)-ylidene)-1H-pyrrolo[2,3-b]pyridine-3-carboxamide T43 as an off-white solid.

Preparation of of Examples T44, T45

Scheme 59

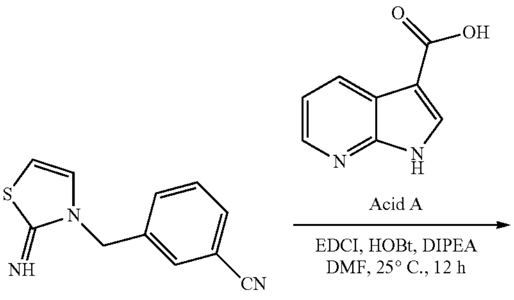

B17

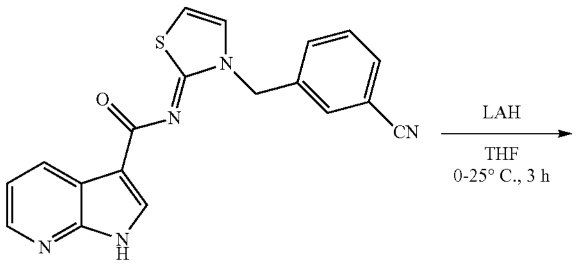

T44

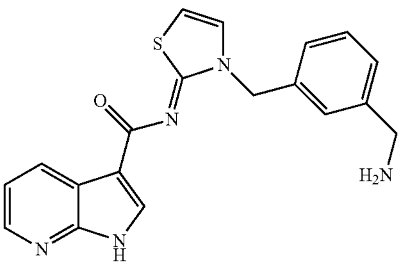

T45

(Z)—N-(3-(3-cyanobenzypthiazol-2(3H)-ylidene)-1H-pyrrolo[2,3-b]pyridine-3-carboxamide T44

To a solution of 1H-pyrrolo[2,3-b]pyridine-3-carboxylic acid A (264 mg, 1.63 mmol, 1.0 eq), HOBt (330 mg, 2.44 mmol, 1.5 eq), EDCI (468 mg, 2.44 mmol, 1.5 eq) and DIPEA (630 mg, 4.88 mmol, 850 μL, 3.0 eq) in DMF (8 mL) was added 3-((2-iminothiazol-3(2H)-yl)methyl)benzonitrile B17 (350 mg, 1.63 mmol, 1.0 eq) at 25° C. The reaction mixture was then stirred at 25° C. for 12 hr. The reaction mixture was diluted with water 50 mL and extracted with EtOAc (3×30 mL). The combined organic layers were washed with brine 50 mL, dried over $Na_2SO_4$, filtered and concentrated under reduced pressure. The residue was diluted with MeOH (20 mL) and stirred for 20 min; the suspension was filtered to collect the solid. The collected solid was washed with MeOH (10 mL) and then dried in vacuum to give 500 mg of (Z)—N-(3-(3-cyanobenzyl)thiazol-2(3H)-ylidene)-1H-pyrrolo[2,3-b]pyridine-3-carboxamide T44 as a yellow solid. 100 mg of the crude product was purified on prep-HPLC to give 62 mg of pure (Z)—N-(3-(3-cyanobenzyl)thiazol-2(3H)-ylidene)-1H-pyrrolo[2,3-b]pyridine-3-carboxamide T44 as a white solid.

(Z)—N-(3-(3-(aminomethyl)benzyl)thiazol-2(3H)-ylidene)-1H-pyrrolo[2,3-b]pyridine-3-carboxamide T45

To a suspension of (Z)—N-(3-(3-cyanobenzyl)thiazol-2(3H)-ylidene)-1H-pyrrolo[2,3-b] pyridine-3-carboxamide T44 (200 mg, 556 μmol, 1.0 eq) in THF (5 mL) was added LAH (63 mg, 1.67 mmol, 3.0 eq) at 0° C. under $N_2$. The reaction mixture was then stirred at 25° C. for 3 h. The reaction mixture was quenched by addition of water (5 mL) and acidified to pH=3 with HCl (4 N), and the mixture was turned to clear. The mixture was directly purified by prep-HPLC to give 76 mg of (Z)—N-(3-(3-(aminomethyl)benzyl)thiazol-2(3H)-ylidene)-1H-pyrrolo[2,3-b]pyridine-3-carboxamide T45 as a white solid.

Preparation of of Examples T46, T47, T48

Scheme 60

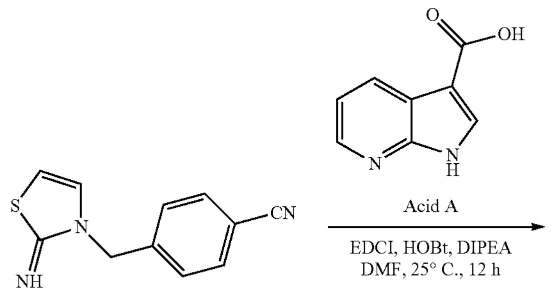

B5

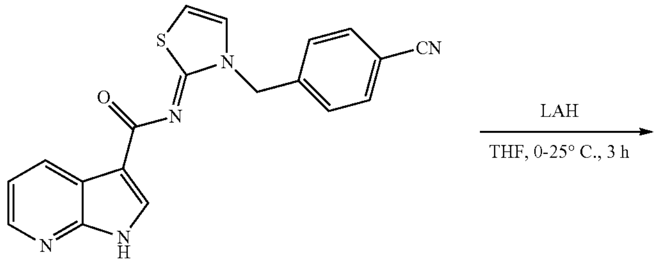

T46

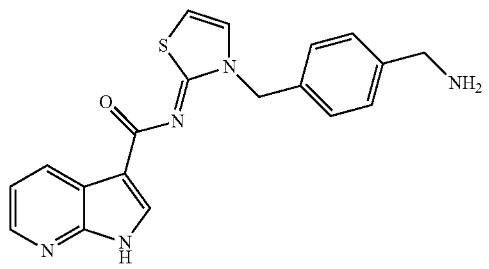

T47

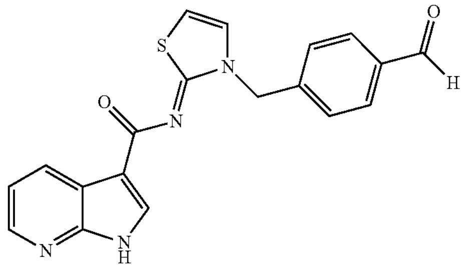

T48

(Z)—N-(3-(4-cyanobenzyl)thiazol-2(3H)-ylidene)-1H-pyrrolo[2,3-b]pyridine-3-carboxamide T46

To a solution of 1H-pyrrolo[2,3-b]pyridine-3-carboxylic acid A (1.09 g, 6.75 mmol, 1.0 eq), HOBt (1.37 g, 10.1 mmol, 1.5 eq), EDCI (1.94 g, 10.1 mmol, 1.5 eq) and DIPEA (2.62 g, 20.3 mmol, 3.5 mL, 3.0 eq) in DMF (20 mL) was added 4-((2-Iminothiazol-3(2H)-yl)methyl)benzonitrile B5 (2.00 g, 6.80 mmol, 1.0 eq) at 25° C. The reaction mixture was stirred at 25° C. for 12 hr. The reaction mixture was diluted with water 150 mL and extracted with EtOAc (3×100 mL). The combined organic layers were washed with brine 200 mL, dried over $Na_2SO_4$, filtered and concentrated under reduced pressure to give a residue. The residue was diluted with MeOH (50 mL) and stirred for 20 min; the suspension was filtered to collect the solid. The filter cake was washed with MeOH (20 mL), dried in vacuum to give 1.8 g of (Z)—N-(3-(4-cyanobenzyl)thiazol-2(3H)-ylidene)-1H-pyrrolo[2,3-b]pyridine-3-carboxamide T46 as a yellow solid. 200 mg of the crude product T46 was purified by prep-HPLC to give 132 mg of pure (Z)—N-(3-(4-cyanobenzyl)thiazol-2(3H)-ylidene)-1H-pyrrolo[2,3-b]pyridine-3-carboxamide T46 as a white solid.

(Z)—N-(3-(4-(aminomethyl)benzyl)thiazol-2(3H)-ylidene)-1H-pyrrolo[2,3-b]pyridine-3-carboxamide T47

(Z)—N-(3-(4-formylbenzyl)thiazol-2(3H)-ylidene)-1H-pyrrolo[2,3-b]pyridine-3-carboxamide T48

To a mixture of (Z)—N-(3-(4-cyanobenzyl)thiazol-2(3H)-ylidene)-1H-pyrrolo [2,3-b]pyridine-3-carboxamide T46 (300 mg, 835 μmol, 1.0 eq) in THF (7 mL) was added LAH (95 mg, 2.5 mmol, 3.0 eq) at 0° C. under $N_2$. The mixture was stirred at 25° C. for 3 h. The reaction mixture was quenched by addition of water (5 mL) and acidified to pH=3 with 4N HCl. The mixture was purified by prep-HPLC to give 108 mg of (Z)—N-(3-(4-(aminomethyl)benzyl)thiazol-2(3H)-ylidene)-1H-pyrrolo[2,3-b]pyridine-3-carboxamide T47 as a white solid and 31 mg of (Z)—N-(3-(4-formylbenzyl)thiazol-2(3H)-ylidene)-1H-pyrrolo[2,3-b]pyridine-3-carboxamide T48 as a white solid.

Preparation of Examples T54 and T64

To a solution of the appropriate imine (1.0 eq) in pyridine was added HBTU (2.0 eq) and 1H-pyrrolo[2,3-b]pyridine-3-carboxylic acid A (1.0 eq). The reaction mixture was stirred at 100° C. for 12 h. The reaction mixture was concentrated under reduced pressure. The residue was purified by prep-HPLC to giveT54 and T64.

Preparation of Example T51

Scheme 61

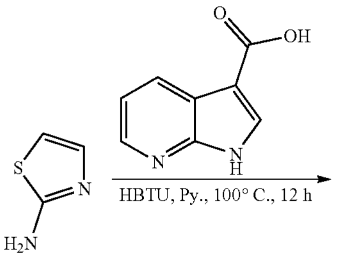

-continued

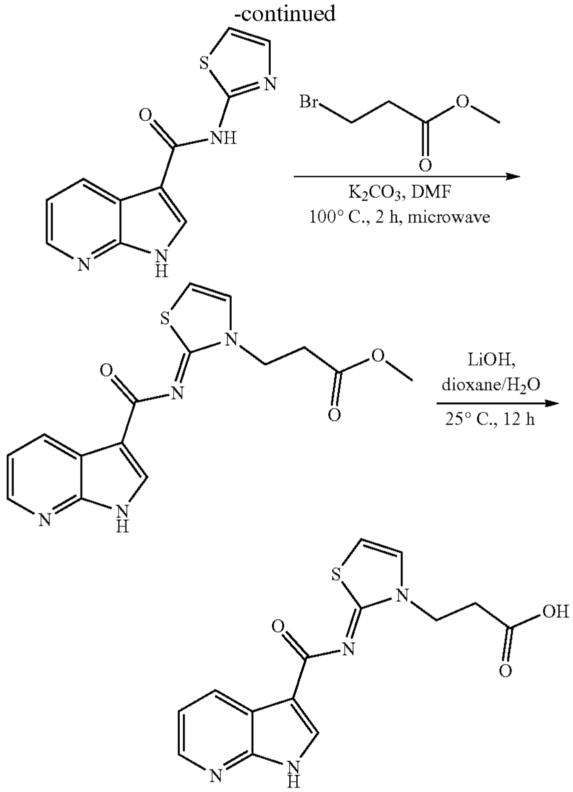

T51

N-(Thiazol-2-yl)-1H-pyrrolo[2,3-b]pyridine-3-carboxamide

To a solution of 1H-pyrrolo[2,3-b]pyridine-3-carboxylic acid A (0.60 g, 3.70 mmol, 1.0 eq) in Pyridine (6 mL) was added HBTU (2.81 g, 7.40 mmol, 2.0 eq) and 2-thiazolamine (556 mg, 5.55 mmol, 1.5 eq) at 0° C. The reaction mixture was slowly heated to 100° C. and stirred at 100° C. for 12 hours. The reaction mixture was poured into ice-water (12 mL). The solid was collected by filtration and washed with $H_2O$ (5×2 mL), dried under reduced pressure. The crude product was re-crystallized by refluxing in MeOH/EtOH (4 mL/4 mL) at 70° C. for 0.5 hour and then cooled to room temperature, filtered to afford 0.41 g of N-(thiazol-2-yl)-1H-pyrrolo[2,3-b]pyridine-3-carboxamide as a brown solid.

Methyl 3-[(2Z)-2-(1H-pyrrolo[2,3-b]pyridine-3-carbonylimino)thiazol-3-yl]propanoate To a solution of N-(thiazol-2-yl)-1H-pyrrolo[2,3-b]pyridine-3-carboxamide (0.29 g, 1.19 mmol, 1.0 eq) in DMF (5 mL) was added $K_2CO_3$ (656 mg, 4.75 mmol, 4.0 eq) and methyl 3-bromopropanoate (595 mg, 3.56 mmol, 3.0 eq). After the addition, the reaction mixture was transferred to a sealed microwave vial and stirred at 100° C. for 2 hours in a microwave reactor. The reaction mixture was quenched by addition of $H_2O$ (10 mL) at 0° C., extracted with EtOAc (2×10 mL). The combined organic layers were washed with $H_2O$ (20 mL), brine (20 mL), dried over $Na_2SO_4$ and filtered. The filtrate was concentrated under reduced pressure. The residue was purified by prep-TLC on silica gel (etroleum ether/ethyl acetate=1:1) to afford 0.30 g of methyl 3-[(2Z)-2-(1H-pyrrolo[2,3-b]pyridine-3-carbonylimino)thiazol-3-yl]propanoate as a brown solid. Part of the residue (0.10 g) was further purified by prep-TLC on silica gel (petroleum ether/ethyl acetate=2:1) twice to afford 20 mg of methyl 3-[(2Z)-2-(1H-pyrrolo[2,3-b]pyridine-3-carbonylimino)thiazol-3-yl]propanoate as a white solid.

Example T51

To a solution of (Z)-methyl 3-(2-(1H-pyrrolo[2,3-b]pyridine-3-carbonyl)imino)thiazol-3(2H)-yl)propanoate (0.20 g, 605 μmol, 1.0 eq) in dioxane (4 mL)/$H_2O$ (1 mL) was added LiOH·$H_2O$ (127 mg, 3.03 mmol, 5.0 eq). The reaction mixture was stirred at 25° C. for 12 hours. The mixture was concentrated. The residue was diluted with water (5 mL) and adjusted to pH<5.0 by addition of HCl (conc). The suspension was filtered. The filter cake was washed with $H_2O$ (5 mL), dried under reduced pressure. The residue was purified by prep-HPLC to afford 52 mg of (Z)-3-(2-((1H-pyrrolo[2,3-b]pyridine-3-carbonyl)imino)thiazol-3(2H)-yl)propanoic acid as a white solid.

Preparation of Example T52

Scheme 62

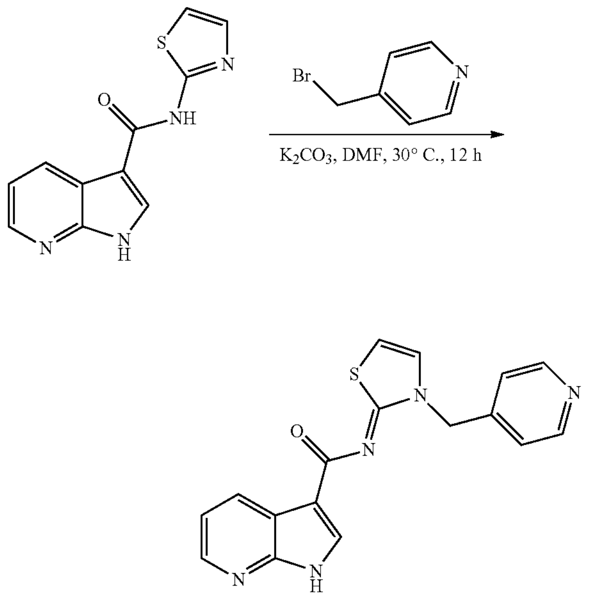

T52

A mixture of N-(thiazol-2-yl)-1H-pyrrolo[2,3-b]pyridine-3-carboxamide (100 mg, 409.38 μmol, 1.0 eq), 4-(bromomethyl)pyridine (104 mg, 409 μmol, 1.0 eq, HBr), $K_2CO_3$ (170 mg, 1.23 mmol, 3.0 eq) in DMF (1 mL) was degassed and purged with $N_2$ for 3 times, and then the reaction mixture was stirred at 30° C. for 12 h under $N_2$ atmosphere. The reaction mixture was concentrated under reduced pressure. The residue was purified by prep-HPLC to give 37 mg of (Z)—N-(3-(pyridin-4-ylmethyl)thiazol-2(3H)-ylidene)-1H-pyrrolo[2,3-b]pyridine-3-carboxamide T52 as a white solid.

Preparation of Example T53

Scheme 63

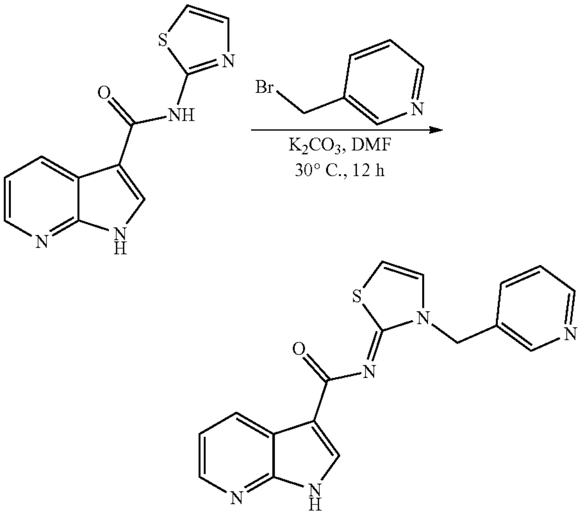

T53

A mixture of N-(thiazol-2-yl)-1H-pyrrolo[2,3-b]pyridine-3-carboxamide (100 mg, 409 μmol, 1.0 eq), 3-(bromomethyl)pyridine (104 mg, 409 μmol, 1.0 eq, HBr), $K_2CO_3$ (170 mg, 1.23 mmol, 3.0 eq) in DMF (1 mL) was degassed and purged with $N_2$ for 3 times, and then the reaction mixture was stirred at 30° C. for 12 h under $N_2$ atmosphere. The reaction mixture was concentrated under reduced pressure. The residue was purified by prep-HPLC to give 32 mg of (Z)—N-(3-(pyridin-3-ylmethyl)thiazol-2(3H)-ylidene)-1H-pyrrolo[2,3-b]pyridine-3-carboxamide T53 was obtained as a white solid.

Preparation of Example T57

Scheme 64

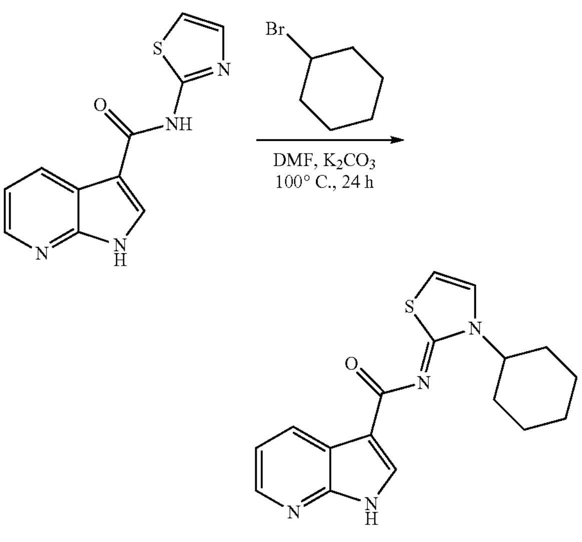

T57

To a solution of N-(thiazol-2-yl)-1H-pyrrolo[2,3-b]pyridine-3-carboxamide (200 mg, 819 μmol, 1.0 eq) in DMF (2 mL) was added $K_2CO_3$ (226 mg, 1.64 mmol, 2.0 eq), followed by addition of bromocyclohexane (2.67 g, 16.4 mmol, 2.02 mL, 20 eq) at room temperature. The reaction mixture was then stirred at 100° C. for 12 h. Additional 10 eq of bromocyclohexane was added into the reaction mixture and the mixture was then stirred at 100° C. for another 12 h under $N_2$. The reaction mixture was diluted with water (50 mL) and extracted with EtOAc (50 mL×3), the combined organic layers were washed with brine (100 mL), dried over $Na_2SO_4$, filtered and the filtrate was concentrated under reduced pressure. The residue was purified by prep-HPLC to give 7.3 mg of (Z)—N-(3-cyclohexylthiazol-2(3H)-ylidene)-1H-pyrrolo[2,3-b]pyridine-3-carboxamide T57 as a white solid. Structure was confirmed with NOE.

Preparation of Example T61

Scheme 65

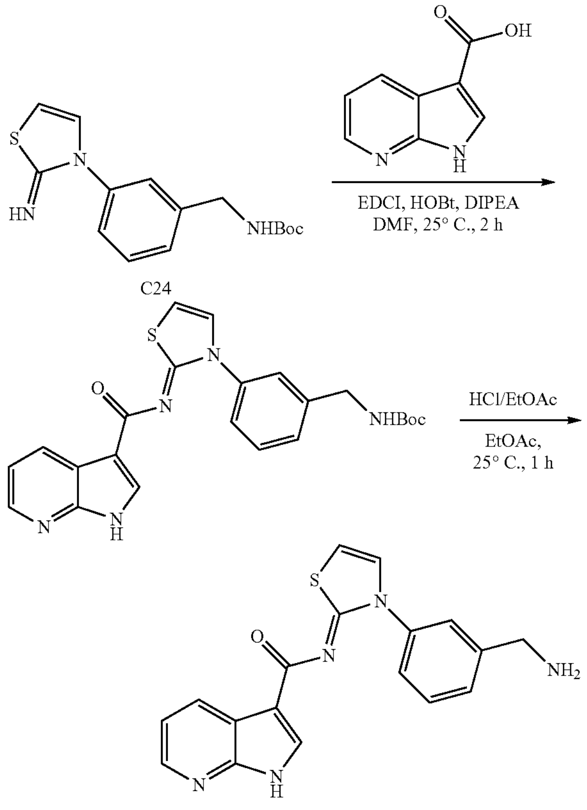

C24

T61

(Z)-Tert-butyl 3-(2-((1H-pyrrolo[2,3-b]pyridine-3-carbonyl)imino)thiazol-3(2H)-y 1)benzylcarbamate To a solution of 1H-pyrrolo[2,3-b]pyridine-3-carboxylic acid A (80 mg, 491 μmol, 1.0 eq) in DMF (2 mL) was added EDCI (141 mg, 737 μmol, 1.5 eq), HOBt (100 mg, 737 μmol, 1.5 eq), DIPEA (190 mg, 1.47 mmol, 257 μL, 3.0 eq) and tert-butyl 3-(2-iminothiazol-3(2H)-yl)benzylcarbamate C24 (150 mg, 491 μmol, 1.0 eq) at 25° C. The reaction mixture was then stirred at 25° C. for 2 hr under $N_2$. The reaction mixture was diluted with water (5 mL) and solid precipitated out. The solid was collected by filtration, washed with water (5 mL and dried under residue pressure to give 170 mg of (Z)-tert-butyl 3-(2-((1H-pyrrolo[2,3-b]pyridine-3-carbonyl)imino)thiazol-3(2H)-yl)benzylcarbamate as a white solid.

(Z)—N-(3-(3-(aminomethyl)phenyl)thiazol-2(3H)-ylidene)-1H-pyrrolo[2,3-b]pyridine-3-carboxamide T61

To a solution of (Z)-tert-butyl 3-(2-((1H-pyrrolo[2,3-b]pyridine-3-carbonyl)imino)thiazol-3(2H)-yl)benzylcarbamate (170 mg, 378 μmol, 1.0 eq) in EtOAc (1 mL) was added HCl/EtOAc (378 μmol, 3 mL, 1.0 eq) at 25° C. The solution was then stirred at 25° C. for 1 h under $N_2$. The reaction mixture was filtered, and the filter cake was washed with EtOAc (30 mL). The filter cake was concentrated under reduced pressure and purified by prep-HPLC to give 52 mg of (Z)—N-(3-(3-(aminomethyl)phenyl)thiazol-2(3H)-ylidene)-1H-pyrrolo[2,3-b]pyridine-3-carboxamide T61 as a white solid.

Preparation of Example T62

Scheme 66

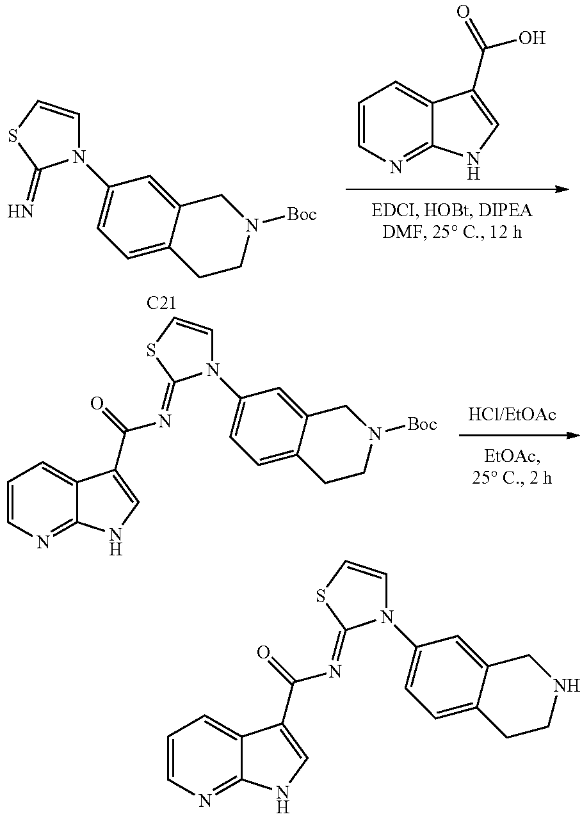

C21

T62

(Z)-Tert-butyl 7-(2-((1H-pyrrolo[2,3-b]pyridine-3-carbonyl)imino)thiazol-3(2H)-yl)-3,4-dihydroisoquinoline-2(1H)-carboxylate To a mixture of 1H-pyrrolo[2,3-b]pyridine-3-carboxylic acid A (80 mg, 493 μmol, 1.0 eq) in DMF (3 mL) was added HOBt (100 mg, 740 μmol, 1.5 eq), EDCI (142 mg, 740 μmol, 1.5 eq), DIPEA (191 mg, 1.48 mmol, 258 μL, 3.0 eq) and tert-butyl 7-(2-iminothiazol-3(2H)-yl)-3,4-dihydroisoquinoline-2(1H)-carboxylate C21 (164 mg, 493 μmol, 1.0 eq) at 25° C. Then the reaction mixture was stirred at 25° C. for 12 h under $N_2$. The reaction mixture was diluted with water (20 mL) and filtered to collect the solid. The collected solid was dried under reduced pressure to give 200 mg of (Z)-tert-butyl 7-(2-((1H-pyrrolo[2,3-b]pyridine-3-carbonyl)imino)thiazol-3(2H)-yl)-3,4-dihydroisoquinoline-2(1H)-carboxylate as brown solid. The crude product will be used directly in next step.

(Z)—N-(3-(1,2,3,4-tetrahydroisoquinolin-7-yl)thiazol-2(3H)-ylidene)-1H-pyrrolo[2,3-b]pyridine-3-carboxamide T62

To a mixture of (Z)-tert-butyl 7-(2-((1H-pyrrolo[2,3-b]pyridine-3-carbonyl) imino)thiazol-3(2H)-yl)-3,4-dihydroisoquinoline-2(1H)-carboxylate (170 mg, 357 μmol, 1.0 eq) in EtOAc (1 mL) was added HCl/EtOAc (4 M, 3 mL, 33 eq) at 25° C. Then the reaction mixture was stirred at 25° C. for 2 h under $N_2$. The solid was collected by filtration and purified by prep-HPLC to give 88 mg of (Z)—N-(3-(1,2,3,4-tetrahydroisoquinolin-7-yl)thiazol-2(3H)-ylidene)-1H-pyrrolo[2,3-b]pyridine-3-carboxamide T62 as a white solid.

Preparation of Example T72

Scheme 67

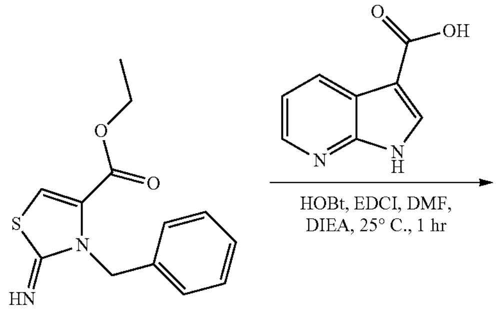

B8

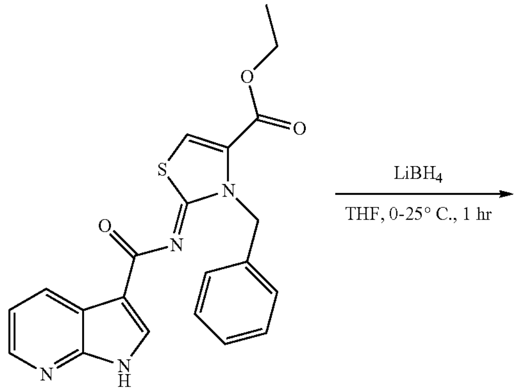

-continued

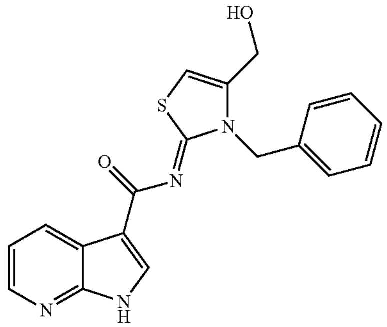

T72

(Z)-Ethyl 2-((1H-pyrrolo[2,3-b]pyridine-3-carbonyl)imino)-3-benzyl-2,3-dihydrothiazole-4-carboxylate To a solution of 1H-pyrrolo[2,3-b]pyridine-3-carboxylic acid (0.238 g, 1.47 mmol, 1.0 eq) in DMF (5 mL) was added EDCI (0.422 g, 2.20 mmol, 1.5 eq), HOBT (0.298 g, 2.20 mmol, 1.5 eq), diisopropylethylamine (0.758 mL, 4.41 mmol, 3.0 eq) and ethyl 3-benzyl-2-imino-2,3-dihydrothiazole-4-carboxylate (0.400 g, 1.47 mmol, 1.0 eq) at 25° C. Then the mixture was stirred at 25° C. for 1 hour. And then the reaction mixture was poured into ice-water (15 mL) causing a solid to precipitate which was collected by filtration. The filter cake was triturated with ethanol (15 mL) at 25° C. three times to afford 0.40 g of (Z)-ethyl 2-(1H-pyrrolo[2,3-b]pyridine-3-carbonyl)imino)-3-benzyl-2,3-dihydrothiazole-4-carboxylate as a white solid. $^1H$ NMR (400 MHz, DMSO-$d_6$): δ 12.27 (br. s, 1H), 8.45-8.42 (m, 1H), 8.26 (dd, J=4.8, 1.2 Hz, 1H), 8.21-8.20 (m, 1H), 7.99 (s, 1H), 7.35-7.31 (m, 2H), 7.27-7.2 (m, 3H), 7.14 (dd, J=8.0, 4.8 Hz, 1H), 5.93 (s, 2H), 4.27 (q, J=7.2 Hz, 2H), 1.25 (t, J=7.2 Hz, 3H). LCMS (m/z $[M+H]^+$): 407.0.

(Z)—N-(3-benzyl-4-(hydroxymethyl)thiazol-2(3H)-ylidene)-1H-pyrrolo[2,3-b]pyridine-3-carboxamide T72

To a suspension of (Z)-ethyl 2-((1H-pyrrolo[2,3-b]pyridine-3-carbonyl)imino)-3-benzyl-2,3-dihydrothiazole-4-carboxylate (0.200 g, 0.407 mmol) in THF (5 mL) was added dropwise a solution of lithium borohydride in THF (2 M, 0.4 mL, 0.8 mmol) at 0° C. under nitrogen atmosphere. After addition, the reaction mixture was warmed to 25° C. and stirred for 1 hour. Then the mixture was added dropwise into water (5 mL) at 25° C., and then a saturated aqueous solution of sodium carbonate (5 mL) was the mixture. The aqueous phase was extracted with ethyl acetate (50 mL×3). The combined organic layers were washed with brine (15 mL), dried over anhydrous sodium sulfate, filtered and concentrated under reduced pressure. The residue was purified by prep-HPLC to afford 32 mg of (Z)—N-(3-benzyl-4-(hydroxymethyl)thiazol-2(3H)-ylidene)-1H-pyrrolo[2,3-b]pyridine-3-carboxamide T72 as a white solid.

Preparation of Example T75

Scheme 68

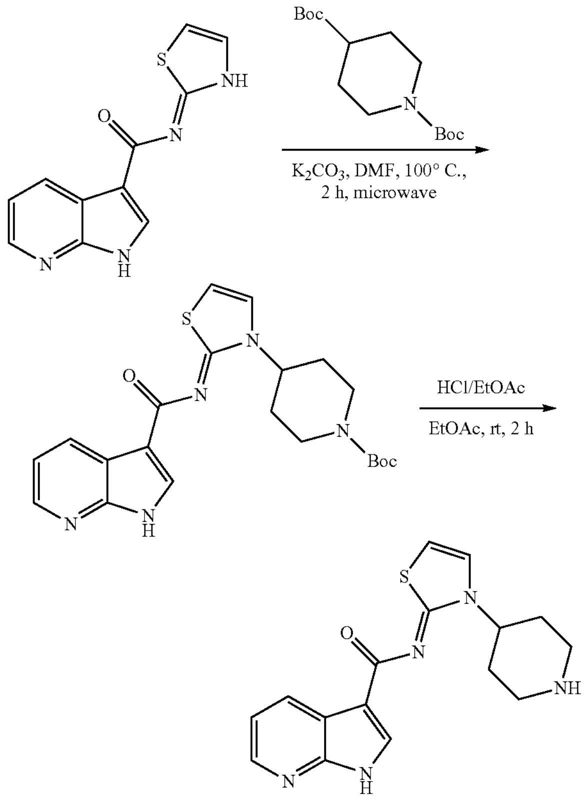

T75

(Z)-Tert-butyl4-(2-((1H-pyrrolo[2,3-b]pyridine-3-carbonyl)imino)thiazol-3(2H)-yl)piperidine-1-carboxylate To a solution of (Z)—N-(thiazol-2(3H)-ylidene)-1H-pyrrolo[2,3-b]pyridine-3-carboxamide (20 mg, 82 μmol, 1.0 eq) in DMF (1 mL) was added $K_2CO_3$ (57 mg, 246 μmol, 3.0 eq) and tert-butyl 4-bromopiperidine-1-carboxylate (216 mg, 819 μmol, 10.0 eq). The reaction mixture was transferred to a microwave tube. The sealed tube was heated at 100° C. for 2 hours in a microwave reactor. The reaction mixture was quenched by addition of water (5 mL), brown precipitate was formed. The solid was collected by filtration and washed with water (2 mL). The filtrate was dried under reduced pressure to afford the crude product (Z)-tert-butyl4-(2-((1H-pyrrolo[2,3-b]pyridine-3-carbonyl)imino)thiazol-3(2H)-yl)piperidine-1-carboxylate (30 mg, crude) as a brown solid.

(Z)—N-(3-(piperidin-4-yl)thiazol-2(3H)-ylidene)-1H-pyrrolo[2,3-b]pyridine-3-carboxamide hydrochloride T75

To a solution of (Z)-tert-butyl 4-(2-((1H-pyrrolo[2,3-b]pyridine-3-carbonyl)imino)thiazol-3(2H)-yl)piperidine-1-carboxylate (0.03 g, 70 umol, 1.0 eq) in EtOAc (1 mL) was added HCl/EtOAc (4 M, 1.2 mL, 68.4 eq) drop-wise slowly. The reaction mixture was stirred at 25° C. for 2 hours. The reaction mixture was concentrated dunder reduced pressure. The residue was purified by prep-HPLC to afford 5 mg of (Z)—N-(3-(piperidin-4-yl)thiazol-2(3H)-ylidene)-1H-pyrrolo[2,3-b]pyridine-3-carboxamide hydrochloride T75 as a white solid.

Preparation of Example T77

Scheme 69

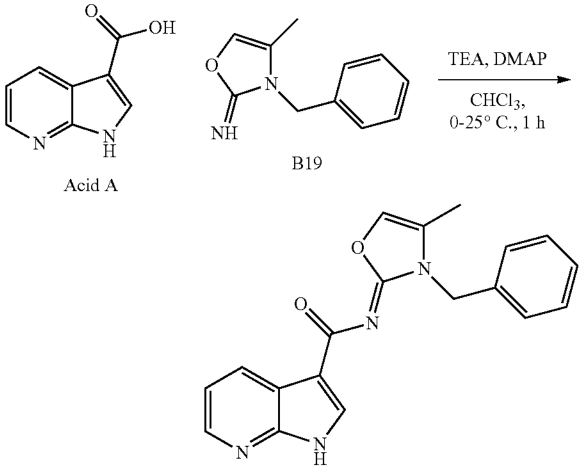

T77

To a solution of 3-benzyl-4-methyloxazol-2(3H)-imine 2,2,2-trifluoroacetate B19 (0.100 g, 0.285 mmol, 1.0 eq) and triethylamine (0.198 mL, 1.43 mmol, 5.0 eq) in chloroform (1 mL) was added N,N-dimethylpyridin-4-amine (3 mg, 0.03 mmol, 0.1 eq) and a solution of 1H-pyrrolo[2,3-b]pyridine-3-carbonyl chloride hydrochloride A (62 mg, 0.28 mmol, 1.0 eq) in chloroform (2 mL) at 0° C. The reaction mixture was warmed to 25° C. and stirred for 1 hour. The mixture was concentrated under reduced pressure, the residue was dissolved in methanol (2 mL), then poured into water (10 mL) causing a solid to precipitate out. The precipitate was collected by filtration and purified by prep-HPLC to afford 8 mg of (Z)—N-(3-benzyl-4-methyloxazol-2(3H)-ylidene)-1H-pyrrolo[2,3-b]pyridine-3-carboxamide T77 as a white solid.

Preparation of Example T78

Scheme 70

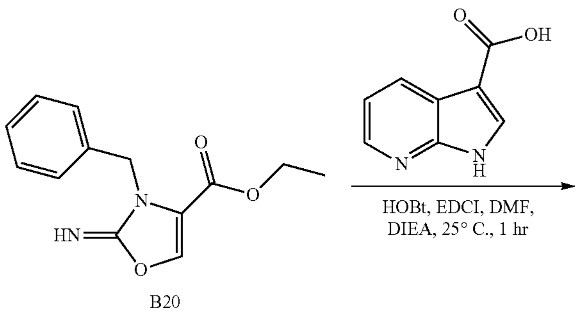

B20

-continued

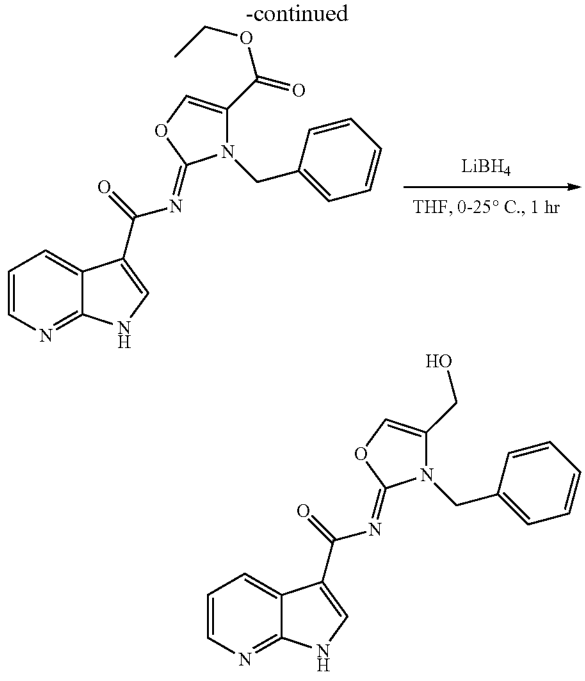

T78

Ethyl (Z)-2-((1H-pyrrolo[2,3-1]pyridine-3-carbonyl) imino)-3-benzyl-2,3-dihydrooxazole-4-carboxylate To a solution of ethyl 3-benzyl-2-imino-2,3-dihydrooxazole-4-carboxylate B20 (0.450 g, 1.83 mmol) and 1H-pyrrolo[2,3-b]pyridine-3-carboxylic acid (Acid A) (0.356 g, 2.19 mmol) in DMF (6 mL) was added DIPEA (1.59 mL, 9.14 mmol), EDCI (0.525 g, 2.74 mmol) and HOBt (0.247 g, 1.83 mmol) at 25° C. The reaction mixture was stirred at 50° C. for 2 hours. The reaction was quenched with water (50 mL) and then extracted with ethyl acetate (30 mL×3). The combined organic layers were washed with saturated aqueous solution of sodium bicarbonate (50 mL×3) and brine (50 mL×3), dried over anhydrous $Na_2SO_4$ and filtered. The filtrate was concentrated under reduced pressure. The crude product was purified by reversed-phase HPLC (0.1% $NH_3 \cdot H_2O$ condition) to afford 0.220 g of (Z)-ethyl 2-((1H-pyrrolo[2,3-b]pyridine-3-carbonyl)imino)-3-benzyl-2, 3-dihydrooxazole-4-carboxylate as a yellow solid. $^1$H NMR (DMSO-$d_6$, 400 MHz) δ 12.18 (br. s, 1H), 8.52 (s, 1H), 8.34 (dd, J=1.6, 6.4 Hz, 1H), 8.24 (dd, J=1.6, 3.2 Hz, 1H), 8.07 (d, J=2.0 Hz, 1H), 7.37-7.36 (m, 4H), 7.33-7.29 (m, 1H), 7.10 (dd, J=3.2, 4.8 Hz, 1H), 5.37 (s, 2H), 4.28 (q, J=7.2 Hz, 2H), 1.25 (t, J=7.2 Hz, 3H). LCMS (m/z [M+H]$^+$): 391.0.

(Z)—N-(3-benzyl-4-(hydroxymethyl)oxazol-2(3H)-ylidene)-1H-pyrrolo[2,3-b]pyridine-3-carboxamide T78

To a solution of (Z)-ethyl 2-((1H-pyrrolo[2,3-b]pyridine-3-carbonyl)imino)-3-benzyl-2,3-dihydrooxazole-4-carboxylate (0.100 g, 0.231 mmol) in THF (3.0 mL) was added a solution of lithium borohydride (0.348 mL, 2 M in THF) dropwise at 0° C. under nitrogen atmosphere. The reaction mixture was stirred at 0° C. for 1 hour. The mixture was poured into water (20 mL) at 25° C., and then saturated aqueous solution of ammonium chloride (20 mL) was added. The aqueous phase was extracted with ethyl acetate (30 mL×3). The combined organic phases were washed with brine (50 mL), dried over anhydrous $Na_2SO_4$, filtered. The filtrate was concentrated under reduced pressure. The mixture was purified by prep-HPLC (column: Phenomenex Gemini-NX $C_{18}$ 75*30 mm*3 um; mobile phase: [water (10 mM $NH_4HCO_3$)-ACN]; B %: 17%-47%, 8 min) to afford 9 mg of (Z)—N-(3-benzyl-4-(hydroxymethyl)oxazol-2(3H)-ylidene)-1-pyrrolo[2,3-b]pyridine-3-carboxamide T78 as a white solid.

Preparation of Examples T79 and T80

Scheme 71

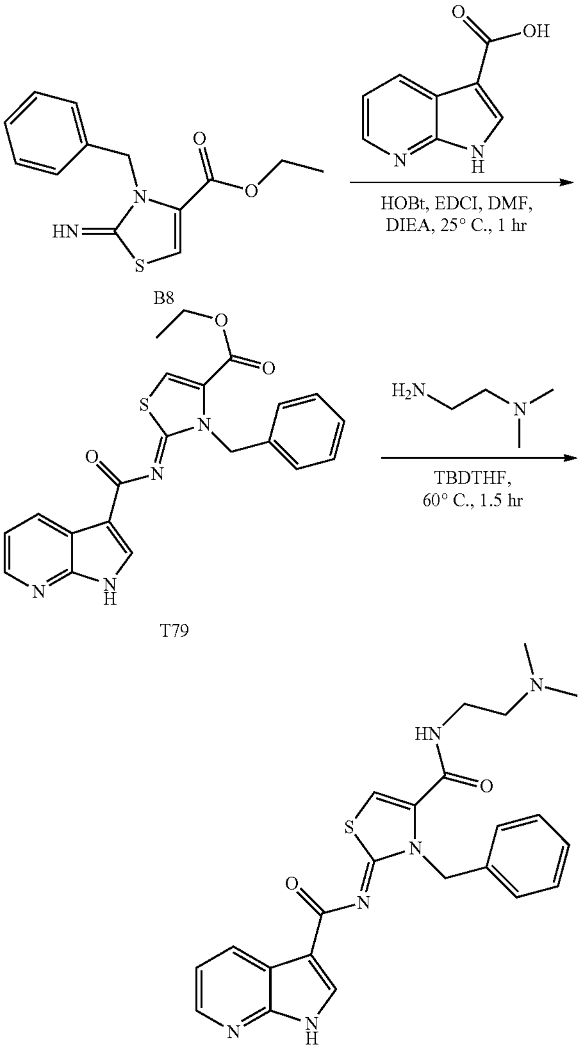

B8

T79

T80

Ethyl (2Z)-3-benzyl-2-(1H-pyrrolo[2,3-b]pyridine-3-carbonylimino)thiazole-4-carboxylate T79

To a solution of 1H-pyrrolo[2,3-b]pyridine-3-carboxylic acid (Acid A) (4.62 g, 28.4 mmol) in DMF (100 mL) were added HOBt (3.08 g, 22.8 mmol), EDCI (8.20 g, 42.8 mmol), DIPEA (14.9 mL, 85.6 mmol) and ethyl 3-benzyl- 2-imino-thiazole-4-carboxylate hydrobromide B8 (10.0 g, 28.5 mmol) at 25° C. The resulting mixture was stirred at 25° C. for 1 hour. The reaction was poured into ice-water (200 mL). The precipitate was collected by filtration and the filter cake was triturated with ethanol (150 mL) to afford 10.0 g of ethyl (2Z)-3-benzyl-2-(1H-pyrrolo[2,3-b]pyridine-3-carbonylimino)thiazole-4-carboxylate T79 as a white solid.

(Z)-3-Benzyl-N-[2-(dimethylamino)ethyl]-2-(1H-pyrrolo[2,3-b]pyridine-3-carbonylimino)thiazole-4-carboxamide T80

To a solution of ethyl (2Z)-3-benzyl-2-(1H-pyrrolo[2,3-b]pyridine-3-carbonylimino) thiazole-4-carboxylate T79 (0.050 g, 0.123 mmol,) and N', N'-dimethylethane-1,2-diamine (0.108 g, 1.23 mmol, 0.134 mL) in THF (1 mL) was added 3, 4, 6, 7, 8, 9-hexahydro-2H-pyrimido[1,2-a]pyrimidine (0.009 g, 0.062 mmol). The mixture was stirred at 60° C. for 1 hour. The reaction mixture was concentrated under reduced pressure. The residue was purified by prep-HPLC (Phenomenex Waters Xbridge 150*25 mm*5 um; mobile phase: [water (10 mM $NH_4HCO_3$)-acetonitrile]; B %: 24%-54%, 10 min) to afford 54 mg of (Z)-3-benzyl-N-[2-(dimethylamino)ethyl]-2-(1H-pyrrolo[2,3-b]pyridine-3-carbonylimino)thiazole-4-carboxamide T80 as a white solid.

General Methods

| LCMS conditions | | | | |
|---|---|---|---|---|
| Instrument | | Agilent 1200\G6110A | | |
| Software | | Agilent ChemStation Rev. B. 04.03[54] | | |
| HPLC | Column | Kinetex@ 5 um EVO C18 30*2.1 mm | | |
| | Mobile Phase | A: 0.0375% TFA in water (v/v) | | |
| | | B: 0.01875% TFA in Acetonitrile (v/v) | | |
| | Gradient | Time(min) | B(%) | Flow(mL/min) |
| | | 0.01 | 5 | 0.8 |
| | | 3.00 | 95 | 0.8 |
| | | 3.5 | 95 | 0.8 |
| | | 3.51 | 5 | 0.8 |
| | | 4.00 | 5 | 0.8 |
| | Column Temp | 50° C. | | |
| | Detector | DAD(220&254 nm) | | |
| MS | Ionization source | ESI | | |
| | Drying Gas | N2 | | |
| | Drying Gas Flow | 11(L/min) | | |
| | Nebulizer Pressure | 60 (psig) | | |
| | Drying Gas Temp | 350(° C.) | | |
| | Capillary Voltage | 3500(V) | | |
| | MS Polarity | Positive | | |
| | MS Mode | Scan | | |
| | Mass range | 100-1000 | | |

IVKA assay at 10 uM method:

The in vitro kinase assay (HTRF KinEASE-STK S1, CisBio 62ST1PEB) was optimized to the linear reaction range of the enzyme Lats1 (Carna 01-123). Reactions were conducted with 10 μM STK1 substrate and 10 μM ATP or 2 mM ATP as shown below. The DMSO concentration was maintained at 0.5% throughout all experiments, and a Janus 384 MDT (PerkinElmer) equipped with a 50 nL Pintool (V&P Scientific, Inc.) was used to add the compounds dissolved in DMSO to the reaction. The enzyme, substrate, ATP, and test compound of the invention were combined in a low-volume 384-well plate and shaken for 50 min at room temperature, unless otherwise indicated. The reaction was stopped by adding the detection reagents, which were prepared at an 8:1 biotin:streptavidin ratio and shaking for 60 min at room temperature. All reactions were conducted in triplicate and a Synergy NEO (Biotek) was used to detect the signal.

Reagents, final assay concentrations for the IVKA at 2 mM ATP: Kit:HTRFKinEASE-STKS1,CisBio62ST1PEB; 1× Kinase Buffer (KB); 5 mMMg$Cl_2$; 1 mMDTT; ATP 2 mM; STK1, 2.5 μM; 50 pg/μL (Lats1, Carna 01-123); BSA 1 mg/mL; the detection reagents in 8:1 biotin:streptavidin ratio Streptavidin-XL665:156 nM to final reaction volume of 10 μL and final detection volume of 20 μL. Assay was carried out in a 384 well plate. Each drug dosage curve was done with 16 points of 3-fold dilutions in 100% DMSO, and triplicate.

Lats1 activities determined as above are listed in the following Table

| Example | LATS1_HTRF_10 uM ATP $IC_{50}$ (nM) | LATS1_HTRF_2 mM ATP $IC_{50}$ (nM) |
|---|---|---|
| T01 | 2.2 | 157.9 |
| T02 | 5841 | |
| T03 | 148.2 | |
| T04 | 158.7 | |
| T05 | | 3258 |
| T06 | 92.2 | |
| T14 | 0.3 | 3.0 |
| T19 | | 0.3 |
| T20 | | 155.2 |
| T21 | | 7.5 |
| T22 | | 720.1 |
| T23 | | 576.2 |
| T24 | | 111.8 |
| T25 | 1.9 | 59.2 |
| T26 | 74.5 | |
| T27 | | 44.9 |
| T28 | | 193.8 |
| T29 | | 20.5 |
| T30 | | 279.4 |
| T31 | | 3799 |
| T32 | | 43.0 |
| T33 | 224.1 | |
| T34 | 6247 | |
| T35 | | 328.8 |
| T36 | | 60.0 |
| T37 | 233 | |
| T38 | 27 | |
| T39 | 1.9 | 59.2 |
| T40 | 88.7 | |
| T41 | 4.4 | 302.5 |
| T42 | 12.9 | |
| T43 | 2.2 | 140.7 |
| T44 | 259.8 | |
| T45 | 30.7 | 309.2 |
| T46 | 390.6 | |
| T47 | 83.2 | |
| T48 | 799.5 | |
| T49 | 2.7 | 0.5 |
| T51 | | 607.2 |
| T52 | | 4876 |
| T53 | | 1102.0 |
| T54 | | 11020 |
| T55 | 2.0 | 4.9 |
| T56 | | 1015.5 |
| T57 | | 0.5 |
| T58 | 127.8 | |
| T59 | | 6056 |
| T60 | | 417.9 |
| T61 | | 18.6 |
| T62 | | 126 |
| T64 | | 7857 |
| T65 | | 0.1 |
| T66 | | 192.7 |
| T67 | | 9.1 |

-continued

| Example | LATS1_HTRF_10 uM ATP $IC_{50}$ (nM) | LATS1_HTRF_2 mM ATP $IC_{50}$ (nM) |
|---|---|---|
| T68 | | 59.5 |
| T69 | | 168.2 |
| T70 | | 89.3 |
| T71 | | 176 |
| T72 | | 0.2 |
| T73 | | 0.8 |
| T74 | | 0.2 |
| T75 | | 92.5 |
| T76 | | 2191 |
| T77 | | 107.1 |
| T78 | | 1.6 |
| T79 | | 22 |
| T80 | | 82 |
| T81 | | 3.67 |
| T82 | | 20 |

The compound T01 was tested extensively to explore its mechanism of action and its utility in regenerating hair cells of the ear. The effects of the compounds were tested on utricles isolated from mice eight to twelve weeks of age. Internal ears were dissected from mice euthanized with fluothane and placed into ice-cold Hank's balanced salt solution, and cultured as previously described by Gnedeva, K. & Hudspeth [*Proc. Natl. Acad. Sci.* 112, 14066-14071 (2015)].

For proliferation assays, utricles were cultured with 10 μM 5-ethynyl-2'-deoxyuridine (EdU) that was detected with click chemistry.

Immunohistochemical analysis demonstrated that T01 drove robust Yap nuclear translocation in supporting cells after 24 hr of treatment at a concentration of 10 μM (quantified as a ratio to the constitutively expressed protein Sall2; control=0.6; T01-treated=1.0; $p<0.0001$ by an unpaired, two-tailed t-test, n=570 control nuclei and 680 treated nuclei), and it caused a striking reduction in the level of Yap phosphorylation as detected by western blot. After 5 days of treatment, T01 evoked robust re-entry into the cell cycle of adult utricular supporting cells, yielding hundreds of EdU+ daughter supporting cells (control=20 EdU+ supporting cells; T01-treated=250 EdU+ supporting cells; p=0.021 by an unpaired, one-tailed t-test, control n=2, T01 n=3).

The invention claimed is:

1. A compound of formula I:

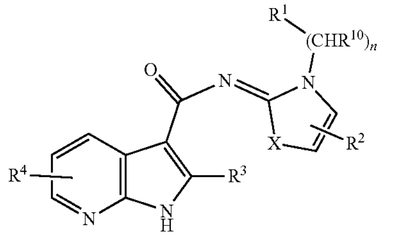

I wherein:

$R^1$ is selected from the group consisting of $(C_1\text{-}C_6)$alkyl, carboxy, $(C_3\text{-}C_7)$carbomonocyclyl, $(C_9\text{-}C_{11})$carbobicyclyl, heteromonocyclyl, and heterobicyclyl, wherein said $(C_1\text{-}C_6)$alkyl, $(C_3\text{-}C_7)$carbomonocyclyl, $(C_9\text{-}C_{11})$ carbobicyclyl, heteromonocyclyl, and heterobicyclyl may be optionally substituted with from one to three substituents selected independently from the group consisting of halogen, cyano, hydroxy, nitro, amino, acetoxy, carboxy, $(C_1\text{-}C_7)$hydrocarbyl, halo$(C_1\text{-}C_6)$alkyl, $(C_1\text{-}C_3)$alkoxy, halo$(C_1\text{-}C_3)$alkoxy, $(C_1\text{-}C_6)$acyl, $(C_1\text{-}C_3)$alkoxy$(C_1\text{-}C_3)$alkyl, hydroxy$(C_1\text{-}C_3)$alkyl, heteroaryl, benzenesulfonyl, $(C_1\text{-}C_3)$alkoxycarbonyl, aminocarbonyl, $(C_1\text{-}C_3)$alkylaminocarbonyl, di$(C_1\text{-}C_3)$alkylaminocarbonyl, $(C_1\text{-}C_3)$alkylamino, di$(C_1\text{-}C_3)$ alkylamino, amino$(C_1\text{-}C_3)$alkyl, $(C_1\text{-}C_3)$alkylamino $(C_1\text{-}C_3)$alkyl $(C_1\text{-}C_3)$dialkylamino$(C_1\text{-}C_3)$alkyl, $(C_1\text{-}C_3)$alkylthio, $(C_1\text{-}C_3)$alkylsulfonylamino, $(C_1\text{-}C_3)$ alkylsulfinyl, $(C_1\text{-}C_3)$alkylsulfonyl, phenoxy, and benzyloxy;

$R^2$ is selected from the group consisting of hydrogen, halogen, $(C_1\text{-}C_7)$hydrocarbyl, halo$(C_1\text{-}C_6)$alkyl, $(C_1\text{-}C_6)$acyl, hydroxy$(C_1\text{-}C_3)$alkyl, $—C(=O)O(C_1\text{-}C_6)$alkyl, $—C(=O)NR^{20}R^{21}$, and $(C_1\text{-}C_6)$oxaalkyl;

$R^3$ is selected from the group consisting of hydrogen, halogen, $(C_1\text{-}C_6)$hydrocarbyl, halo$(C_1\text{-}C_6)$alkyl, $(C_1\text{-}C_6)$acyl, and $(C_1\text{-}C_3)$alkoxy;

$R^4$ is selected from the group consisting of hydrogen, halogen, $(C_1\text{-}C_6)$hydrocarbyl, halo$(C_1\text{-}C_6)$alkyl, $(C_1\text{-}C_6)$acyl, and $(C_1\text{-}C_3)$alkoxy;

$R^{10}$ is selected independently in each instance from the group consisting of hydrogen and methyl;

$R^{20}$ is selected from the group consisting of hydrogen and $(C_1\text{-}C_6)$hydrocarbyl;

$R^{21}$ is selected from the group consisting of hydrogen, $(C_1\text{-}C_6)$hydrocarbyl, $(C_1\text{-}C_6)$oxaalkyl, amino$(C_1\text{-}C_6)$ alkyl, $(C_1\text{-}C_3)$alkylamino$(C_1\text{-}C_6)$alkyl, di$(C_1\text{-}C_3)$alkylamino$(C_1\text{-}C_6)$alkyl, and $—(CH_2)_m$-Het, wherein Het is an aliphatic mono- or bicyclic heterocycle, optionally substituted with a substituent selected from the group consisting hydroxy, amino, acetoxy, carboxy, $(C_1\text{-}C_7)$ hydrocarbyl, halo$(C_1\text{-}C_6)$alkyl, $(C_1\text{-}C_3)$alkoxy, halo $(C_1\text{-}C_3)$alkoxy, $(C_1\text{-}C_6)$acyl, $(C_1\text{-}C_3)$alkoxy$(C_1\text{-}C_3)$alkyl, hydroxy$(C_1\text{-}C_3)$alkyl, aminocarbonyl, $(C_1\text{-}C_3)$ alkylaminocarbonyl, di$(C_1\text{-}C_3)$alkylaminocarbonyl, $(C_1\text{-}C_3)$alkylamino, and di$(C_1\text{-}C_3)$alkylamino;

or, taken together with the nitrogen to which they are attached, $R^{20}$ and $R^{21}$ form an aliphatic heterocycle;

n is zero, one or two;

m is zero, one or two; and

X is S; or, when n is 1 and $R^1$ is optionally substituted phenyl, X is S or O;

with the proviso that, when $R^1$ is phenyl, X is sulfur, and n is one, at least one of $R^2$, $R^3$, $R^4$, and $R^{10}$ is other than hydrogen.

2. A compound according to claim 1 wherein $R^2$ is selected from the group consisting of $—C(=O)O(C_1\text{-}C_6)$ alkyl, $—C(=O)NR^{20}R^{21}$, and $(C_1\text{-}C_6)$oxaalkyl.

3. A compound according to claim 2 wherein $R^{20}$ is chosen from hydrogen and methyl, and and $R^{21}$ is chosen from hydrogen, methyl, $(C_1\text{-}C_6)$oxaalkyl, dimethylamino $(C_1\text{-}C_6)$alkyl, and $—(CH_2)_m$-Het.

4. A compound according to claim 1 wherein $R^{20}$ and $R^{21}$ taken together with the nitrogen to which they are attached form a 4-7-membered aliphatic heterocycle.

5. A compound according to claim 1 of formula:

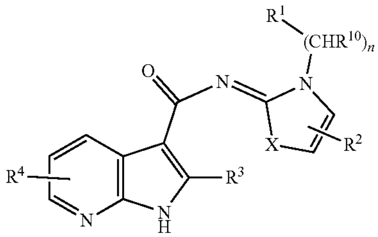

wherein:

$R^1$ is selected from the group consisting of $(C_1-C_6)$alkyl, carboxy, $(C_3-C_7)$carbomonocyclyl, $(C_9-C_{11})$carbobicyclyl, heteromonocyclyl, and heterobicyclyl, wherein said $(C_1-C_6)$alkyl, $(C_3-C_7)$carbomonocyclyl, $(C_9-C_{11})$ carbobicyclyl, heteromonocyclyl, and heterobicyclyl may be optionally substituted with from one to three substituents selected independently from the group consisting of halogen, cyano, hydroxy, nitro, amino, acetoxy, carboxy, $(C_1-C_7)$hydrocarbyl, halo$(C_1-C_6)$alkyl, $(C_1-C_3)$alkoxy, halo$(C_1-C_3)$alkoxy, $(C_1-C_6)$acyl, $(C_1-C_3)$alkoxy$(C_1-C_3)$alkyl, hydroxy$(C_1-C_3)$alkyl, heteroaryl, benzenesulfonyl, $(C_1-C_3)$alkoxycarbonyl, aminocarbonyl, $(C_1-C_3)$alkylaminocarbonyl, $(C_1-C_3)$alkylamino, di$(C_1-C_3)$alkylamino, amino$(C_1-C_3)$alkyl, $(C_1-C_3)$alkylamino$(C_1-C_3)$alkyl $(C_1-C_3)$dialkylamino$(C_1-C_3)$alkyl, $(C_1-C_3)$alkylthio, $(C_1-C_3)$ alkylsulfonylamino, $(C_1-C_3)$alkylsulfinyl, $(C_1-C_3)$ alkylsulfonyl, phenoxy, and benzyloxy;

$R^2$ is selected from the group consisting of hydrogen, halogen, $(C_1-C_6)$hydrocarbyl, halo$(C_1-C_6)$alkyl, $(C_1-C_6)$acyl, hydroxy$(C_1-C_3)$alkyl, and $(C_1-C_3)$alkoxy;

$R^3$ is selected from the group consisting of hydrogen, halogen, $(C_1-C_6)$hydrocarbyl, halo$(C_1-C_6)$alkyl, $(C_1-C_6)$acyl, and $(C_1-C_3)$alkoxy;

$R^4$ is selected from the group consisting of hydrogen, halogen, $(C_1-C_6)$hydrocarbyl, halo$(C_1-C_6)$alkyl, $(C_1-C_6)$acyl, and $(C_1-C_3)$alkoxy;

$R^{10}$ is selected independently in each instance from the group consisting of hydrogen and methyl;

n is zero, one or two; and

X is O or S;

with the proviso that, when $R^1$ is phenyl, X is sulfur, and n is one, at least one of $R^2$, $R^3$, $R^4$, and $R^{10}$ is other than hydrogen.

6. A compound according to claim 1 wherein n is zero.

7. A compound according to claim 1 wherein n is one.

8. A compound according to claim 7 wherein $R^{10}$ is hydrogen.

9. A compound according to claim 1 wherein $R^1$ is selected from the group consisting of carboxy and optionally substituted $(C_1-C_4)$alkyl, phenyl, cyclohexyl, 5-membered heterocyclyl, 6-membered heterocyclyl and heterobicyclyl.

10. A compound according to claim 9 wherein $R^1$ is selected from the group consisting of methyl, ethyl, aminobutyl, and carboxyethyl.

11. A compound according to claim 9 wherein $R^1$ is optionally substituted cyclohexyl.

12. A compound according to claim 9 wherein $R^1$ is optionally substituted phenyl.

13. A compound according to claim 9 wherein $R^1$ is optionally substituted heterocyclyl.

14. A compound according to claim 13 wherein $R^1$ is selected from the group consisting of pyridinyl, pyrazolyl, piperidinyl, tetrahydropyranyl, tetrahydrofuranyl, and tetrahydroisoquinolinyl, each optionally substituted.

15. A compound according to claim 12 wherein $R^1$ is phenyl or phenyl substituted with one or two substituents selected independently from the group consisting of halogen, cyano, hydroxy, amino, carboxy, $(C_1-C_6)$hydrocarbyl, trifluoromethyl, methoxy, acetyl, formyl, hydroxy$(C_1-C_3)$ alkyl, methoxycarbonyl, carboxamido, methanesulfonylamino, and amino$(C_1-C_3)$alkyl.

16. A compound according to claim 15 wherein $R^1$ is phenyl substituted at the ortho position and n is zero.

17. A compound according to claim 14 wherein $R^1$ is selected from the group consisting of pyridinyl, pyrazolyl, piperidinyl, tetrahydropyranyl, and tetrahydroisoquinolinyl, each optionally substituted with one or two substituents selected independently from the group consisting of amino, hydroxy and $(C_1-C_6)$hydrocarbyl.

18. A compound according to claim 9 wherein X is S.

19. A compound according to claim 9 wherein X is O.

20. A compound according to claim 9 wherein $R^3$ and $R^4$ are selected independently from the group consisting of hydrogen, chloro and methyl.

21. A compound according to claim 9 wherein $R^2$ is selected from the group consisting of hydrogen, methyl, ethyl, propyl, cyclopropyl, hydroxymethyl, and trifluoromethyl.

22. A compound according to claim 1 chosen from the compounds in the table below:

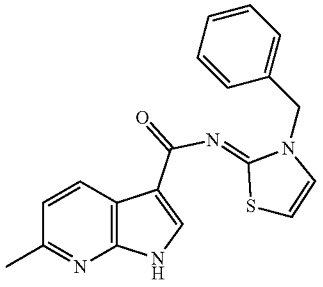 [SMILES: Cc1ccc2c(C(=O)/N=c3\sccn3Cc3ccccc3)c[nH]c2n1]

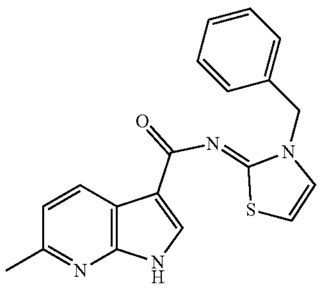 [SMILES: Cc1ccc2c(C(=O)/N=c3\sccn3Cc3ccccc3)c[nH]c2n1]

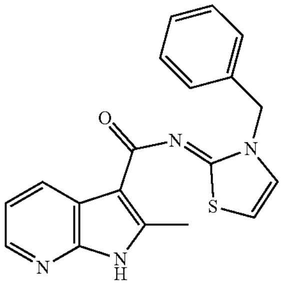 [SMILES: Cc1[nH]c2ncccc2c1C(=O)/N=c1\sccn1Cc1ccccc1]

-continued
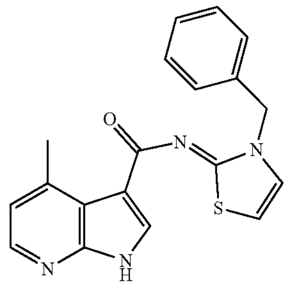 [SMILES: Cc1ccnc2[nH]cc(C(=O)/N=c3\sccn3Cc3ccccc3)c12]
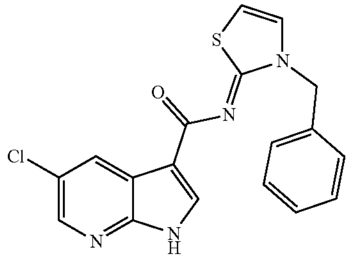 [SMILES: O=C(/N=c1\sccn1Cc1ccccc1)c1c[nH]c2ncc(Cl)cc12]
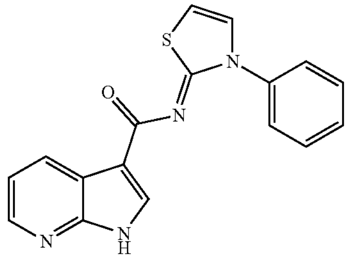 [SMILES: O=C(/N=c1\sccn1-c1ccccc1)c1c[nH]c2ncccc12]
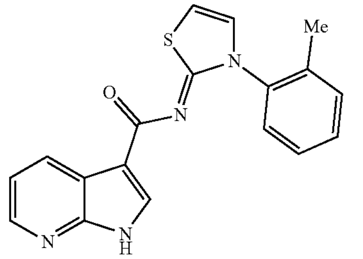 [SMILES: Cc1ccccc1-n1ccs/c1=N\C(=O)c1c[nH]c2ncccc12]
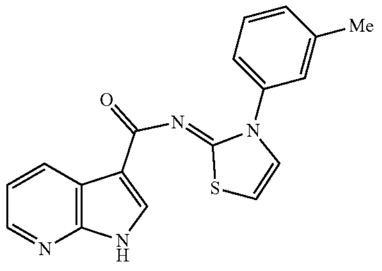 [SMILES: Cc1cccc(-n2ccs/c2=N\C(=O)c2c[nH]c3ncccc23)c1]
-continued
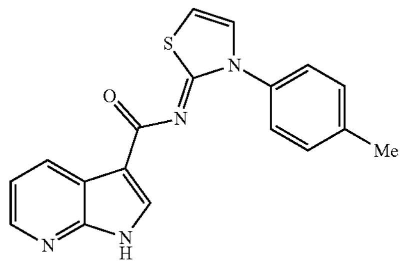 [SMILES: Cc1ccc(-n2ccs/c2=N\C(=O)c2c[nH]c3ncccc23)cc1]
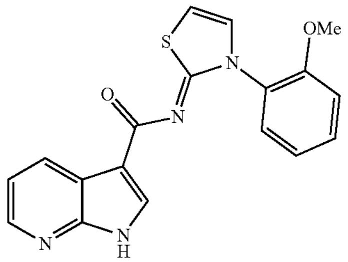 [SMILES: COc1ccccc1-n1ccs/c1=N\C(=O)c1c[nH]c2ncccc12]
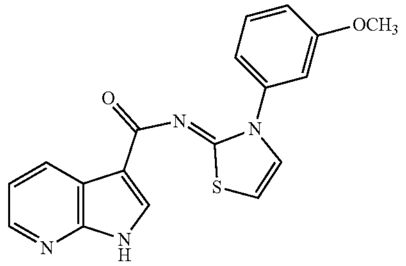 [SMILES: COc1cccc(-n2ccs/c2=N\C(=O)c2c[nH]c3ncccc23)c1]
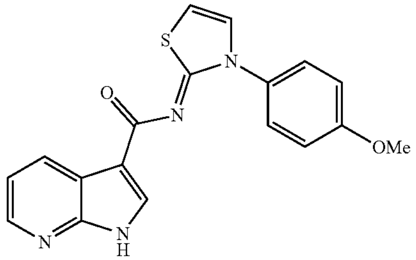 [SMILES: COc1ccc(-n2ccs/c2=N\C(=O)c2c[nH]c3ncccc23)cc1]
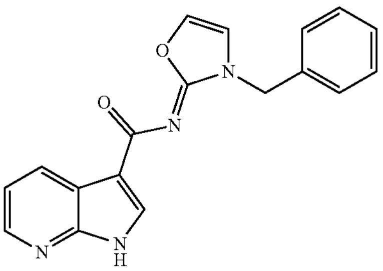 [SMILES: O=C(/N=c1\occn1Cc1ccccc1)c1c[nH]c2ncccc12]

-continued
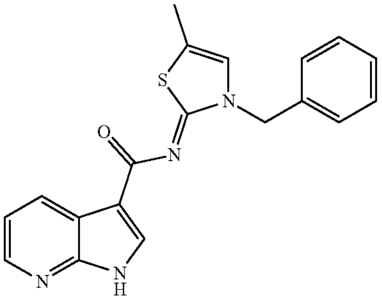 [SMILES: Cc1cn(Cc2ccccc2)/c(=N/C(=O)c2c[nH]c3ncccc23)s1]
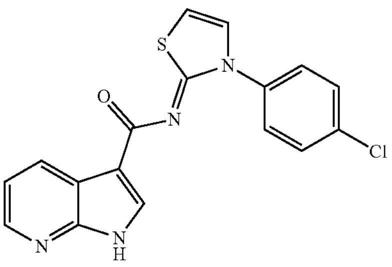 [SMILES: O=C(/N=c1\sccn1-c1ccc(Cl)cc1)c1c[nH]c2ncccc12]
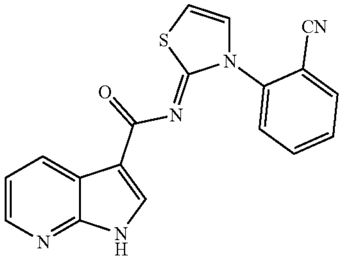 [SMILES: N#Cc1ccccc1-n1ccs/c1=N\C(=O)c1c[nH]c2ncccc12]
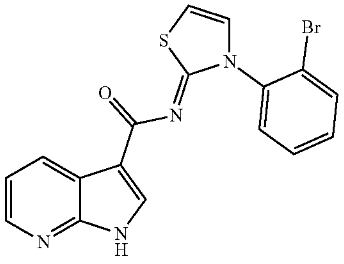 [SMILES: O=C(/N=c1\sccn1-c1ccccc1Br)c1c[nH]c2ncccc12]
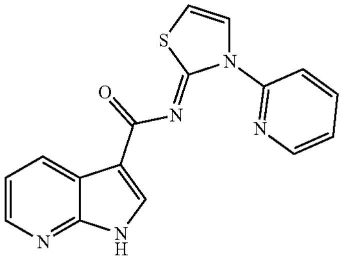 [SMILES: O=C(/N=c1\sccn1-c1ccccn1)c1c[nH]c2ncccc12]
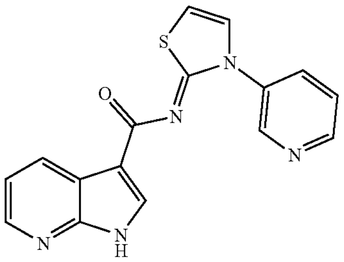 [SMILES: O=C(/N=c1\sccn1-c1cccnc1)c1c[nH]c2ncccc12]
-continued
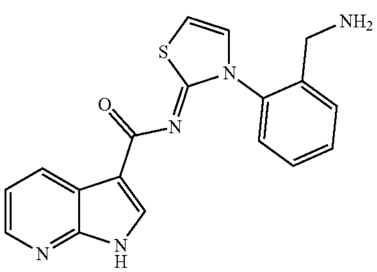 [SMILES: NCc1ccccc1-n1ccs/c1=N\C(=O)c1c[nH]c2ncccc12]
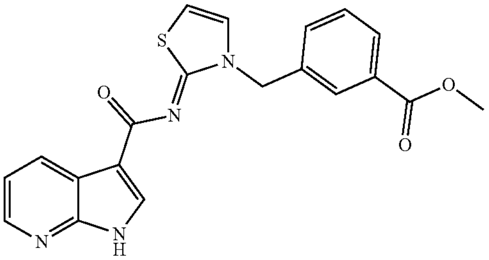 [SMILES: COC(=O)c1cccc(Cn2ccs/c2=N\C(=O)c2c[nH]c3ncccc23)c1]
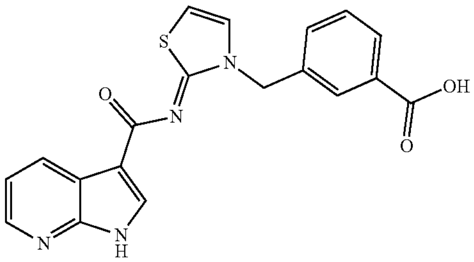 [SMILES: O=C(O)c1cccc(Cn2ccs/c2=N\C(=O)c2c[nH]c3ncccc23)c1]
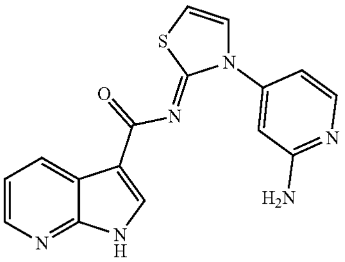 [SMILES: Nc1cc(-n2ccs/c2=N\C(=O)c2c[nH]c3ncccc23)ccn1]
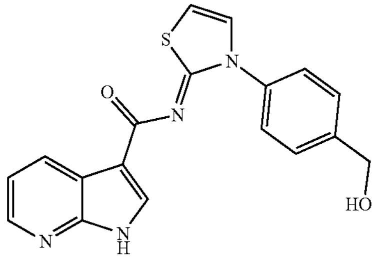 [SMILES: O=C(/N=c1\sccn1-c1ccc(CO)cc1)c1c[nH]c2ncccc12]
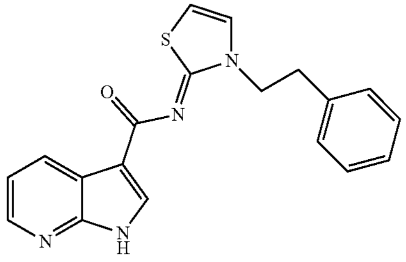 [SMILES: O=C(/N=c1\sccn1CCc1ccccc1)c1c[nH]c2ncccc12]

-continued
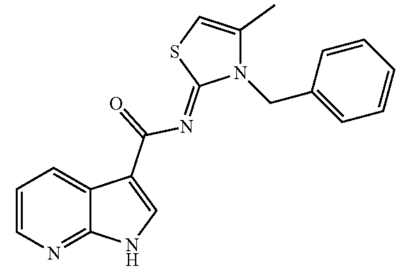 [SMILES: Cc1cs/c(=N\C(=O)c2c[nH]c3ncccc23)n1Cc1ccccc1]
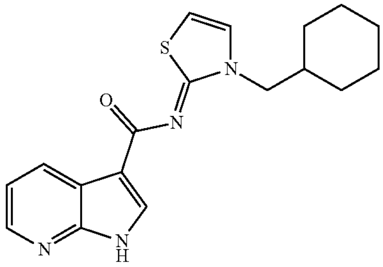 [SMILES: O=C(/N=c1\sccn1CC1CCCCC1)c1c[nH]c2ncccc12]
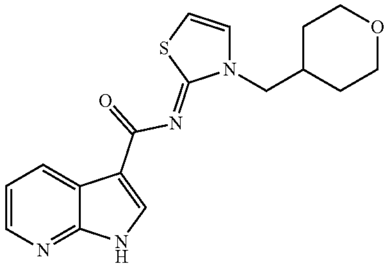 [SMILES: O=C(/N=c1\sccn1CC1CCOCC1)c1c[nH]c2ncccc12]
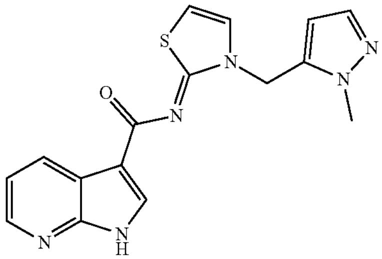 [SMILES: Cn1nccc1Cn1ccs/c1=N\C(=O)c1c[nH]c2ncccc12]
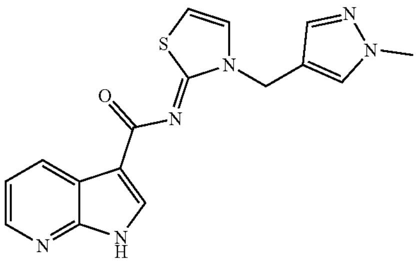 [SMILES: Cn1cc(Cn2ccs/c2=N\C(=O)c2c[nH]c3ncccc23)cn1]
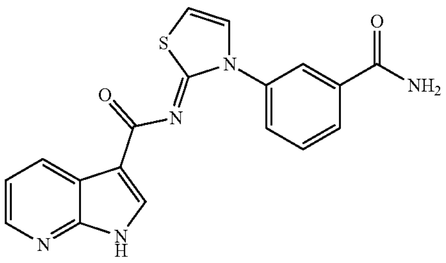 [SMILES: NC(=O)c1cccc(-n2ccs/c2=N\C(=O)c2c[nH]c3ncccc23)c1]
-continued
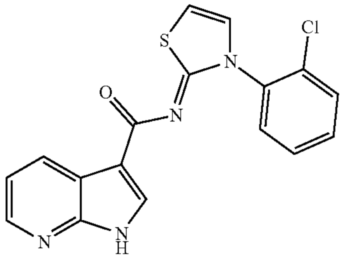 [SMILES: O=C(/N=c1\sccn1-c1ccccc1Cl)c1c[nH]c2ncccc12]
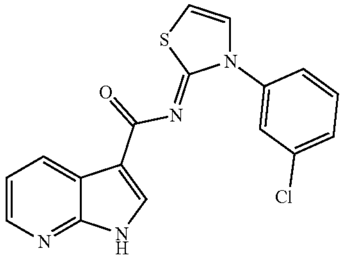 [SMILES: O=C(/N=c1\sccn1-c1cccc(Cl)c1)c1c[nH]c2ncccc12]
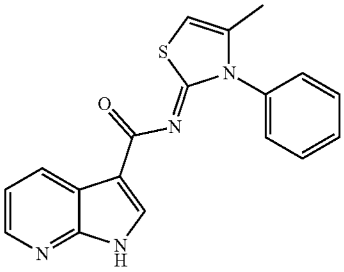 [SMILES: Cc1cs/c(=N\C(=O)c2c[nH]c3ncccc23)n1-c1ccccc1]
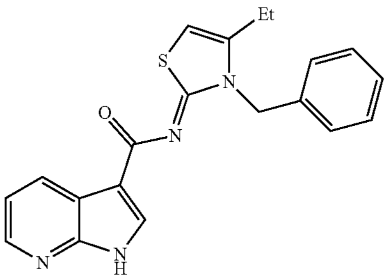 [SMILES: CCc1cs/c(=N\C(=O)c2c[nH]c3ncccc23)n1Cc1ccccc1]
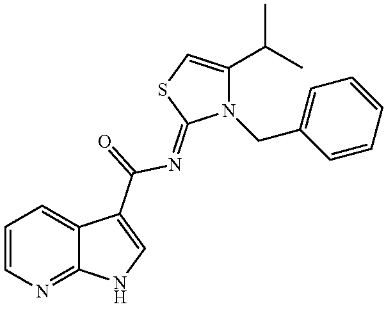 [SMILES: CC(C)c1cs/c(=N\C(=O)c2c[nH]c3ncccc23)n1Cc1ccccc1]

-continued
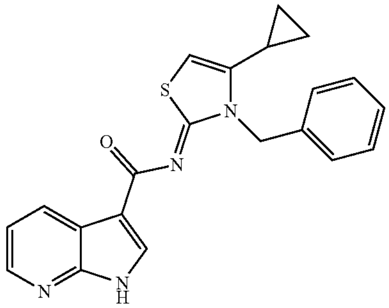 [SMILES: O=C(/N=c1\scc(C2CC2)n1Cc1ccccc1)c1c[nH]c2ncccc12]
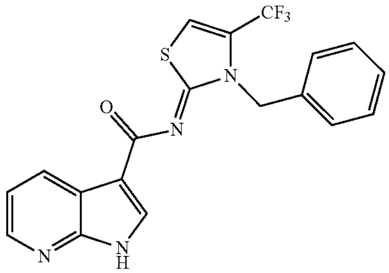 [SMILES: O=C(/N=c1\scc(C(F)(F)F)n1Cc1ccccc1)c1c[nH]c2ncccc12]
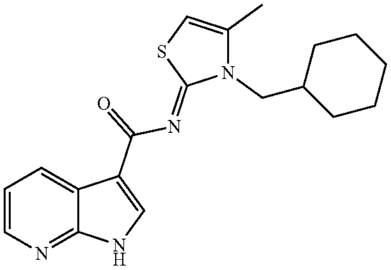 [SMILES: Cc1cs/c(=N\C(=O)c2c[nH]c3ncccc23)n1CC1CCCCC1]
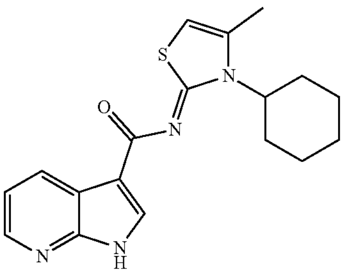 [SMILES: Cc1cs/c(=N\C(=O)c2c[nH]c3ncccc23)n1C1CCCCC1]
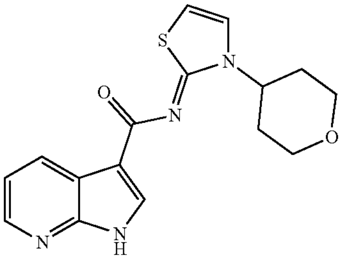
-continued
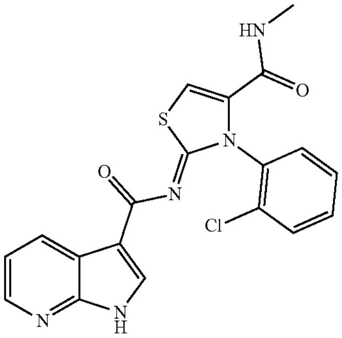 [SMILES: CNC(=O)c1cs/c(=N\C(=O)c2c[nH]c3ncccc23)n1-c1ccccc1Cl]
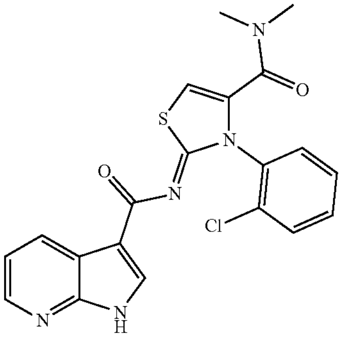 [SMILES: CN(C)C(=O)c1cs/c(=N\C(=O)c2c[nH]c3ncccc23)n1-c1ccccc1Cl]
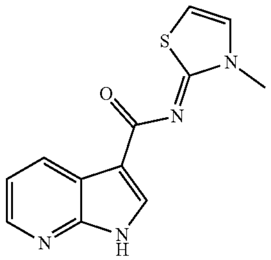 [SMILES: Cn1ccs/c1=N\C(=O)c1c[nH]c2ncccc12]
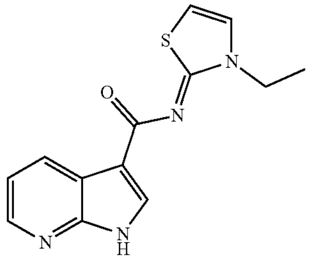 [SMILES: CCn1ccs/c1=N\C(=O)c1c[nH]c2ncccc12]
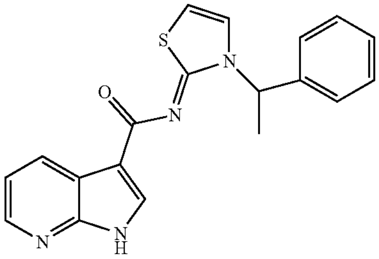 [SMILES: CC(c1ccccc1)n1ccs/c1=N\C(=O)c1c[nH]c2ncccc12]

-continued
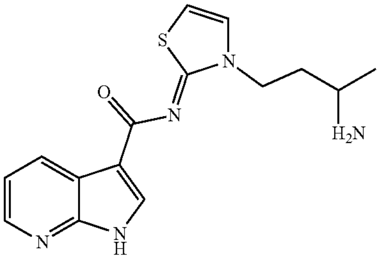 [SMILES: CC(N)CCn1ccs/c1=N\C(=O)c1c[nH]c2ncccc12]
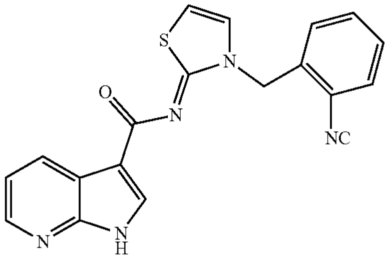
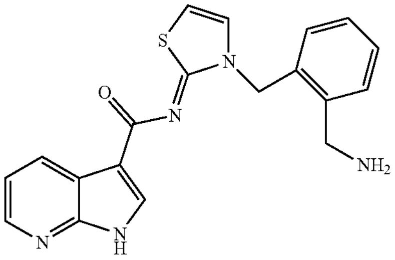 [SMILES: NCc1ccccc1Cn1ccs/c1=N\C(=O)c1c[nH]c2ncccc12]
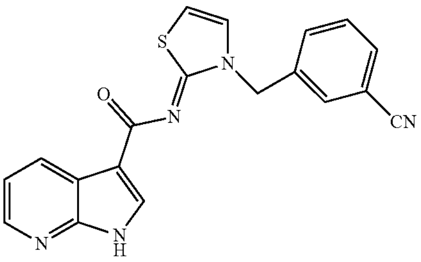 [SMILES: N#Cc1cccc(Cn2ccs/c2=N\C(=O)c2c[nH]c3ncccc23)c1]
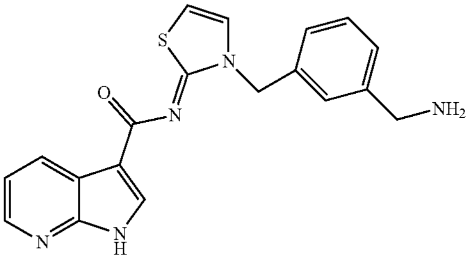 [SMILES: NCc1cccc(Cn2ccs/c2=N\C(=O)c2c[nH]c3ncccc23)c1]
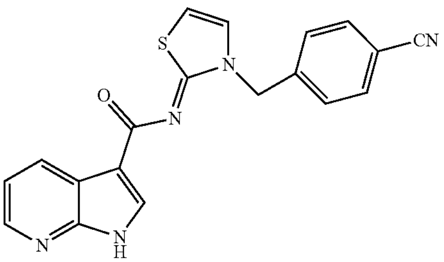 [SMILES: N#Cc1ccc(Cn2ccs/c2=N\C(=O)c2c[nH]c3ncccc23)cc1]
-continued
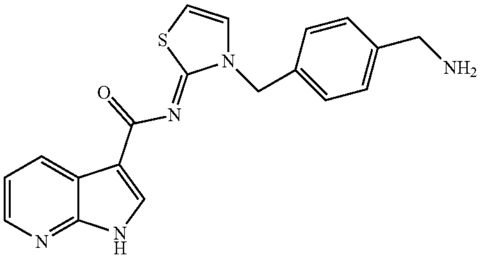 [SMILES: NCc1ccc(Cn2ccs/c2=N\C(=O)c2c[nH]c3ncccc23)cc1]
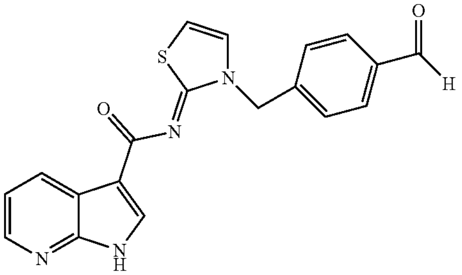 [SMILES: O=Cc1ccc(Cn2ccs/c2=N\C(=O)c2c[nH]c3ncccc23)cc1]
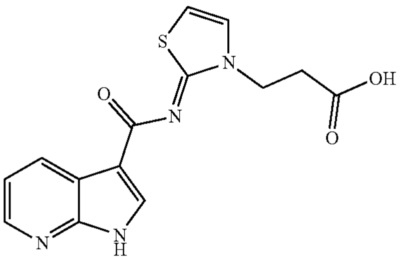 [SMILES: O=C(O)CCn1ccs/c1=N\C(=O)c1c[nH]c2ncccc12]
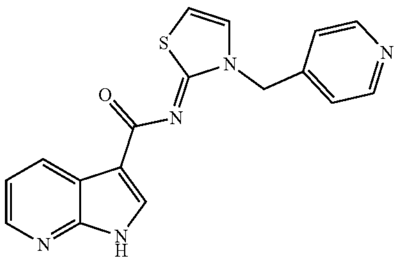 [SMILES: O=C(/N=c1\sccn1Cc1ccncc1)c1c[nH]c2ncccc12]
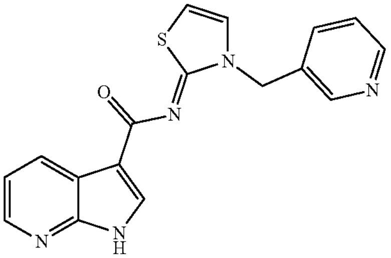 [SMILES: O=C(/N=c1\sccn1Cc1cccnc1)c1c[nH]c2ncccc12]
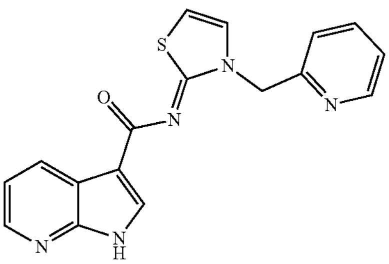 [SMILES: O=C(/N=c1\sccn1Cc1ccccn1)c1c[nH]c2ncccc12]

-continued
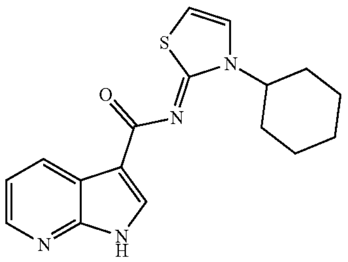 [SMILES: O=C(/N=c1\sccn1C1CCCCC1)c1c[nH]c2ncccc12]
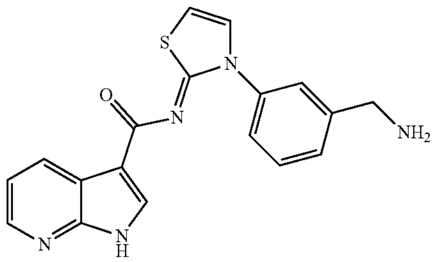 [SMILES: NCc1cccc(-n2ccs/c2=N\C(=O)c2c[nH]c3ncccc23)c1]
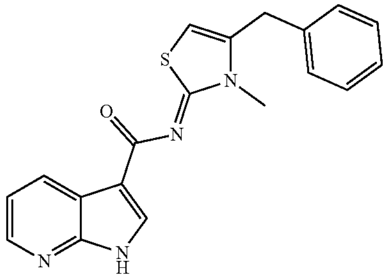 [SMILES: Cn1c(Cc2ccccc2)cs/c1=N\C(=O)c1c[nH]c2ncccc12]
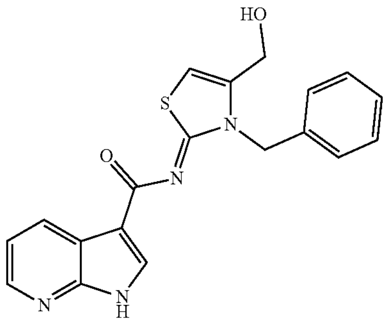 [SMILES: O=C(/N=c1\scc(CO)n1Cc1ccccc1)c1c[nH]c2ncccc12]
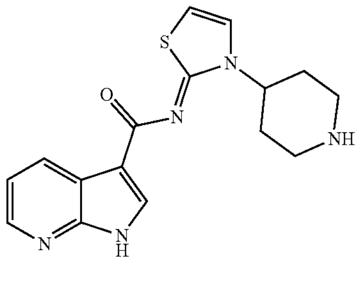 [SMILES: O=C(/N=c1\sccn1C1CCNCC1)c1c[nH]c2ncccc12]
-continued
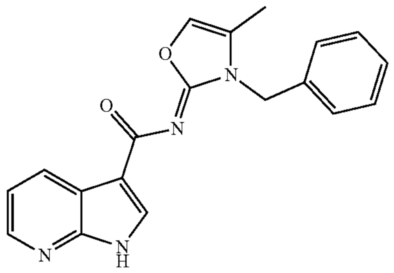 [SMILES: Cc1co/c(=N\C(=O)c2c[nH]c3ncccc23)n1Cc1ccccc1]
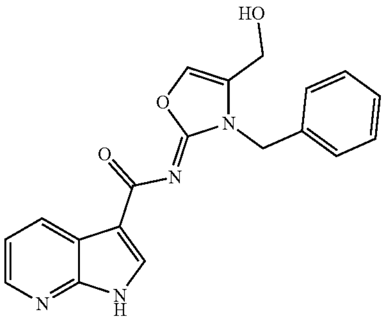 [SMILES: O=C(/N=c1\occ(CO)n1Cc1ccccc1)c1c[nH]c2ncccc12]
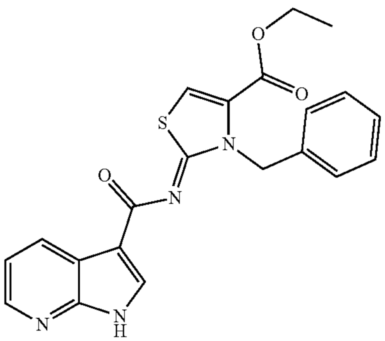 [SMILES: CCOC(=O)c1cs/c(=N\C(=O)c2c[nH]c3ncccc23)n1Cc1ccccc1]
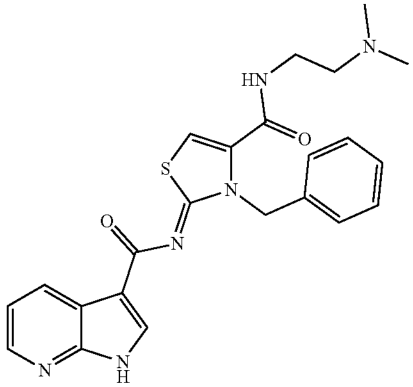 [SMILES: CN(C)CCNC(=O)c1cs/c(=N\C(=O)c2c[nH]c3ncccc23)n1Cc1ccccc1]
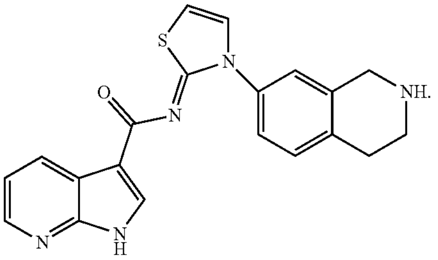 [SMILES: O=C(/N=c1\sccn1-c1ccc2c(c1)CNCC2)c1c[nH]c2ncccc12]

23. A pharmaceutical composition comprising a pharmaceutically acceptable carrier and a compound according to claim 1.

24. A method for stimulating hair cell regeneration comprising exposing a supporting-cell population to a compound of formula:

I

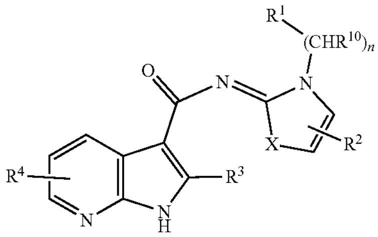

wherein:

$R^1$ is selected from the group consisting of $(C_1-C_6)$alkyl, carboxy, $(C_3-C_7)$carbomonocyclyl, $(C_9-C_{11})$carbobicyclyl, heteromonocyclyl, and heterobicyclyl, wherein said $(C_1-C_6)$alkyl, $(C_3-C_7)$carbomonocyclyl, $(C_9-C_{11})$ carbobicyclyl, heteromonocyclyl, and heterobicyclyl may be optionally substituted with from one to three substituents selected independently from the group consisting of halogen, cyano, hydroxy, nitro, amino, acetoxy, carboxy, $(C_1-C_7)$hydrocarbyl, halo$(C_1-C_6)$alkyl, $(C_1-C_3)$alkoxy, halo$(C_1-C_3)$alkoxy, $(C_1-C_6)$acyl, $(C_1-C_3)$alkoxy$(C_1-C_3)$alkyl, hydroxy$(C_1-C_3)$alkyl, heteroaryl, benzenesulfonyl, $(C_1-C_3)$alkoxycarbonyl, aminocarbonyl, $(C_1-C_3)$alkylaminocarbonyl, di$(C_1-C_3)$alkylaminocarbonyl, $(C_1-C_3)$alkylamino, di$(C_1-C_3)$ alkylamino, amino$(C_1-C_3)$alkyl, $(C_1-C_3)$alkylamino $(C_1-C_3)$alkyl $(C_1-C_3)$dialkylamino$(C_1-C_3)$alkyl, $(C_1-C_3)$alkylthio, $(C_1-C_3)$alkylsulfonylamino, $(C_1-C_3)$alkylsulfinyl, $(C_1-C_3)$alkylsulfonyl, phenoxy, and benzyloxy;

$R^2$ is selected from the group consisting of hydrogen, halogen, $(C_1-C_6)$hydrocarbyl, halo$(C_1-C_6)$alkyl, $(C_1-C_6)$acyl, hydroxy$(C_1-C_3)$alkyl, $—C(=O)O(C_1-C_6)$alkyl, $—C(=O)NR^{20}R^{21}$, and $(C_1-C_6)$oxaalkyl;

$R^3$ is selected from the group consisting of hydrogen, halogen, $(C_1-C_6)$hydrocarbyl, halo$(C_1-C_6)$alkyl, $(C_1-C_6)$acyl, and $(C_1-C_3)$alkoxy;

$R^4$ is selected from the group consisting of hydrogen, halogen, $(C_1-C_6)$hydrocarbyl, halo$(C_1-C_6)$alkyl, $(C_1-C_6)$acyl, and $(C_1-C_3)$alkoxy;

$R^{10}$ is selected independently in each instance from the group consisting of hydrogen and methyl;

$R^{20}$ is selected from the group consisting of hydrogen and $(C_1-C_6)$hydrocarbyl;

$R^{21}$ is selected from the group consisting of hydrogen, $(C_1-C_6)$hydrocarbyl, $(C_1-C_6)$oxaalkyl, amino$(C_1-C_6)$ alkyl, $(C_1-C_3)$alkylamino$(C_1-C_6)$alkyl, di$(C_1-C_3)$alkylamino$(C_1-C_6)$alkyl, and $—(CH_2)_m$-Het, wherein Het is an aliphatic mono- or bicyclic heterocycle, optionally substituted with a substituent selected from the group consisting hydroxy, amino, acetoxy, carboxy, $(C_1-C_7)$ hydrocarbyl, halo$(C_1-C_6)$alkyl, $(C_1-C_3)$alkoxy, halo $(C_1-C_3)$alkoxy, $(C_1-C_6)$acyl, $(C_1-C_3)$alkoxy$(C_1-C_3)$alkyl, hydroxy$(C_1-C_3)$alkyl, aminocarbonyl, $(C_1-C_3)$ alkylaminocarbonyl, di$(C_1-C_3)$alkylaminocarbonyl, $(C_1-C_3)$alkylamino, and di$(C_1-C_3)$alkylamino;

or, taken together with the nitrogen to which they are attached, $R^{20}$ and $R^{21}$ form an aliphatic heterocyle;

n is zero, one or two;

m is zero, one or two; and

X is S; or, when n is 1 and $R^1$ is optionally substituted phenyl, X is S or O.

25. A method of treating a subject having or at risk of developing hearing loss, comprising administering to the subject an effective amount of the compound of claim 1.

* * * * *